(12) United States Patent
Yonezawa et al.

(10) Patent No.: US 8,703,785 B2
(45) Date of Patent: Apr. 22, 2014

(54) 2-AMINOPYRIMIDIN-4-ONE AND 2-AMINOPYRIDINE DERIVATIVES BOTH HAVING BACE1-INHIBITING ACTIVITY

(75) Inventors: Shuji Yonezawa, Hokkaido (JP); Yuuji Kooriyama, Osaka (JP); Gaku Sakaguchi, Shiga (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 13/123,761

(22) PCT Filed: Oct. 22, 2009

(86) PCT No.: PCT/JP2009/068200
§ 371 (c)(1),
(2), (4) Date: Jun. 9, 2011

(87) PCT Pub. No.: WO2010/047372
PCT Pub. Date: Apr. 29, 2010

(65) Prior Publication Data
US 2011/0237576 A1   Sep. 29, 2011

(30) Foreign Application Priority Data

Oct. 22, 2008   (JP) .................................. 2008-272305

(51) Int. Cl.
*A01N 43/54* (2006.01)
*A61K 31/505* (2006.01)
*C07D 239/02* (2006.01)

(52) U.S. Cl.
USPC .......................................... 514/272; 544/320

(58) Field of Classification Search
USPC .......................................... 514/272; 544/320
See application file for complete search history.

(56) References Cited

U.S. PATENT DOCUMENTS

| | | | |
|---|---|---|---|
| 2,899,426 A | 8/1959 | Bloom et al. | |
| 3,115,494 A | 12/1963 | Joseph et al. | |
| 3,227,713 A | 1/1966 | Behner et al. | |
| 3,235,551 A | 2/1966 | Schubert et al. | |
| 3,577,428 A | 5/1971 | Suh et al. | |
| 3,636,116 A | 1/1972 | Trepanier | |
| 3,719,674 A | 3/1973 | Trepanier | |
| 3,775,409 A | 11/1973 | Harsanyi et al. | |
| 4,311,840 A | 1/1982 | Condon | |
| 4,895,841 A | 1/1990 | Sugimoto et al. | |
| 4,906,626 A | 3/1990 | Amrein et al. | |
| 5,100,901 A | 3/1992 | Sugimoto et al. | |
| 5,236,942 A | 8/1993 | Miller | |
| 5,328,915 A | 7/1994 | Long et al. | |
| 5,880,147 A | 3/1999 | Yoshida et al. | |
| 5,952,374 A | 9/1999 | Clarkson, Jr. et al. | |
| 6,096,753 A * | 8/2000 | Spohr et al. ............... | 514/269 |
| 6,590,123 B2 | 7/2003 | Bekesi et al. | |
| 6,713,276 B2 | 3/2004 | Cordell et al. | |
| 7,183,070 B2 | 2/2007 | Cordell et al. | |

(Continued)

FOREIGN PATENT DOCUMENTS

| | | |
|---|---|---|
| DE | 140144 | 2/1980 |
| EP | 0 798 292 | 10/1995 |

(Continued)

OTHER PUBLICATIONS

Co-pending U.S. Appl. No. 13/508,899, entitled Aminothiazine or Aminooxazine Derivative Having Amino Linker, filed May 9, 2012.

(Continued)

*Primary Examiner* — Jeffrey S. Lundgren
*Assistant Examiner* — Michael Schmitt
(74) *Attorney, Agent, or Firm* — Hamre, Schumann, Mueller & Larson, P.C.

(57) ABSTRACT

The present invention provides a compound which has an effect of inhibiting amyloid-β production and is useful as a therapeutic agent for diseases induced by production, secretion and/or deposition of amyloid-β proteins. The present invention relates to a compound represented by formula (I) or a pharmaceutically acceptable salt or solvate thereof:

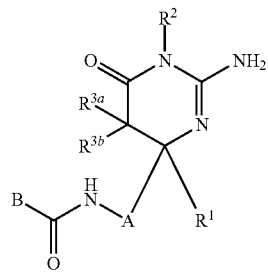

(I)

wherein A is optionally substituted carbocyclic diyl or optionally substituted heterocyclic diyl; B is an optionally substituted carbocyclic group or an optionally substituted heterocyclic group; $R^1$ is a group such as optionally substituted lower alkyl; $R^2$ is a group such as hydrogen; and $R^{3a}$ and $R^{3b}$ are each independently a group such as hydrogen, provided that the following compound is excluded.

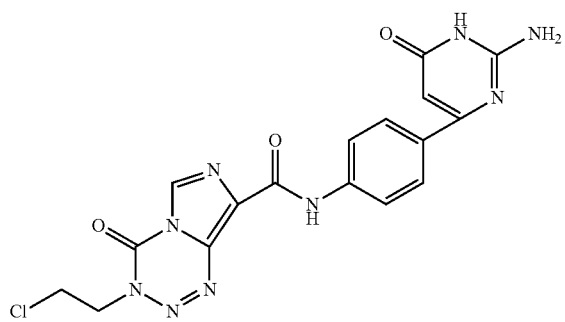

9 Claims, No Drawings

(56) References Cited

U.S. PATENT DOCUMENTS

| | | |
|---|---|---|
| 7,309,706 B2 | 12/2007 | Rupp et al. |
| 7,326,792 B2 | 2/2008 | Shum et al. |
| 7,414,050 B2 | 8/2008 | Illig et al. |
| 7,763,609 B2 | 7/2010 | Zhu et al. |
| 7,902,238 B2 | 3/2011 | Galley et al. |
| 8,173,642 B2 | 5/2012 | Kobayashi et al. |
| 2002/0019427 A1 | 2/2002 | Carry et al. |
| 2005/0165080 A1 | 7/2005 | Rupp et al. |
| 2006/0173006 A1 | 8/2006 | Sun et al. |
| 2006/0183790 A1 | 8/2006 | Cole et al. |
| 2006/0183792 A1 | 8/2006 | Fobare et al. |
| 2006/0183943 A1 | 8/2006 | Hu |
| 2007/0004730 A1 | 1/2007 | Zhou et al. |
| 2007/0004786 A1 | 1/2007 | Malamas et al. |
| 2007/0027199 A1 | 2/2007 | Malamas et al. |
| 2007/0224656 A1 | 9/2007 | Cordell et al. |
| 2008/0200445 A1* | 8/2008 | Zhu et al. ............ 514/210.02 |
| 2009/0023729 A1 | 1/2009 | Nakamuta et al. |
| 2009/0082560 A1 | 3/2009 | Kobayashi et al. |
| 2010/0075957 A1 | 3/2010 | Tamura et al. |
| 2010/0093999 A1 | 4/2010 | Motoki et al. |
| 2010/0125087 A1 | 5/2010 | Holenz et al. |
| 2010/0160290 A1 | 6/2010 | Kobayashi et al. |
| 2010/0234365 A1 | 9/2010 | Liu et al. |
| 2010/0261727 A1 | 10/2010 | Chi et al. |
| 2011/0009395 A1 | 1/2011 | Audia et al. |
| 2011/0046122 A1 | 2/2011 | Andreini et al. |
| 2011/0065695 A1 | 3/2011 | Beauchamp et al. |
| 2011/0190279 A1 | 8/2011 | Hori et al. |
| 2012/0015961 A1 | 1/2012 | Tamura et al. |
| 2012/0016116 A1 | 1/2012 | Kobayashi et al. |
| 2012/0022249 A1 | 1/2012 | Kobayashi et al. |
| 2012/0172355 A1 | 7/2012 | Tamura et al. |
| 2012/0238548 A1 | 9/2012 | Gabellieri et al. |
| 2012/0253035 A1 | 10/2012 | Narquizian et al. |
| 2012/0258962 A1 | 10/2012 | Hilpert et al. |
| 2012/0295900 A1 | 11/2012 | Hilpert et al. |

FOREIGN PATENT DOCUMENTS

| | | |
|---|---|---|
| EP | 0 713 704 | 5/1996 |
| EP | 0 718 294 | 6/1996 |
| EP | 0717040 | 6/1996 |
| EP | 1043312 | 10/2000 |
| EP | 1 283 039 | 2/2003 |
| EP | 1 577 294 | 9/2005 |
| EP | 1 942 105 | 7/2008 |
| EP | 1942105 | 7/2008 |
| EP | 2147914 | 1/2010 |
| EP | 2151435 | 2/2010 |
| EP | 2 233 474 | 9/2010 |
| EP | 2 305 672 | 4/2011 |
| EP | 2332943 | 6/2011 |
| EP | 2 360 155 | 8/2011 |
| EP | 2415756 | 2/2012 |
| GB | 1001093 | 8/1965 |
| JP | 62-120374 | 6/1987 |
| JP | 8-231521 | 9/1996 |
| JP | 9-67355 | 3/1997 |
| JP | 10-505862 | 6/1998 |
| JP | 11-349572 | 12/1999 |
| JP | 2005-509651 | 4/2004 |
| JP | 2004-149429 | 5/2004 |
| JP | 2005-517634 | 6/2005 |
| JP | 2005-526005 | 9/2005 |
| JP | 2005-531520 | 10/2005 |
| JP | 2006-519758 | 8/2006 |
| JP | 2009-051828 | 3/2009 |
| JP | 2009-520685 | 5/2009 |
| WO | 94/12165 | 6/1994 |
| WO | 95/09619 | 4/1995 |
| WO | 96/09286 | 3/1996 |
| WO | 96/14842 | 5/1996 |
| WO | 96/18608 | 6/1996 |
| WO | 97/07098 | 2/1997 |
| WO | 97/14686 | 4/1997 |
| WO | 97/38977 | 10/1997 |
| WO | 99/18960 | 4/1999 |
| WO | 00/00200 | 1/2000 |
| WO | 01/19788 | 3/2001 |
| WO | 01/78709 | 10/2001 |
| WO | 01/87293 | 11/2001 |
| WO | 02/062766 | 8/2002 |
| WO | 02/088101 | 11/2002 |
| WO | 02/096897 | 12/2002 |
| WO | 03/039446 | 5/2003 |
| WO | 03/040096 | 5/2003 |
| WO | 03/040115 | 5/2003 |
| WO | 03/040142 | 5/2003 |
| WO | 03/082191 | 10/2003 |
| WO | 2004/009549 | 1/2004 |
| WO | 2004/014843 | 2/2004 |
| WO | 2004/031154 | 4/2004 |
| WO | 2004/039404 | 5/2004 |
| WO | 2004/043916 | 5/2004 |
| WO | 2004/096795 | 11/2004 |
| WO | 2005/014555 | 2/2005 |
| WO | 2005/032493 | 4/2005 |
| WO | 2005/058311 | 6/2005 |
| WO | 2005/097767 | 10/2005 |
| WO | 2005/111031 | 11/2005 |
| WO | 2005/121100 | 12/2005 |
| WO | 2006/009655 | 1/2006 |
| WO | 2006/023750 | 3/2006 |
| WO | 2006/029850 | 3/2006 |
| WO | 2006/041404 | 4/2006 |
| WO | 2006/041405 | 4/2006 |
| WO | 2006/065204 | 6/2006 |
| WO | 2006/065277 | 6/2006 |
| WO | 2006/076284 | 7/2006 |
| WO | 2006/099379 | 9/2006 |
| WO | 2006/138192 | 12/2006 |
| WO | 2006/138217 | 12/2006 |
| WO | 2006/138265 | 12/2006 |
| WO | 2006/138304 | 12/2006 |
| WO | 2007/002220 | 1/2007 |
| WO | 2007/005366 | 1/2007 |
| WO | 2007/005404 | 1/2007 |
| WO | 2007/016012 | 2/2007 |
| WO | 2007/038271 | 4/2007 |
| WO | 2007/049532 | 5/2007 |
| WO | 2007/058580 | 5/2007 |
| WO | 2007/058582 | 5/2007 |
| WO | 2007/058583 | 5/2007 |
| WO | 2007/058601 | 5/2007 |
| WO | 2007/058602 | 5/2007 |
| WO | 2007/073284 | 6/2007 |
| WO | 2007/078813 | 7/2007 |
| WO | 2007/092846 | 8/2007 |
| WO | 2007/092854 | 8/2007 |
| WO | 2007/114771 | 10/2007 |
| WO | 2007/120096 | 10/2007 |
| WO | 2007/14622 | 12/2007 |
| WO | 2008/011560 | 1/2008 |
| WO | 2008/022024 | 2/2008 |
| WO | 2008/073365 | 6/2008 |
| WO | 2008/073370 | 6/2008 |
| WO | 2008/103351 | 8/2008 |
| WO | 2008/133273 | 11/2008 |
| WO | 2008/133274 | 11/2008 |
| WO | 2009/010454 | 1/2009 |
| WO | 2009/064418 | 5/2009 |
| WO | 2009/097278 | 8/2009 |
| WO | 2009/097401 | 8/2009 |
| WO | 2009/097578 | 8/2009 |
| WO | 2009/103626 | 8/2009 |
| WO | 2009/131974 | 10/2009 |
| WO | 2009/131975 | 10/2009 |
| WO | 2009/134617 | 11/2009 |
| WO | 2009/151098 | 12/2009 |
| WO | 2010/013302 | 2/2010 |
| WO | 2010/013794 | 2/2010 |
| WO | 2010/019392 | 2/2010 |

(56) References Cited

FOREIGN PATENT DOCUMENTS

| WO | 2010/019393 | 2/2010 |
| WO | 2010/047372 | 4/2010 |
| WO | 2010/056194 | 5/2010 |
| WO | 2010/056195 | 5/2010 |
| WO | 2010/056196 | 5/2010 |
| WO | 2010/113848 | 10/2010 |
| WO | 2010/128058 | 11/2010 |
| WO | 2010/129864 | 11/2010 |
| WO | 2011/005738 | 1/2011 |
| WO | 2011/009897 | 1/2011 |
| WO | 2011/009898 | 1/2011 |
| WO | 2011/009943 | 1/2011 |
| WO | 2011/020806 | 2/2011 |
| WO | 2011/029803 | 3/2011 |
| WO | 2011/044181 | 4/2011 |
| WO | 2011/044184 | 4/2011 |
| WO | 2011/044185 | 4/2011 |
| WO | 2011/044187 | 4/2011 |
| WO | 2011/058763 | 5/2011 |
| WO | 2011/060207 | 5/2011 |
| WO | 2011/069934 | 6/2011 |
| WO | 2011/070029 | 6/2011 |
| WO | 2011/070781 | 6/2011 |
| WO | 2011/071057 | 6/2011 |
| WO | 2011/071109 | 6/2011 |
| WO | 2011/071135 | 6/2011 |
| WO | 2011/077726 | 6/2011 |
| WO | 2011/080176 | 7/2011 |
| WO | 2011/138293 | 11/2011 |
| WO | 2011/154374 | 12/2011 |
| WO | 2011/154431 | 12/2011 |
| WO | 2012/000933 | 1/2012 |
| WO | 2012/006953 | 1/2012 |
| WO | 2012/095469 | 1/2012 |
| WO | WO 2012/019966 | 2/2012 |
| WO | 2012/038438 | 3/2012 |
| WO | 2012/057247 | 5/2012 |
| WO | 2012/057248 | 5/2012 |
| WO | 2012/085038 | 6/2012 |
| WO | 2012/093148 | 7/2012 |
| WO | 2012/095521 | 7/2012 |
| WO | 2012/098064 | 7/2012 |
| WO | 2012/098213 | 7/2012 |
| WO | 2012/098461 | 7/2012 |
| WO | 2012/104263 | 8/2012 |
| WO | 2012/107371 | 8/2012 |
| WO | 2012/110440 | 8/2012 |
| WO | 2012/110441 | 8/2012 |
| WO | 2012/110459 | 8/2012 |
| WO | 2012/117027 | 9/2012 |
| WO | 2012/119883 | 9/2012 |
| WO | 2012/120023 | 9/2012 |
| WO | 2012/126791 | 9/2012 |
| WO | 2012/136603 | 10/2012 |
| WO | 2012/139993 | 10/2012 |
| WO | 2012/147762 | 11/2012 |
| WO | 2012/147763 | 11/2012 |
| WO | 2012/156284 | 11/2012 |
| WO | 2012/162330 | 11/2012 |
| WO | 2012/162334 | 11/2012 |
| WO | 2012/163790 | 12/2012 |
| WO | 2012/168164 | 12/2012 |
| WO | 2012/168175 | 12/2012 |

OTHER PUBLICATIONS

Co-pending U.S. Appl. No. 13/513,839, entitled Oxazine Derivatives, filed Jun. 4, 2012.
Co-pending U.S. Appl. No. 13/514,516, entitled Substituted Aminothiazine Derivative, filed Jun. 7, 2012.
Co-pending U.S. Appl. No. 13/518,285, entitled 4-Amino-1,3-Thiazine or Oxazine Derivative, filed Jun. 21, 2012.
Co-pending U.S. Appl. No. 13/514,907, entitled Fused Heterocyclic Compound Having Amino Group, filed Jun. 8, 2012.

Bol'but et al., Heterocyclizations of Functionalized Heterocumulenes with C,N- and C,O-Dinucleophiles: III.* Cyclization of N-(1-Aryl-1-chloro-2,2,2-trifluoroethyl)-N'-arylcarbodiimides with 3-Substituted 1-Phenylpyrazol-5-ones, Russian Journal of Organic Chemistry, 2003, vol. 29, No. 2, pp. 1789-1791.
Trepanier et al., "Synthesis and screening for antidepressant activity of some aminoindanooxazolines, aminoindanooxazines, and aminoacenaphthoxazolines," Journal of Medicinal Chemistry, 1970, vol. 13, No. 4, pp. 729-733.
Sayed et al., "α-Enones in heterocyclic synthesis of indazole, thiazine, chromene and quinolone derivatives with their antimicrobial activities," Journal of Chemical Research, 2009, vol. 12, pp. 726-728.
Database Caplus [Online] Chemical Abstracts Service, Columbus, Ohio, US; Xu, Yungen et al: "Preparation of benzimidazolyl and benzothiazolyl isothiourea derivatives as nitric oxide synthase inhibitors", XP002679913, retrieved from STN Database accession No. 2005:46620 *abstract* Accessed Jul. 13, 2012.
Bol'but et al., "Synthesis of 4-imino-2-trifluoromethyl-3,4-dihydro-2h-Benzo-[1,3]Thiazines," Chemistry of Heterocyclic Compounds, 2001, vol. 37, No. 4, pp. 522-523.
Vovk et al., "Intramolecular thermal cyclization of N-(1-Aryl-1-aryloxy-2,2,2-trifluoroethyl)-N'-arylcarbodiimides," Russian Journal of Organic Chemistry, 2000, vol. 36, No. 12, pp. 1739-1742.
Vovk et al., "Regioselective cyclization of 1-chloroalkylcarbodiimides with 1,1- and 1,2-bifunctional nucleophilic reagents," Russian Journal of Organic Chemistry, 1997, vol. 22, No. 1, pp. 96-102.
Potts et al., "N-Acyl-β-enamino Ketones: Versatile Heterocyclic Synthons," J. Org. Chem., 1983, 48, pp. 625-626.
Rivkin et al., "Piperazinyl pyrimidine derivatives as potent γ-secretase modulators," Bioorganic & Medicinal Chemistry Letters, 2010, 20, pp. 1269-1271.
Rivkin et al., "Purine derivatives as potent γ-secretase modulators," Bioorganic & Medicinal Chemistry Letters, 2010, 20, pp. 2279-2282.
Clark, et al., "Antitumor Imidazotetrazines. 32.[1] Synthesis of Novel Imidazotetrazinones and Related Bicyclic Heterocycles to Probe the Mode of Action of the Antitumor Drug Temozolomide", J. Med. Chem., vol. 38, 1995, pp. 1493-1504.
Edwards, et al., "Application of Fragment-Based Lead Generation to the Discovery of Novel, Cyclic Amidine β-Secretase Inhibitors with Nanomolar Potency, Cellular Activity, and High Ligand Efficiency[§]", J. Med. Chem., vol. 50, 2007, pp. 5912-5925.
Congreve, et al., "Application of Fragment Screening by X-ray Crystallography to the Discovery of Aminopyridines as Inhibitors of β-Secretase[§]", J. Med. Chem., vol. 50, 2007, pp. 1124-1132.
Huang, et al., "Progress in the Development of Nonpeptidomimetic BACE I Inhibitors for Alzheimer's Disease", Current Medicinal Chemistry, vol. 16, 2009, pp. 1806-1820.
Cohen et al. "Synthesis of 2-Amino-5, +-dihydro-4H-1, 3-thiazines and Related Compounds by Acid Catalyzed Cyclization of Allylic Isothiuronium Salts." Journal of Heterocyclic Chemistry 14(5), 1977, p. 717-723.
Kuo et al. "A Synthesis of Estrone via Novel Intermediates. Mechanism of Coupling Reaction of a Vinyl Carbinol with a β Diketone." Journal of Organic Chemistry 33(8), Aug. 1968, p. 3126-3132.
Liebscher et al. "2-Arylimino-3-Thiazolines—Formation of Unusual Tautomers of 2-Arylamino-Thiazolines—A Revision." Tetrahedron Letters, 26(35), 1985, p. 4179-4180.
Fernández et al. "Syntheses and Spectral Properties of β-Iodoureas ans 2-Amino-4, 4-diphenyl-2-oxazolines." Journal of Heterocyclic Chemistry, 28(3), Apr.-May 1991, p. 777-780.
Schaumann et al. "Stickstofthaltige Funfring-Heterocyclen aus Carbodiimiden orderKeteniminen mit 3-Dimethylamino-2H-azirinen." Liebigs Annalen der Chemie, 1981, p. 290-305.
Fernández et al. "Syntheses of β-iodourea derivatives of carbohydrates and glycosylamino-ozazolines." Carbohydrate Research, 216, 1991, p. 21-32.
Cambie et al. "vic-Iodothiocyanates and Iodoisothiocyanates. Part 2. New Syntheses of Thiazolidin-2-ones and 2-Amino-thiazolines." Journal of the Chemical Society, Perkin Transactions I, 3, 1979, p. 765-770.

(56) References Cited

OTHER PUBLICATIONS

Kondrat'eva et al. "Noncyclic dimer of 4-methyl-2-(dimenthylamino)oxazole." Akademii Nauk SSSR, Seriya Khimicheskaya, 7, 1977, p. 1680-1682.
Hünig et al. "Azo dyes by oxidative coupling, XVIII. Synthesis of 3-substituted 2-thiazolone hydrazones and 2-thiazolone benzenesulfonylhydrazones." Ann. 647, 1961, p. 66-76.
Koriyama et al., "Reversal of diastereofacial selectivity in the nucleophilic addition reaction to chiral N-sulfinimine and application to the synthesis of indrizidine 223AB," Tetrahedron, vol. 58, 2002, pp. 9621-9628.
Fujisawa et al., "Switchover of diastereofacial selectivity in the condensation reaction of optically active N-sulfinimine with ester enolate," Tetrahedron Letters, vol. 37, No. 22, 1996, pp. 3881-3884.
Vilaivan et al., "Recent Advances in Catalytic Asymmetric Addition to Imines and Related C=N Systems," Current Organic Chemistry, vol. 9, 2005, pp. 1315-1392.
Hua et al., "N-Alkylidenesulfinamides," Sulfur Reports, vol. 21, 1999, pp. 211-239.
Savoca et al., "1,5-Diazabicyclo[4.3.0]non-5-ene[1]," Encyclopedia of Reagents for Organic Synthesis, 2006, 10 pages total.
Creeke et al., "Synthesis and elaboration of heterocycles via iodocyclisation of unsaturated thioureas," Tetrahedron Letters, 1989, vol. 30, No. 33, pp. 4435-4438.
Mellor et al.,"A general route to spirocycles by radical additions to exocyclic unsaturated sulphides and related compounds," Tetrahedron Letters, 1991, vol. 32, No. 48, pp. 7111-7114.
Murai et al., "Iodo-cyclization of N-homoallyl thioamides leading to 2,4-diaryl-5,6-dihydro-4H-1,3-thiazines," Chemistry Letters, 2004, vol. 33, No. 5, pp. 508-509.
Singh et al., "Synthesis of heterocyclic compounds via enamines. Part 8[†]. Acid-catalysed transformations in a 4,4,6-trimethyl-1,4-dihydropyrimidine-2(3H)-thione derivatives and related compounds," J. Chem. Soc., Perkin Trans. 1, 1980, pp. 1013-1018.
Vippagunta et al. "Crystalline Solids". Advanced Drug Delivery Reviews, vol. 48, 2001, pp. 3-26.
Gavezzotti. "Are Crystal Structures Predictable". Accounts of Chemical Research, vol. 27, 1994, pp. 309-314.
Database Registry [Online], Chemical Abstracts Service, Columbus, Ohio, US; May 29, 2007, "2H-Indol-2-ome,4-(-2-amino-5,6-dihydro-4H-1,3-thiazin-4-yl)-1,3-dihydro-", XP002646872, Database accession No. 935998-84-8.
Schubert et al., "Neue synthesen von 2-Amino-5,6-dihydro-4H-1,3-thiazinen," Archie der Pharmazie, 1968, vol. 301, No. 10, pp. 750-762.
Huang et al., "Pharmacophore model construction of β-secretase inhibitors," 2008, Acta Chimica Sinica, vol. 66, No. 16, pp. 1889-1897 (English language abstract provided).
Goodyer et al., "Synthesis of N-benzyl- and N-phenyl-2-amino-4,5-dihydrothiazoles and thioureas and evaluation as modulators of the isoforms of nitric oxide synthase," Bioorganic & Medicinal Chemistry, 2003, vol. 11, pp. 4189-4206.
Siddiqui et al., "Some extensions of Von Bruan (BrCN) reaction on organic bases," Proc. Pakistan Acad. Sci., 1988, vol. 25, No. 3, pp. 231-240.
Ozawa et al., Pharmacological actions of 2-Aminoethylisothiuronium (AET) derivatives. I[1]), Yakugaku Zasshi, 1968, vol. 88, No. 2, pp. 156-162.
Curtis et al., The byozynsethis of Phenols. Part VIII. The synthesis of (2-carboxy-3,5-dihydroxyphynyl)propan-2-one (C-acetyl-o-orsellinic acid). Journal of the Chemical Society, 1964, pp. 5382-5385.
Burton et al., "Addition reactions of quinones. Part I. The reaction of cysteine and thiourea and its derivatives with some quinones," Journal of the Chemical Society, 1952, pp. 2193-2196.
Matsui, "Yomo bochuzai no kenkyu (the 6th report) Kagaku kozo to yomo shokugai boshi koka tono kankei (III)," Journal of Synthetic Organic Chemistry, Japan, 1950, vol. 8, No. 10, pp. Ho61-Ho65.
Desai et al., "The condensation of thiocarbamides with monochloroacetic acide and the conversion of arylformamidinethiolacetic acids into pseudothiohydantoin derivatives," Recuil des Travaux Chimiques des Pays-Bas et de la Belgique, 1935, pp. 118-121.
Cole et al., "Acylguanidines as small-molecule beta-secretase inhibitors," J. Med. Chem., 2006, pp. 6158-6161.
Co-pending Application U.S. Appl. No. 13/243,874, entitled Aminodihydrothiazine Derivatives, filed Sep. 23, 2011.
Co-pending Application U.S. Appl. No. 13/243,971, entitled Aminodihydrothiazine Derivatives, filed Sep. 23, 2011.
Co-pending U.S. Appl. No. 13/260,103, entitled Isothiourea Derivatives or Isourea Derivatives Having Bace 1 Inhibitory Activity, filed Sep. 23, 2011.
STN a the Web, RN 79005-45-1, 1964.
Zhu et al., Two novel Diastereoselective Three-Component Reactions of Alkenes or 3,4-Dihydro-(2H)-pyran with Urea/Thiourea-Aldehyde Mixtures: [4 + 2] Cycloaddition vs Biginelli-Type Reaction, Organic Letters, 2006, vol. 8, No. 12, pp. 2599-2602.
Kiselyov et al., "Design and chemical synthesis of [1,2,4]triazol[1,5-c]pyrimidin-5-yl amines, a novel class of VEGFR-2 kinase inhibitors," 2009, Tetrahedron Letters, vol. 50, pp. 3809-3812.
Mulcahy et al., "A stereoselective synthesis of (+)-Gonyautoxin 3," Journal of the American Chemical Society, 2008, vol. 130, pp. 12630-12631.
"Diphenyl Cyanocarbonimidate," e-EROS Encyclopedia of Reagents for Organic Synthesis, 2001, 2 pages total.
Shafik et al., "Synthesis of novel 2-[2-(substituted amino)phenethyl]-1H-benzimidazoles; 3,4-dihydro and 1,2,3,4-tetrahydropyrimido[1,6-α]-benzimidazoles as potential antiulcer agents," 2004, Pharmazie, vol. 59, No. 12, pp. 899-905.
Pohl et al., "Synthesis of partially saturated condensed triazoles by reaction of ω-Aminoalkyl-1,2,4-triazoles with electrophiles," Journal fuer Praktische Chemie Chemiker-Zeitung, 1992, vol. 334, pp. 630-636.
Buschauer et al., "Isohistamine und Homologe als Bausteine von H$_2$-Antagonisten," Arzneimittel-Forschung, 1985, vol. 35, pp. 1025-1029 (English language abstract provided).
Buschauer et al., "7,8-Dihydroimidazo[1,2-c]pyrimidin-5(6H)-one, -5(6H)-thione and -5(6H)-ylidencyanamide," Chemische Berichte, 1984, vol. 117, pp. 2597-2614.
Borchers et al., "H$_2$-Antihystaminika, 19. Mitt[1)]. Syntheses und H$_2$-antihistaminische Wirkung N$^α$-substituierter Histamine," Archiv der Pharmazie (Weinheim, Germany), 1984, vol. 317, pp. 455-459.
Cheong et al., "Pharmacophore elucidation for a new series of 2-arylpyrazolo-triazolo-pyrimidines as potent human A$_3$ adenosine receptor antagonists," Bioorganic & Medicinal Chemistry Letters, 2011, vol. 21, pp. 2898-2905.
Xu et al., "Copper-catalyzed cascade synthesis of benzimidazoquinazoline derivatives under mild condition," Chemical Communications, 2011, vol. 47, pp. 5596-5598.
Kishore et al., "QSAR of adenosine receptor antagonists: exploring physicochemical requirements for binding of pyrazolo[4,3-e]-1-2,4-triazolo[1,5-c]pyrimidine derivatives with human adenosine A$_3$ receptor subtype," Bioorganic & Medicinal Chemistry Letters, 2011, vol. 21, No. 2, pp. 818-823.
Dolzhenko et al., "8-methy1-2-[4-(trifluoromethyl)phenyl]-8H-pyrazolo[4,3-e][1,2,4]triazolo[1,5-c]-pyrimidin-5-amine methanol disolvate," Acta Crystallographica, Section E: Structure Reports Online, E66(7), 12 pages total, Jul. 2010.
Beaton et al., "3,4-dihydro-1-isoquinolinamines: a novel class of nitric oxide synthase inhibitors with a range of isoform selectivity and potency," Bioorganic & Medicinal Chemistry Letters, 2001, vol. 11, pp. 1023-1026.
Beaton et al., "The synthesis of 1-aminodihydroisoquinolines by an imine addition cyclisation reaction," 1998, Tetrahedron Letters, vol. 39, pp. 1227-1230.
Tian et al., "Radiosynthesis of 8-Fluoro-3-(4-[$^{18}$F]Fluorophenyl)-3,4-Dihydro-1-Isoquinolinamine ([$^{18}$F]FFDI), a potential PET radiotracer for the inducible nitric oxide synthase," 2008, Current Radiopharmaceuticals, vol. 1, pp. 49-53.
Weinhardt, et al. "Synthesis and antidepressant profiles of phenyl-substituted 2-amino- and 2-((alkoxycarbonyl)amino)1,4,5,6-tetrahydropyrimidines," Journal of Medicinal Chemistry, vol. 28, No. 6, 1985, pp. 694-698.

(56) References Cited

OTHER PUBLICATIONS

Meschino et al., "2-Amino-5,6-dihydro-1,3-oxazines. The reduction of carboxylic esters with sodium borohydride," J. Org. Chem., vol. 28, 1963, pp. 3129-3134.

Poos et al., "2-amino-5-aryl-2-oxazolines. Potent new anorectic agent," J. Med. Chem., vol. 6, 1963, pp. 266-272.

Sandin et al., "A fast and parallel route to cyclic isothioureas and guanidines with use of microwave-assisted chemistry," J. Org. Chem., vol. 69, 2004, pp. 1571-1580.

Weinhardt et al., "Synthesis and central nervous system propreties of 2-[(Alkoxycarbonyl)amino]-4(5)-phenyl-2-imidazolines," Journal of Medicinal Chemistry, vol. 27, No. 5, 1984, pp. 616-627.

Woodgate et al., "A new synthesis of 2-amino-2-thiazolines," Heterocycles, vol. 7, No. 1, 1977, pp. 109-112.

Co-pending U.S. Appl. No. 13/881,112, entitled Fused Aminodihydropyrimidine Derivative, filed Apr. 23, 2013.

Co-pending U.S. Appl. No. 13/881,250, entitled Naphthyridine Derivative, filed Apr. 24, 2013.

Calabrese et al. "NO Synthase and NO-Dependent Signal Pathways in Brain Aging and Neurodegenerative Disorders: The Role of Oxidant/Antioxidant Balance". Neurochemical Balance, vol. 25, No. 9/10, pp. 1315-1341 (2000).

Kavya et al. "Nitric oxide synthase regulation and diversity: Implications in Parkinson's Disease". Nitric Oxide: Biology and Chemistry, vol. 15, No. 4, pp. 280-294 (2006).

Chiou et al. "Review: Effects of Nitric Oxide on Eye Diseases and Their Treatment". Journal of Ocular Pharmacology and Therapeutics, vol. 17, No. 2, pp. 189-198 (2001).

Ishii et al. "Subacute NO generation induced by Alzheimer's β-amyloid in the living brain: reversal by inhibition of the inducible NO synthase". The Federation of American Societies for Experimental Biology Journal, vol. 14, pp. 1485-1489 (2000).

Pak et al. "Morphine via nitric oxide modulates β-amyloid metabolism: anovel protective mechanism for Alzheimer's disease". Medical Science Monitor, vol. 11, No. 10, pp. BR357-BR366 (2005).

Dörwald, "Side reactions in organic synthesis: a guide to successful synthesis design" 2005 Wiley-VCH Verlag GmbH & Co., KGaA, Wienheim, chapter 1, 32 pages total.

Wermuth; Practice of Medicinal Chemistry, Third Ed., 2008, Elsevier, chapter 15, 54 pages total.

\* cited by examiner

2-AMINOPYRIMIDIN-4-ONE AND 2-AMINOPYRIDINE DERIVATIVES BOTH HAVING BACE1-INHIBITING ACTIVITY

TECHNICAL FIELD

The present invention relates to a compound which has an effect of inhibiting amyloid-β production and is useful as a therapeutic agent for diseases induced by production, secretion and/or deposition of amyloid-β proteins.

BACKGROUND ART

In the brains of patients with Alzheimer's disease, peptides each consisting of approximately 40 amino acids, called amyloid-β proteins, which widely accumulate outside neurons to form insoluble plaques (senile plaques) are observed. These senile plaques are thought to kill neurons and cause the onset of Alzheimer's disease. As therapeutic agents for Alzheimer's disease, agents promoting degradation of amyloid-β proteins and amyloid-β vaccines have been studied.

Secretases are enzymes which cleave a protein called amyloid-β precursor protein (APP) within a cell and generate an amyloid-β protein. An enzyme which produces N-terminals of amyloid-β proteins is called as BACE1 (beta-site APP-cleaving enzyme 1, β-secretase). It is considered that production of amyloid-β proteins may be suppressed by inhibiting this enzyme, and thus a substance with such an effect can serve as a therapeutic agent for Alzheimer's disease.

Non-Patent Document 1 discloses a 2-aminopyrimidin-4-one derivative which has a structure similar to that of the compound of the present invention. However, the document only discloses that this substance is useful as an antitumor drug.

Further, 2-aminopyrimidin-4-one derivatives in Patent Documents 1 to 7 and Non-Patent Document 2, 2-aminopyridine derivatives in Patent Document 8 and Non-Patent Document 3, and an aminodihydrothiazine derivative in Patent Document 9 are known as BACE1 inhibitors. However, each of these substances has a structure different from that of the compound of the present invention.

Patent Document 1: WO 2006/041404
Patent Document 2: WO 2006/041405
Patent Document 3: WO 2005/058311
Patent Document 4: WO 2006/065277
Patent Document 5: WO 2007/058580
Patent Document 6: WO 2007/146225
Patent Document 7: WO 2007/114771
Patent Document 8: WO 2006/065204
Patent Document 9: WO 2007/049532
Non-Patent Document 1: Journal of Medicinal Chemistry, 1995, 38, 1493-1504
Non-Patent Document 2: Journal of Medicinal Chemistry, 2007, 50, 5912-5925
Non-Patent Document 3: Journal of Medicinal Chemistry, 2007, 50, 1124-1132

SUMMARY OF THE INVENTION

The present invention provides a compound which has an effect of inhibiting amyloid-β production, in particular a BACE1 inhibitory effect, and is useful as a therapeutic agent for diseases induced by production, secretion or deposition of amyloid-β proteins.

The present invention aims to provide the following 1) to 10).

1) A compound represented by formula (I) or a pharmaceutically acceptable salt or solvate thereof,

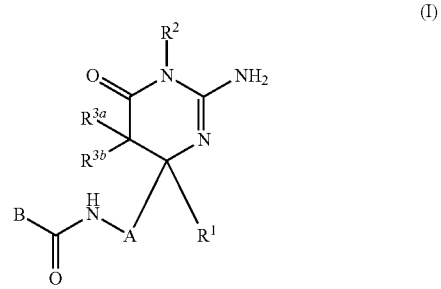

wherein A is optionally substituted carbocyclic diyl or optionally substituted heterocyclic diyl;

B is an optionally substituted carbocyclic group or an optionally substituted heterocyclic group;

$R^1$ is optionally substituted lower alkyl, optionally substituted lower alkenyl or optionally substituted lower alkynyl;

$R^2$ is hydrogen, optionally substituted lower alkyl, optionally substituted lower alkenyl, optionally substituted lower alkynyl, optionally substituted acyl or optionally substituted lower alkoxycarbonyl; and $R^{3a}$ and $R^{3b}$ are each independently hydrogen, halogen, hydroxy, optionally substituted lower alkyl, optionally substituted lower alkenyl, optionally substituted acyl, optionally substituted lower alkoxy, optionally substituted aralkyl, optionally substituted heteroarylalkyl, optionally substituted aralkyloxy, optionally substituted heteroarylalkyloxy, optionally substituted lower alkylthio, carboxy, optionally substituted lower alkoxycarbonyl, optionally substituted amino, optionally substituted carbamoyl, an optionally substituted carbocyclic group or an optionally substituted heterocyclic group, or $R^{3a}$ or $R^{3b}$ forms a bond together with $R^1$, provided that the following compound is excluded.

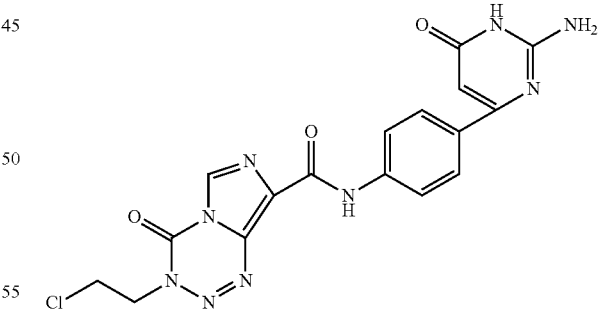

2) The compound or a pharmaceutically acceptable salt or solvate thereof according to the above 1),
wherein A is optionally substituted benzenediyl, optionally substituted pyridinediyl, optionally substituted pyrazinediyl or optionally substituted benzofurandiyl.

3) The compound or a pharmaceutically acceptable salt or solvate thereof according to the above 1) or 2),
wherein B is an optionally substituted heterocyclic group.

4) The compound or a pharmaceutically acceptable salt or solvate thereof according to the above 3), wherein the substituent of the heterocyclic group for B is substituted lower alkoxy, optionally substituted lower alkenyloxy or optionally substituted lower alkynyloxy.

5) The compound or a pharmaceutically acceptable salt or solvate thereof according to any one of the above 1) to 4),
wherein $R^{3a}$ and $R^{3b}$ are both hydrogen.

6) The compound or a pharmaceutically acceptable salt or solvate thereof according to any one of the above 1) to 4),
wherein $R^1$ and $R^{3a}$ together form a bond, and $R^{3b}$ is hydrogen.

7) The compound or a pharmaceutically acceptable salt or solvate thereof according to any one of the above 1) to 5),
wherein $R^1$ is C1-C3 alkyl.

8) The compound or a pharmaceutically acceptable salt or solvate thereof according to any one of the above 1) to 7),
wherein $R^2$ is optionally substituted lower alkyl.

9) A pharmaceutical composition, comprising
the compound or a pharmaceutically acceptable salt or solvate thereof according to any one of the above 1) to 8) as an active ingredient.

10) The pharmaceutical composition according to the above 9), which has a BACE1 inhibitory activity.

The present invention also aims to provide the following 11) to 18).

11) A compound represented by formula (II) or a pharmaceutically acceptable salt or solvate thereof,

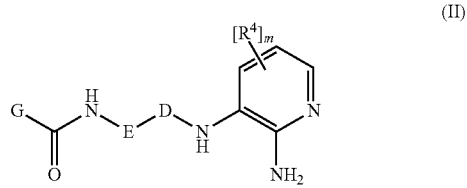

(II)

wherein E is optionally substituted carbocyclic diyl or optionally substituted heterocyclic diyl;
G is an optionally substituted carbocyclic group or an optionally substituted heterocyclic group;
D is lower alkylene, lower alkenylene or lower alkynylene;
$R^4$ is each independently hydrogen, halogen, hydroxy, optionally substituted lower alkyl, optionally substituted lower alkenyl, optionally substituted acyl, optionally substituted lower alkoxy, optionally substituted aralkyl, optionally substituted heteroarylalkyl, optionally substituted aralkyloxy, optionally substituted heteroarylalkyloxy, optionally substituted lower alkylthio, carboxy, optionally substituted lower alkoxycarbonyl, optionally substituted amino, optionally substituted carbamoyl, an optionally substituted carbocyclic group or an optionally substituted heterocyclic group; and
m is an integer of 0 to 3.

12) The compound or a pharmaceutically acceptable salt or solvate thereof according to the above 11),
wherein E is optionally substituted benzenediyl, optionally substituted pyridinediyl, optionally substituted pyrazinediyl or optionally substituted benzofurandiyl.

13) The compound or a pharmaceutically acceptable salt or solvate thereof according to the above 11) or 12),
wherein G is an optionally substituted heterocyclic group.

14) The compound or a pharmaceutically acceptable salt or solvate thereof according to the above 13),
wherein the substituent on the heterocyclic group of G is substituted lower alkoxy, optionally substituted lower alkenyloxy or optionally substituted lower alkynyloxy.

15) The compound or a pharmaceutically acceptable salt or solvate thereof according to any one of the above 11) to 14),
wherein D is lower alkylene.

16) The compound or a pharmaceutically acceptable salt or solvate thereof according to any one of the above 11) to 15),
wherein $R^4$ is each independently hydrogen, halogen or lower alkyl.

17) A pharmaceutical composition, comprising
the compound or a pharmaceutically acceptable salt or solvate thereof according to any one of the above 11) to 16) as an active ingredient.

18) The pharmaceutical composition according to the above 17), which has a BACE1 inhibitory activity.

The present invention further aims to provide the following 19) to 30).

19) The pharmaceutical composition according to the above 10), which is an amyloid-β production inhibitor.

20) The pharmaceutical composition according to the above 10), which is a therapeutic agent for diseases induced by production, secretion and/or deposition of amyloid-β proteins.

21) The pharmaceutical composition according to the above 10), which is an agent for treating Alzheimer's disease.

22) A method for treating diseases induced by production, secretion or deposition of amyloid-β proteins, the method comprising
administering the compound of formula (I) or a pharmaceutically acceptable salt or solvate thereof in the above 1).

23) Use of the compound of formula (I) or a pharmaceutically acceptable salt or solvate thereof in the above 1) in the manufacture of a medicament for treating diseases induced by production, secretion or deposition of amyloid-β proteins.

24) The compound of formula (I) or a pharmaceutically acceptable salt or solvate thereof in the above 1) for the use as the treatment of diseases induced by production, secretion or deposition of amyloid-β proteins.

25) A method for treating diseases due to BACE1, the method comprising
administering the compound of formula (I) or a pharmaceutically acceptable salt or solvate thereof in the above 1).

26) Use of the compound of formula (I) or a pharmaceutically acceptable salt or solvate thereof in the above 1) in the manufacture of a medicament for treating diseases due to BACE1.

27) The compound of formula (I) or a pharmaceutically acceptable salt or solvate thereof in the above 1) for the use as the treatment of diseases due to BACE1.

28) A method for treating Alzheimer's disease, comprising
administering the compound of formula (I) or a pharmaceutically acceptable salt or solvate thereof in the above 1).

29) Use of the compound of formula (I) or a pharmaceutically acceptable salt or solvate thereof in the above 1) in the manufacture of a medicament for treating Alzheimer's disease.

30) The compound of formula (I) or a pharmaceutically acceptable salt or solvate thereof in the above 1) for the use as the treatment of Alzheimer's disease.

The present invention still further aims to provide the following 31) to 42).

31) The pharmaceutical composition according to the above 18), which is an amyloid-β production inhibitor.

32) The pharmaceutical composition according to the above 18), which is a therapeutic agent for diseases induced by production, secretion and/or deposition of amyloid-β proteins.

33) The pharmaceutical composition according to the above 18), which is an agent for treating Alzheimer's disease.

34) A method for treating diseases induced by production, secretion or deposition of amyloid-β proteins, the method comprising
administering the compound of formula (II) or a pharmaceutically acceptable salt or solvate thereof in the above 11).

35) Use of the compound of formula (II) or a pharmaceutically acceptable salt or solvate thereof in the above 11) in the manufacture of a medicament for treating diseases induced by production, secretion or deposition of amyloid-β proteins.

36) The compound of formula (II) or a pharmaceutically acceptable salt or solvate thereof in the above 11) for the use as the treatment of diseases induced by production, secretion or deposition of amyloid-β proteins.

37) A method for treating diseases due to BACE1, the method comprising
administering the compound of formula (II) or a pharmaceutically acceptable salt or solvate thereof in the above 11).

38) Use of the compound of formula (II) or a pharmaceutically acceptable salt or solvate thereof in the above 11) in the manufacture of a medicament for treating diseases due to BACE1.

39) The compound of formula (II) or a pharmaceutically acceptable salt or solvate thereof in the above 11) for the use as the treatment of diseases due to BACE1.

40) A method for treating Alzheimer's disease, comprising
administering the compound of formula (II) or a pharmaceutically acceptable salt or solvate thereof in the above 11).

41) Use of the compound of formula (II) or a pharmaceutically acceptable salt or solvate thereof in the above 11) in the manufacture of a medicament for treating Alzheimer's disease.

42) The compound of formula (II) or a pharmaceutically acceptable salt or solvate thereof in the above 11) for the use as the treatment of Alzheimer's disease.

The compound of the present invention is useful as a therapeutic agent for diseases (e.g. Alzheimer's disease) induced by production, secretion or deposition of amyloid-β proteins.

MODES FOR CARRYING OUT THE INVENTION

The term "halogen" herein includes fluorine, chlorine, bromine and iodine.

The halogen portions in "halogeno lower alkyl" and "halogeno lower alkoxycarbonyl" are as defined above for the "halogen".

The term "lower alkyl" herein includes C1-C15, preferably C1-C10, more preferably C1-C6, and further preferably C1-C3 linear or branched alkyl. Examples thereof include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl and n-decyl.

The lower alkyl portions in "lower alkoxy", "halogeno lower alkyl", "hydroxy lower alkoxy", "lower alkoxycarbonyl", "halogeno lower alkoxycarbonyl", "lower alkylamino", "hydroxyimino lower alkyl", "lower alkoxyimino lower alkyl", "amino lower alkyl", "lower alkoxy lower alkoxy", "lower alkoxy lower alkenyloxy", "lower alkoxy lower alkynyloxy", "lower alkylcarbamoyl", "hydroxy lower alkylcarbamoyl", "lower alkoxyimino", "lower alkylthio", "lower alkylsulfonyl", "lower alkylsulfamoyl", "lower alkylsulfinyl", "carbocyclic lower alkyl", "carbocyclic lower alkoxy", "carbocyclic lower alkoxycarbonyl", "carbocyclic lower alkylamino", "carbocyclic lower alkylcarbamoyl", "cycloalkyl lower alkyl", "cycloalkyl lower alkoxy", "cycloalkyl lower alkylamino", "cycloalkyl lower alkoxycarbonyl", "cycloalkyl lower alkylcarbamoyl", "aryl lower alkyl", "aryl lower alkoxy", "aryl lower alkylamino", "aryl lower alkoxycarbonyl", "aryl lower alkylcarbamoyl", "heterocyclic lower alkyl", "heterocyclic lower alkoxy", "heterocyclic lower alkylamino", "heterocyclic lower alkoxycarbonyl" and "heterocyclic lower alkylcarbamoyl" are as defined above for the "lower alkyl".

The "optionally substituted lower alkyl" may be substituted by one or more groups selected from the substituent group α.

The substituent group α herein consists of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, imino, hydroxyimino, lower alkoxyimino, lower alkylthio, carbamoyl, lower alkylcarbamoyl, hydroxy lower alkylcarbamoyl, sulfamoyl, lower alkylsulfamoyl, lower alkylsulfinyl, cyano, nitro, carbocyclic groups and heterocyclic groups.

The substituents in "optionally substituted lower alkoxy", "optionally substituted lower alkoxycarbonyl" and "optionally substituted lower alkylthio" may be one or more groups selected from the substituent group α.

The substituent in "substituted lower alkoxy" is the same as any of the above substituents.

The term "lower alkylidene" herein includes divalent forms of the "lower alkyl". Examples thereof include methylidene, ethylidene, propylidene, isopropylidene, butylidene, pentylidene and hexylidene.

The term "lower alkenyl" herein includes C2-C15, preferably C2-C10, more preferably C2-C6, and further preferably C2-C4 linear or branched alkenyl having one or more double bonds at any position. Specific examples thereof include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl and pentadecenyl.

The term "lower alkynyl" herein includes C2-C10, preferably C2-C8, and more preferably C3-C6 linear or branched alkynyl having one or more triple bonds at any position. Specific examples thereof include ethynyl, propynyl, butynyl, pentynyl, hexynyl, heptynyl, octynyl, nonynyl and decynyl. These groups may further have a double bond at any position.

The substituents in "optionally substituted lower alkenyl", "optionally substituted lower alkenyloxy", "optionally substituted lower alkynyl" and "optionally substituted lower alkynyloxy" may be one or more groups selected from the substituent group α.

The lower alkenyl portions in "lower alkoxy lower alkenyloxy", "lower alkenyloxy", "lower alkenylthio" and "lower alkenylamino" are as defined above for the "lower alkenyl".

The lower alkynyl portions in "lower alkynyloxy", "lower alkoxy lower alkynyloxy", "lower alkynylthio" and "lower alkynylamino" are as defined above for the "lower alkynyl".

The substituents in the "optionally substituted amino" and "optionally substituted carbamoyl" may be one or two groups selected from lower alkyl, acyl, hydroxy, lower alkoxy, lower alkoxycarbonyl, carbocyclic groups, heterocyclic groups and the like.

The term "acyl" herein includes C1-C10 aliphatic acyl, carbocyclic carbonyl and heterocyclic carbonyl. Specific examples thereof include formyl, acetyl, propionyl, butyryl, isobutyryl, valeryl, pivaloyl, hexanoyl, acryloyl, propioloyl, methacryloyl, crotonoyl, benzoyl, cyclohexane carbonyl, pyridine carbonyl, furan carbonyl, thiophene carbonyl, benzothiazole carbonyl, pyrazine carbonyl, piperidine carbonyl and thiomorpholino.

The acyl portions in "acylamino" and "acyloxy" are the same as mentioned above.

The substituent in "optionally substituted acyl" may be one or more groups selected from the substituent group α. The cyclic portions in carbocyclic carbonyl and heterocyclic carbonyl may be substituted by one or more groups selected from lower alkyl, the substituent group α and lower alkyl substituted by one or more groups selected from the substituent group α.

The term "carbocyclic group" herein includes cycloalkyl, cycloalkenyl, aryl and fused non-aromatic carbocyclic groups.

The term "cycloalkyl" herein includes C3-C10, preferably C3-C8, and more preferably C4-C8 carbocyclic groups. Examples thereof include cyclopropyl, cyclobutyl, cyclopentyl, cyclohexyl, cycloheptyl, cyclooctyl, cyclononyl and cyclodecyl.

The cycloalkyl portions in "cycloalkyl lower alkyl", "cycloalkyloxy", "cycloalkyloxycarbonyl", "cycloalkyl lower alkoxy", "cycloalkylthio", "cycloalkylamino", "cycloalkyl lower alkylamino", "cycloalkyl sulfamoyl", "cycloalkyl sulfonyl", "cycloalkylcarbamoyl", "cycloalkyl lower alkylcarbamoyl" and "cycloalkyl lower alkoxycarbonyl" are as defined above for the "cycloalkyl".

The term "cycloalkenyl" herein includes those having one or more double bonds at any position in the ring of the cycloalkyl. Specific examples thereof include cyclopropenyl, cyclobutenyl, cyclopentenyl, cyclohexenyl, cycloheptynyl, cyclooctynyl and cyclohexadienyl.

The term "aryl" herein includes phenyl, naphthyl, anthryl and phenanthryl. Phenyl is particularly preferable among these.

The term "fused non-aromatic carbocyclic group" herein includes groups formed by fusion of two or more cyclic groups selected from the above "cycloalkyl", "cycloalkenyl" and "aryl". Specific examples thereof include indanyl, indenyl, tetrahydronaphthyl and fluorenyl.

The carbocyclic portions in "carbocyclic diyl", "carbocyclic oxy", "carbocyclic lower alkyl", "carbocyclic lower alkoxy", "carbocyclic lower alkoxycarbonyl", "carbocyclic thio", "carbocyclic amino", "carbocyclic lower alkylamino", "carbocyclic carbonyl", "carbocyclic sulfamoyl", "carbocyclic sulfonyl", "carbocyclic carbamoyl", "carbocyclic lower alkylcarbamoyl" and "carbocyclic oxycarbonyl" are the same as the carbocycle of the "carbocyclic group".

The aryl portions in "aralkyl", "aralkyloxy", "aryl lower alkyl", "aryloxy", "aryloxycarbonyl", "aryl lower alkoxycarbonyl", "arylthio", "arylamino", "aryl lower alkoxy", "aryl lower alkylamino", "arylsulfonyl", "arylsulfamoyl", "arylcarbamoyl" and "aryl lower alkylcarbamoyl" are as defined above for the "aryl".

The substituents in "optionally substituted aralkyl" and "optionally substituted aralkyloxy" may be one or more groups selected from the substituent group α.

The term "heterocyclic group" herein includes heterocyclic groups having one or more hetero atoms arbitrarily selected from O, S and N in the ring. Specific examples thereof include:

5- or 6-membered heteroaryls such as pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, triazolyl and thiadiazolyl;

non-aromatic heterocyclic groups such as dioxanyl, thiiranyl, oxiranyl, oxetanyl, oxathioranyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl and tetrahydropyridazinyl;

fused bicyclic heterocyclic groups such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzotriazolyl, benzisoxazolyl, benzoxazolyl, benzoxadiazolyl, benzoisothiazolyl, benzothiazolyl, benzothiadiazolyl, benzofuryl, isobenzofuryl, benzothienyl, benzotriazolyl, thienopyridyl, thienopyrrolyl, thienopyrazolyl, thienopyrazinyl, furopyrrolyl, thienothienyl, imidazopyrazyl, imidazopyridyl, pyrazolopyridyl, thiazolopyridyl, pyrazolopyrimidinyl, pyrrolopyrimidinyl, pyrazolotriazinyl, pyridazolopyridyl, triazolopyridyl, imidazothiazolyl, pirazinopyridazinyl, quinazolinyl, quinolyl, isoquinolyl, naphthyridinyl, dihydrothiazolopyrimidinyl, tetrahydroquinolyl, tetrahydroisoquinolyl, dihydrobenzofuryl, dihydrobenzoxazinyl, dihydrobenzimidazolyl, tetrahydrobenzothienyl, tetrahydrobenzofuryl, benzodioxolyl, benzodioxonyl, chromanyl, chromenyl, octahydrochromenyl, dihydrobenzodioxinyl, dihydrobenzooxedinyl, dihydrobenzodioxepinyl and dihydrothienodioxinyl; and fused tricyclic heterocyclic groups such as carbazolyl, acridinyl, xanthenyl, phenothiazinyl, phenoxathiinyl, phenoxazinyl, dibenzofuryl, imidazoquinolyl and tetrahydrocarbazolyl. Preferable among these are 5- or 6-membered heteroaryls or non-aromatic heterocyclic groups.

The heterocyclic portions in "heterocyclic diyl", "heterocyclic lower alkyl", "heterocyclic oxy", "heterocyclic thio", "heterocyclic carbonyl", "heterocyclic lower alkoxy", "heterocyclic amino", "heterocyclic sulfamoyl", "heterocyclic sulfonyl", "heterocyclic carbamoyl", "heterocyclic oxycarbonyl", "heterocyclic lower alkylamino", "heterocyclic lower alkoxycarbonyl" and "heterocyclic lower alkylcarbamoyl" are the same as the heterocycle of the above "heterocyclic group".

The bond(s) in "heterocyclic group" and "heterocyclic diyl" may be positioned in any ring.

The substituents in "optionally substituted carbocyclic diyl", "optionally substituted benzenediyl", "optionally substituted heterocyclic diyl", "optionally substituted pyridinediyl", "optionally substituted pyrazinediyl", "optionally substituted benzofurandiyl", "optionally substituted carbocyclic group" and "optionally substituted heterocyclic group" for A, B, E and G may be as follows:

substituents selected from the substituent group α;

lower alkyl which may be substituted by one or more groups selected from the substituent group α, hydroxyimino and lower alkoxyimino (preferable examples of the substituent(s) include halogen, hydroxy, lower alkoxy and lower alkoxycarbonyl);

amino lower alkyl substituted by one or more groups selected from the substituent group α (preferable examples of the substituent(s) include acyl, lower alkyl and/or lower alkoxy);

hydroxyimino lower alkyl; lower alkoxyimino lower alkyl;

lower alkenyl which may be substituted by one or more groups selected from the substituent group α (preferable examples of the substituent(s) include lower alkoxycarbonyl, halogen and/or halogeno lower alkoxycarbonyl);

lower alkynyl which may be substituted by one or more groups selected from the substituent group α (preferable examples of the substituent(s) include lower alkoxycarbonyl);

lower alkoxy which may be substituted by one or more groups selected from the substituent group α (preferable examples of the substituent(s) include halogen, carbamoyl, oxetane, lower alkylcarbamoyl and hydroxy lower alkylcarbamoyl);

lower alkoxy lower alkoxy which may be substituted by one or more groups selected from the substituent group α;

lower alkenyloxy which may be substituted by one or more groups selected from the substituent group α (preferable examples of the substituent(s) include halogen, hydroxy, amino and lower alkylamino);

lower alkoxy lower alkenyloxy which may be substituted by one or more groups selected from the substituent group α;

lower alkynyloxy which may be substituted by one or more groups selected from the substituent group α (preferable examples of the substituent(s) include halogen and hydroxy);

lower alkoxy lower alkynyloxy which may be substituted by one or more groups selected from the substituent group α;

lower alkylthio which may be substituted by one or more groups selected from the substituent group α;

lower alkenylthio which may be substituted by one or more groups selected from the substituent group α;

lower alkynylthio which may be substituted by one or more groups selected from the substituent group α;

lower alkylamino substituted by one or more groups selected from the substituent group α;

lower alkenylamino substituted by one or more groups selected from the substituent group α;

lower alkynylamino substituted by one or more groups selected from the substituent group α;

aminooxy which may be substituted by one or more groups selected from the substituent group α and lower alkylidene;

acyl substituted by one or more groups selected from the substituent group α;

lower alkylsulfonyl which may be substituted by one or more groups selected from the substituent group α;

lower alkylsulfinyl which may be substituted by one or more groups selected from the substituent group α; sulfamoyl;

lower alkylsulfamoyl which may be substituted by one or more groups selected from the substituent group α;

carbocyclic groups which may be substituted by one or more groups selected from the substituent group α, azide, lower alkyl and halogeno lower alkyl (preferable examples thereof include cycloalkyl and aryl);

heterocyclic groups which may be substituted by one or more groups selected from the substituent group α, azide, lower alkyl and halogeno lower alkyl;

carbocyclic lower alkyl which may be substituted by one or more groups selected from the substituent group α, azide, lower alkyl and halogeno lower alkyl (preferable examples thereof include cycloalkyl lower alkyl and aryl lower alkyl);

heterocyclic lower alkyl which may be substituted by one or more groups selected from the substituent group α, azide, lower alkyl and halogeno lower alkyl;

carbocyclic oxy which may be substituted by one or more groups selected from the substituent group α, azide, lower alkyl and halogeno lower alkyl (preferable examples thereof include cycloalkyloxy and aryloxy)

heterocyclic oxy which may be substituted by one or more groups selected from the substituent group α, azide, lower alkyl and halogeno lower alkyl;

carbocyclic lower alkoxy which may be substituted by one or more groups selected from the substituent group α, azide, lower alkyl and halogeno lower alkyl (preferable examples thereof include cycloalkyl lower alkoxy and aryl lower alkoxy);

heterocyclic lower alkoxy which may be substituted by one or more groups selected from the substituent group α, azide, lower alkyl and halogeno lower alkyl;

carbocyclic lower alkoxycarbonyl which may be substituted by one or more groups selected from the substituent group α, azide, lower alkyl and halogeno lower alkyl (preferable examples thereof include cycloalkyl lower alkoxycarbonyl, aryl lower alkoxycarbonyl);

heterocyclic lower alkoxycarbonyl which may be substituted by one or more groups selected from the substituent group α, azide, lower alkyl and halogeno lower alkyl;

carbocyclic thio which may be substituted by one or more groups selected from the substituent group α, azide, lower alkyl and halogeno lower alkyl (preferable examples thereof include cycloalkylthio and arylthio);

heterocyclic thio which may be substituted by one or more groups selected from the substituent group α, azide, lower alkyl and halogeno lower alkyl;

carbocyclic amino which may be substituted by one or more groups selected from the substituent group α, azide, lower alkyl and halogeno lower alkyl (preferable examples thereof include cycloalkylamino and arylamino);

heterocyclic amino which may be substituted by one or more groups selected from the substituent group α, azide, lower alkyl and halogeno lower alkyl;

carbocyclic lower alkylamino which may be substituted by one or more groups selected from the substituent group α, azide, lower alkyl and halogeno lower alkyl (preferable examples thereof include cycloalkyl lower alkylamino, aryl lower alkylamino);

heterocyclic lower alkylamino which may be substituted by one or more groups selected from the substituent group α, azide, lower alkyl and halogeno lower alkyl;

lower alkylsulfamoyl which may be substituted by one or more groups selected from the substituent group α;

carbocyclic sulfamoyl which may be substituted by one or more groups selected from the substituent group α, azide, lower alkyl and halogeno lower alkyl (preferable examples thereof include cycloalkylsulfamoyl and arylsulfamoyl);

heterocyclic sulfamoyl which may be substituted by one or more groups selected from the substituent group α, azide, lower alkyl and halogeno lower alkyl;

carbocyclic sulfonyl which may be substituted by one or more groups selected from the substituent group α, azide, lower alkyl and halogeno lower alkyl (preferable examples thereof include cycloalkylsulfonyl and arylsulfonyl);

heterocyclic sulfonyl which may be substituted by one or more groups selected from the substituent group α, azide, lower alkyl and halogeno lower alkyl;

carbocyclic carbamoyl which may be substituted by one or more groups selected from the substituent group α, azide, lower alkyl and halogeno lower alkyl (preferable examples thereof include cycloalkylcarbamoyl and arylcarbamoyl);

heterocyclic carbamoyl which may be substituted by one or more groups selected from the substituent group α, azide, lower alkyl and halogeno lower alkyl;

carbocyclic lower alkylcarbamoyl which may be substituted by one or more groups selected from the substituent group α, azide, lower alkyl and halogeno lower alkyl (preferable examples thereof include cycloalkyl lower alkylcarbamoyl and aryl lower alkylcarbamoyl);

heterocyclic lower alkylcarbamoyl which may be substituted by one or more groups selected from the substituent group α, azide, lower alkyl and halogeno lower alkyl;

carbocyclic oxycarbonyl which may be substituted by one or more groups selected from the substituent group α, azide, lower alkyl and halogeno lower alkyl (preferable examples thereof include cycloalkyloxycarbonyl and aryloxycarbonyl);

heterocyclic oxycarbonyl which may be substituted by one or more groups selected from the substituent group a, azide, lower alkyl and halogeno lower alkyl;

lower alkylenedioxy which may be substituted by halogen; oxo; and azide. The above groups may be substituted by one or more groups selected from these groups.

The substituents in "optionally substituted carbocyclic group" and "optionally substituted heterocyclic group" for groups other than A, B, E and G may be one or more groups selected from the group consisting of lower alkyl and the substituent group α.

The term "heteroaryl" herein includes aromatic heterocyclic groups which are included in the "heterocyclic group".

The heteroaryl portions in "heteroarylalkyl" and "heteroarylalkyloxy" are as defined above for the "heteroaryl".

The substituents in "optionally substituted heteroarylalkyl" and "optionally substituted heteroarylalkyloxy" may be one or more groups selected from the substituent group α.

The term "lower alkylene" herein includes C1-C10, preferably C1-C6, and more preferably C1-C3 linear or branched divalent carbon chains. Specific examples thereof include methylene, dimethylene, trimethylene, tetramethylene and methyl trimethylene.

The lower alkylene portion in the "lower alkylenedioxy" is as defined above for the "lower alkylene".

The term "lower alkenylene" herein includes C2-C10, preferably C2-C6, and more preferably C2-C4 linear or branched divalent carbon chains having a double bond at any position. Specific examples thereof include vinylene, propenylene, butenylene, butadienylene, methyl propenylene, pentenylene and hexenylene.

The term "lower alkynylene" herein includes C2-C10, more preferably C2-C6, and more preferably C2-C4 linear or branched divalent carbon chains having a triple bond at any position and optionally having a double bond. Specific examples thereof include ethynylene, propynylene, butynylene, pentynylene and hexynylene.

The phrase "$R^{3a}$ or $R^{3b}$ forms a bond together with $R^1$" means that $R^{3a}$ or $R^{3b}$ forms a bond together with $R^1$ so that a carbon-carbon double bond is formed between the carbon to which $R^{3a}$ and $R^{3b}$ are bonded and the carbon to which $R^1$ is bonded.

The term "solvate" herein includes, for example, solvates with organic solvents and hydrates. In the case that a hydrate is formed, the compound or salt may be coordinated with any number of water molecules.

The compound of formula (I) and the compound of formula (II) include pharmaceutically acceptable salts thereof. Examples thereof include salts with alkaline metals (e.g. lithium, sodium and potassium), alkaline earth metals (e.g. magnesium and calcium), ammonium, organic bases and amino acids, and salts with inorganic acids (e.g. hydrochloric acid, sulfuric acid, nitric acid, hydrobromic acid, phosphoric acid and hydroiodic acid) and organic acids (e.g. acetic acid, trifluoroacetic acid, citric acid, lactic acid, tartaric acid, oxalic acid, maleic acid, fumaric acid, mandelic acid, glutaric acid, malic acid, benzoic acid, phthalic acid, benzenesulfonic acid, p-toluenesulfonic acid, methanesulfonic acid and ethanesulfonic acid). Specifically preferable are hydrochloric acid, phosphoric acid, tartaric acid and methanesulfonic acid. These salts may be formed by a routine method.

The compound of formula (I) and the compound of formula (II) are each not limited to a specific isomer, and include any possible isomers (e.g. keto-enol isomers, imine-enamine isomers, diastereoisomers, optical isomers and rotamers) and racemic mixtures.

The present invention relates to the compound of formula (I) which has a 2-aminopyrimidin-4-one structure as its core and has a side chain (B) bonding to the core via a linker moiety (A) and an amide linkage, and the compound of formula (II) which has a 2-aminopyridine structure as its core and has a side chain (G) bonding to the core via a linker moiety (E) and an amide linkage. The compounds having the above respective cores have the same linker moiety and the side chain. The functional groups in each of the compounds are under the same definition mentioned above.

In the compound of formula (I), A is preferably optionally substituted benzenediyl, optionally substituted pyridinediyl, optionally substituted pyrazinediyl or optionally substituted benzofurandiyl.

B is preferably an optionally substituted heterocyclic group.

The substituent of the heterocyclic group for B is preferably substituted lower alkoxy, optionally substituted lower alkenyloxy or optionally substituted lower alkynyloxy.

$R^{3a}$ and $R^{3b}$ are both preferably hydrogen.

$R^1$ is preferably C1-C3 alkyl.

$R^2$ is preferably optionally substituted lower alkyl.

B is preferably an optionally substituted aromatic carbocyclic group or an optionally substituted aromatic heterocyclic group.

B is preferably a carbocyclic group substituted with other than oxo or a heterocyclic group substituted with other than oxo.

In the compound of formula (II), the carbocycle or heterocycle of the carbocyclic diyl or heterocyclic diyl for E is preferably an optionally substituted benzene ring, an optionally substituted pyridine ring, an optionally substituted pyrazine ring or an optionally substituted benzofuran ring.

G is preferably an optionally substituted heterocyclic group.

The substituent in the heterocyclic group for G is preferably substituted lower alkoxy, optionally substituted lower alkenyloxy or optionally substituted lower alkynyloxy.

D is preferably lower alkylene.

$R^4$ is each independently preferably hydrogen, halogen or lower alkyl.

Compound (1) of the present invention may be produced by the following method.

Synthesis of 2-aminopyrimidin-4-one derivative (I-1)

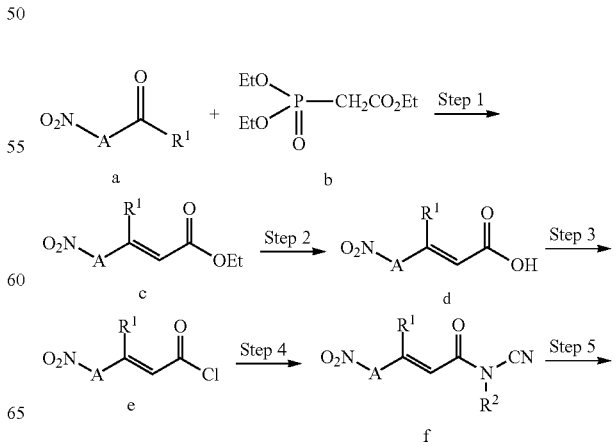

-continued

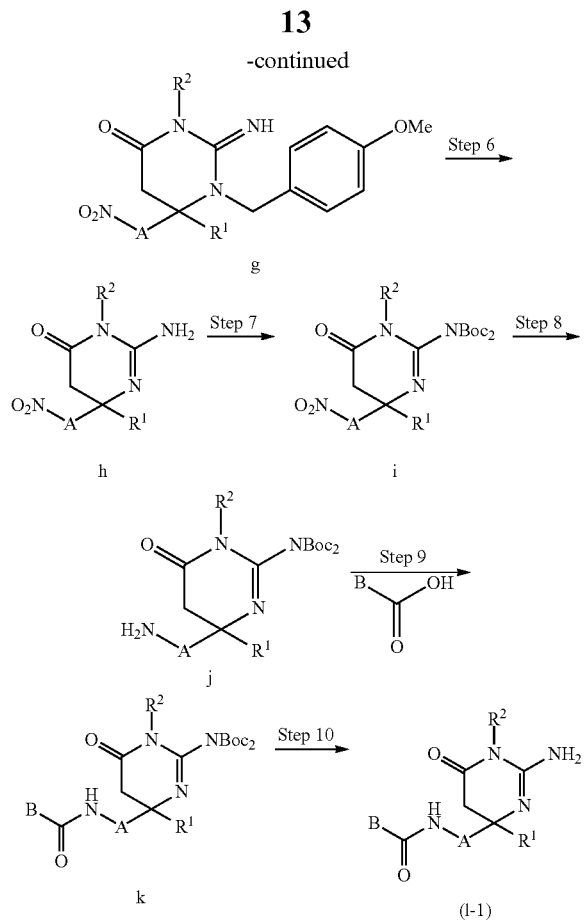

In the scheme, each symbol is under the same definition mentioned above.

Step 1

Compound b is mixed with an alkyl metal reagent such as n-butyl lithium, t-butyl lithium, sodium bis(trimethylsilyl) amide or lithium diisopropylamide, a metal hydride reagent such as sodium hydride or potassium hydride, a metal alkoxide reagent such as potassium t-butoxide or sodium t-butoxide and the like in a solvent such as tetrahydrofuran at −50° C. to −100° C., preferably −30° C. to −90° C., and reacted with each other at 0° C. to 100° C., preferably 10° C. to 30° C., for 1 to 90 minutes, preferably 20 to 60 minutes. Compound a which is commercially available or prepared by a common method is added thereto over 1 to 90 minutes, preferably 20 to 60 minutes, and further reacted for 1 to 90 minutes, preferably 20 to 70 minutes. The resulting mixture is heated up to room temperature, and is reacted for 1 to 30 hours, preferably 10 to 24 hours. Compound c is thereby obtained.

Step 2

Compound c is mixed with a base such as sodium hydroxide, potassium hydroxide or lithium hydroxide in a mixed solvent such as methanol-water. They are reacted for 0.5 to 30 hours, preferably 1 to 24 hours, at room temperature. Compound d is thereby obtained.

Step 3

Compound d is mixed with a mixture of oxalyl chloride and a catalytic amount of dimethyl formamide, or a chlorinating reagent such as thionyl chloride, phosphorus trichloride and phosphorus pentachloride in a solvent such as dichloromethane. They are reacted for 10 minutes to 5 hours, preferably 1 to 3 hours, at room temperature. Compound e is thereby obtained.

Step 4

Bromine cyanide is mixed with a base such as potassium carbonate, sodium carbonate or sodium hydrogencarbonate in a solvent such as tetrahydrofuran at −30° C. to −100° C., preferably −50° C. to −80° C., and then mixed with an $R^2$-amine solution. The resulting mixture is reacted for 10 minutes to 5 hours, preferably 1 to 3 hours, at −30° C. to −100° C., preferably −40° C. to −80° C. The reaction solution is filtered, and the filtrate is mixed with Compound e which is dissolved in tetrahydrofuran, and an organic base such as diisopropylethylamine, diazabicycloundecene or diazabicyclononan at −30° C. to −100° C., preferably −40° C. to −80° C. The mixture is stirred for 10 minutes to 8 hours, preferably 2 to 6 hours, at the same temperature. Compound f is thereby obtained.

Step 5

Compound f is mixed with 4-methoxybenzylamine in a solvent such as dimethylformamide, dimethylacetamide or N-methylpyrrolidone. They are reacted for 3 to 30 hours, preferably 5 to 24 hours, at room temperature. Compound g is thereby obtained.

Step 6

Compound g is reacted with an oxidant such as diammonium cerium nitrate (CAN), 2,3-dichloro-5,6-dicyano-p-benzoquinoline (DDQ) or ozone, or it is electrooxidated, in a mixed solvent of water and an organic solvent such as acetonitrile, dichloromethane or chloroform, for 10 minutes to 8 hours, preferably 2 to 6 hours, at 10° C. to 100° C., preferably 50° C. to 100° C. Compound h is thereby obtained.

Step 7

Compound h is mixed with di-t-butyl dicarbonate and a base, if necessary, such as 4-dimethylaminopyridine, triethylamine, pyridine or potassium carbonate in a solvent such as dichloromethane, chloroform, acetonitrile, tetrahydrofuran or water or in a mixed solvent. They are reacted for 10 minutes to 2 hours, preferably 30 to 60 minutes at room temperature. Compound i is thereby obtained.

Step 8

Compound i is mixed with $Pd(OH)_2$, palladium-carbon, platinum-carbon or Raney nickel in a solvent such as methanol, ethanol, ethyl acetate or dioxane. They are reacted for 10 minutes to 8 hours, preferably 2 to 6 hours, at room temperature under hydrogen atmosphere. Compound j is thereby obtained.

Step 9

A carboxylic acid which is suitable for the target compound is mixed with an organic base such as triethylamine, pyridine or diisopropylethylamine, and then mixed with Compound j, in a solvent such as dimethylformamide in the presence of a condensation agent such as HATU (O-(7-azabenzotriazol-1-yl)-N,N,N',N'-tetramethyluronium hexafluoro phosphate), DCC (dicyclohexyl carbodiimide), WSCD (water-soluble carbodiimide), chlorocarbonic acid ester or carbonyldiimidazole. They are reacted for 0.5 to 7 hours, preferably 1 to 5 hours, at room temperature. Compound k is thereby obtained.

Step 10

Compound k is mixed with trifluoroacetic acid (TFA), sulfuric acid, methanesulfonic acid, formic acid, hydrochloric acid, hydrobromic acid or the like in a solvent such as dichloromethane under ice-cold conditions.

They are reacted for 10 minutes to 5 hours, preferably 45 minutes to 3 hours, at room temperature. Compound (1-1) is thereby obtained.

Compound a' which is commercially available or prepared by a common method may be used instead of the above Compound a. In this case, the ring portion may be formed to prepare Compound i' in a similar manner, and then Compound j may be prepared by the following method.

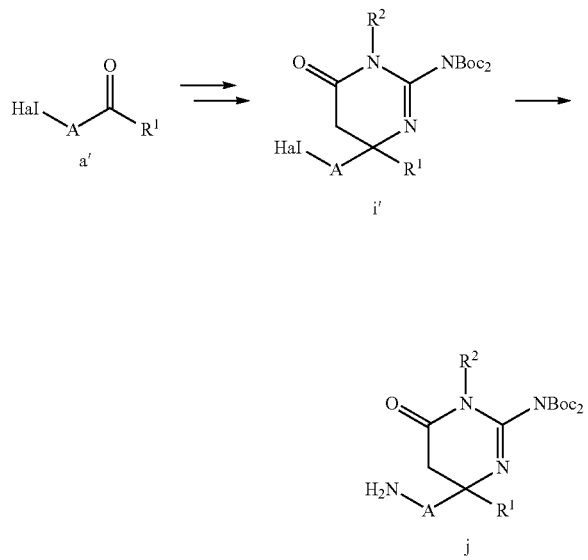

In the scheme, Hal means halogen, and the other symbols are under the same definitions mentioned above.

In a solvent such as tetrahydrofuran, toluene or xylene, Compound i' is mixed with tris dibenzylideneacetone dipalladium, palladium acetate or palladium(0) prepared in situ and a phosphine ligand such as tri-tert-butylphosphine or dicyclohexylbiphenylphosphine, then mixed with lithium hexamethyldisilazide at −40° C. to 30° C., and thereafter mixed with lithium amide, or gaseous ammonia or liquid ammonia. They are reacted for 0.5 to 48 hours, preferably 3 to 20 hours, at −40° C. to 100° C., preferably 0° C. to 60° C. Compound j is thereby obtained.

Compound (II) of the present invention may be produced by the following method.

Synthesis of 2-Aminopyridine Derivative (II-1)

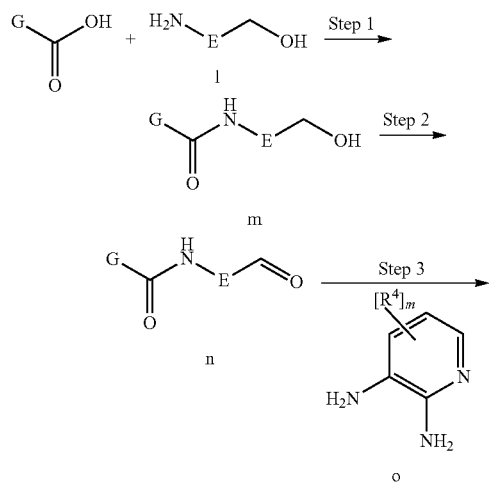

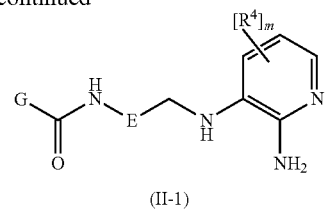

In the scheme, each symbol is under the same definition mentioned above.

Step 1

Compound l which is commercially available or prepared by a common method is mixed with an organic base such as triethylamine, pyridine or diisopropylethylamine in the presence of a carboxylic acid which is suitable for the target compound and a condensation agent such as HATU, DCC, WSCD, chlorocarbonic acid ester or carbonyl dimidazole in a solvent such as dimethylformamide, dimethylacetamide or dimethylsulfoxide. They are reacted for 10 minutes to 5 hours, preferably 30 minutes to 2 hours, at room temperature. Compound m is thereby obtained.

Step 2

Compound m is mixed with an oxidant such as a Dess-Martin reagent, 2-iodoxyacetic acid, a Swern oxidation reagent, pyridinium dichromate or pyridinium chlorochromate in a solvent such as dichloromethane or dimethylsulfoxide under a nitrogen stream. They are reacted for 10 minutes to 5 hours, preferably 1 to 3 hours, at room temperature. Compound n is thereby obtained.

Step 3

Compound n and Compound o which is commercially available or prepared by a common method are mixed with a catalytic amount of acetic acid and a hydrogenation reagent such as sodium triacetoxyborohydride, sodium cyanoborohydride, sodium borohydride, pyridine borane complex or sodium borohydride in a solvent such as dichloromethane, tetrahydrofuran or acetonitrile. They are reacted for 0.5 to 20 hours, preferably 5 to 10 hours, at room temperature. Compound (II-1) is thereby obtained.

In the above reaction, a carboxylic acid which is suitable for the target compound may be prepared by reacting an ester which is suitable for the target compound with a base such as sodium hydroxide, lithium hydroxide or potassium carbonate for 10 minutes to 24 hours, preferably 1 to 5 hours, at 0° C. to 50° C., preferably 10° C. to 40° C., in the presence of a solvent such as methanol, ethanol or water, or a mixed solvent thereof.

In the above reaction, the amide linkage between the side chain and the linker moiety may be formed by the following method.

The linker moiety is reacted with a substance which has a side chain suitable for the target compound, selected from acid chlorides, acid anhydrides, chlorocarbonic acid esters, isocyanates and the like, for 0.1 to 24 hours, preferably 1 to 12 hours, at −80° C. to 100° C., preferably −20° C. to 40° C., with or without a solvent such as tetrahydrofuran or dichloromethane and with or without a base such as pyridine or triethylamine.

Compounds used for forming the linker moieties (A) and (E) or the side chains (B) and (G) may be commercially available or may be produced by the following method or a method of the reference examples mentioned later.

Method for Forming Linker Moiety

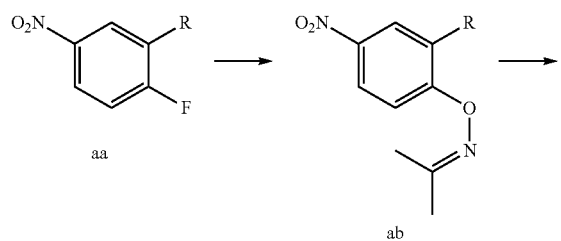

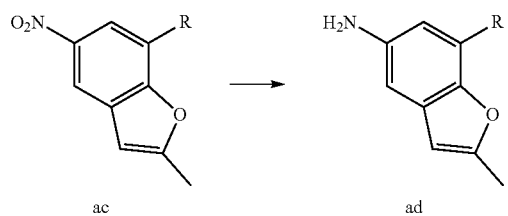

Compound aa which is suitable for the target compound is mixed with propan-2-one oxime, and a base such as potassium t-butoxide, potassium hydride, sodium hydride or sodium ethoxide in an organic solvent such as dimethylformamide, dimethylacetamide or N-methylpyrrolidone. They are reacted for 1 to 24 hours, preferably 1 to 12 hours at room temperature. Compound ab is thereby obtained.

Compound ab is reacted with hydrogen chloride, sulfuric acid, trifluoroacetoxy triflate or the like in a solvent such as acetic acid, formic acid or ethanol for 1 to 24 hours, preferably 1 to 12 hours, at 10° C. to 150° C., preferably 80° C. to 120° C. Compound ac is thereby obtained.

Compound ac is mixed with Pd(OH)$_2$, palladium-carbon, platinum-carbon, Raney nickel or the like in a solvent such as methanol or ethyl acetate under hydrogen atmosphere.

They are reacted for 1 to 24 hours, preferably 1 to 12 hours, at room temperature. Compound ad is thereby obtained.

Method for Producing Carboxylic Acid af

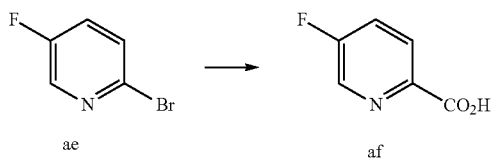 [SMILES: Fc1ccc(Br)nc1 ; O=C(O)c1ccc(F)cn1]

Compound ae is dissolved in a solvent such as toluene, hexane, dichloromethane or tetrahydrofuran, or a mixed solvent thereof. A solution of n-butyl lithium, s-butyl lithium or tert-butyl lithium is dropwise added thereto at −100° C. to 0° C., preferably −80° C. to 0° C. Dry ice is added thereto at the same temperature, and they are reacted for 10 minutes to 5 hours, preferably 1 to 3 hours. Compound of is thereby obtained.

A compound which forms a side chain such as the below-listed B2 may be obtained in the same manner.

Method for Producing Carboxylic Acid ah

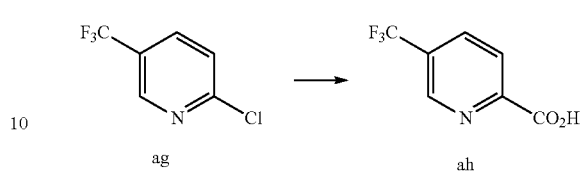

Compound ag is dissolved in a solvent such as 2-propanol or dimethylformamide or a mixed solvent thereof.

A catalytic amount of palladium (II) acetate, 1,1′-bis(diphenylphosphino)ferrocene or a catalyst such as tetrakis(triphenylphosphine)palladium or dichlorobis(triphenylphosphine)palladium, and a base such as potassium acetate, sodium hydroxide, potassium hydroxide, triethylamine or tri-n-butylamine are added thereto. They are reacted for 1 to 48 hours, preferably 4 to 24 hours, at 50° C. to 100° C., preferably 70° C. to 90° C., under carbon monoxide atmosphere. Compound ah is thereby obtained.

Method for Producing Carboxylic Acid ak

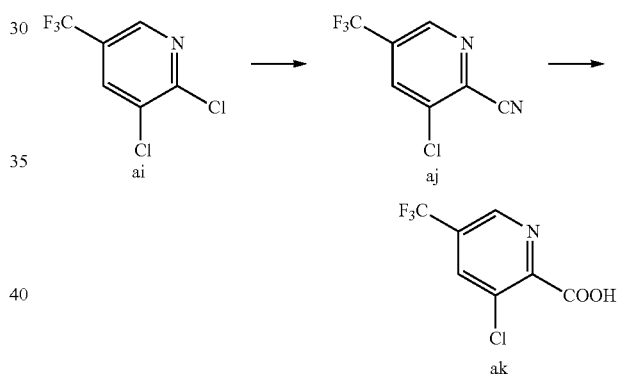

Compound ai is dissolved in a solvent such as dimethylformamide, dimethylacetamide or N-methylpiperidone. An aqueous solution of sodium cyanide or potassium cyanide is added thereto, and they are reacted for 1 to 24 hours, preferably 1 to 12 hours, at 0° C. to 100° C., preferably 20° C. to 50° C. Compound aj is thereby obtained.

Compound aj is mixed and reacted with an aqueous solution of sodium hydroxide or potassium hydroxide for 1 to 24 hours, preferably 1 to 12 hours, at 20° C. to 100° C., preferably 20° C. to 50° C. Compound ak is thereby obtained.

Method for Producing Carboxylic Acid an

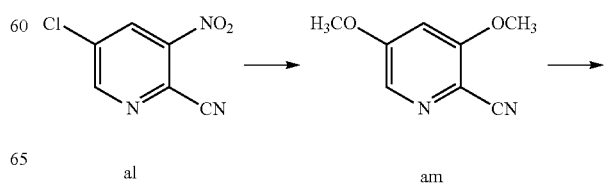

-continued

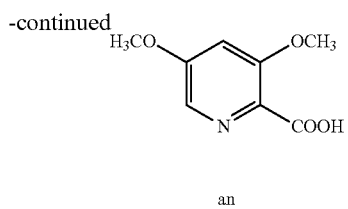

an

Compound al is dissolved in methanol. Sodium methoxide is added thereto, and they are reacted for 1 to 24 hours, preferably 1 to 12 hours, at 0° C. to 60° C., preferably 20° C. to 50° C. Compound am is thereby obtained.

Concentrated hydrochloric acid or concentrated sulfuric acid is added thereto, and they are reacted for 1 to 12 hours, preferably 1 to 6 hours, while being heated to reflux. Compound an is thereby obtained.

Method for Producing Carboxylic Acid ap

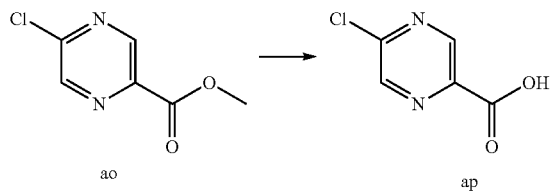

Compound ao is dissolved in a solvent such as methanol, ethanol or water, or a mixed solvent thereof. A base such as an aqueous solution of sodium hydroxide, potassium hydroxide or lithium hydroxide is added thereto. They are reacted for 1 to 24 hours, preferably 1 to 12 hours, at 0° C. to 80° C., preferably 20° C. to 50° C. Compound ap is thereby obtained.

Method for Producing Carboxylic Acid av

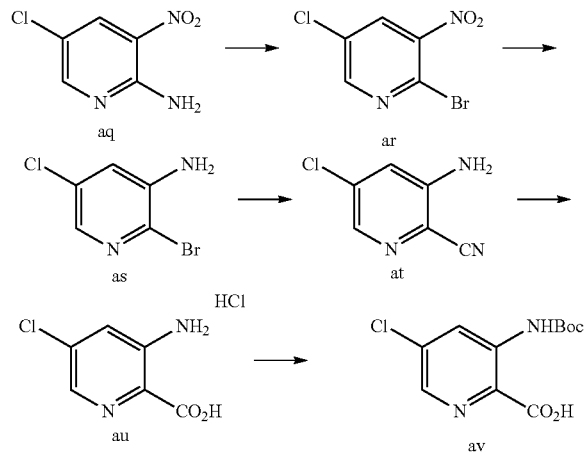

Compound aq is reacted with bromine or potassium bromide, copper bromide or the like in an aqueous solution of hydrobromic acid in the presence of a nitrite ester such as sodium nitrite or isoamyl nitrite for 0.5 to 5 hours, preferably 1 to 2 hours, at −20° C. to 20° C., preferably −10° C. to 10° C. Compound ar is thereby obtained.

The obtained Compound ar is dissolved in an organic solvent such as toluene, tetrahydrofuran or methanol and water. Metal such as iron, tin or zinc and ammonium chloride or hydrochloric acid are added thereto, and they are reacted for 1 to 8 hours, preferably 2 to 5 hours, at 30° C. to 150° C., preferably 50° C. to 120° C. Compound as is thereby obtained.

The obtained Compound as is dissolved in an organic solvent such as dimethylformamide, dimethylacetamide or N-methylpyrrolidone. A catalytic amount of tetrakis(triphenylphosphine)palladium and 0.3 to 1 equivalent zinc cyanide are added thereto, and they are reacted for 3 to 20 hours at 50° C. to 150° C., or reacted for 5 to 30 minutes at 50° C. to 120° C. with microwave irradiation. Compound at is thereby obtained.

Compound at is mixed with concentrated hydrochloric acid or concentrated sulfuric acid. They are reacted for 6 to 30 hours, preferably 12 to 24 hours, at 50° C. to 150° C. Compound au is thereby obtained.

Compound au is mixed with di-t-butyl dicarbonate and a base such as 4-dimethylaminopyridine, triethylamine, pyridine, potassium carbonate or sodium hydroxide in a solvent such as dichloromethane, acetonitrile, tetrahydrofuran or water, or a mixed solvent thereof. They are reacted for 10 minutes to 2 hours, preferably 30 to 60 minutes, at room temperature. Compound av is thereby obtained.

Method for Producing Carboxylic Acid ba

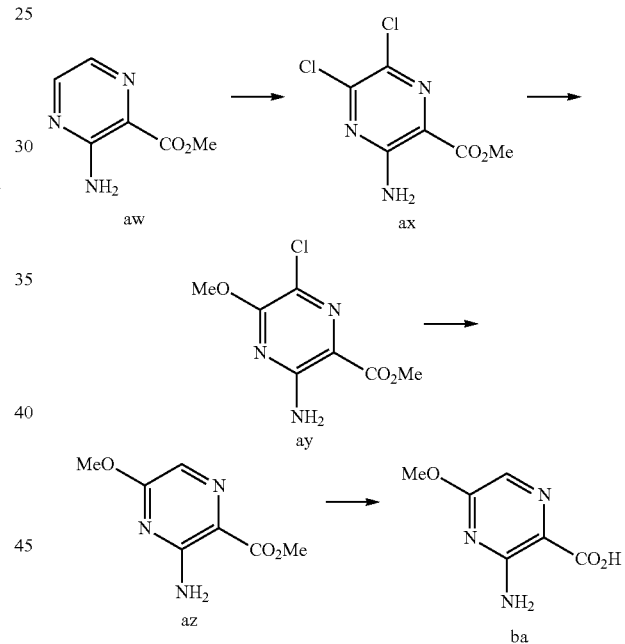

Compound aw is dissolved in an organic solvent such as toluene or benzene. A largely excessive amount of chlorinating agent such as sulfuryl chloride or thionyl chloride is added thereto. They are reacted for 2 to 10 hours, preferably 3 to 6 hours, at 30° C. to 150° C., preferably 60° C. to 100° C. Compound ax is thereby obtained.

The obtained Compound ax is dissolved in methanol. Sodium methoxide is added thereto, and they are reacted for 1 to 5 hours, preferably 2 to 4 hours, at 20° C. to 70° C., preferably 30° C. to 60° C. Compound ay is thereby obtained.

The obtained Compound ay is dissolved in an organic solvent such as ethanol, methanol, ethyl acetate or tetrahydrofuran. A catalytic reduction catalyst such as palladium-carbon or platinum-carbon is added thereto, and they are reacted for 1 to 24 hours, preferably 5 to 12 hours, at room temperature under hydrogen atmosphere. Compound az is thereby obtained.

The obtained Compound az is dissolved in a solvent such as tetrahydrofuran, methanol or water, or a mixed solvent thereof. An aqueous solution of sodium hydroxide, lithium hydroxide, potassium hydroxide or the like is added thereto, and they are reacted for 1 to 24 hours, preferably 1 to 12 hours, at 0° C. to 60° C., preferably 20° C. to 40° C. Compound ba is thereby obtained.

Method for Producing Carboxylic Acid bg

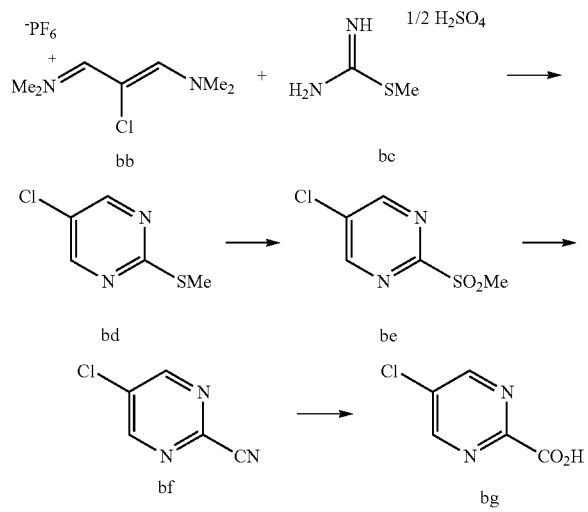

Compounds bb and bc are dissolved in methanol. Sodium methoxide is added thereto, and they are reacted for 3 to 7 hours at 0° C. to 20° C. Compound bd is thereby obtained.

The obtained Compound bd is dissolved in an organic solvent such as dichloromethane, dimethylformamide, dimethylacetamide or N-methylpyrrolidone. An oxidant such as metachloroperbenzoic acid, hydrogen peroxide or potassium permanganate is added thereto. They are reacted for 1 to 12 hours, preferably 2 to 8 hours, at 0° C. to 50° C., preferably 10° C. to 30° C. Compound be is thereby obtained.

The obtained Compound be is dissolved in an organic solvent such as dimethylformamide, dimethylacetamide or N-methylpyrrolidone. A cyanating agent such as potassium cyanide or sodium cyanide is added thereto. They are reacted for 1 to 8 hours, preferably 2 to 6 hours, at 0° C. to 50° C., preferably 10° C. to 30° C. Compound bf is thereby obtained.

The obtained Compound bf is dissolved in a solvent such as tetrahydrofuran, methanol or water, or a mixed solvent thereof. An aqueous solution of sodium hydroxide, lithium hydroxide, potassium hydroxide or the like is added thereto. They are reacted for 1 to 8 hours, preferably 2 to 5 hours, at 0° C. to 100° C., preferably 40° C. to 80° C. Compound bg is thereby obtained.

Method for Producing Benzofuran Derivative

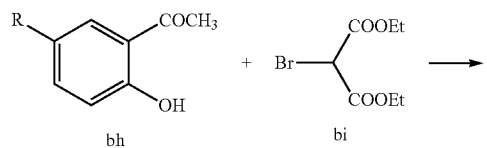

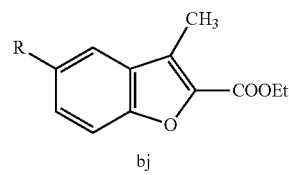

Compound bh which is suitable for the target compound is mixed with Compound bi and a base such as potassium carbonate, sodium carbonate or sodium hydride in a solvent such as acetone, methylethylketone, tetrahydrofuran, dioxane, dichloromethane or dimethylformamide. They are reacted for 0.5 to 12 hours, preferably 1 to 8 hours, while being heated to reflux. Compound bj is thereby obtained.

Method for Producing 5-Membered Ring Compounds bn and bo

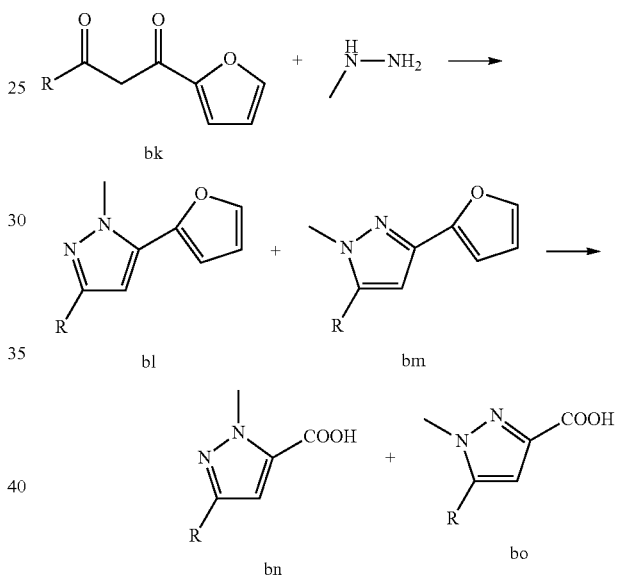

Compound bk which is suitable for the target compound is mixed with methylhydrazine in acetic acid. They are reacted for 10 minutes to 5 hours, preferably 30 minutes to 2 hours, at room temperature. A mixture of Compound bl and Compound bm is thereby obtained.

This mixture is reacted with an oxidant such as potassium permanganate or sodium periodate for 30 minutes to 10 hours, preferably 1 to 5 hours, at 0° C. to 100° C., preferably 20° C. to 50° C., in a mixed solvent of acetone, water and the like. A mixture of Compound bn and Compound bo is thereby obtained. A required isomer can be obtained by a common purifying process.

Method for Producing 5-Membered Ring Compound bq

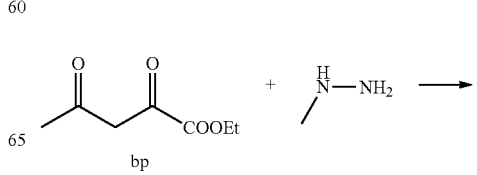

Method for Producing 5-Membered Ring Compound bx

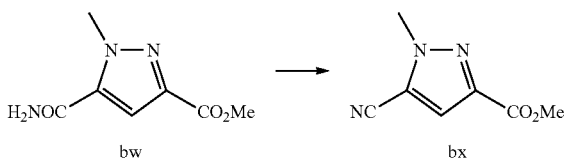

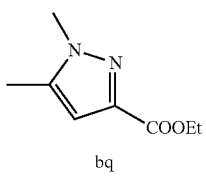

Acetic acid, Compound bp, and methylhydrazine are mixed with each other in a solvent such as tetrahydrofuran, dimethylformamide or N-methylpyrrolidone. They are reacted for 1 to 24 hours, preferably 1 to 12 hours, at 20° C. to 60° C. Compound bq is thereby obtained.

Method for Producing 5-Membered Ring Compound bt

Compound bw is dissolved, if necessary, in a solvent such as dichloromethane, and it is mixed with trifluoroacetic anhydride or methanesulfonyl chloride and a base such as pyridine or triethylamine. They are reacted for 1 to 12 hours, preferably 1 to 6 hours, at 0° C. to 30° C. Compound bx is thereby obtained.

Method for Producing Fused Cyclic Compound

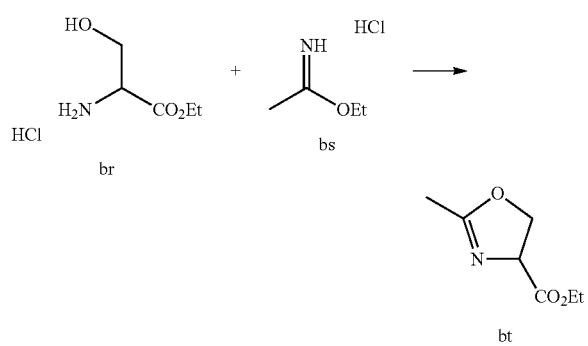

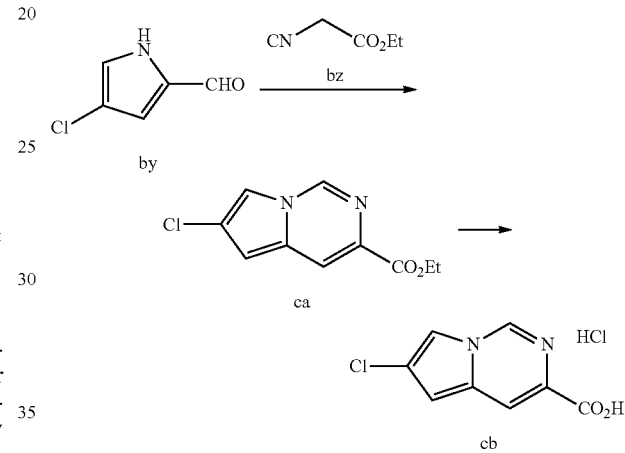

Compound br and Compound bs are mixed with triethylamine in the presence of a solvent such as tetrahydrofuran or dichloromethane. They are reacted for 1 to 24 hours, preferably 1 to 12 hours, at 20° C. to 60° C. Compound bt is thereby obtained.

Method for Producing 5-Membered Ring Compound bv

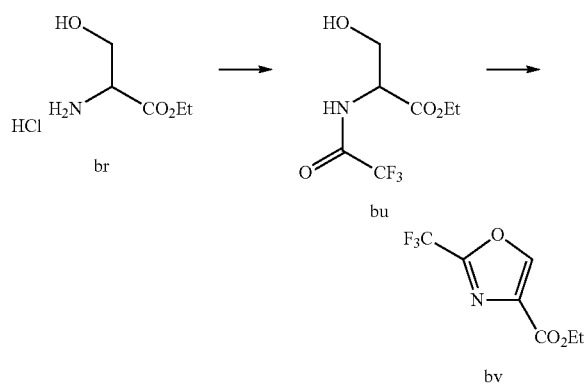

Compound by and Compound bz are dissolved in a solvent such as dichloromethane or tetrahydrofuran, and a base such as diazabicycloundecene, diazabicyclononane or diisopropylethylamine is added thereto. They are reacted for 1 to 24 hours, preferably 1 to 12 hours, at 20° C. to 60° C. Compound ca is thereby obtained.

Hydrochloric acid is added to the obtained Compound ca, and they are reacted for 1 to 12 hours, preferably 1 to 6 hours, while being heated to reflux. Compound cb is thereby obtained.

A compound which forms a side chain such as the below-listed B134 may be prepared in the same manner as mentioned above.

Modification of Side Chain End

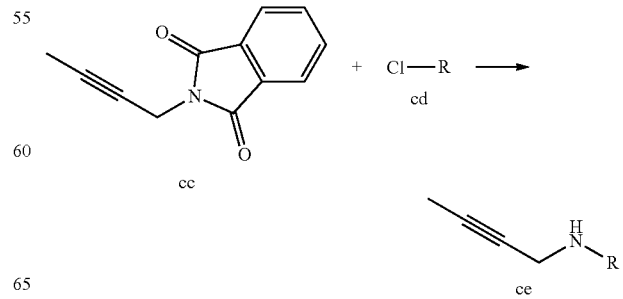

Compound br is mixed with trifluoroacetic anhydride and a base such as triethylamine or pyridine in the presence of a solvent such as tetrahydrofuran or dichloromethane. They are reacted for 1 to 12 hours, preferably 1 to 6 hours, at 0° C. to 40° C. Compound bu is thereby obtained.

This compound is dissolved in a solvent such as tetrahydrofuran or dichloromethane, and bromotrichloromethane and a base such as diazabicycloundecene or diazabicyclononane are added thereto at −20° C. to 20° C. They are reacted for 1 to 24 hours, preferably 1 to 12 hours, at 0° C. to 20° C. Compound by is thereby obtained.

Compound cc is mixed with Compound cd which is suitable for the target compound and hydrazine in a solvent such as ethanol. They are reacted for 1 to 48 hours, preferably 1 to 24 hours, at 0° C. to 100° C., preferably 20° C. to 50° C. Compound ce is thereby obtained.

Modification of Side Chain End

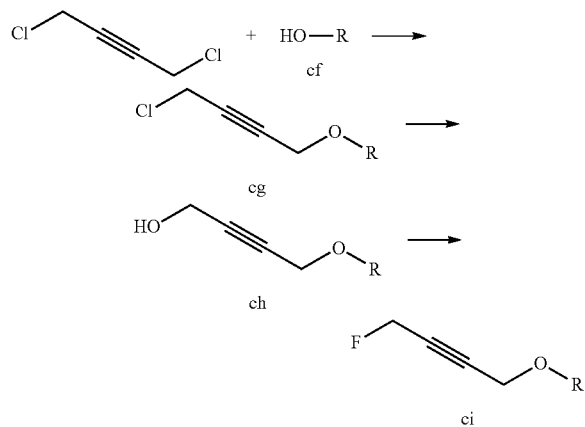

Compound cf which is suitable for the target compound is mixed with 1,4-dichloro-2-butyne and a base such as potassium carbonate, sodium carbonate, sodium hydride or potassium t-butoxide in a solvent such as dimethylformamide. They are reacted for 1 to 24 hours, preferably 1 to 4 hours, at 0° C. to 100° C., preferably 20° C. to 70° C. Compound cg is thereby obtained.

Compound cg is mixed with a base such as sodium hydride, sodium hydroxide, potassium hydroxide or potassium carbonate in the presence of water or a mixed solvent of water and a water-compatible solvent. They are reacted for 1 to 48 hours, preferably 1 to 24 hours, at 0° C. to 100° C., preferably 20° C. to 50° C. Compound ch is thereby obtained.

This is mixed with a fluorinating reagent such as (diethylamino)sulfur trifluoride or tetrabutylammonium fluoride in a solvent such as dichloromethane. They are reacted for 1 to 5 hours, preferably 2 to 4 hours, at −20° C. to 50° C., preferably 0° C. to 30° C. Compound ci is thereby obtained.

Modification of Side Chain End

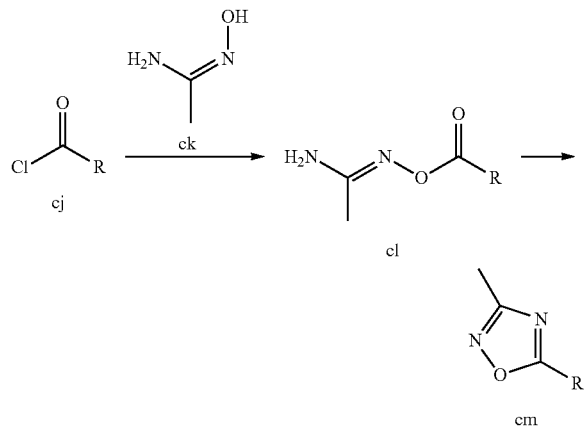

Compound cj which is suitable for the target compound is mixed with Compound ck and a tertiary amine such as triethylamine, diisopropylethylamine or dimethylaminopyridine in a solvent such as chloroform, dichloromethane, tetrahydrofuran or dioxane. They are reacted for 1 to 24 hours, preferably 1 to 4 hours, at 0° C. to 50° C., preferably 20° C. to 40° C. Compound cl is thereby obtained.

This is mixed, if needed, with an appropriate amount of acetic acid, trifluoroacetic acid, hydrochloric acid, sulfuric acid, molecular sieves and the like in a solvent such as toluene or DMF. They are reacted for 1 to 5 hours, preferably 2 to 4 hours, at 10° C. to 100° C., preferably 20° C. to 40° C. Compound cm is thereby obtained.

Modification of Side Chain End

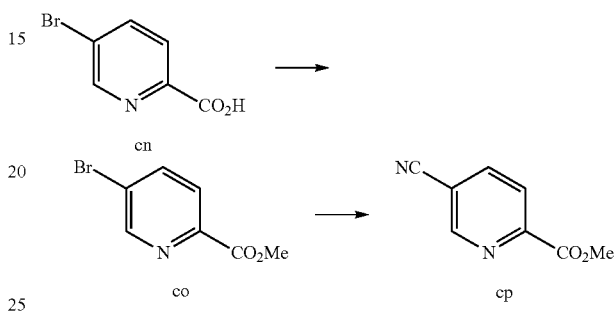

Compound cn is dissolved in methanol, and thionyl chloride is added thereto. They are reacted for 1 to 12 hours, preferably 1 to 6 hours, at 20° C. to 80° C. Compound co is thereby obtained.

The obtained Compound co is dissolved in an organic solvent such as dimethylformamide, dimethylacetamide or N-methylpyrrolidone, and a catalytic amount of tetrakis(triphenylphosphine)palladium (0) and zinc cyanide are added thereto. They are reacted for 1 to 12 hours, preferably 1 to 6 hours, at 80° C. to 120° C. Compound cp is thereby obtained.

Modification of Side Chain End

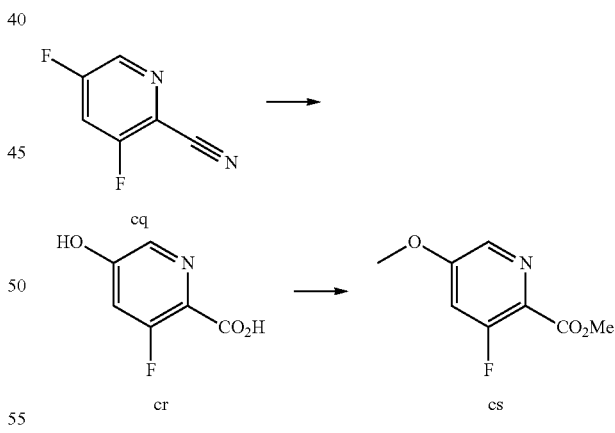

Compound cq is mixed with a base such as potassium hydroxide or sodium hydroxide in a mixed solvent of t-butyl alcohol and water. They are reacted for 1 to 12 hours, preferably 1 to 6 hours, at 20° C. to 80° C. Compound cr is thereby obtained.

The obtained Compound cr is mixed with a methylating agent such as methyl iodide or dimethyl sulfate and a base such as potassium carbonate or cesium carbonate in a solvent such as dimethylformamide. They are reacted for 1 to 12 hours, preferably 1 to 6 hours, at 20° C. to 80° C. Compound cs is thereby obtained.

Modification of Side Chain End

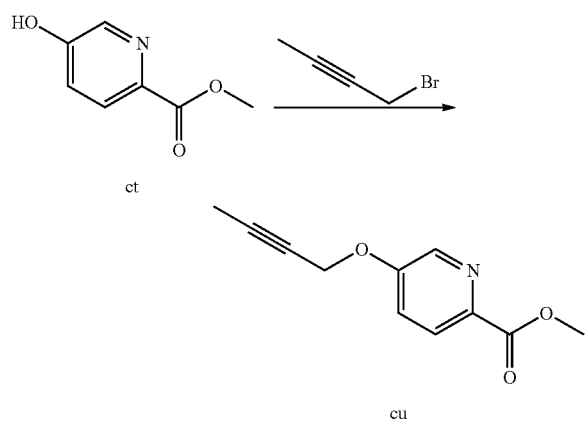

ct cu

Compound ct is dissolved in a solvent such as dimethylformamide, and 1-bromo-2-butyne and a base such as potassium carbonate or cesium carbonate are added thereto at room temperature. They are reacted for 1 to 24 hours, preferably 1 to 12 hours, at 0° C. to 80° C., preferably 20° C. to 50° C. Compound cu is thereby obtained.

A compound which forms a side chain such as the below-listed B24 may be prepared in the same manner as mentioned above.

Modification of Side Chain End

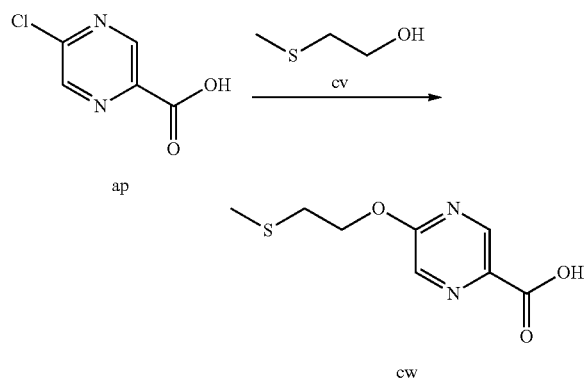

ap cw

Compound ap is dissolved in a solvent such as tetrahydrofuran or toluene, and Compound cv and a base such as sodium hydride, potassium t-butoxide or sodium methoxide are added thereto. They are reacted for 1 to 24 hours, preferably 1 to 12 hours, at 0° C. to 80° C., preferably 20° C. to 50° C. Compound cw is thereby obtained.

Modification of Side Chain End

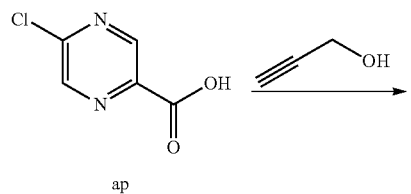

ap

-continued

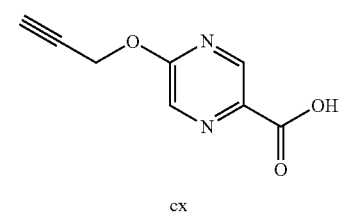

cx

Compound ap is dissolved in a solvent such as dimethylformamide, and a base such as potassium t-butoxide and propargyl alcohol are added thereto. They are reacted for 1 to 24 hours, preferably 1 to 12 hours, at 0° C. to 80° C., preferably 20° C. to 50° C. Compound cx is thereby obtained.

A compound which forms a side chain such as the below-listed B60 may be prepared in the same manner as mentioned above.

Modification of Side Chain End

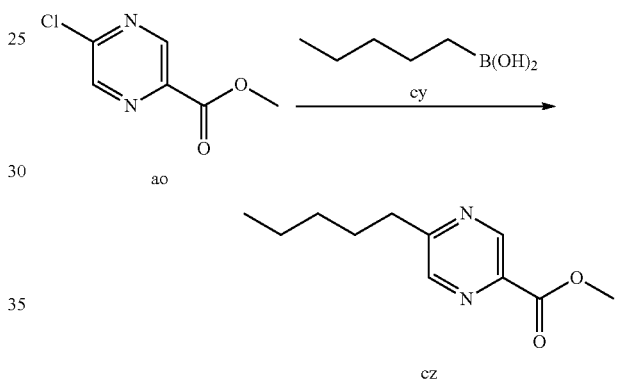

ao cz

Compound ao is dissolved in a mixed solvent of water and an organic solvent such as dimethylformamide, tetrahydrofuran or dimethoxyethane or the like solvent. Compound cy, a catalytic amount of a catalyst such as 1,1'-bis(diphenylphosphino)ferrocene palladium (II) chloride, tetrakis(triphenylphosphine)palladium or dichlorobis(triphenylphosphine)palladium, and a base such as potassium carbonate, sodium carbonate or sodium hydroxide are added thereto. They are reacted for 1 to 24 hours, preferably 1 to 12 hours, at 20° C. to 100° C., preferably 50° C. to 100° C. Compound cz is thereby obtained.

A compound which forms a side chain such as the below-listed B80 may be prepared in the same manner as mentioned above.

Modification of Side Chain End

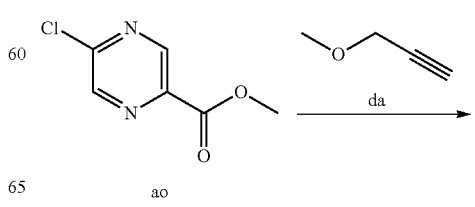

ao

Modification of Side Chain End

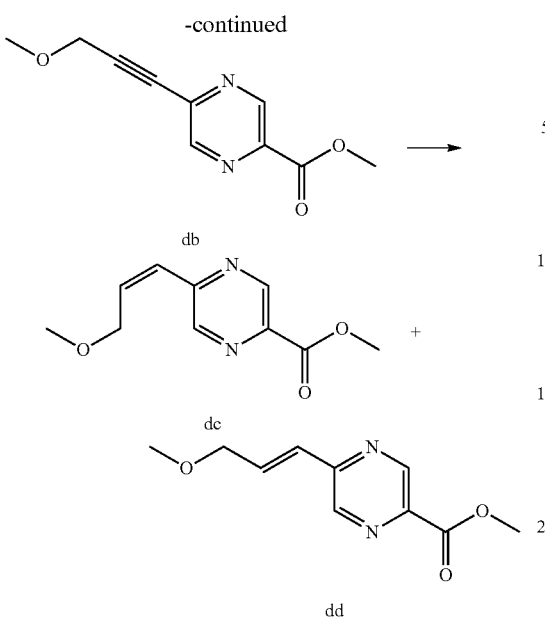

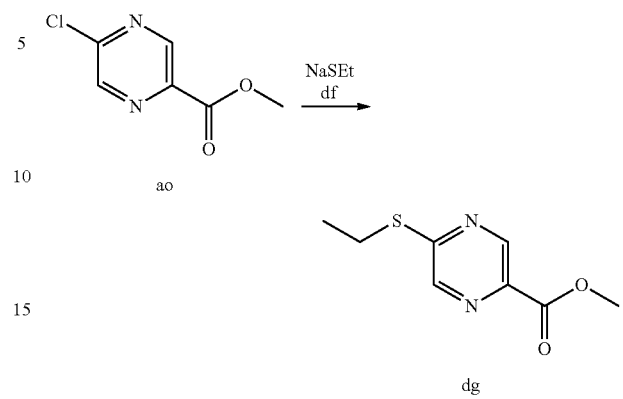

Compound ao is dissolved in a solvent such as dimethylformamide, dimethylacetamide or N-methylpyrrolidone. Compound da, copper (I) iodide, a catalytic amount of a catalyst such as bis(triphenylphosphine)palladium chloride or tetrakis(triphenylphosphine)palladium, and a base such as triethylamine, diethylamine, tri-n-butylamine, n-propylamine, n-butylamine or diisopropylethylamine are added thereto. They are reacted for 1 to 24 hours, preferably 1 to 12 hours, at 20° C. to 100° C., preferably 50° C. to 100° C. Compound db is thereby obtained.

This is dissolved in a solvent such as quinoline or toluene, and a Lindlar catalyst is added thereto. They are reacted for 1 to 24 hours, preferably 1 to 12 hours, at 20° C. to 50° C. under hydrogen atmosphere. A mixture of Compound dc and Compound dd is thereby obtained. Compound dc and Compound dd can be separated and isolated by a common purifying process.

Modification of Side Chain End

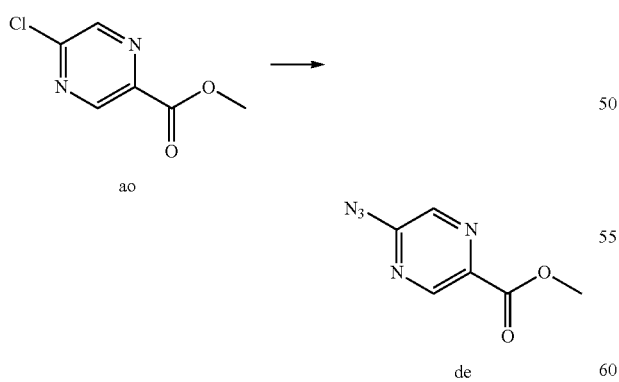

Compound ao is dissolved in a solvent such as dimethylformamide, dimethylacetamide or N-methylpyrrolidone, and sodium azide is added thereto. They are reacted for 1 to 24 hours, preferably 1 to 12 hours, at 20° C. to 100° C., preferably 20° C. to 60° C. Compound de is thereby obtained.

Compound ao is dissolved in a solvent such as dimethylformamide, dimethylacetamide or N-methylpyrrolidone, and Compound df is added thereto. They are reacted for 1 to 24 hours, preferably 1 to 12 hours, at 20° C. to 100° C., preferably 20° C. to 60° C. Compound dg is thereby obtained.

Modification of Side Chain End

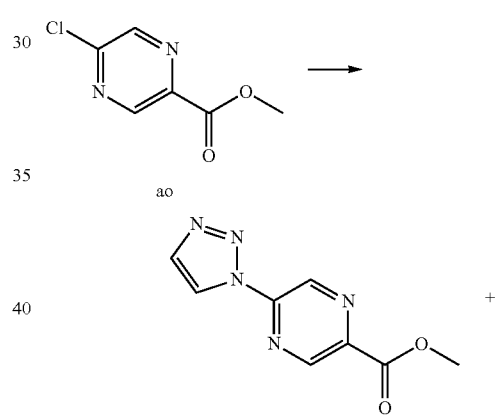

Compound ao is dissolved in a solvent such as dimethylformamide, dimethylacetamide or N-methylpyrrolidone, and 1H-1,2,3-triazole and a base such as potassium carbonate or sodium hydride are added thereto. They are reacted under microwave irradiation. Compound dh and Compound di are thereby obtained. Compound dh and Compound di can be separated and isolated by a common purifying method.

A compound which forms a side chain such as the below-listed B72 may be prepared in the same manner as mentioned above.

Modification of Side Chain End

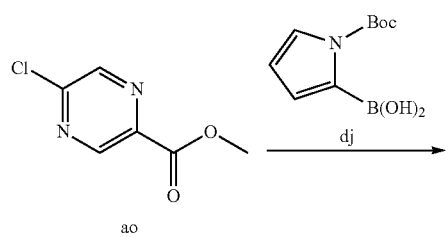

ao

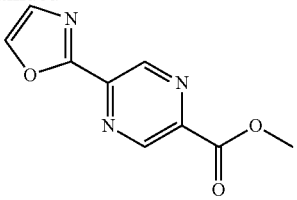

dn

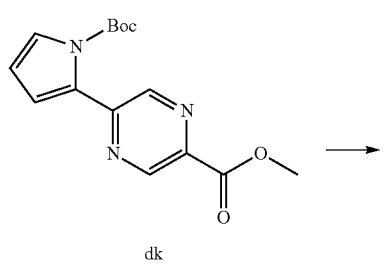

dk

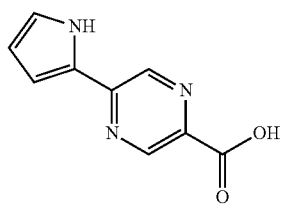

dl

Compound ao is mixed with Compound dj, a base such as sodium carbonate, potassium carbonate, cesium carbonate or sodium hydroxide, and a catalytic amount of a catalyst such as tetrakis(triphenylphosphine)palladium (0) or bis(triphenylphosphine)palladium chloride in a mixed solvent of water and an organic solvent such as dimethylformamide, tetrahydrofuran or dimethoxyethane. They are reacted for 1 to 12 hours, preferably 1 to 6 hours, while being heated to reflux. Compound dk is thereby obtained.

This is dissolved in a solvent such as tetrahydrofuran, methanol or water, or a mixed solvent thereof, and an aqueous solution of sodium hydroxide, lithium hydroxide, potassium hydroxide or the like is added thereto. They are reacted for 1 to 24 hours, preferably 1 to 12 hours, at 0° C. to 60° C., preferably 20° C. to 40° C. Compound dl is thereby obtained.

Modification of Side Chain End

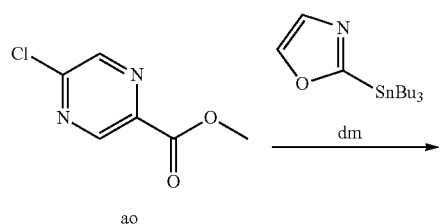

ao

Compound ao is mixed with Compound dm and a catalytic amount of a catalyst such as tetrakis(triphenylphosphine) palladium (0) or bis(triphenylphosphine)palladium chloride in a solvent such as toluene, tetrahydrofuran, dimethylformamide or N-methylpyrrolidone. They are reacted for 1 to 24 hours, preferably 1 to 12 hours, at 20° C. to 100° C., preferably 60° C. to 100° C. Compound do is thereby obtained.

In the case that a substituent which inhibits a reaction (e.g. hydroxy, mercapto, amino, formyl, carbonyl and carboxy) exists in any of the above steps, the substituent may be preliminarily protected by, for example, the method described in "Protective Groups in Organic Synthesis, Theodora W Green (John Wiley & Sons)", and the protecting group may be removed at a desired step.

Further, during all the above-mentioned steps, the order of the steps to be performed may be appropriately changed. In each step, an intermediate may be isolated and then used in the next step.

The compound according to the present invention is preferably as follows.

1) A compound of formula (I'):

(I')

wherein is any one of the following.

TABLE 1

| | |
|---|---|
| A1 | 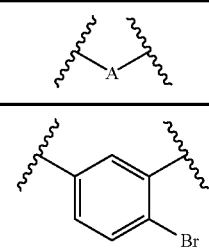 |

TABLE 1-continued

| | |
|---|---|
| A2 | 2-chloro-1,4-phenylene (Cl at 4-position) |
| A3 | 2-methoxy... (OMe) |
| A4 | 2-methyl... (Me) |
| A5 | 2-NMe₂... (NMe₂) |
| A6 | 2-SMe... (SMe) |
| A7 | 5-fluoro-1,3-phenylene (F) |
| A8 | 5-bromo-1,3-phenylene (Br) |
| A9 | 5-chloro-1,3-phenylene (Cl) |
| A10 | 5-methoxy-1,3-phenylene (OMe) |
| A11 | 5-methyl-1,3-phenylene (Me) |
| | A |
| A12 | 3,4-difluoro-1,5-phenylene (F, F) |
| A13 | 2-methylbenzofuran-5,7-diyl |
| A14 | pyridine-2,6-diyl |
| A15 | pyridine-3,5-diyl |
| A16 | pyridine-2,4-diyl |
| A17 | 2-chloropyridine-3,5-diyl (Cl) |
| A18 | pyrazine-2,6-diyl |
| A19 | 1,3-phenylene |

TABLE 1-continued
| | |
|---|---|
| A20 | 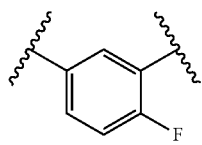 [SMILES: *c1ccc(F)c(*)c1] |
| A21 | 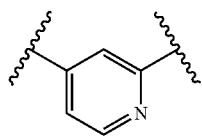 [SMILES: *c1ccnc(*)c1] |
2) A compound of formula (I'):
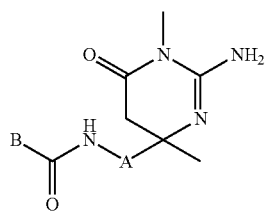
wherein
is any one of the following.
TABLE 2
| | B⏜ |
|---|---|
| B1 | 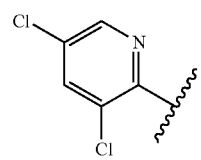 [SMILES: *c1ncc(Cl)cc1Cl] |
| B2 | 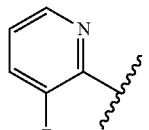 |
| B3 | 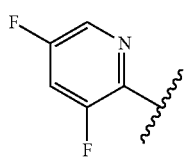 [SMILES: *c1ncc(F)cc1F] |
TABLE 2-continued
| | |
|---|---|
| B4 | 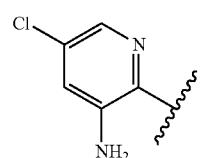 |
| B5 | 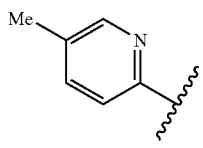 [SMILES: *c1ccc(C)cn1] |
| B6 | 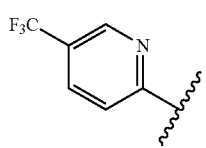 |
| B7 | 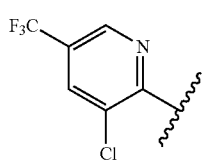 |
| B8 | 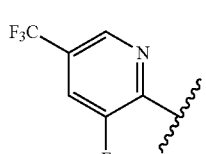 |
| B9 | 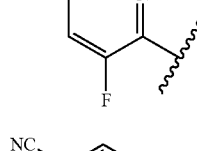 |
| B10 | 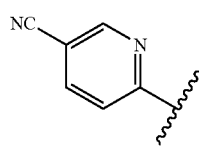 [SMILES: *c1ccc(C#N)cn1] |
| B11 | 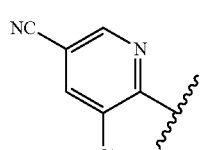 |
| B12 | 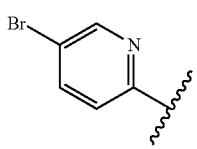 |
| B13 | 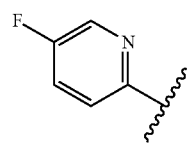 |

TABLE 2-continued
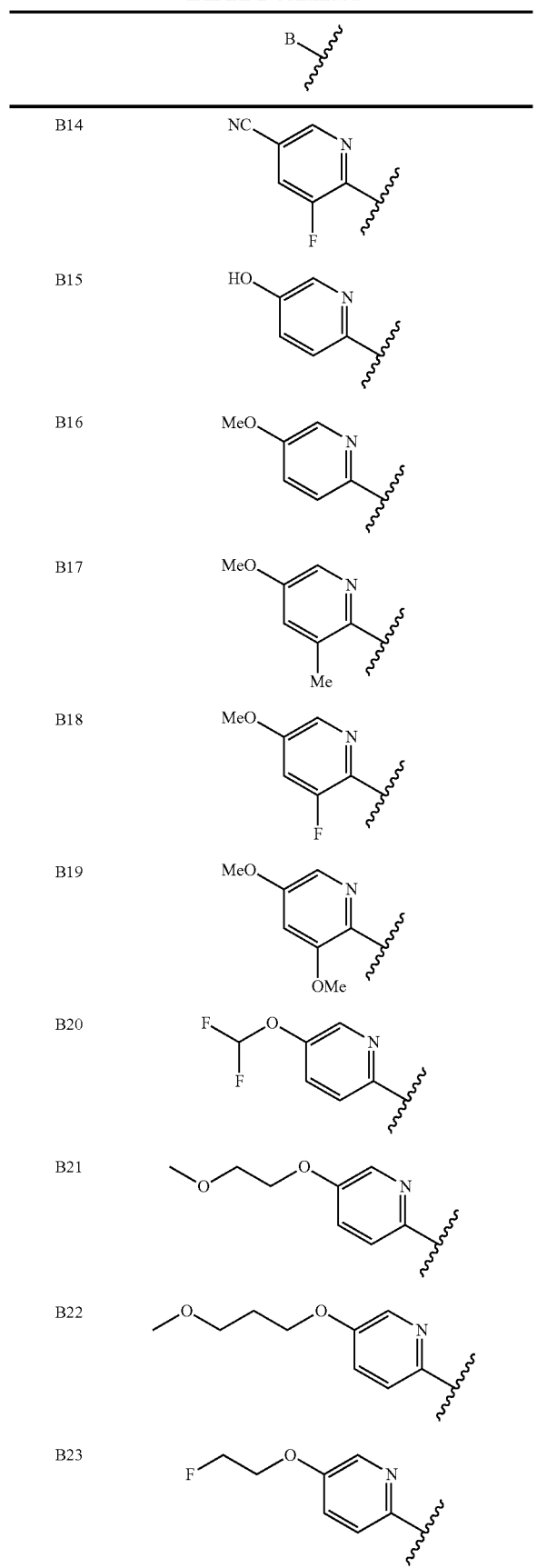
TABLE 2-continued
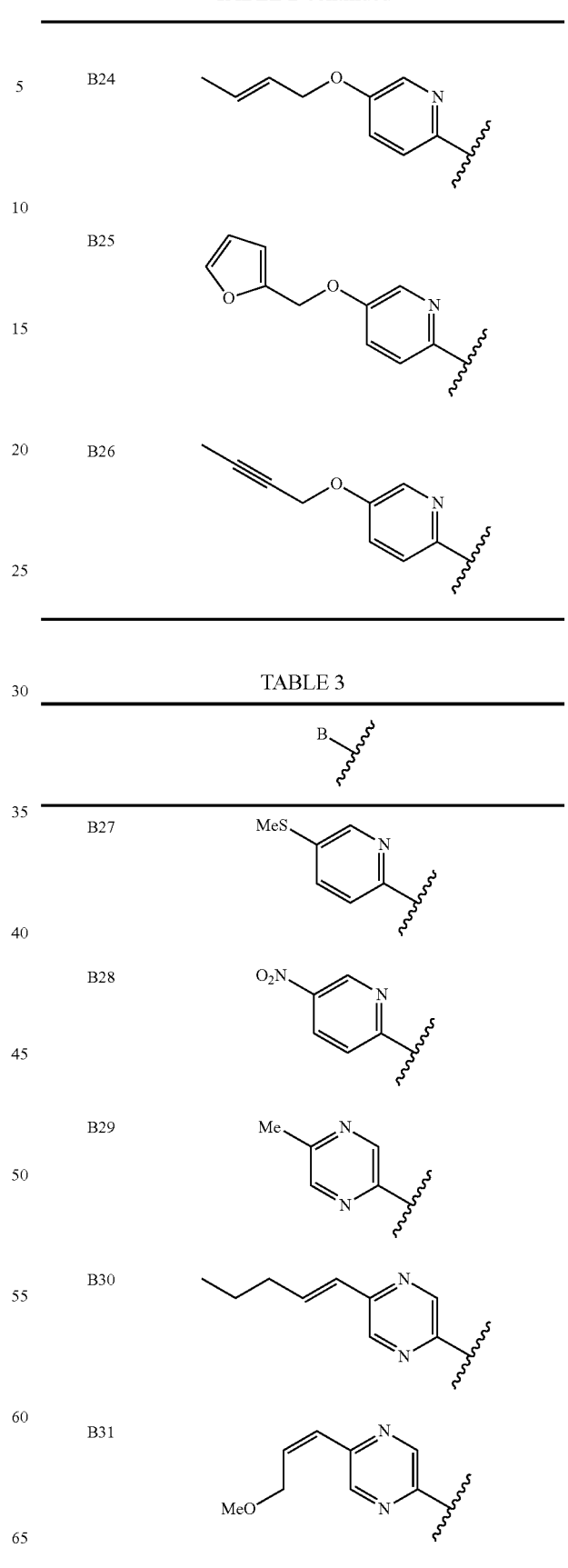
TABLE 3

TABLE 3-continued
| | | | | |
|---|---|---|---|---|
| B32 | 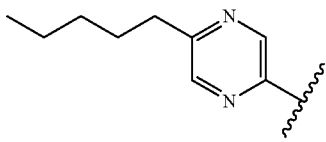 [SMILES: *c1cnc(CCCCC)cn1] | | B41 | 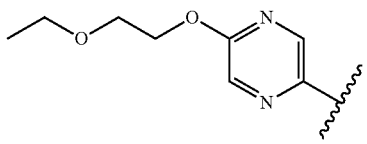 |
| B33 | 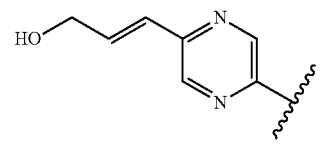 [SMILES: *c1cnc(/C=C/CO)cn1] | | B42 | 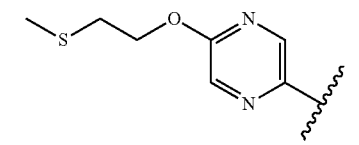 |
| B34 | 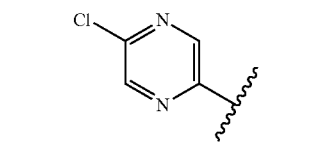 [SMILES: *c1cnc(Cl)cn1] | | B43 | 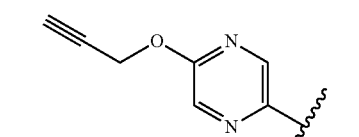 |
| B35 | 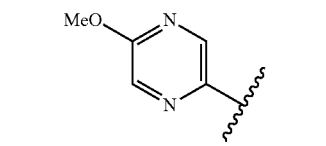 [SMILES: *c1cnc(OC)cn1] | | B44 | 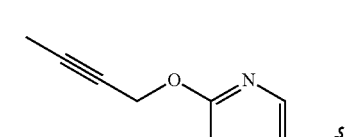 |
| B36 | 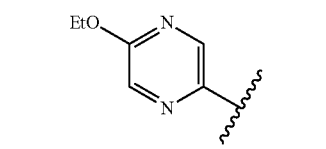 [SMILES: *c1cnc(OCC)cn1] | | B45 | 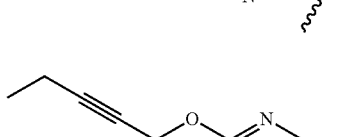 |
| B37 | 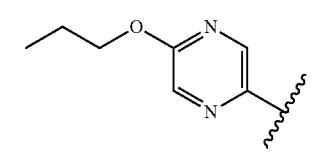 [SMILES: *c1cnc(OCCC)cn1] | | B46 | 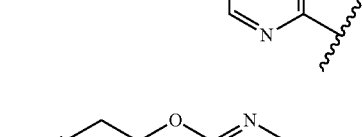 |
| B38 | 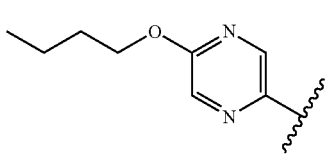 [SMILES: *c1cnc(OCCCC)cn1] | | B47 | 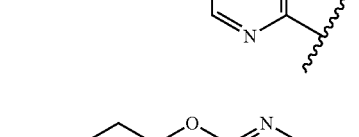 |
| B39 | 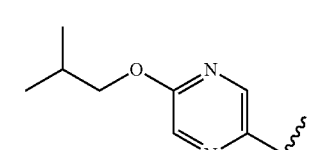 | | B48 | 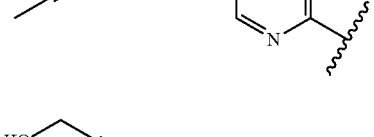 |
| | 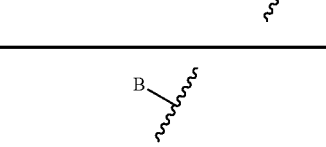 | | | |
| B40 |  | | B49 | 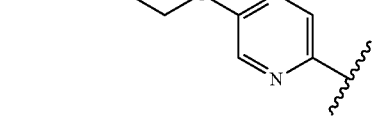 |

TABLE 3-continued
| | |
|---|---|
| B50 | 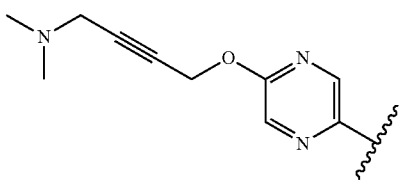 [SMILES: *c1cnc(OCC#CCN(C)C)cn1] |
| B51 | 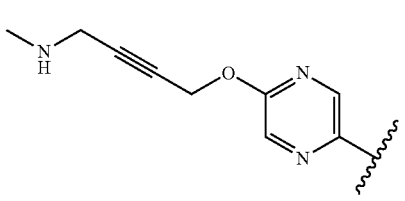 [SMILES: *c1cnc(OCC#CCNC)cn1] |
| B52 | 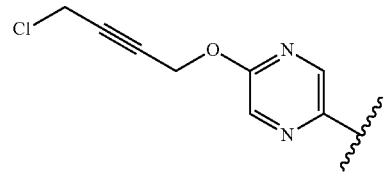 [SMILES: *c1cnc(OCC#CCCl)cn1] |
TABLE 4
| | |
|---|---|
| B53 | 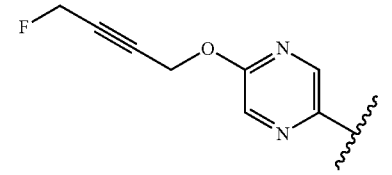 [SMILES: *c1cnc(OCC#CCF)cn1] |
| B54 | 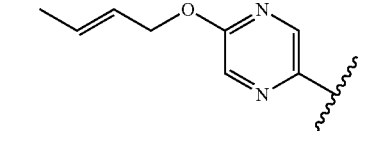 [SMILES: *c1cnc(OC/C=C/C)cn1] |
| B55 | 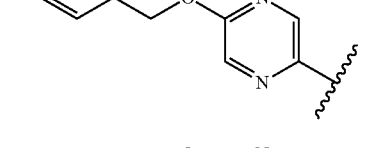 |
| B56 | 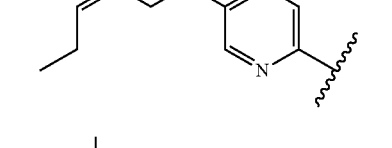 |
| B57 | 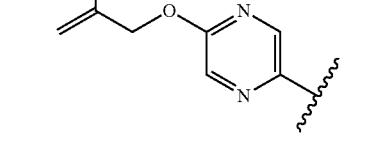 |
TABLE 4-continued
| | |
|---|---|
| B58 | 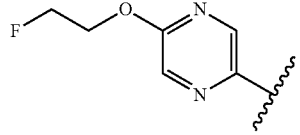 |
| B59 | 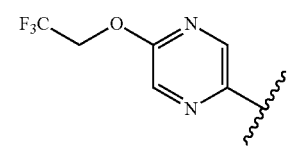 [SMILES: *c1cnc(OCC(F)(F)F)cn1] |
| B60 | 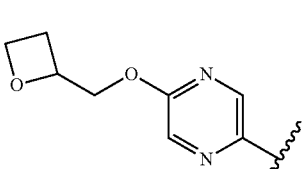 |
| B61 | 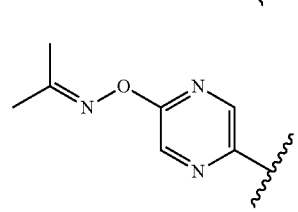 |
| B62 | 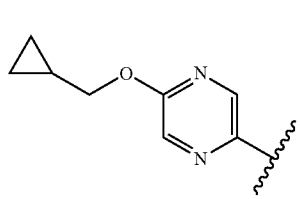 [SMILES: *c1cnc(OCC2CC2)cn1] |
| B63 | 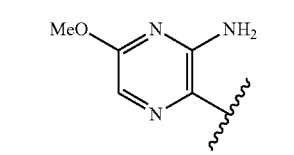 [SMILES: *c1ncc(OC)nc1N] |
| B64 | 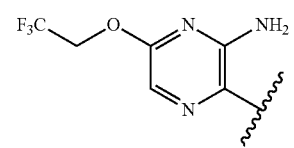 [SMILES: *c1ncc(OCC(F)(F)F)nc1N] |
| B65 | 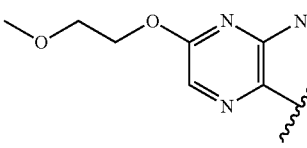 |
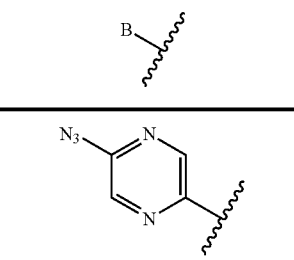
| | |
|---|---|
| B66 | (continued) |

TABLE 4-continued

| | |
|---|---|
| B67 | [structure: but-2-yn-1-ylamino pyrazine] |
| B68 | [structure: 5-(methylthio)pyrazine] |
| B69 | [structure: 5-(ethylthio)pyrazine] |
| B70 | [structure: 2H-1,2,3-triazol-2-yl pyrazine] |
| B71 | [structure: 1H-1,2,3-triazol-1-yl pyrazine] |
| B72 | [structure: 1H-1,2,4-triazol-1-yl pyrazine] |
| B73 | [structure: 1H-pyrazol-1-yl pyrazine] |
| B74 | [structure: 1H-pyrrol-2-yl pyrazine] |

TABLE 4-continued

| | |
|---|---|
| B75 | [structure: oxazol-2-yl pyrazine] |
| B76 | [structure: thiazol-2-yl pyrazine] |
| B77 | [structure: thiophen-3-yl pyrazine] |
| B78 | [structure: 3,5-dimethylisoxazol-4-yl pyrazine] |

TABLE 5

B—[wavy bond]

| | |
|---|---|
| B79 | [structure: furan-3-yl pyrazine] |
| B80 | [structure: furan-2-yl pyrazine] |

TABLE 5-continued
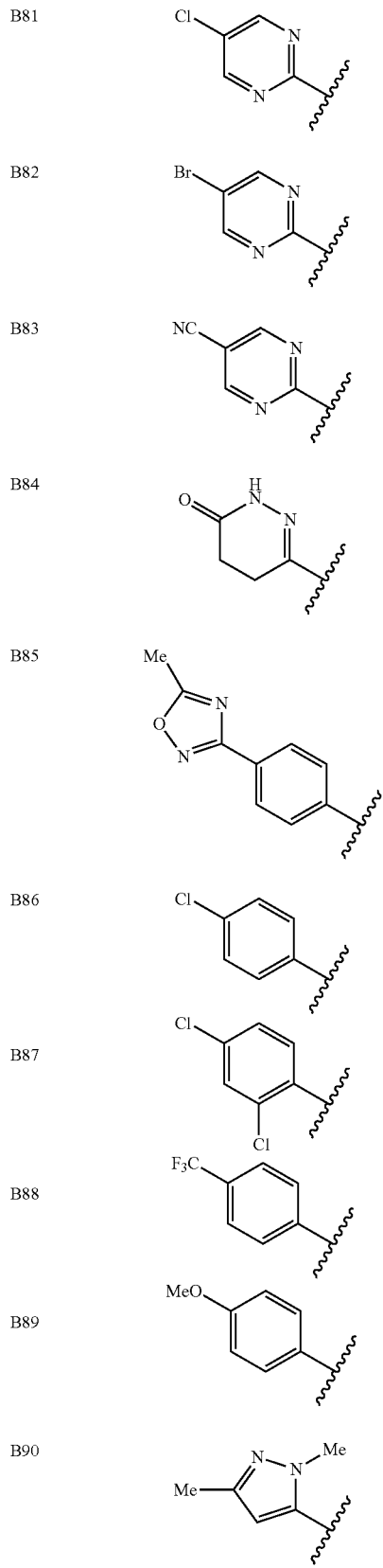
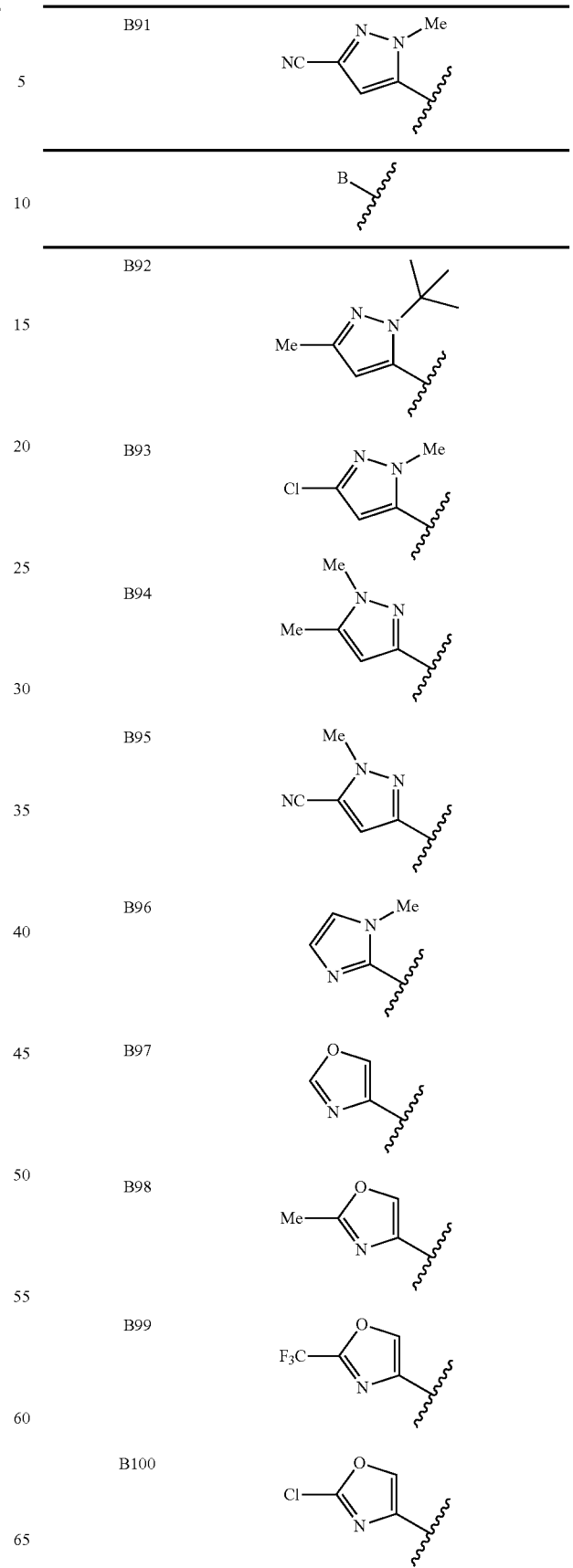

TABLE 5-continued
B101 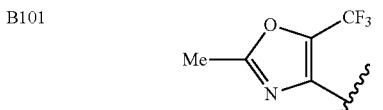
B102 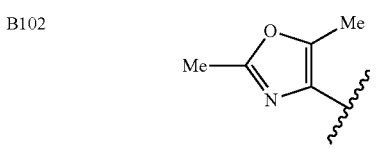
B103 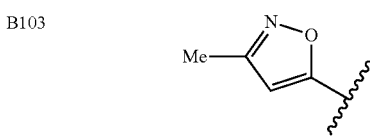
B104 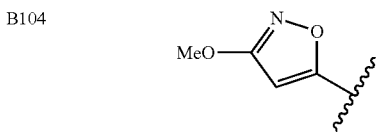
TABLE 6
B105 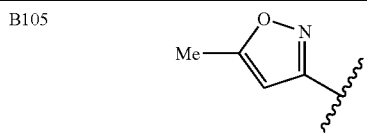
B106 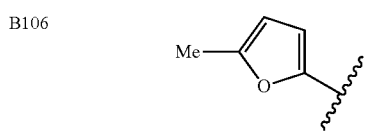
B107 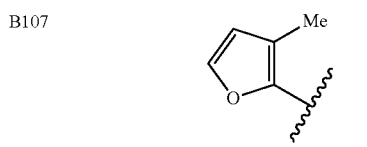
B108 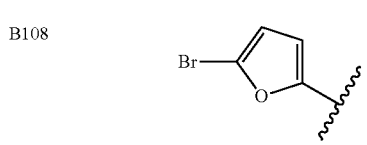
B109 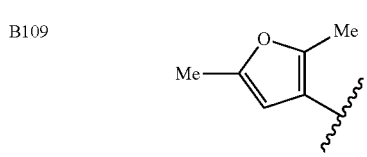
TABLE 6-continued
B110 
B111 
B112 
B113 
B114 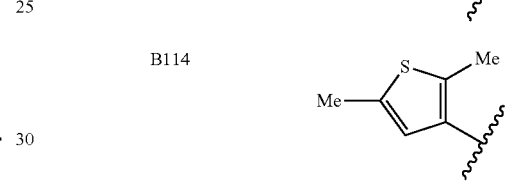
B115 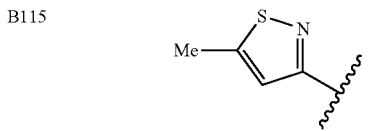
B116 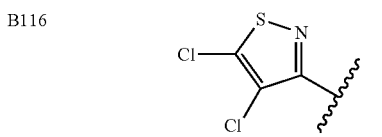
B117 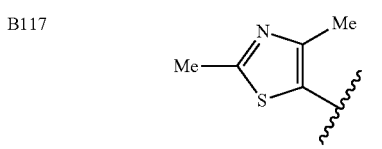
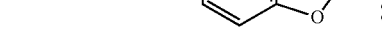
B118 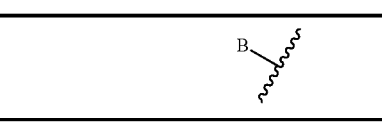
B119 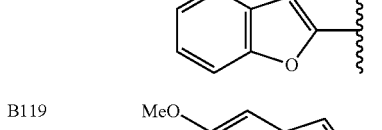
B120 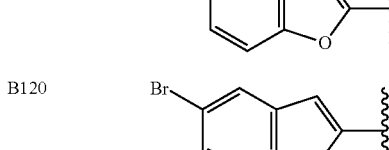

TABLE 6-continued

| | |
|---|---|
| B121 | 5-chloro-benzofuran-2-yl |
| B122 | 3-methyl-benzofuran-2-yl |
| B123 | 5-bromo-3-methyl-benzofuran-2-yl |
| B124 | 5-chloro-3-methyl-benzofuran-2-yl |
| B125 | 5-fluoro-3-methyl-benzofuran-2-yl |
| B126 | 5-hydroxy-3-methyl-benzofuran-2-yl |
| B127 | 5-methyl-3-methyl-benzofuran-2-yl |
| B128 | 5-methoxy-3-methyl-benzofuran-2-yl |
| B129 | 5-bromo-3-amino-benzofuran-2-yl |
| B130 | 1H-indol-2-yl |

TABLE 7

B—

| | |
|---|---|
| B131 | 5-fluoro-1H-indol-2-yl |
| B132 | benzothiophen-2-yl |
| B133 | 5-hydroxy-3-methyl-benzothiophen-2-yl |
| B134 | pyrrolo[1,2-c]pyrimidin-3-yl |
| B135 | chloro-pyrrolo[1,2-c]pyrimidin-3-yl |
| B136 | 2-methyl-imidazo[1,2-a]pyrazin-6-yl |
| B137 | 2-trifluoromethyl-imidazo[1,2-a]pyrazin-6-yl |
| B138 | 2-cyano-imidazo[1,2-a]pyrazin-6-yl |
| B139 | quinoxalin-2-yl |
| B140 | quinolin-3-yl |

TABLE 7-continued

B141 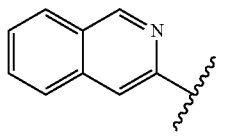 [SMILES: *c1cc2ccccc2cn1]

B142 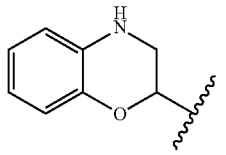 [SMILES: *C1CNc2ccccc2O1]

B143 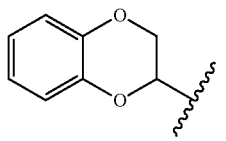 [SMILES: *C1COc2ccccc2O1]

B 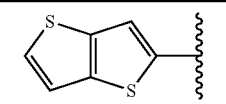

B144 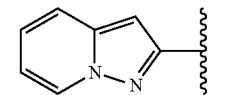 [SMILES: *c1cc2ccccn2n1]

B145 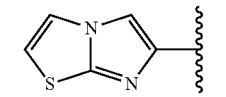 [SMILES: *c1cn2ccsc2n1]

B146 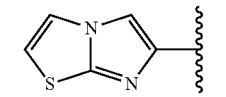 [SMILES: *c1cn2ccsc2n1]

3) A compound of formula (I'):

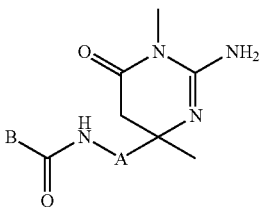

wherein the combination of

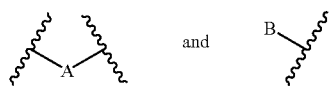 and is as follows:
(A1, B1), (A1, B2), (A1, B3), (A1, B4), (A1, B5), (A1, B6), (A1, B7), (A1, B8), (A1, B9), (A1, B10), (A1, B11), (A1, B12), (A1, B13), (A1, B14), (A1, B15), (A1, B16), (A1, B17), (A1, B18), (A1, B19), (A1, B20), (A1, B21), (A1, B22), (A1, B23), (A1, B24), (A1, B25), (A1, B26), (A1, B27), (A1, B28), (A1, B29), (A1, B30), (A1, B31), (A1, B32), (A1, B33), (A1, B34), (A1, B35), (A1, B36), (A1, B37), (A1, B38), (A1, B39), (A1, B40), (A1, B41), (A1, B42), (A1, B43), (A1, B44), (A1, B45), (A1, B46), (A1, B47), (A1, B48), (A1, B49), (A1, B50), (A1, B51), (A1, B52), (A1, B53), (A1, B54), (A1, B55), (A1, B56), (A1, B57), (A1, B58), (A1, B59), (A1, B60), (A1, B61), (A1, B62), (A1, B63), (A1, B64), (A1, B65), (A1, B66), (A1, B67), (A1, B68), (A1, B69), (A1, B70), (A1, B71), (A1, B72), (A1, B73), (A1, B74), (A1, B75), (A1, B76), (A1, B77), (A1, B78), (A1, B79), (A1, B80), (A1, B81), (A1, B82), (A1, B83), (A1, B84), (A1, B85), (A1, B86), (A1, B87), (A1, B88), (A1, B89), (A1, B90), (A1, B91), (A1, B92), (A1, B93), (A1, B94), (A1, B95), (A1, B96), (A1, B97), (A1, B98), (A1, B99), (A1, B100), (A1, B101), (A1, B102), (A1, B103), (A1, B104), (A1, B105), (A1, B106), (A1, B107), (A1, B108), (A1, B109), (A1, B110), (A1, B111), (A1, B112), (A1, B113), (A1, B114), (A1, B115), (A1, B116), (A1, B117), (A1, B118), (A1, B119), (A1, B120), (A1, B121), (A1, B122), (A1, B123), (A1, B124), (A1, B125), (A1, B126), (A1, B127), (A1, B128), (A1, B129), (A1, B130), (A1, B131), (A1, B132), (A1, B133), (A1, B134), (A1, B135), (A1, B136), (A1, B137), (A1, B138), (A1, B139), (A1, B140), (A1, B141), (A1, B142), (A1, B143), (A1, B144), (A1, B145), (A1, B146),
(A2, B1), (A2, B2), (A2, B3), (A2, B4), (A2, B5), (A2, B6), (A2, B7), (A2, B8), (A2, B9), (A2, B10), (A2, B11), (A2, B12), (A2, B13), (A2, B14), (A2, B15), (A2, B16), (A2, B17), (A2, B18), (A2, B19), (A2, B20), (A2, B21), (A2, B22), (A2, B23), (A2, B24), (A2, B25), (A2, B26), (A2, B27), (A2, B28), (A2, B29), (A2, B30), (A2, B31), (A2, B32), (A2, B33), (A2, B34), (A2, B35), (A2, B36), (A2, B37), (A2, B38), (A2, B39), (A2, B40), (A2, B41), (A2, B42), (A2, B43), (A2, B44), (A2, B45), (A2, B46), (A2, B47), (A2, B48), (A2, B49), (A2, B50), (A2, B51), (A2, B52), (A2, B53), (A2, B54), (A2, B55), (A2, B56), (A2, B57), (A2, B58), (A2, B59), (A2, B60), (A2, B61), (A2, B62), (A2, B63), (A2, B64), (A2, B65), (A2, B66), (A2, B67), (A2, B68), (A2, B69), (A2, B70), (A2, B71), (A2, B72), (A2, B73), (A2, B74), (A2, B75), (A2, B76), (A2, B77), (A2, B78), (A2, B79), (A2, B80), (A2, B81), (A2, B82), (A2, B83), (A2, B84), (A2, B85), (A2, B86), (A2, B87), (A2, B88), (A2, B89), (A2, B90), (A2, B91), (A2, B92), (A2, B93), (A2, B94), (A2, B95), (A2, B96), (A2, B97), (A2, B98), (A2, B99), (A2, B100), (A2, B101), (A2, B102), (A2, B103), (A2, B104), (A2, B105), (A2, 3106), (A2, B107), (A2, B108), (A2, B109), (A2, B110), (A2, B111), (A2, B112), (A2, B113), (A2, B114), (A2, B115), (A2, B116), (A2, B117), (A2, B118), (A2, B119), (A2, B120), (A2, B121), (A2, B122), (A2, B123), (A2, B124), (A2, B125), (A2, B126), (A2, B127), (A2, B128), (A2, B129), (A2, B130), (A2, B131), (A2, B132), (A2, B133), (A2, B134), (A2, B135), (A2, B136), (A2, B137), (A2, B138), (A2, B139), (A2, B140), (A2, B141), (A2, B142), (A2, B143), (A2, B144), (A2, B145), (A2, B146),
(A3, B1), (A3, B2), (A3, B3), (A3, B4), (A3, B5), (A3, B6), (A3, B7), (A3, B8), (A3, B9), (A3, B10), (A3, B11), (A3, B12), (A3, B13), (A3, B14) (A3, B15), (A3, B16), (A3, B17), (A3, B18) (A3, B19) (A3, B20), (A3, B21), (A3, B22), (A3, B23), (A3, B24), (A3, B25) (A3, B26), (A3, B27) (A3, B28), (A3, B29), (A3, B30), (A3, B31) (A3, B32), (A3, B33), (A3, B34) (A3, B35) (A3, B36), (A3, B37), (A3, B38), (A3, B39), (A3, B40), (A3, B41), (A3, B42), (A3, B43), (A3, B44) (A3, B45) (A3, B46), (A3, B47), (A3, B48), (A3, B49), (A3, B50) (A3, B51) (A3, B52), (A3, B53), (A3, B54), (A3, B55) (A3, B56), (A3, B57) (A3, B58), (A3, B59) (A3, B60), (A3, B61), (A3, B62) (A3, B63), (A3, B64), (A3, B65) (A3, B66), (A3, B67) (A3, B68), (A3, B69), (A3, B70) (A3, B71), (A3, B72), (A3, B73), (A3, B74), (A3, B75), (A3, B76), (A3, B77), (A3, B78), (A3, B79), (A3, B80), (A3, B81), (A3, B82), (A3, B83), (A3, B84), (A3, B85) (A3, B86) (A3, B87) (A3, B88), (A3, B89) (A3, B90), (A3, B91), (A3, B92), (A3, B93), (A3, B94), (A3, B95), (A3, B96), (A3, B97), (A3, B98), (A3, B99), (A3, B100), (A3, B101), (A3, B102), (A3, B103), (A3, B104), (A3, B105) (A3, B106), (A3, B107), (A3, B108), (A3, B109), (A3, B110), (A3, B111), (A3, B112), (A3, B113), (A3, B114), (A3, B115), (A3, B116), (A3, B117), (A3, B118), (A3, B119), (A3, B120), (A3, B121) (A3, B122), (A3, B123), (A3, B124), (A3, B125), (A3, B126), (A3, B127), (A3, B128), (A3, B129), (A3, B130), (A3, B131), (A3, B132), (A3, B133), (A3, B134), (A3, B135), (A3, B136), (A3, B137), (A3, B138), (A3, B139), (A3, B140), (A3, B141), (A3, B142), (A3, B143) (A3, B144), (A3, B145), (A3, B146)
(A4, B1) (A4, B2), (A4, B3), (A4, B4), (A4, B5), (A4, B6), (A4, B7), (A4, B8), (A4, B9), (A4, B10), (A4, B11), (A4, B12), (A4, B13), (A4, B14), (A4, B15) (A4, B16), (A4, B17), (A4, B18), (A4, B19) (A4, B20), (A4, B21), (A4, B22), (A4, B23), (A4, B24), (A4, B25), (A4, B26), (A4, B27) (A4, B28), (A4, B29) (A4, B30), (A4, B31), (A4, B32) (A4, B33), (A4, B34) (A4, B35), (A4, B36), (A4, B37), (A4, B38), (A4, B39), (A4, B40), (A4, B41), (A4, B42), (A4, B43), (A4, B44), (A4, B45), (A4, B46), (A4, B47), (A4, B48), (A4, B49), (A4, B50), (A4, B51), (A4, B52), (A4, B53), (A4, B54) (A4, B55), (A4, B56), (A4, B57), (A4, B58), (A4, B59), (A4, B60), (A4, B61), (A4, B62), (A4, B63), (A4, B64), (A4, B65), (A4, B66), (A4, B67), (A4, B68), (A4, B69), (A4, B70), (A4, B71), (A4, B72), (A4, B73), (A4, B74), (A4, B75), (A4, B76), (A4, B77), (A4, B78), (A4, B79), (A4, B80), (A4, B81), (A4, B82), (A4, B83), (A4, B84), (A4, B85), (A4, B86), (A4, B87), (A4, B88), (A4, B89), (A4, B90) (A4, B91), (A4, B92), (A4, B93), (A4, B94), (A4, B95), (A4, B96), (A4, B97), (A4, B98), (A4, B99), (A4, B100), (A4, B101), (A4, B102), (A4, B103), (A4, B104), (A4, B105), (A4, B106), (A4, B107), (A4, B108), (A4, B109), (A4, B110), (A4, B111) (A4, B112) (A4, B113), (A4, B114), (A4, B115), (A4, B116), (A4, B117) (A4, B118), (A4, B119), (A4, B120), (A4, B121), (A4, B122), (A4, B123), (A4, B124), (A4, B125), (A4, B126), (A4, B127), (A4, B128) (A4, B129), (A4, B130), (A4, B131), (A4, B132), (A4, B133), (A4, B134), (A4, B135) (A4, B136), (A4, B137), (A4, B138), (A4, B139) (A4, B140), (A4, B141), (A4, B142), (A4, B143), (A4, B144), (A4, B145), (A4, B146)
(A5, B1), (A5, B2) (A5, B3), (A5, B4), (A5, B5) (A5, B6) (A5, B7), (A5, B8), (A5, B9), (A5, B10), (A5, B11) (A5, B12), (A5, B13), (A5, B14), (A5, B15), (A5, B16), (A5, B17), (A5, B18), (A5, B19), (A5, B20), (A5, B21), (A5, B22), (A5, B23), (A5, B24) (A5, B25) (A5, B26), (A5, B27), (A5, B28), (A5, B29), (A5, B30), (A5, B31), (A5, B32), (A5, B33), (A5, B34), (A5, B35), (A5, B36), (A5, B37) (A5, B38), (A5, B39), (A5, B40) (A5, B41), (A5, B42), (A5, B43), (A5, B44), (A5, B45) (A5, B46), (A5, B47), (A5, B48), (A5, B49), (A5, B50), (A5, B51), (A5, B52), (A5, B53), (A5, B54), (A5, B55), (A5, B56), (A5, B57), (A5, B58), (A5, B59), (A5, B60), (A5, B61), (A5, B62) (A5, B63), (A5, B64), (A5, B65), (A5, B66), (A5, B67), (A5, B68), (A5, B69), (A5, B70), (A5, B71), (A5, B72), (A5, B73), (A5, B74), (A5, B75), (A5, B76), (A5, B77), (A5, B78), (A5, B79), (A5, B80), (A5, B81), (A5, B82), (A5, B83), (A5, B84), (A5, B85), (A5, B86), (A5, B87), (A5, B88), (A5, B89), (A5, B90), (A5, B91), (A5, B92), (A5, B93), (A5, B94), (A5, B95), (A5, B96), (A5, B97), (A5, B98), (A5, B99), (A5, B100), (A5, B101), (A5, B102), (A5, B103), (A5, B104), (A5, B105), (A5, B106), (A5, B107), (A5, B108), (A5, B109), (A5, B110), (A5, B111), (A5, B112), (A5, B113), (A5, B114), (A5, B115), (A5, B116), (A5, B117), (A5, B118), (A5, B119), (A5, B120), (A5, B121), (A5, B122), (A5, B123), (A5, B124), (A5, B125), (A5, B126), (A5, B127), (A5, B128), (A5, B129), (A5, B130), (A5, B131), (A5, B132), (A5, B133), (A5, B134), (A5, B135), (A5, B136), (A5, B137), (A5, B138), (A5, B139), (A5, B140), (A5, B141), (A5, B142), (A5, B143), (A5, B144), (A5, B145), (A5, B146),
(A6, B1), (A6, B2), (A6, B3), (A6, B4), (A6, B5), (A6, B6), (A6, B7), (A6, B8), (A6, B9), (A6, B10), (A6, B11), (A6, B12), (A6, B13), (A6, B14), (A6, B15), (A6, B16), (A6, B17), (A6, B18), (A6, B19), (A6, B20), (A6, B21), (A6, B22), (A6, B23), (A6, B24), (A6, B25), (A6, B26), (A6, B27), (A6, B28), (A6, B29), (A6, B30), (A6, B31), (A6, B32), (A6, B33), (A6, B34), (A6, B35), (A6, B36), (A6, B37), (A6, B38), (A6, B39), (A6, B40), (A6, B41), (A6, B42), (A6, B43), (A6, B44), (A6, B45), (A6, B46), (A6, B47), (A6, B48), (A6, B49), (A6, B50), (A6, B51), (A6, B52), (A6, B53), (A6, B54), (A6, B55), (A6, B56), (A6, B57), (A6, B58), (A6, B59), (A6, B60), (A6, B61), (A6, B62), (A6, B63), (A6, B64), (A6, B65), (A6, B66), (A6, B67), (A6, B68), (A6, B69), (A6, B70), (A6, B71), (A6, B72), (A6, B73), (A6, B74), (A6, B75), (A6, B76), (A6, B77), (A6, B78), (A6, B79), (A6, B80), (A6, B81), (A6, B82), (A6, B83), (A6, B84), (A6, B85), (A6, B86), (A6, B87), (A6, B88), (A6, B89), (A6, B90), (A6, B91), (A6, B92), (A6, B93), (A6, B94), (A6, B95), (A6, B96), (A6, B97), (A6, B98), (A6, B99), (A6, B100), (A6, B101), (A6, B102), (A6, B103), (A6, B104), (A6, B105), (A6, B106), (A6, B107), (A6, B108), (A6, B109), (A6, B110), (A6, B111), (A6, B112), (A6, B113), (A6, B114), (A6, B115), (A6, B116), (A6, B117), (A6, B118), (A6, B119), (A6, B120), (A6, B121), (A6, B122), (A6, B123), (A6, B124), (A6, B125), (A6, B126), (A6, B127), (A6, B128) (A6, B129), (A6, B130), (A6, B131), (A6, B132), (A6, B133), (A6, B134), (A6, B135), (A6, B136), (A6, B137), (A6, B138), (A6, B139), (A6, B140) (A6, B141) (A6, B142), (A6, B143), (A6, B144), (A6, B145), (A6, B146),
(A7, B1), (A7, B2), (A7, B3), (A7, B4), (A7, B5), (A7, B6), (A7, B7), (A7, B8), (A7, B9), (A7, B10), (A7, B11), (A7, B12), (A7, B13), (A7, B14), (A7, B15), (A7, B16), (A7, B17), (A7, B18), (A7, B19), (A7, B20), (A7, B21), (A7, B22), (A7, B23), (A7, B24), (A7, B25), (A7, B26), (A7, B27), (A7, B28) (A7, B29), (A7, B30), (A7, B31), (A7, B32), (A7, B33) (A7, B34), (A7, B35), (A7, B36), (A7, B37), (A7, B38), (A7, B39), (A7, B40), (A7, B41) (A7, B42), (A7, B43), (A7, B44) (A7, B45), (A7, B46), (A7, B47), (A7, B48), (A7, B49) (A7, B50), (A7, B51), (A7, B52), (A7, B53), (A7, B54), (A7, B55), (A7, B56), (A7, B57), (A7, B58), (A7, B59), (A7, B60), (A7, B61), (A7, B62), (A7, B63), (A7, B64), (A7, B65), (A7, B66), (A7, B67) (A7, B68), (A7, B69), (A7, B70), (A7, B71), (A7, B72), (A7, B73), (A7, B74), (A7, B75), (A7, B76), (A7, B77), (A7, B78), (A7, B79), (A7, B80), (A7, B81), (A7, B82), (A7, B83), (A7, B84), (A7, B85), (A7, B86), (A7, B87), (A7, B88) (A7, B89), (A7, B90), (A7, B91), (A7, B92), (A7, B93) (A7, B94), (A7, B95), (A7, B96), (A7, B97), (A7, B98), (A7, B99), (A7, B100), (A7, B101), (A7, B102), (A7, B103), (A7, B104), (A7, B105), (A7, B106), (A7, B107), (A7, B108), (A7, B109), (A7, B110), (A7, B111), (A7, B112), (A7, B113), (A7, B114), (A7, B115) (A7, B116), (A7, B117), (A7, B118), (A7, B119), (A7, B120), (A7, B121) (A7, B122), (A7, B123), (A7, B124) (A7, B125), (A7, B126), (A7, B127) (A7, B128) (A7, B129), (A7, B130), (A7, B131), (A7, B132), (A7, B133), (A7, B134), (A7, B135) (A7, B136), (A7, B137), (A7, B138), (A7, B139), (A7, B140), (A7, B141), (A7, B142), (A7, B143), (A7, B144), (A7, B145), (A7, B146), (A8, B1), (A8, B2), (A8, B3), (A8, B4), (A8, B5), (A8, B6), (A8, B7), (A8, B8), (A8, B9), (A8, B10), (A8, B11), (A8, B12), (A8, B13), (A8, B14), (A8, B15), (A8, B16), (A8, B17), (A8, B18), (A8, B19), (A8, B20), (A8, B21), (A8, B22), (A8, B23), (A8, B24), (A8, B25), (A8, B26), (A8, B27), (A8, B28), (A8, B29), (A8, B30), (A8, B31), (A8, B32), (A8, B33), (A8, B34), (A8, B35), (A8, B36), (A8, B37), (A8, B38), (A8, B39), (A8, B40), (A8, B41), (A8, B42), (A8, B43), (A8, B44), (A8, B45), (A8, B46), (A8, B47), (A8, B48), (A8, B49), (A8, B50), (A8, B51), (A8, B52), (A8, B53), (A8, B54), (A8, B55), (A8, B56), (A8, B57), (A8, B58), (A8, B59), (A8, B60), (A8, B61), (A8, B62), (A8, B63), (A8, B64), (A8, B65), (A8, B66), (A8, B67), (A8, B68), (A8, B69), (A8, B70), (A8, B71), (A8, B72), (A8, B73), (A8, B74), (A8, B75), (A8, B76), (A8, B77), (A8, B78), (A8, B79), (A8, B80), (A8, B81), (A8, B82), (A8, B83), (A8, B84), (A8, B85), (A8, B86), (A8, B87), (A8, B88), (A8, B89), (A8, B90), (A8, B91), (A8, B92), (A8, B93), (A8, B94), (A8, B95), (A8, B96), (A8, B97), (A8, B98), (A8, B99), (A8, B100), (A8, B101), (A8, B102), (A8, B103), (A8, B104), (A8, B105), (A8, B106), (A8, B107), (A8, B108), (A8, B109), (A8, B110), (A8, B111), (A8, B112), (A8, B113), (A8, B114), (A8, B115), (A8, B116), (A8, B117), (A8, B118), (A8, B119), (A8, B120), (A8, B121), (A8, B122), (A8, B123), (A8, B124), (A8, B125), (A8, B126), (A8, B127), (A8, B128), (A8, B129), (A8, B130), (A8, B131), (A8, B132), (A8, B133), (A8, B134), (A8, B135), (A8, B136), (A8, B137), (A8, B138), (A8, B139), (A8, B140), (A8, B141), (A8, B142), (A8, B143), (A8, B144), (A8, B145), (A8, B146), (A9, B1), (A9, B2), (A9, B3), (A9, B4), (A9, B5), (A9, B6), (A9, B7), (A9, B8), (A9, B9), (A9, B10), (A9, B11), (A9, B12), (A9, B13), (A9, B14), (A9, B15), (A9, B16), (A9, B17), (A9, B18), (A9, B19), (A9, B20), (A9, B21), (A9, B22), (A9, B23), (A9, B24), (A9, B25), (A9, B26), (A9, B27), (A9, B28), (A9, B29), (A9, B30), (A9, B31), (A9, B32), (A9, B33), (A9, B34), (A9, B35), (A9, B36), (A9, B37), (A9, B38), (A9, B39), (A9, B40), (A9, B41), (A9, B42), (A9, B43), (A9, B44), (A9, B45), (A9, B46), (A9, B47), (A9, B48), (A9, B49), (A9, B50), (A9, B51), (A9, B52), (A9, B53), (A9, B54), (A9, B55), (A9, B56), (A9, B57), (A9, B58), (A9, B59) (A9, B60) (A9, B61), (A9, B62), (A9, B63), (A9, B64), (A9, B65), (A9, B66), (A9, B67), (A9, B68), (A9, B69) (A9, B70), (A9, B71), (A9, B72) (A9, B73), (A9, B74) (A9, B75) (A9, B76), (A9, B77), (A9, B78), (A9, B79) (A9, B80), (A9, B81), (A9, B82), (A9, B83) (A9, B84) (A9, B85), (A9, B86), (A9, B87), (A9, B88), (A9, B89), (A9, B90), (A9, B91) (A9, B92), (A9, B93), (A9, B94), (A9, B95), (A9, B96), (A9, B97), (A9, B98), (A9, B99), (A9, B100), (A9, B101), (A9, B102), (A9, B103), (A9, B104), (A9, B105) (A9, B106), (A9, B107), (A9, B108), (A9, B109), (A9, B110), (A9, B111), (A9, B112), (A9, B113), (A9, B114) (A9, B115), (A9, B116) (A9, B117) (A9, B118), (A9, B119), (A9, B120), (A9, B121), (A9, B122), (A9, B123), (A9, B124), (A9, B125), (A9, B126), (A9, B127), (A9, B128), (A9, B129), (A9, B130), (A9, B131), (A9, B132), (A9, B133), (A9, B134), (A9, B135), (A9, B136), (A9, B137), (A9, B138), (A9, B139), (A9, B140), (A9, B141), (A9, B142), (A9, B143), (A9, B144), (A9, B145), (A9, B146), (A10, B1), (A10, B2), (A10, B3), (A10, B4), (A10, B5), (A10, B6), (A10, B7), (A10, B8), (A10, B9), (A10, B10), (A10, B11), (A10, B12), (A10, B13), (A10, B14), (A10, B15), (A10, B16) (A10, B17), (A10, B18), (A10, B19), (A10, B20), (A10, B21), (A10, B22), (A10, B23), (A10, B24) (A10, B25), (A10, B26), (A10, B27) (A10, B28) (A10, B29), (A10, B30), (A10, B31), (A10, B32), (A10, B33), (A10, B34), (A10, B35), (A10, B36) (A10, B37), (A10, B38), (A10, B39), (A10, B40), (A10, B41), (A10, B42), (A10, B43), (A10, B44), (A10, B45), (A10, B46), (A10, B47) (A10, B48), (A10, B49), (A10, B50), (A10, B51), (A10, B52), (A10, B53), (A10, B54), (A10, B55), (A10, B56) (A10, B57), (A10, B58), (A10, B59), (A10, B60), (A10, B61), (A10, B62), (A10, B63) (A10, B64), (A10, B65), (A10, B66), (A10, B67), (A10, B68), (A10, B69), (A10, B70), (A10, B71), (A10, B72), (A10, B73), (A10, B74), (A10, B75), (A10, B76), (A10, B77), (A10, B78), (A10, B79), (A10, B80), (A10, B81), (A10, B82), (A10, B83), (A10, B84), (A10, B85), (A10, B86), (A10, B87), (A10, B88), (A10, B89), (A10, B90), (A10, B91), (A10, B92), (A10, B93), (A10, B94), (A10, B95), (A10, B96), (A10, B97), (A10, B98), (A10, B99), (A10, B100), (A10, B101), (A10, B102), (A10, B103), (A10, B104), (A10, B105), (A10, B106), (A10, B107), (A10, B108), (A10, B109), (A10, B110), (A10, B111), (A10, B112), (A10, B113), (A10, B114), (A10, B115), (A10, B116), (A10, B117), (A10, B118), (A10, B119), (A10, B120), (A10, B121), (A10, B122), (A10, B123), (A10, B124), (A10, B125), (A10, B126), (A10, B127), (A10, B128), (A10, B129), (A10, B130), (A10, B131), (A10, B132), (A10, B133), (A10, B134), (A10, B135), (A10, B136), (A10, B137), (A10, B138), (A10, B139), (A10, B140), (A10, B141), (A10, B142), (A10, B143), (A10, B144), (A10, B145), (A10, B146), (A11, B1), (A11, B2), (A11, B3), (A11, B4), (A11, B5), (A11, B6), (A11, B7), (A11, B8), (A11, B9), (A11, B10), (A11, B11), (A11, B12), (A11, B13), (A11, B14), (A11, B15), (A11, B16), (A11, B17), (A11, B18), (A11, B19), (A11, B20), (A11, B21), (A11, B22), (A11, B23), (A11, B24), (A11, B25), (A11, B26), (A11, B27), (A11, B28), (A11, B29), (A11, B30), (A11, B31), (A11, B32), (A11, B33), (A11, B34), (A11, B35), (A11, B36), (A11, B37), (A11, B38), (A11, B39), (A11, B40), (A11, B41), (A11, B42), (A11, B43), (A11, B44), (A11, B45), (A11, B46), (A11, B47), (A11, B48), (A11, B49), (A11, B50), (A11, B51), (A11, B52), (A11, B53), (A11, B54), (A11, B55), (A11, B56), (A11, B57), (A11, B58), (A11, B59), (A11, B60), (A11, B61), (A11, B62), (A11, B63), (A11, B64), (A11, B65), (A11, B66), (A11, B67), (A11, B68), (A11, B69), (A11, B70), (A11, B71), (A11, B72), (A11, B73), (A11, B74), (A11, B75), (A11, B76), (A11, B77), (A11, B78), (A11, B79), (A11, B80), (A11, B81), (A11, B82), (A11, B83), (A11, B84), (A11, B85), (A11, B86), (A11, B87), (A11, B88), (A11, B89), (A11, B90), (A11, B91), (A11, B92), (A11, B93), (A11, B94), (A11, B95), (A11, B96), (A11, B97), (A11, B98), (A11, B99), (A11, B100), (A11, B101), (A11, B102), (A11, B103), (A11, B104), (A11, B105), (A11, B106), (A11, B107), (A11, B108), (A11, B109), (A11, B110), (A11, B111), (A11, B112), (A11, B113), (A11, B114), (A11, B115), (A11, B116), (A11, B117), (A11, B118), (A11, B119), (A11, B120), (A11, B121), (A11, B122), (A11, B123), (A11, B124), (A11, B125), (A11, B126), (A11, B127), (A11, B128), (A11, B129), (A11, B130), (A11, B131), (A11, B132), (A11, B133), (A11, B134), (A11, B135), (A11, B136), (A11, B137), (A11, B138), (A11, B139), (A11, B140), (A11, B141), (A11, B142), (A11, B143), (A11, B144), (A11, B145), (A11, B146), (A12, B1), (A12, B2), (A12, B3), (A12, B4), (A12, B5), (A12, B6), (A12, B7), (A12, B8), (A12, B9), (A12, B10), (A12, B11), (A12, B12), (A12, B13), (A12, B14), (A12, B15), (A12, B16), (A12, B17), (A12, B18), (A12, B19), (A12, B20), (A12, B21), (A12, B22), (A12, B23), (A12, B24), (A12, B25), (A12, B26), (A12, B27), (A12, B28), (A12, B29), (A12, B30), (A12, B31), (A12, B32), (A12, B33), (A12, B34), (A12, B35), (A12, B36), (A12, B37), (A12, B38), (A12, B39), (A12, B40), (A12, B41), (A12, B42), (A12, B43), (A12, B44), (A12, B45), (A12, B46), (A12, B47), (A12, B48), (A12, B49), (A12, B50), (A12, B51), (A12, B52), (A12, B53), (A12, B54), (A12, B55), (A12, B56), (A12, B57), (A12, B58), (A12, B59), (A12, B60), (A12, B61), (A12, B62), (A12, B63), (A12, B64), (A12, B65), (A12, B66), (A12, B67), (A12, B68), (A12, B69), (A12, B70), (A12, B71), (A12, B72), (A12, B73), (A12, B74), (A12, B75), (A12, B76), (A12, B77), (A12, B78), (A12, B79), (A12, B80), (A12, B81), (A12, B82), (A12, B83), (A12, B84), (A12, B85), (A12, B86), (A12, B87), (A12, B88), (A12, B89), (A12, B90), (A12, B91), (A12, B92), (A12, B93), (A12, B94), (A12, B95), (A12, B96), (A12, B97), (A12, B98), (A12, B99), (A12, B100), (A12, B101), (A12, B102), (A12, B103), (A12, B104), (A12, B105), (A12, B106), (A12, B107), (A12, B108), (A12, B109), (A12, B110), (A12, B111), (A12, B112), (A12, B113), (A12, B114), (A12, B115), (A12, B116), (A12, B117), (A12, B118), (A12, B119), (A12, B120), (A12, B121), (A12, B122), (A12, B123), (A12, B124), (A12, B125), (A12, B126), (A12, B127), (A12, B128), (A12, B129), (A12, B130), (A12, B131), (A12, B132), (A12, B133), (A12, B134), (A12, B135), (A12, B136), (A12, B137), (A12, B138), (A12, B139), (A12, B140), (A12, B141), (A12, B142), (A12, B143), (A12, B144), (A12, B145), (A12, B146), (A13, B1), (A13, B2), (A13, B3), (A13, B4), (A13, B5), (A13, B6), (A13, B7), (A13, B8), (A13, B9), (A13, B10), (A13, B11), (A13, B12), (A13, B13), (A13, B14), (A13, B15), (A13, B16), (A13, B17), (A13, B18), (A13, B19), (A13, B20), (A13, B21), (A13, B22), (A13, B23), (A13, B24), (A13, B25), (A13, B26), (A13, B27), (A13, B28), (A13, B29), (A13, B30), (A13, B31), (A13, B32), (A13, B33), (A13, B34), (A13, B35), (A13, B36), (A13, B37), (A13, B38), (A13, B39), (A13, B40), (A13, B41), (A13, B42), (A13, B43), (A13, B44), (A13, B45), (A13, B46), (A13, B47), (A13, B48), (A13, B49), (A13, B50), (A13, B51), (A13, B52), (A13, B53), (A13, B54), (A13, B55), (A13, B56), (A13, B57), (A13, B58), (A13, B59), (A13, B60), (A13, B61), (A13, B62), (A13, B63), (A13, B64), (A13, B65), (A13, B66), (A13, B67), (A13, B68), (A13, B69), (A13, B70), (A13, B71), (A13, B72), (A13, B73), (A13, B74), (A13, B75), (A13, B76), (A13, B77), (A13, B78), (A13, B79), (A13, B80), (A13, B81), (A13, B82), (A13, B83), (A13, B84), (A13, B85), (A13, B86), (A13, B87), (A13, B88), (A13, B89), (A13, B90), (A13, B91), (A13, B92), (A13, B93), (A13, B94), (A13, B95), (A13, B96), (A13, B97), (A13, B98), (A13, B99), (A13, B100), (A13, B101), (A13, B102), (A13, B103), (A13, B104), (A13, B105), (A13, B106), (A13, B107), (A13, B108), (A13, B109), (A13, B110), (A13, B111), (A13, B112), (A13, B113), (A13, B114), (A13, B115), (A13, B116), (A13, B117), (A13, B118), (A13, B119), (A13, B120), (A13, B121), (A13, B122), (A13, B123), (A13, B124), (A13, B125), (A13, B126), (A13, B127), (A13, B128), (A13, B129), (A13, B130), (A13, B131), (A13, B132), (A13, B133), (A13, B134), (A13, B135), (A13, B136), (A13, B137), (A13, B138), (A13, B139), (A13, B140), (A13, B141), (A13, B142), (A13, B143), (A13, B144), (A13, B145), (A13, B146), (A14, B1), (A14, B2), (A14, B3), (A14, B4), (A14, B5), (A14, B6), (A14, B7), (A14, B8), (A14, B9), (A14, B10), (A14, B11), (A14, B12), (A14, B13), (A14, B14), (A14, B15), (A14, B16), (A14, B17), (A14, B18), (A14, B19) (A14, B20), (A14, B21), (A14, B22), (A14, B23), (A14, B24), (A14, B25), (A14, B26) (A14, B27), (A14, B28), (A14, B29), (A14, B30), (A14, B31), (A14, B32), (A14, B33), (A14, B34), (A14, B35), (A14, B36) (A14, B37), (A14, B38), (A14, B39), (A14, B40), (A14, B41), (A14, B42), (A14, B43), (A14, B44), (A14, B45), (A14, B46), (A14, B47), (A14, B48), (A14, B49), (A14, B50), (A14, B51) (A14, B52), (A14, B53), (A14, B54) (A14, B55), (A14, B56), (A14, B57), (A14, B58), (A14, B59), (A14, B60), (A14, B61), (A14, B62), (A14, B63), (A14, B64), (A14, B65), (A14, B66), (A14, B67), (A14, B68), (A14, B69), (A14, B70), (A14, B71), (A14, B72), (A14, B73), (A14, B74), (A14, B75), (A14, B76), (A14, B77), (A14, B78), (A14, B79), (A14, B80), (A14, B81), (A14, B82), (A14, B83), (A14, B84), (A14, B85), (A14, B86), (A14, B87), (A14, B88), (A14, B89), (A14, B90), (A14, B91), (A14, B92), (A14, B93), (A14, B94), (A14, B95), (A14, B96), (A14, B97), (A14, B98), (A14, B99), (A14, B100), (A14, B101), (A14, B102), (A14, B103), (A14, B104), (A14, B105), (A14, B106), (A14, B107), (A14, B108), (A14, B109), (A14, B110), (A14, B111), (A14, B112), (A14, B113), (A14, B114), (A14, B115), (A14, B116), (A14, B117), (A14, B118), (A14, B119), (A14, B120), (A14, B121), (A14, B122), (A14, B123), (A14, B124), (A14, B125), (A14, B126), (A14, B127), (A14, B128), (A14, B129), (A14, B130), (A14, B131), (A14, B132), (A14, B133), (A14, B134), (A14, B135), (A14, B136), (A14, B137), (A14, B138), (A14, B139), (A14, B140), (A14, B141), (A14, B142) (A14, B143), (A14, B144), (A14, B145), (A14, B146), (A15, B1), (A15, B2), (A15, B3), (A15, B4), (A15, B5), (A15, B6), (A15, B7), (A15, B8), (A15, B9), (A15, B10), (A15, B11), (A15, B12), (A15, B13), (A15, B14), (A15, B15), (A15, B16), (A15, B17), (A15, B18), (A15, B19), (A15, B20), (A15, B21), (A15, B22), (A15, B23), (A15, B24), (A15, B25), (A15, B26), (A15, B27), (A15, B28), (A15, B29), (A15, B30), (A15, B31), (A15, B32), (A15, B33), (A15, B34), (A15, B35), (A15, B36), (A15, B37), (A15, B38), (A15, B39), (A15, B40), (A15, B41), (A15, B42), (A15, B43), (A15, B44), (A15, B45), (A15, B46), (A15, B47), (A15, B48), (A15, B49), (A15, B50), (A15, B51), (A15, B52), (A15, B53), (A15, B54), (A15, B55), (A15, B56), (A15, B57), (A15, B58), (A15, B59), (A15, B60), (A15, B61), (A15, B62), (A15, B63), (A15, B64), (A15, B65), (A15, B66), (A15, B67), (A15, B68), (A15, B69), (A15, B70), (A15, B71), (A15, B72), (A15, B73), (A15, B74), (A15, B75), (A15, B76), (A15, B77), (A15, B78), (A15, B79), (A15, B80), (A15, B81), (A15, B82), (A15, B83), (A15, B84), (A15, B85), (A15, B86), (A15, B87), (A15, B88), (A15, B89), (A15, B90), (A15, B91), (A15, B92), (A15, B93), (A15, B94), (A15, B95), (A15, B96), (A15, B97), (A15, B98), (A15, B99), (A15, B100), (A15, B101), (A15, B102), (A15, B103), (A15, B104), (A15, B105), (A15, B106), (A15, B107), (A15, B108), (A15, B109), (A15, B110), (A15, B111), (A15, B112), (A15, B113), (A15, B114), (A15, B115), (A15, B116), (A15, B117), (A15, B118), (A15, B119), (A15, B120), (A15, B121), (A15, B122), (A15, B123), (A15, B124), (A15, B125), (A15, B126), (A15, B127), (A15, B128), (A15, B129), (A15, B130), (A15, B131), (A15, B132), (A15, B133), (A15, B134), (A15, B135), (A15, B136), (A15, B137), (A15, B138), (A15, B139), (A15, B140), (A15, B141), (A15, B142), (A15, B143), (A15, B144), (A15, B145), (A15, B146), (A16, B1), (A16, B2), (A16, B3), (A16, B4), (A16, B5), (A16, B6), (A16, B7), (A16, B8), (A16, B9), (A16, B10), (A16, B11), (A16, B12), (A16, B13), (A16, B14), (A16, B15), (A16, B16), (A16, B17), (A16, B18), (A16, B19), (A16, B20), (A16, B21), (A16, B22), (A16, B23), (A16, B24), (A16, B25), (A16, B26), (A16, B27), (A16, B28), (A16, B29), (A16, B30), (A16, B31), (A16, B32), (A16, B33), (A16, B34), (A16, B35), (A16, B36), (A16, B37), (A16, B38), (A16, B39), (A16, B40), (A16, B41), (A16, B42), (A16, B43), (A16, B44), (A16, B45), (A16, B46), (A16, B47), (A16, B48), (A16, B49), (A16, B50), (A16, B51), (A16, B52), (A16, B53), (A16, B54), (A16, B55), (A16, B56), (A16, B57), (A16, B58), (A16, B59), (A16, B60), (A16, B61), (A16, B62), (A16, B63), (A16, B64), (A16, B65), (A16, B66), (A16, B67), (A16, B68), (A16, B69), (A16, B70), (A16, B71), (A16, B72), (A16, B73), (A16, B74), (A16, B75), (A16, B76), (A16, B77), (A16, B78), (A16, B79), (A16, B80), (A16, B81), (A16, B82), (A16, B83), (A16, B84), (A16, B85), (A16, B86), (A16, B87), (A16, B88), (A16, B89), (A16, B90), (A16, B91), (A16, B92), (A16, B93), (A16, B94), (A16, B95), (A16, B96), (A16, B97), (A16, B98), (A16, B99), (A16, B100), (A16, B101), (A16, B102), (A16, B103), (A16, B104), (A16, B105), (A16, B106), (A16, B107), (A16, B108), (A16, B109), (A16, B110), (A16, B111), (A16, B112), (A16, B113), (A16, B114), (A16, B115), (A16, B116), (A16, B117), (A16, B118), (A16, B119), (A16, B120), (A16, B121), (A16, B122), (A16, B123), (A16, B124), (A16, B125), (A16, B126), (A16, B127), (A16, B128), (A16, B129), (A16, B130), (A16, B131), (A16, B132), (A16, B133), (A16, B134), (A16, B135), (A16, B136), (A16, B137), (A16, B138), (A16, B139), (A16, B140), (A16, B141), (A16, B142), (A16, B143), (A16, B144), (A16, B145), (A16, B146), (A17, B1), (A17, B2), (A17, B3), (A17, B4), (A17, B5), (A17, B6), (A17, B7), (A17, B8), (A17, B9), (A17, B10), (A17, B11), (A17, B12), (A17, B13), (A17, B14), (A17, B15), (A17, B16), (A17, B17), (A17, B18), (A17, B19), (A17, B20), (A17, B21), (A17, B22), (A17, B23), (A17, B24), (A17, B25), (A17, B26), (A17, B27), (A17, B28), (A17, B29), (A17, B30), (A17, B31), (A17, B32), (A17, B33), (A17, B34), (A17, B35), (A17, B36), (A17, B37), (A17, B38), (A17, B39), (A17, B40), (A17, B41), (A17, B42), (A17, B43), (A17, B44), (A17, B45), (A17, B46), (A17, B47), (A17, B48), (A17, B49), (A17, B50), (A17, B51), (A17, B52), (A17, B53), (A17, B54), (A17, B55), (A17, B56), (A17, B57), (A17, B58), (A17, B59), (A17, B60), (A17, B61), (A17, B62), (A17, B63), (A17, B64), (A17, B65), (A17, B66), (A17, B67), (A17, B68), (A17, B69), (A17, B70), (A17, B71), (A17, B72), (A17, B73), (A17, B74), (A17, B75), (A17, B76), (A17, B77), (A17, B78), (A17, B79), (A17, B80), (A17, B81), (A17, B82), (A17, B83), (A17, B84), (A17, B85), (A17, B86), (A17, B87), (A17, B88), (A17, B89), (A17, B90), (A17, B91), (A17, B92), (A17, B93), (A17, B94), (A17, B95), (A17, B96), (A17, B97), (A17, B98), (A17, B99), (A17, B100), (A17, B101), (A17, B102), (A17, B103), (A17, B104), (A17, B105), (A17, B106), (A17, B107), (A17, B108), (A17, B109), (A17, B110), (A17, B111), (A17, B112), (A17, B113), (A17, B114), (A17, B115), (A17, B116), (A17, B117), (A17, B118), (A17, B119), (A17, B120), (A17, B121), (A17, B122), (A17, B123), (A17, B124), (A17, B125), (A17, B126), (A17, B127), (A17, B128), (A17, B129), (A17, B130), (A17, B131), (A17, B132), (A17, B133), (A17, B134), (A17, B135), (A17, B136), (A17, B137), (A17, B138), (A17, B139), (A17, B140), (A17, B141), (A17, B142), (A17, B143), (A17, B144), (A17, B145), (A17, B146), (A18, B1), (A18, B2), (A18, B3), (A18, B4), (A18, B5), (A18, B6), (A18, B7), (A18, B8), (A18, B9), (A18, B10), (A18, B11), (A18, B12), (A18, B13), (A18, B14), (A18, B15), (A18, B16), (A18, B17), (A18, B18), (A18, B19), (A18, B20), (A18, B21), (A18, B22), (A18, B23), (A18, B24), (A18, B25), (A18, B26), (A18, B27), (A18, B28), (A18, B29), (A18, B30), (A18, B31), (A18, B32), (A18, B33), (A18, B34), (A18, B35), (A18, B36), (A18, B37), (A18, B38), (A18, B39), (A18, B40), (A18, B41), (A18, B42), (A18, B43), (A18, B44), (A18, B45), (A18, B46), (A18, B47), (A18, B48), (A18, B49), (A18, B50), (A18, B51), (A18, B52), (A18, B53), (A18, B54), (A18, B55), (A18, B56), (A18, B57), (A18, B58), (A18, B59), (A18, B60), (A18, B61), (A18, B62), (A18, B63), (A18, B64), (A18, B65), (A18, B66), (A18, B67), (A18, B68), (A18, B69), (A18, B70), (A18, B71), (A18, B72), (A18, B73), (A18, B74), (A18, B75), (A18, B76), (A18, B77), (A18, B78), (A18, B79), (A18, B80), (A18, B81), (A18, B82), (A18, B83), (A18, B84), (A18, B85), (A18, B86), (A18, B87), (A18, B88), (A18, B89), (A18, B90), (A18, B91), (A18, B92), (A18, B93), (A18, B94), (A18, B95), (A18, B96), (A18, B97), (A18, B98), (A18, B99), (A18, B100), (A18, B101), (A18, B102), (A18, B103), (A18, B104), (A18, B105), (A18, B106), (A18, B107), (A18, B108), (A18, B109), (A18, B110), (A18, B111), (A18, B112), (A18, B113), (A18, B114), (A18, B115), (A18, B116), (A18, B117), (A18, B118), (A18, B119), (A18, B120), (A18, B121), (A18, B122), (A18, B123), (A18, B124), (A18, B125), (A18, B126), (A18, B127), (A18, B128), (A18, B129), (A18, B130), (A18, B131), (A18, B132), (A18, B133), (A18, B134), (A18, B135), (A18, B136), (A18, B137), (A18, B138), (A18, B139), (A18, B140), (A18, B141), (A18, B142), (A18, B143), (A18, B144), (A18, B145), (A18, B146), (A19, B1), (A19, B2), (A19, B3), (A19, B4), (A19, B5), (A19, B6), (A19, B7), (A19, B8), (A19, B9), (A19, B10), (A19, B11), (A19, B12), (A19, B13), (A19, B14), (A19, B15), (A19, B16), (A19, B17), (A19, B18), (A19, B19), (A19, B20), (A19, B21), (A19, B22), (A19, B23), (A19, B24), (A19, B25), (A19, B26), (A19, B27), (A19, B28), (A19, B29), (A19, B30), (A19, B31), (A19, B32), (A19, B33), (A19, B34), (A19, B35), (A19, B36), (A19, B37), (A19, B38), (A19, B39), (A19, B40), (A19, B41), (A19, B42), (A19, B43), (A19, B44), (A19, B45), (A19, B46), (A19, B47), (A19, B48), (A19, B49), (A19, B50), (A19, B51), (A19, B52), (A19, B53), (A19, B54), (A19, B55), (A19, B56), (A19, B57), (A19, B58), (A19, B59), (A19, B60), (A19, B61), (A19, B62), (A19, B63), (A19, B64), (A19, B65), (A19, B66), (A19, B67), (A19, B68), (A19, B69), (A19, B70), (A19, B71), (A19, B72), (A19, B73), (A19, B74), (A19, B75), (A19, B76), (A19, B77), (A19, B78), (A19, B79), (A19, B80), (A19, B81), (A19, B82), (A19, B83), (A19, B84), (A19, B85), (A19, B86), (A19, B87), (A19, B88), (A19, B89), (A19, B90), (A19, B91), (A19, B92), (A19, B93), (A19, B94), (A19, B95), (A19, B96), (A19, B97), (A19, B98), (A19, B99), (A19, B100), (A19, B101), (A19, B102), (A19, B103), (A19, B104), (A19, B05), (A19, B106), (A19, B107), (A19, B108), (A19, B109), (A19, B110), (A19, B111), (A19, B112), (A19, B113), (A19, B114), (A19, B115), (A19, B116), (A19, B117), (A19, B118), (A19, B119), (A19, B120), (A19, B121), (A19, B122), (A19, B123), (A19, B124), (A19, B125), (A19, B126), (A19, B127), (A19, B128), (A19, B129), (A19, B130), (A19, B131), (A19, B132), (A19, B133), (A19, B134), (A19, B135), (A19, B136), (A19, B137), (A19, B138), (A19, B139), (A19, B140), (A19, B141), (A19, B142), (A19, B143), (A19, B144), (A19, B145), (A19, B146), (A20, B1), (A20, B2), (A20, B3), (A20, B4), (A20, B5), (A20, B6), (A20, B7), (A20, B8), (A20, B9), (A20, B10), (A20, B11), (A20, B12), (A20, B13), (A20, B14), (A20, B15), (A20, B16), (A20, B17), (A20, B18), (A20, B19), (A20, B20), (A20, B21), (A20, B22), (A20, B23), (A20, B24), (A20, B25), (A20, B26), (A20, B27), (A20, B28), (A20, B29), (A20, B30), (A20, B31), (A20, B32), (A20, B33), (A20, B34), (A20, B35), (A20, B36), (A20, B37), (A20, B38), (A20, B39), (A20, B40), (A20, B41), (A20, B42), (A20, B43), (A20, B44), (A20, B45), (A20, B46), (A20, B47), (A20, B48), (A20, B49), (A20, B50), (A20, B51), (A20, B52), (A20, B53), (A20, B54), (A20, B55), (A20, B56), (A20, B57), (A20, B58), (A20, B59), (A20, B60), (A20, B61), (A20, B62), (A20, B63), (A20, B64), (A20, B65), (A20, B66), (A20, B67), (A20, B68), (A20, B69), (A20, B70), (A20, B71), (A20, B72), (A20, B73), (A20, B74), (A20, B75), (A20, B76), (A20, B77), (A20, B78), (A20, B79), (A20, B80), (A20, B81), (A20, B82), (A20, B83), (A20, B84), (A20, B85), (A20, B86), (A20, B87), (A20, B88), (A20, B89), (A20, B90), (A20, B91), (A20, B92), (A20, B93), (A20, B94), (A20, B95), (A20, B96), (A20, B97), (A20, B98), (A20, B99), (A20, B100), (A20, B101), (A20, B102), (A20, B103), (A20, B104), (A20, B105), (A20, B106), (A20, B107), (A20, B108), (A20, B109), (A20, B110), (A20, B111), (A20, B112), (A20, B113), (A20, B114), (A20, B115), (A20, B116), (A20, B117), (A20, B118), (A20, B119), (A20, B120), (A20, B121), (A20, B122), (A20, B123), (A20, B124), (A20, B125), (A20, B126), (A20, B127), (A20, B128), (A20, B129), (A20, B130), (A20, B131), (A20, B132), (A20, B133), (A20, B134), (A20, B135), (A20, B136), (A20, B137), (A20, B138), (A20, B139), (A20, B140), (A20, B141), (A20, B142), (A20, B143), (A20, B144), (A20, B145), (A20, B146), (A21, B1), (A21, B2), (A21, B3), (A21, B4), (A21, B5), (A21, B6), (A21, B7), (A21, B8), (A21, B9), (A21, B10), (A21, B11), (A21, B12), (A21, B13), (A21, B14), (A21, B15), (A21, B16), (A21, B17), (A21, B18), (A21, B19), (A21, B20), (A21, B21), (A21, B22), (A21, B23), (A21, B24), (A21, B25), (A21, B26), (A21, B27), (A21, B28), (A21, B29), (A21, B30), (A21, B31), (A21, B32), (A21, B33), (A21, B34), (A21, B35), (A21, B36), (A21, B37), (A21, B38), (A21, B39), (A21, B40), (A21, B41), (A21, B42), (A21, B43), (A21, B44), (A21, B45), (A21, B46), (A21, B47), (A21, B48), (A21, B49), (A21, B50), (A21, B51), (A21, B52), (A21, B53), (A21, B54), (A21, B55), (A21, B56), (A21, B57), (A21, B58), (A21, B59), (A21, B60), (A21, B61), (A21, B62), (A21, B63), (A21, B64), (A21, B65), (A21, B66), (A21, B67), (A21, B68), (A21, B69), (A21, B70), (A21, B71), (A21, B72), (A21, B73), (A21, B74), (A21, B75), (A21, B76), (A21, B77), (A21, B78), (A21, B79), (A21, B80), (A21, B81), (A21, B82), (A21, B83), (A21, B84), (A21, B85), (A21, B86), (A21, B87), (A21, B88), (A21, B89), (A21, B90), (A21, B91), (A21, B92), (A21, B93), (A21, B94), (A21, B95), (A21, B96), (A21, B97), (A21, B98), (A21, B99), (A21, B100), (A21, B101), (A21, B102), (A21, B103), (A21, B104), (A21, B105), (A21, B106), (A21, B107), (A21, B108), (A21, B109), (A21, B110), (A21, B111), (A21, B112), (A21, B113), (A21, B114), (A21, B115), (A21, B116), (A21, B117), (A21, B118), (A21, B119), (A21, B120), (A21, B121), (A21, B122), (A21, B123), (A21, B124), (A21, B125), (A21, B126), (A21, B127), (A21, B128), (A21, B129), (A21, B130), (A21, B131), (A21, B132), (A21, B133), (A21, B134), (A21, B135), (A21, B136), (A21, B137), (A21, B138), (A21, B139), (A21, B140), (A21, B141), (A21, B142), (A21, B143), (A21, B144), (A21, B145), (A21, B146).

In particular, the following compounds are preferable.

TABLE 8

| Compound No. | Structural formula |
|---|---|
| 1 | *[5-chloropyridine-2-carboxamide derivative structure]* |
| 2 | *[5-bromopyridine-2-carboxamide derivative structure]* |
| 3 | *[5-fluoropyridine-2-carboxamide derivative structure]* |
| 4 | *[3,5-dichloropyridine-2-carboxamide derivative structure]* |
| 5 | *[3-fluoropyridine-2-carboxamide derivative structure]* |
| 6 | *[3,5-difluoropyridine-2-carboxamide derivative structure]* |

TABLE 8-continued

| Compound No. | Structural formula |
|---|---|
| 7 | (5-chloro-3-amino-pyridine-2-carboxamide linked to 3-(2-amino-1-methyl-6-oxo-1,4,5,6-tetrahydropyrimidin-4-yl with methyl)phenyl) |
| 8 | (5-methyl-pyridine-2-carboxamide linked to 3-(2-amino-1-methyl-6-oxo-1,4,5,6-tetrahydropyrimidin-4-yl with methyl)phenyl) |

TABLE 9

| Compound No. | Structural formula |
|---|---|
| 9 | (5-trifluoromethyl-pyridine-2-carboxamide linked to 3-(2-amino-1-methyl-6-oxo-1,4,5,6-tetrahydropyrimidin-4-yl with methyl)phenyl) |
| 10 | (5-trifluoromethyl-3-chloro-pyridine-2-carboxamide linked to 3-(2-amino-1-methyl-6-oxo-1,4,5,6-tetrahydropyrimidin-4-yl with methyl)phenyl) |
| 11 | (5-trifluoromethyl-3-fluoro-pyridine-2-carboxamide linked to 3-(2-amino-1-methyl-6-oxo-1,4,5,6-tetrahydropyrimidin-4-yl with methyl)phenyl) |
| 12 | (5-cyano-pyridine-2-carboxamide linked to 3-(2-amino-1-methyl-6-oxo-1,4,5,6-tetrahydropyrimidin-4-yl with methyl)phenyl) |

TABLE 9-continued

| Compound No. | Structural formula |
|---|---|
| 13 | (5-cyano-3-chloro-pyridine-2-carboxamide linked to 3-(2-amino-1-methyl-6-oxo-1,4,5,6-tetrahydropyrimidin-4-yl with methyl)phenyl) |
| 14 | (5-cyano-3-fluoro-pyridine-2-carboxamide linked to 3-(2-amino-1-methyl-6-oxo-1,4,5,6-tetrahydropyrimidin-4-yl with methyl)phenyl) |
| 15 | (5-hydroxy-pyridine-2-carboxamide linked to 3-(2-amino-1-methyl-6-oxo-1,4,5,6-tetrahydropyrimidin-4-yl with methyl)phenyl) |
| 16 | (5-methoxy-pyridine-2-carboxamide linked to 3-(2-amino-1-methyl-6-oxo-1,4,5,6-tetrahydropyrimidin-4-yl with methyl)phenyl) |

TABLE 10
| Compound No. | Structural formula |
| --- | --- |
| 17 | 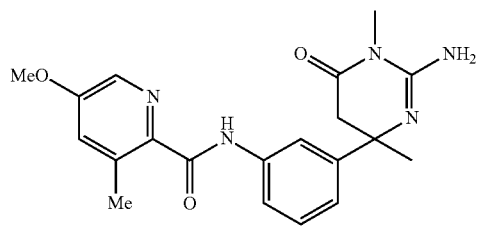 [SMILES: COc1cnc(C(=O)Nc2cccc(C3(C)CC(=O)N(C)C(N)=N3)c2)c(C)c1] |
| 18 | 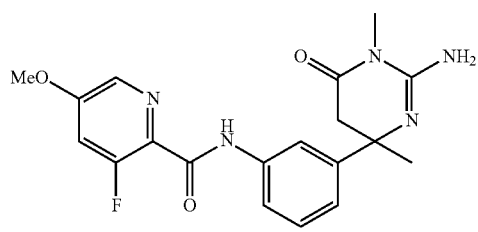 [SMILES: COc1cnc(C(=O)Nc2cccc(C3(C)CC(=O)N(C)C(N)=N3)c2)c(F)c1] |
| 19 | 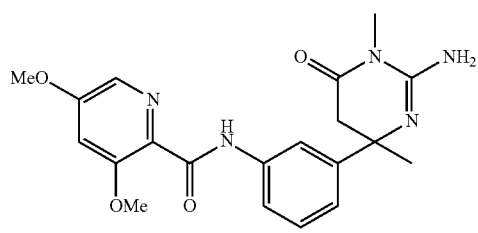 [SMILES: COc1cnc(C(=O)Nc2cccc(C3(C)CC(=O)N(C)C(N)=N3)c2)c(OC)c1] |
| 20 | 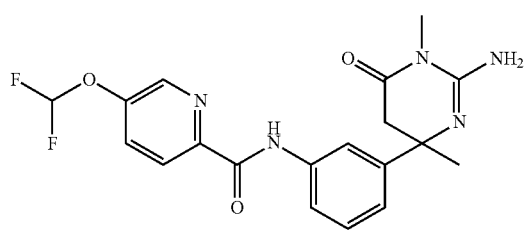 [SMILES: CN1C(=O)CC(C)(c2cccc(NC(=O)c3ccc(OC(F)F)cn3)c2)N=C1N] |
| 21 | 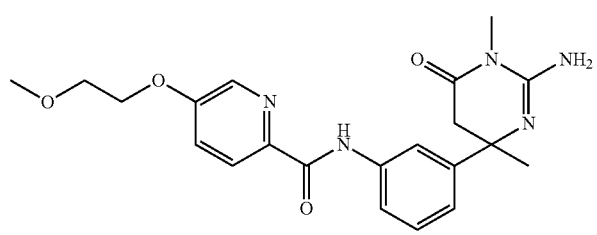 [SMILES: COCCOc1ccc(C(=O)Nc2cccc(C3(C)CC(=O)N(C)C(N)=N3)c2)nc1] |
| 22 | 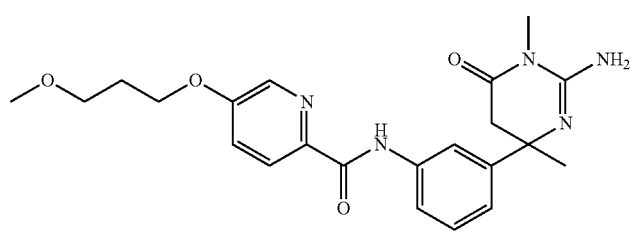 [SMILES: COCCCOc1ccc(C(=O)Nc2cccc(C3(C)CC(=O)N(C)C(N)=N3)c2)nc1] |

TABLE 10-continued
| Compound No. | Structural formula |
|---|---|
| 23 | 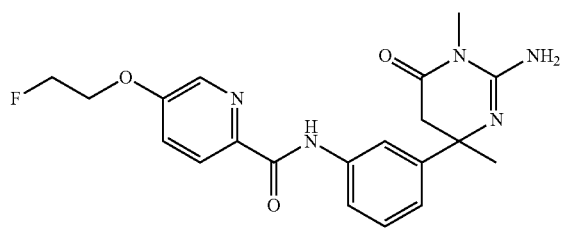 [SMILES: CN1C(=O)CC(C)(c2cccc(NC(=O)c3ccc(OCCF)cn3)c2)N=C1N] |
| 24 | 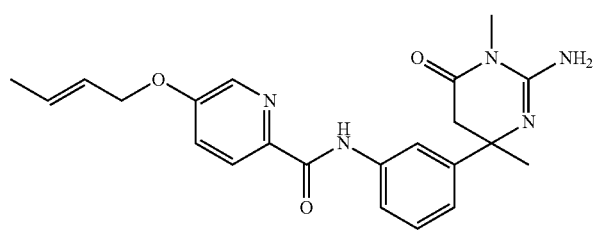 |
TABLE 11
| Compound No. | Structural formula |
|---|---|
| 25 | 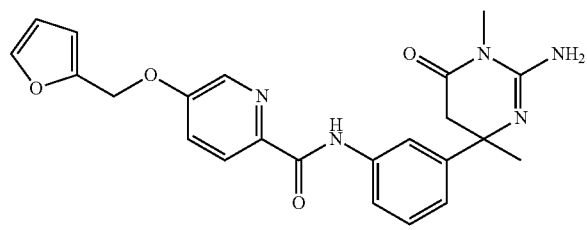 |
| 26 | 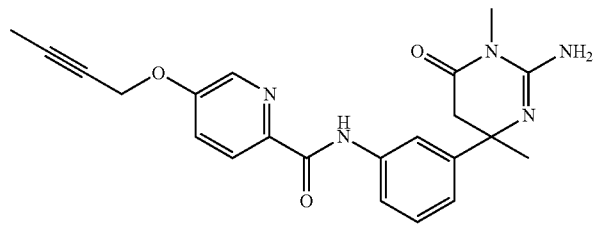 [SMILES: CC#CCOc1ccc(C(=O)Nc2cccc(C3(C)CC(=O)N(C)C(N)=N3)c2)nc1] |
| 27 | 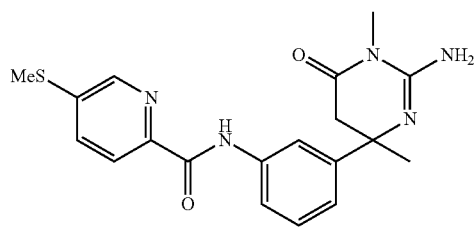 |
| 28 | 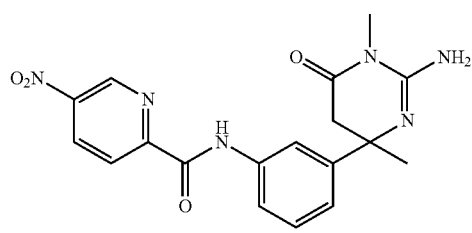 [SMILES: CN1C(=O)CC(C)(c2cccc(NC(=O)c3ccc([N+](=O)[O-])cn3)c2)N=C1N] |

TABLE 11-continued
| Compound No. | Structural formula |
|---|---|
| 29 | 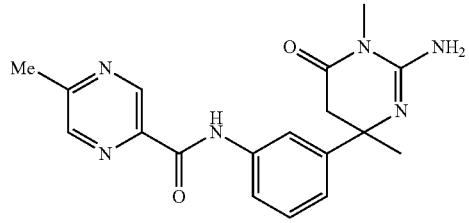 |
| 30 | 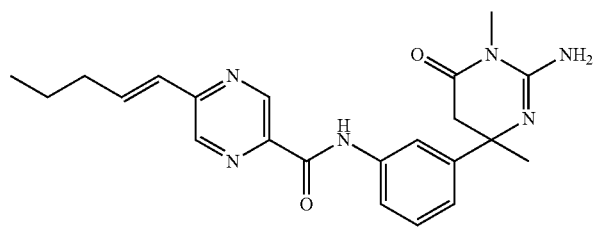 |
| 31 | 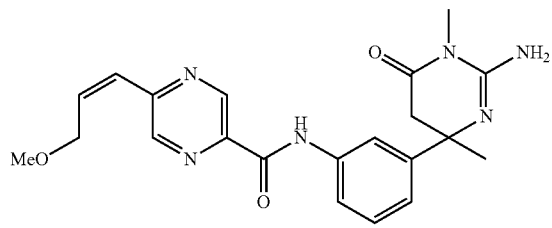 [SMILES: COC/C=C\c1cnc(C(=O)Nc2cccc(C3(C)CC(=O)N(C)C(N)=N3)c2)cn1] |
| 32 | 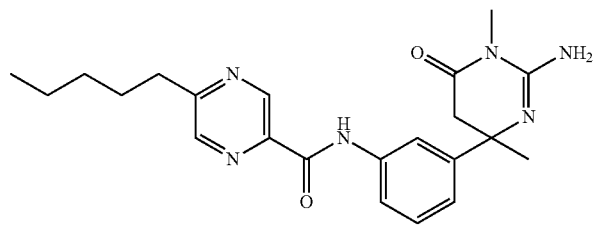 |
TABLE 12
| Compound No. | Structural formula |
|---|---|
| 33 | 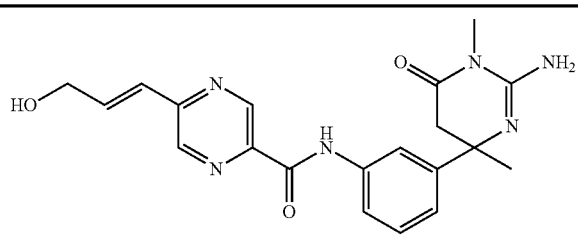 |
| 34 | 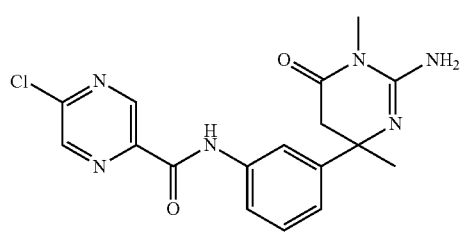 |

TABLE 12-continued
| Compound No. | Structural formula |
|---|---|
| 35 | 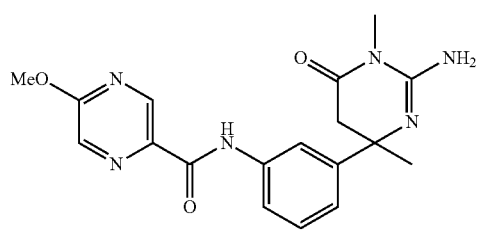 [SMILES: COc1cnc(C(=O)Nc2cccc(C3(C)CC(=O)N(C)C(N)=N3)c2)cn1] |
| 36 | 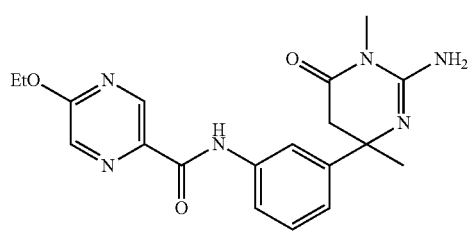 [SMILES: CCOc1cnc(C(=O)Nc2cccc(C3(C)CC(=O)N(C)C(N)=N3)c2)cn1] |
| 37 | 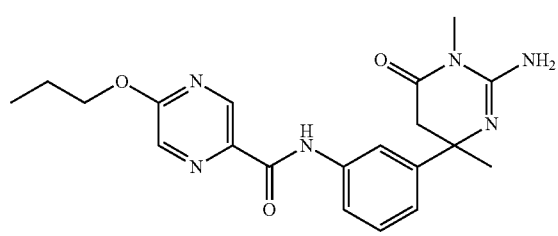 [SMILES: CCCOc1cnc(C(=O)Nc2cccc(C3(C)CC(=O)N(C)C(N)=N3)c2)cn1] |
| 38 | 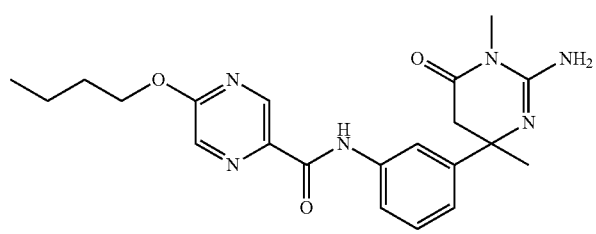 |
| 39 | 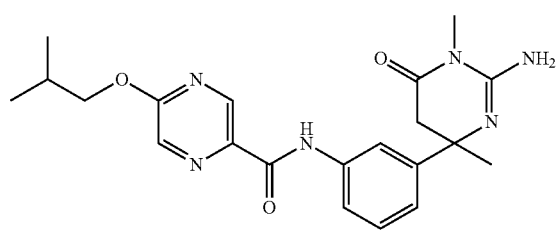 |
| 40 | 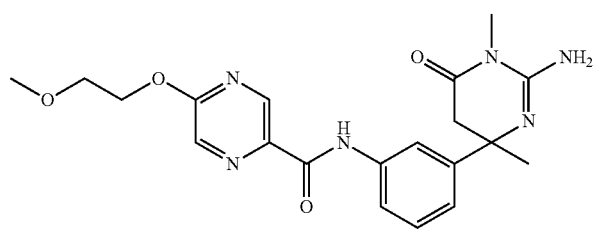 |

TABLE 13
| Compound No. | Structural formula |
| --- | --- |
| 41 | 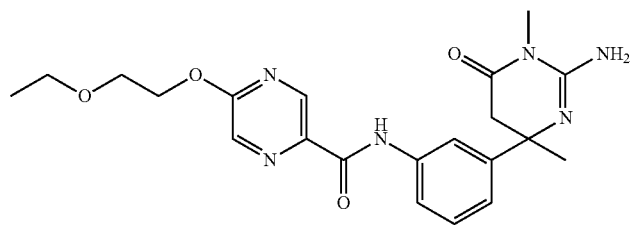 [SMILES: CCOCCOc1cnc(C(=O)Nc2cccc(C3(C)CC(=O)N(C)C(N)=N3)c2)cn1] |
| 42 | 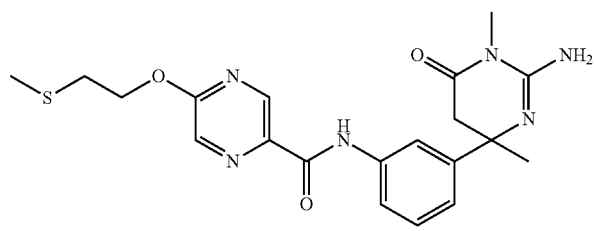 |
| 43 | 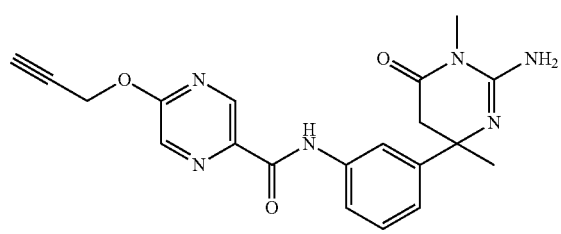 [SMILES: C#CCOc1cnc(C(=O)Nc2cccc(C3(C)CC(=O)N(C)C(N)=N3)c2)cn1] |
| 44 | 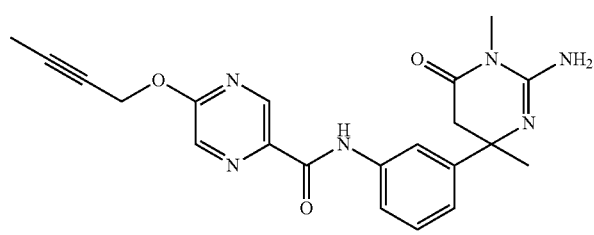 |
| 45 | 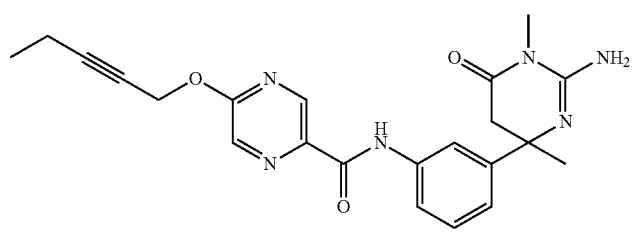 [SMILES: CCC#CCOc1cnc(C(=O)Nc2cccc(C3(C)CC(=O)N(C)C(N)=N3)c2)cn1] |
| 46 | 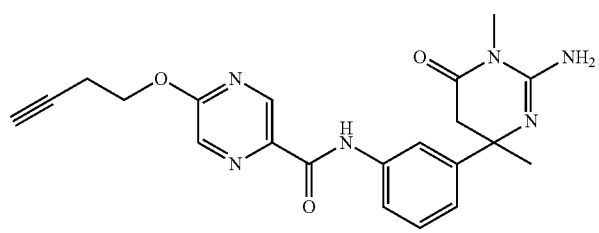 |

TABLE 13-continued
| Compound No. | Structural formula |
|---|---|
| 47 | 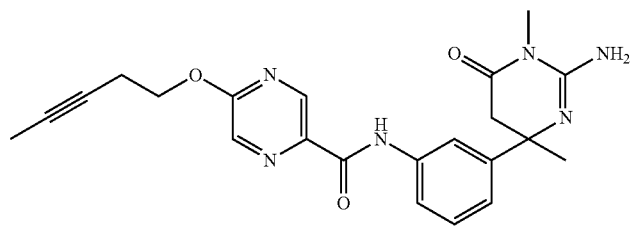 [SMILES: CC#CCCOc1cnc(C(=O)Nc2cccc(C3(C)CC(=O)N(C)C(N)=N3)c2)cn1] |
| 48 | 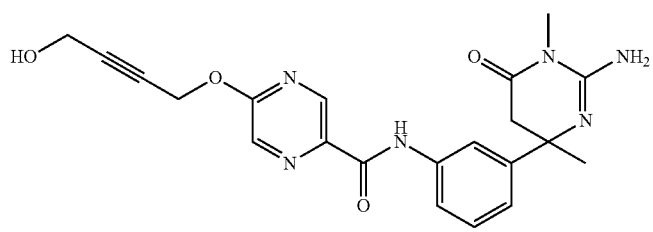 [SMILES: CN1C(=O)CC(C)(c2cccc(NC(=O)c3cnc(OCC#CCO)cn3)c2)N=C1N] |
TABLE 14
| Compound No. | Structural formula |
|---|---|
| 49 | 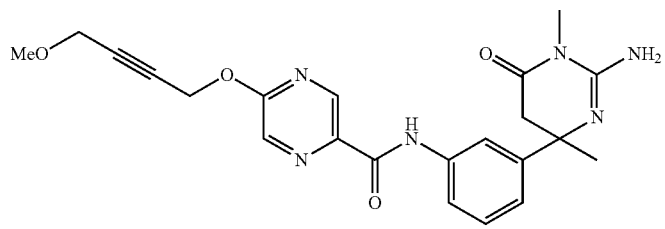 [SMILES: COCC#CCOc1cnc(C(=O)Nc2cccc(C3(C)CC(=O)N(C)C(N)=N3)c2)cn1] |
| 50 | 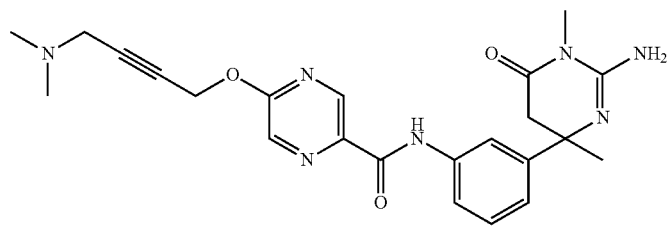 [SMILES: CN(C)CC#CCOc1cnc(C(=O)Nc2cccc(C3(C)CC(=O)N(C)C(N)=N3)c2)cn1] |
| 51 | 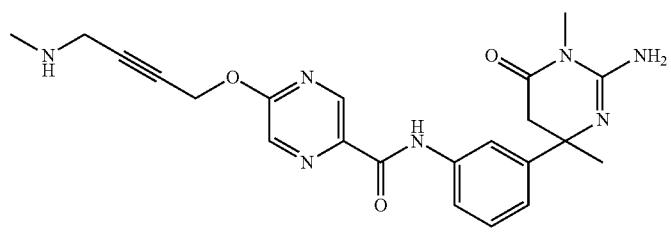 [SMILES: CNCC#CCOc1cnc(C(=O)Nc2cccc(C3(C)CC(=O)N(C)C(N)=N3)c2)cn1] |
| 52 | 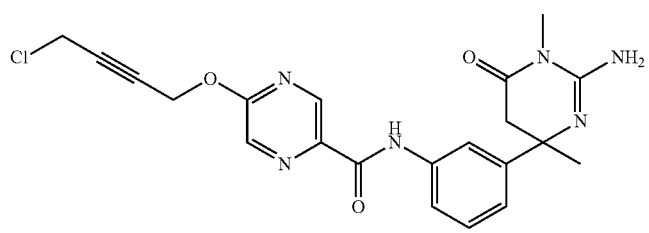 [SMILES: CN1C(=O)CC(C)(c2cccc(NC(=O)c3cnc(OCC#CCCl)cn3)c2)N=C1N] |

TABLE 14-continued
| Compound No. | Structural formula |
|---|---|
| 53 | 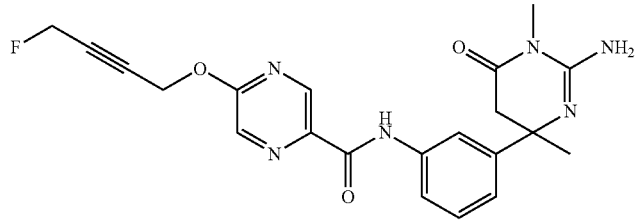 [SMILES: CN1C(=O)CC(C)(c2cccc(NC(=O)c3cnc(OCC#CCF)cn3)c2)N=C1N] |
| 54 | 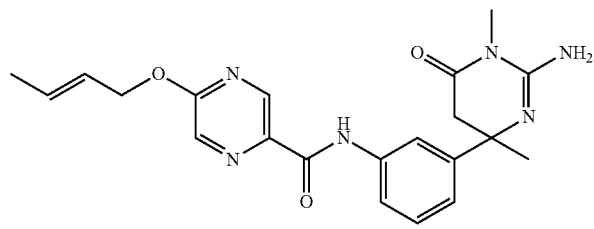 |
| 55 | 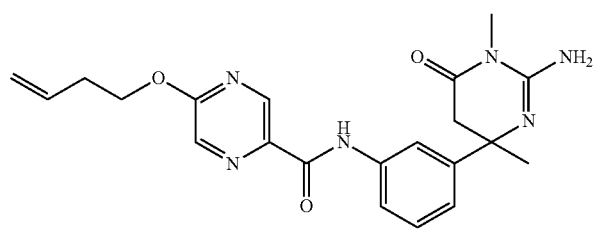 |
| 56 | 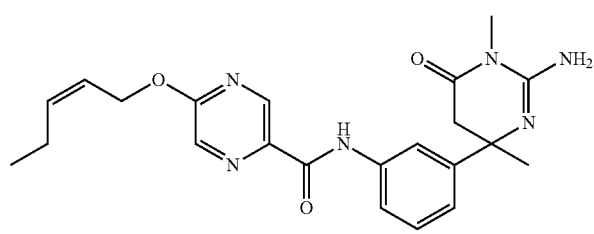 |
TABLE 15
| Compound No. | Structural formula |
|---|---|
| 57 | 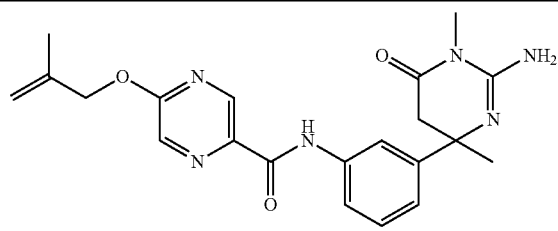 |
| 58 | 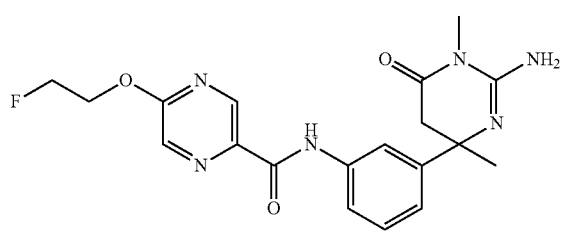 [SMILES: CN1C(=O)CC(C)(c2cccc(NC(=O)c3cnc(OCCF)cn3)c2)N=C1N] |

TABLE 15-continued
Compound No. Structural formula
59 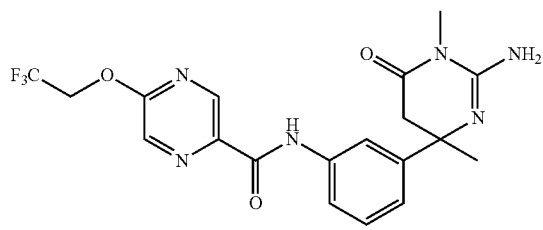 [SMILES: CN1C(=O)CC(C)(c2cccc(NC(=O)c3cnc(OCC(F)(F)F)cn3)c2)N=C1N]
60 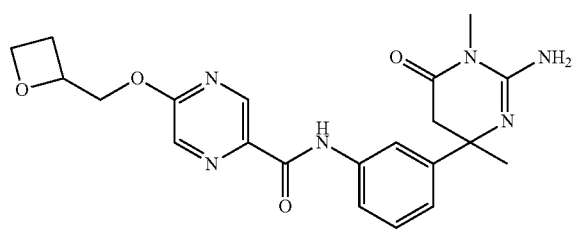 [SMILES: CN1C(=O)CC(C)(c2cccc(NC(=O)c3cnc(OCC4CCO4)cn3)c2)N=C1N]
61 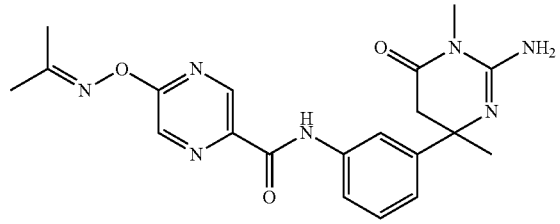
62 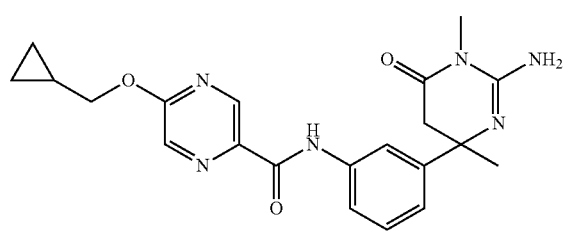
63 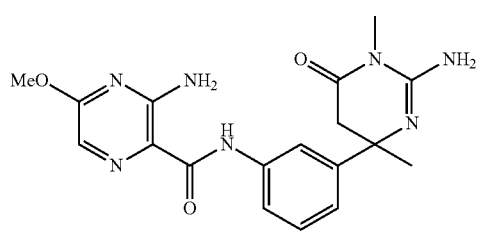 [SMILES: COc1cnc(C(=O)Nc2cccc(C3(C)CC(=O)N(C)C(N)=N3)c2)c(N)n1]
64 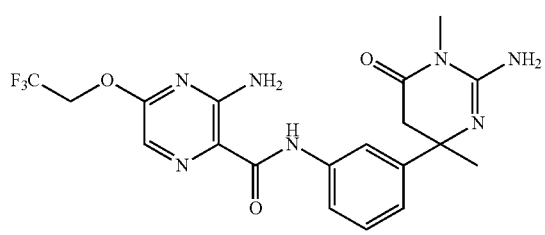 [SMILES: CN1C(=O)CC(C)(c2cccc(NC(=O)c3ncc(OCC(F)(F)F)nc3N)c2)N=C1N]

TABLE 16
| Compound No. | Structural formula |
|---|---|
| 65 | 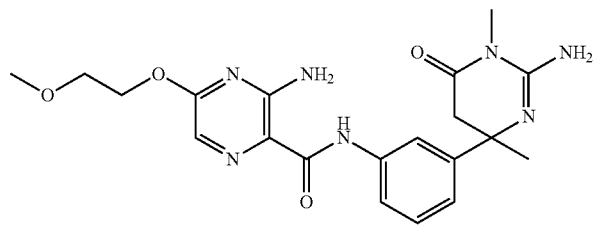 |
| 66 | 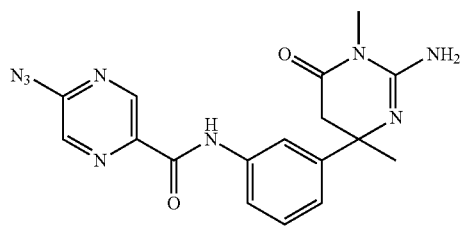 [SMILES: CN1C(=O)CC(C)(c2cccc(NC(=O)c3cnc(N=[N+]=[N-])cn3)c2)N=C1N] |
| 67 | 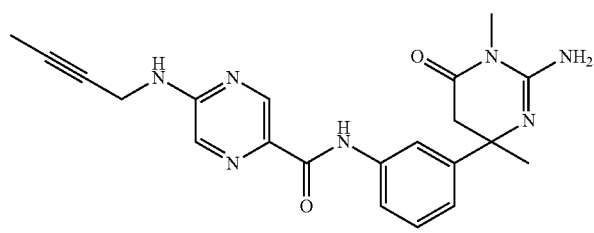 |
| 68 | 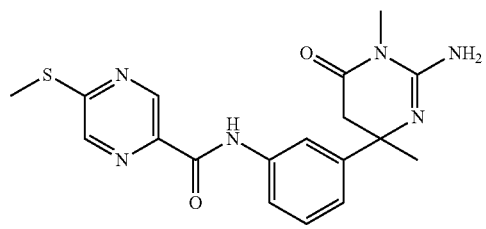 [SMILES: CSc1cnc(C(=O)Nc2cccc(C3(C)CC(=O)N(C)C(N)=N3)c2)cn1] |
| 69 | 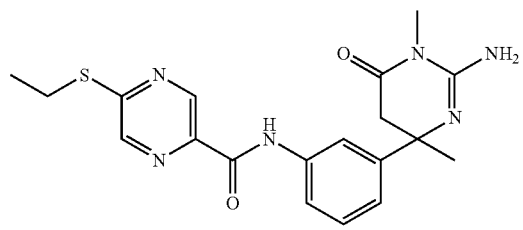 |
| 70 | 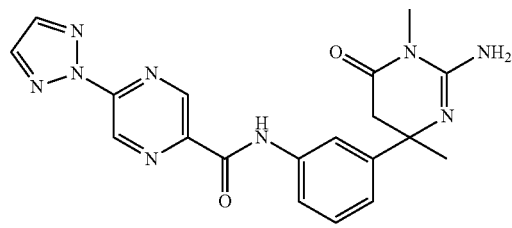 |

TABLE 16-continued
| Compound No. | Structural formula |
|---|---|
| 71 | 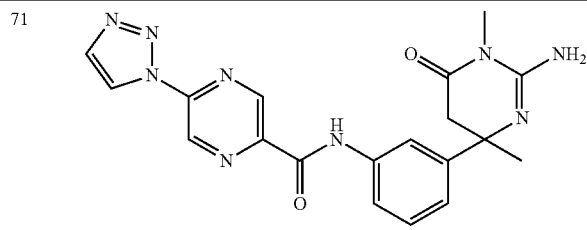 |
| 72 | 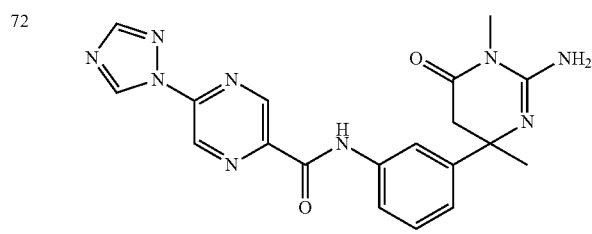 |
TABLE 17
| Compound No. | Structural formula |
|---|---|
| 73 | 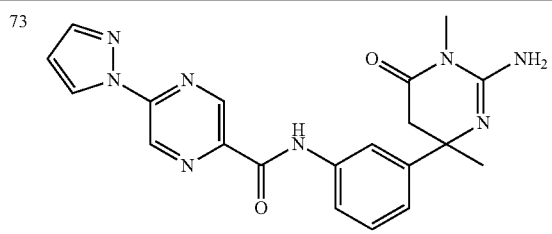 |
| 74 | 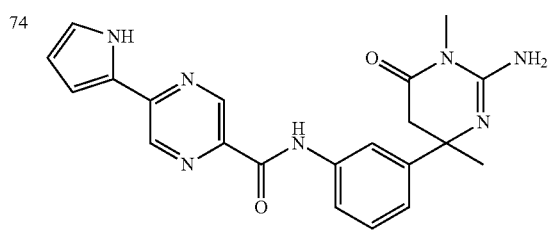 |
| 75 | 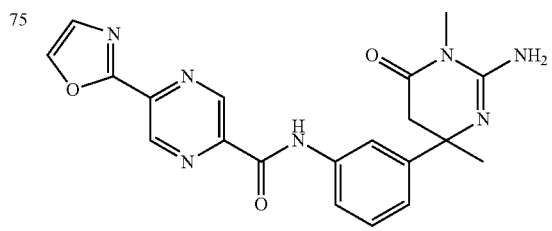 |
| 76 | 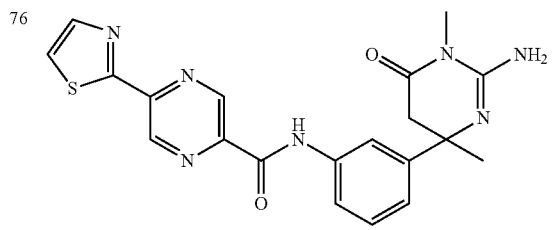 |
TABLE 17-continued
| Compound No. | Structural formula |
|---|---|
| 77 | 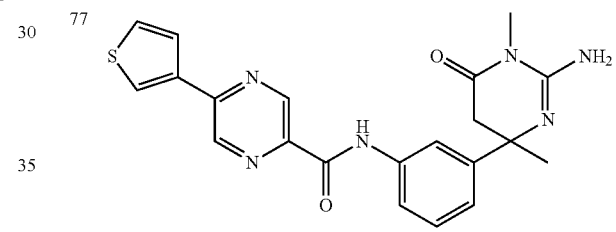 |
| 78 | 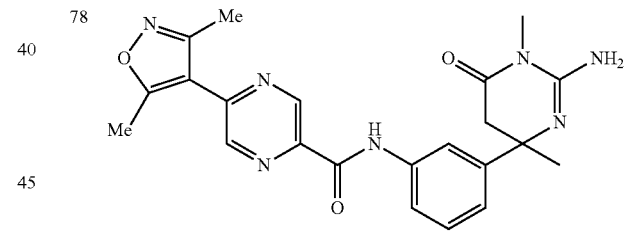 |
| 79 | 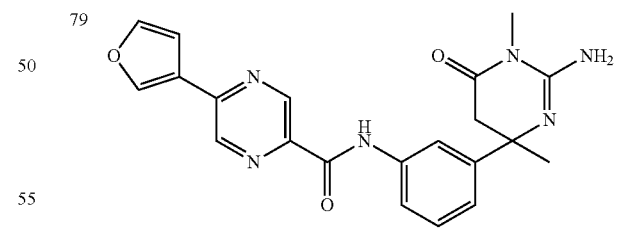 |
| 80 | 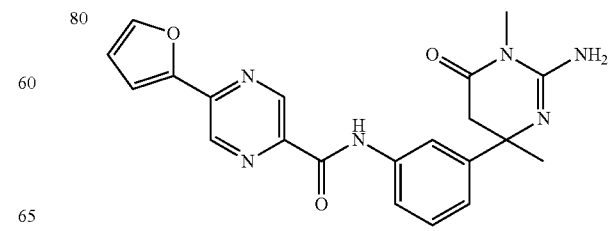 |

TABLE 18

| Compound No. | Structural formula |
|---|---|
| 81 | 5-chloropyrimidine-2-carboxamide derivative |
| 82 | 5-bromopyrimidine-2-carboxamide derivative |
| 83 | 5-cyanopyrimidine-2-carboxamide derivative |
| 84 | 6-oxo-1,4,5,6-tetrahydropyridazine-3-carboxamide derivative |
| 85 | 4-(5-methyl-1,2,4-oxadiazol-3-yl)benzamide derivative |
| 86 | 4-chlorobenzamide derivative |

TABLE 18-continued

| Compound No. | Structural formula |
|---|---|
| 87 | 2,4-dichlorobenzamide derivative |
| 88 | 4-trifluoromethylbenzamide derivative |

TABLE 19

| Compound No. | Structural formula |
|---|---|
| 89 | 4-methoxybenzamide derivative |
| 90 | 1,3-dimethyl-1H-pyrazole-5-carboxamide derivative |
| 91 | 3-cyano-1-methyl-1H-pyrazole-5-carboxamide derivative |
| 92 | 1-tert-butyl-3-methyl-1H-pyrazole-5-carboxamide derivative |

TABLE 19-continued

| Compound No. | Structural formula |
|---|---|
| 93 | (structure) |
| 94 | (structure) |
| 95 | (structure) |
| 96 | (structure) |

TABLE 20

| Compound No. | Structural formula |
|---|---|
| 97 | (structure) |
| 98 | (structure) |
| 99 | (structure) |
| 100 | (structure) |
| 101 | (structure) |
| 102 | (structure) |
| 103 | (structure) |
| 104 | (structure) |

TABLE 21

| Compound No. | Structural formula |
|---|---|
| 105 | (5-methylisoxazol-3-yl)carboxamide derivative |
| 106 | (5-methylfuran-2-yl)carboxamide derivative |
| 107 | (3-methylfuran-2-yl)carboxamide derivative |
| 108 | (5-bromofuran-2-yl)carboxamide derivative |
| 109 | (2,5-dimethylfuran-3-yl)carboxamide derivative |
| 110 | (5-methylthiophen-2-yl)carboxamide derivative |

TABLE 21-continued

| Compound No. | Structural formula |
|---|---|
| 111 | (4-methylthiazol-2-yl)carboxamide derivative |
| 112 | (5-bromothiophen-2-yl)carboxamide derivative |

TABLE 22

| Compound No. | Structural formula |
|---|---|
| 113 | (5-methylthiothiophen-2-yl)carboxamide derivative |
| 114 | (2,5-dimethylthiophen-3-yl)carboxamide derivative |
| 115 | (5-methylisothiazol-3-yl)carboxamide derivative |
| 116 | (4,5-dichloroisothiazol-3-yl)carboxamide derivative |

TABLE 22-continued
| Compound No. | Structural formula |
|---|---|
| 117 | 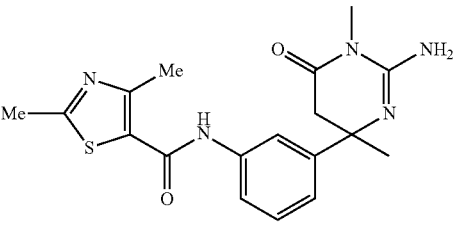 [SMILES: Cc1nc(C)c(C(=O)Nc2cccc(C3(C)CC(=O)N(C)C(N)=N3)c2)s1] |
| 118 | |
| 119 | |
| 120 | |
TABLE 23
| Compound No. | Structural formula |
|---|---|
| 121 | 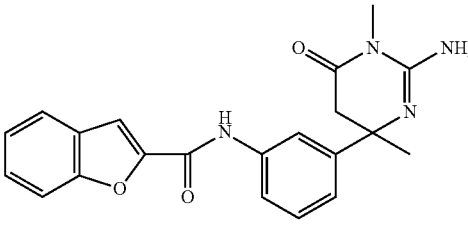 |
| 122 | |
TABLE 23-continued
| Compound No. | Structural formula |
|---|---|
| 123 | 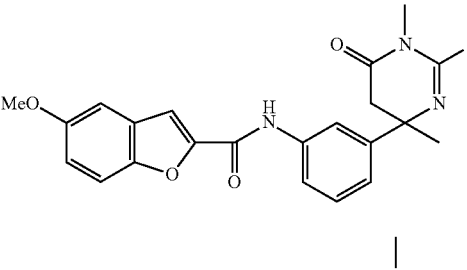 |
| 124 | |
| 125 | |
| 126 | 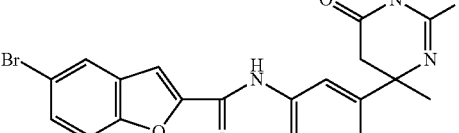 |
| 127 | 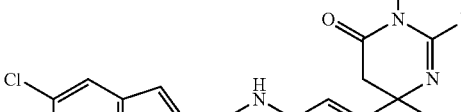 |
| 128 | 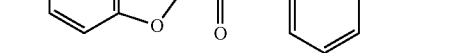 |

TABLE 24
| Compound No. | Structural formula |
|---|---|
| 129 | 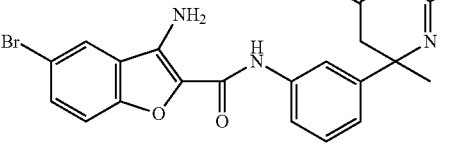 |
| 130 | |
| 131 | |
| 132 | |
| 133 | |
| 134 | |
TABLE 24-continued
| Compound No. | Structural formula |
|---|---|
| 135 | 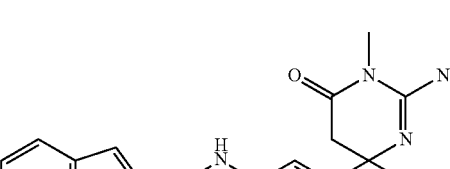 |
| 136 | |
TABLE 25
| Compound No. | Structural formula |
|---|---|
| 137 | |
| 138 | |
| 139 | |
| 140 | |

TABLE 25-continued

| Compound No. | Structural formula |
|---|---|
| 141 | isoquinoline-3-carboxamide derivative |
| 142 | 3,4-dihydro-2H-benzo[b][1,4]oxazine-2-carboxamide derivative |
| 143 | 2,3-dihydro-1,4-benzodioxine-2-carboxamide derivative |
| 144 | thieno[3,2-b]thiophene-2-carboxamide derivative |

TABLE 26

| Compound No. | Structural formula |
|---|---|
| 145 | pyrazolo[1,5-a]pyridine-2-carboxamide derivative |
| 146 | imidazo[2,1-b]thiazole-6-carboxamide derivative |

TABLE 27

| Compound No. | Structural formula |
|---|---|
| 147 | 5-chloropyridine-2-carboxamide, 4-fluorophenyl derivative |
| 148 | 5-bromopyridine-2-carboxamide, 4-fluorophenyl derivative |
| 149 | 5-fluoropyridine-2-carboxamide, 4-fluorophenyl derivative |
| 150 | 3,5-dichloropyridine-2-carboxamide, 4-fluorophenyl derivative |
| 151 | 3-fluoropyridine-2-carboxamide, 4-fluorophenyl derivative |
| 152 | 3,5-difluoropyridine-2-carboxamide, 4-fluorophenyl derivative |

TABLE 27-continued
| Compound No. | Structural formula |
|---|---|
| 153 |  |
| 154 | |
TABLE 28
| Compound No. | Structural formula |
|---|---|
| 155 | 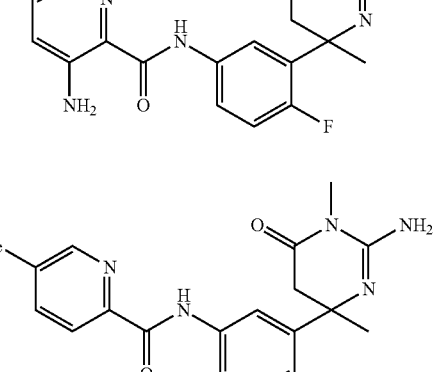 |
| 156 | |
| 157 | |
TABLE 28-continued
| Compound No. | Structural formula |
|---|---|
| 158 | 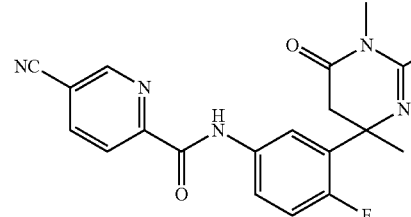 |
| 159 | |
| 160 | |
| 161 | 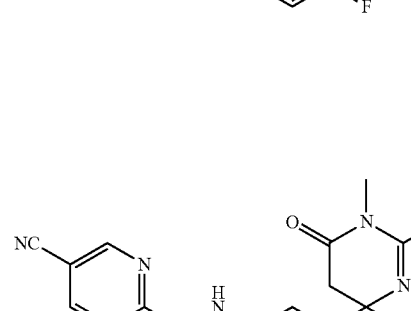 |
| 162 | |

TABLE 29

| Compound No. | Structural formula |
| --- | --- |
| 163 | |
| 164 | |
| 165 | |
| 166 | |
| 167 | |
| 168 | |

TABLE 29-continued
| Compound No. | Structural formula |
|---|---|
| 169 | 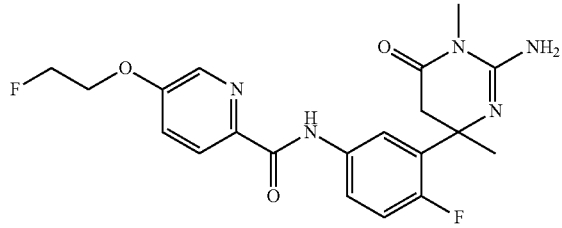 [SMILES: CN1C(=O)CC(C)(c2cc(NC(=O)c3ccc(OCCF)cn3)ccc2F)N=C1N] |
| 170 | 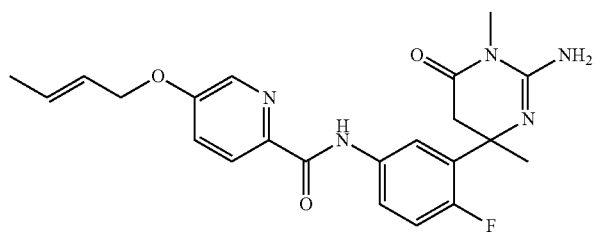 [SMILES: C/C=C/COc1ccc(C(=O)Nc2ccc(F)c(C3(C)CC(=O)N(C)C(N)=N3)c2)nc1] |
TABLE 30
| Compound No. | Structural formula |
|---|---|
| 171 | 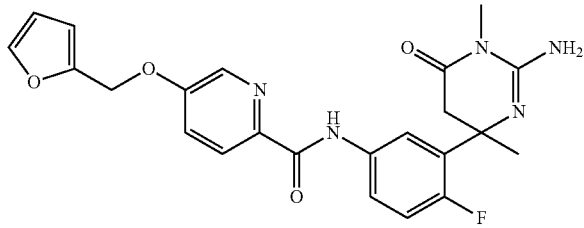 [SMILES: CN1C(=O)CC(C)(c2cc(NC(=O)c3ccc(OCc4ccco4)cn3)ccc2F)N=C1N] |
| 172 | 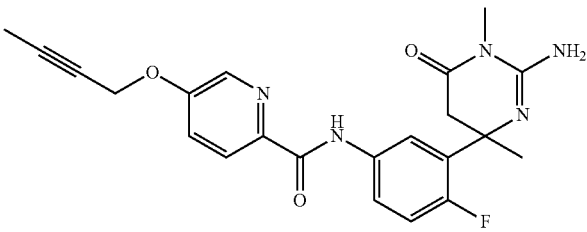 [SMILES: CC#CCOc1ccc(C(=O)Nc2ccc(F)c(C3(C)CC(=O)N(C)C(N)=N3)c2)nc1] |
| 173 | 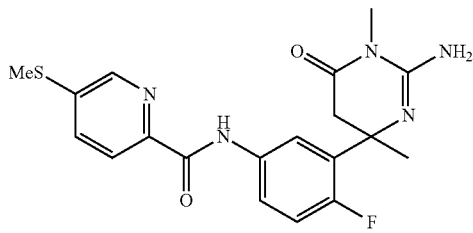 [SMILES: CSc1ccc(C(=O)Nc2ccc(F)c(C3(C)CC(=O)N(C)C(N)=N3)c2)nc1] |
| 174 | 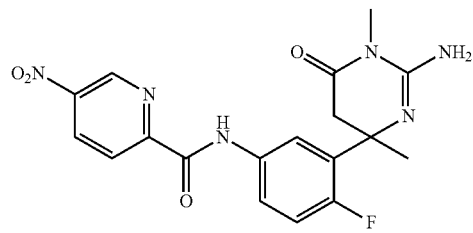 [SMILES: CN1C(=O)CC(C)(c2cc(NC(=O)c3ccc([N+](=O)[O-])cn3)ccc2F)N=C1N] |

TABLE 30-continued

| Compound No. | Structural formula |
| --- | --- |
| 175 | |
| 176 | |
| 177 | |
| 178 | |

TABLE 31

| Compound No. | Structural formula |
| --- | --- |
| 179 | |
| 180 | |

TABLE 31-continued

| Compound No. | Structural formula |
|---|---|
| 181 | |
| 182 | |
| 183 | |
| 184 | |
| 185 | |
| 186 | |

TABLE 32

| Compound No. | Structural formula |
|---|---|
| 187 | |
| 188 | |
| 189 | |
| 190 | |
| 191 | |
| 192 | |

TABLE 32-continued

| Compound No. | Structural formula |
| --- | --- |
| 193 | |
| 194 | |

TABLE 33

| Compound No. | Structural formula |
| --- | --- |
| 195 | |
| 196 | |
| 197 | |
| 198 | |

TABLE 33-continued

| Compound No. | Structural formula |
|---|---|
| 199 | |
| 200 | |
| 201 | |
| 202 | |

TABLE 34

| Compound No. | Structural formula |
|---|---|
| 203 | |
| 204 | |

TABLE 34-continued

| Compound No. | Structural formula |
|---|---|
| 205 | |
| 206 | |
| 207 | |
| 208 | |
| 209 | |
| 210 | |

TABLE 35

| Compound No. | Structural formula |
| --- | --- |
| 211 | |
| 212 | |
| 213 | |
| 214 | |
| 215 | |
| 216 | |

TABLE 35-continued

| Compound No. | Structural formula |
|---|---|
| 217 | (triazolyl-pyrazine-carboxamide-fluorophenyl-methyl-aminopyrimidinone derivative) |
| 218 | (triazolyl-pyrazine-carboxamide-fluorophenyl-methyl-aminopyrimidinone derivative) |

TABLE 36

| Compound No. | Structural formula |
|---|---|
| 219 | (pyrazolyl-pyrazine-carboxamide-fluorophenyl-methyl-aminopyrimidinone derivative) |
| 220 | (pyrrolyl-pyrazine-carboxamide-fluorophenyl-methyl-aminopyrimidinone derivative) |
| 221 | (oxazolyl-pyrazine-carboxamide-fluorophenyl-methyl-aminopyrimidinone derivative) |
| 222 | (thiazolyl-pyrazine-carboxamide-fluorophenyl-methyl-aminopyrimidinone derivative) |
| 223 | (thienyl-pyrazine-carboxamide-fluorophenyl-methyl-aminopyrimidinone derivative) |
| 224 | (dimethylisoxazolyl-pyrazine-carboxamide-fluorophenyl-methyl-aminopyrimidinone derivative) |
| 225 | (furan-3-yl-pyrazine-carboxamide-fluorophenyl-methyl-aminopyrimidinone derivative) |
| 226 | (furan-2-yl-pyrazine-carboxamide-fluorophenyl-methyl-aminopyrimidinone derivative) |

TABLE 36-continued
| Compound No. | Structural formula |
|---|---|
TABLE 37
| Compound No. | Structural formula |
|---|---|
| 227 | 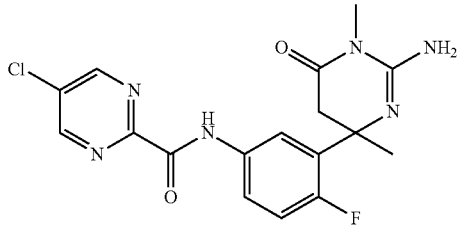 |
| 228 | 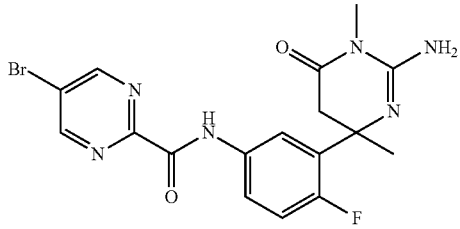 [SMILES: CN1C(=O)CC(C)(c2cc(NC(=O)c3ncc(Cl)cn3)ccc2F)N=C1N] |
| 229 | 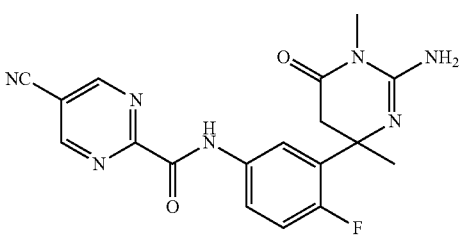 [SMILES: CN1C(=O)CC(C)(c2cc(NC(=O)c3ncc(C#N)cn3)ccc2F)N=C1N] |
| 230 | 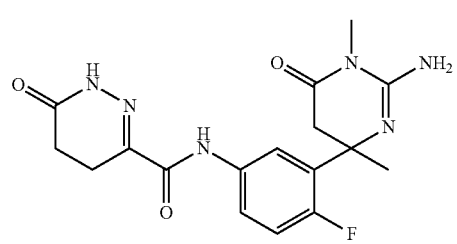 [SMILES: CN1C(=O)CC(C)(c2cc(NC(=O)C3=NNC(=O)CC3)ccc2F)N=C1N] |
| 231 | 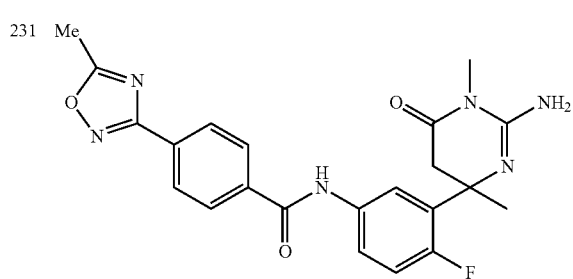 |
TABLE 37-continued
| Compound No. | Structural formula |
|---|---|
| 232 | |
| 233 | |
| 234 | |
TABLE 38
| Compound No. | Structural formula |
|---|---|
| 235 | |
| 236 | |

TABLE 38-continued

| Compound No. | Structural formula |
|---|---|
| 237 | |
| 238 | |
| 239 | |
| 240 | |
| 241 | |
| 242 | |

TABLE 39

| Compound No. | Structural formula |
|---|---|
| 243 | |
| 244 | |
| 245 | |
| 246 | |
| 247 | |
| 248 | |

TABLE 39-continued
| Compound No. | Structural formula |
|---|---|
| 249 | 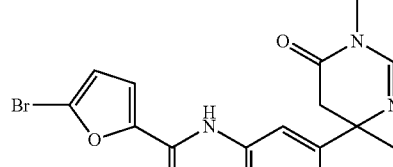 |
| 250 | |
TABLE 40
| Compound No. | Structural formula |
|---|---|
| 251 | 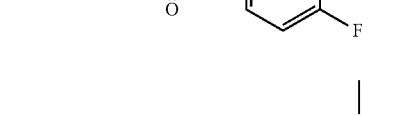 |
| 252 | |
| 253 | |
TABLE 40-continued
| Compound No. | Structural formula |
|---|---|
| 254 | 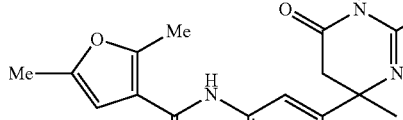 |
| 255 | |
| 256 | 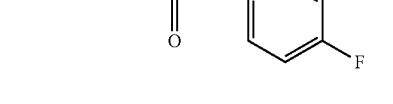 |
| 257 | |
| 258 | |

TABLE 41

| Compound No. | Structural formula |
|---|---|
| 259 | |
| 260 | |
| 261 | |
| 262 | |
| 263 | |
| 264 | |

TABLE 41-continued

| Compound No. | Structural formula |
|---|---|
| 265 | |
| 266 | |

TABLE 42

| Compound No. | Structural formula |
|---|---|
| 267 | |
| 268 | |
| 269 | |
| 270 | |

TABLE 42-continued
| Compound No. | Structural formula |
|---|---|
| 271 | 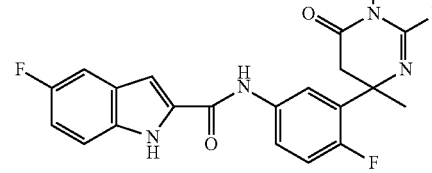 |
| 272 | |
| 273 | |
| 274 | |
TABLE 43
| Compound No. | Structural formula |
|---|---|
| 275 | 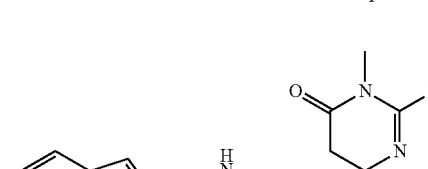 |
| 276 | |
TABLE 43-continued
| Compound No. | Structural formula |
|---|---|
| 277 | 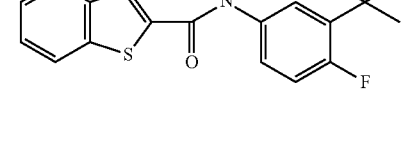 |
| 278 | |
| 279 | 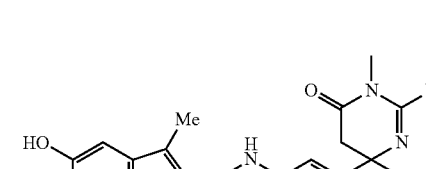 |
| 280 | 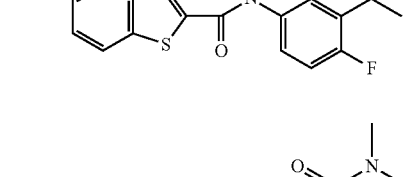 |
| 281 | |
| 282 | 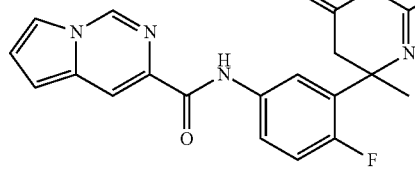 |

TABLE 44
| Compound No. | Structural formula |
|---|---|
| 283 | 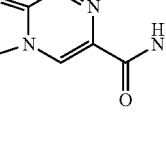 |
| 284 | |
| 285 | |
| 286 | |
| 287 | |
| 288 | |
TABLE 44-continued
| Compound No. | Structural formula |
|---|---|
| 289 | 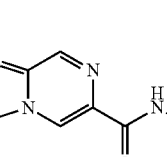 |
| 290 | |
TABLE 45
| Compound No. | Structural formula |
|---|---|
| 291 | 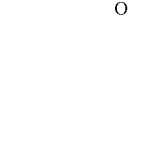 |
| 292 | |
TABLE 46
| Compound No. | Structural formula |
|---|---|
| 293 |  |

TABLE 46-continued

| Compound No. | Structural formula |
|---|---|
| 294 | |
| 295 | |
| 296 | |
| 297 | |
| 298 | |
| 299 | |

TABLE 46-continued

| Compound No. | Structural formula |
|---|---|
| 300 | |

TABLE 47

| Compound No. | Structural formula |
|---|---|
| 301 | |
| 302 | |
| 303 | |
| 304 | |

TABLE 47-continued

| Compound No. | Structural formula |
|---|---|
| 305 | (structure) |
| 306 | (structure) |
| 307 | (structure) |
| 308 | (structure) |

TABLE 48

| Compound No. | Structural formula |
|---|---|
| 309 | (structure) |
| 310 | (structure) |
| 311 | (structure) |
| 312 | (structure) |

TABLE 48-continued

| Compound No. | Structural formula |
|---|---|
| 313 | |
| 314 | |
| 315 | |
| 316 | |

TABLE 49

| Compound No. | Structural formula |
|---|---|
| 317 | |
| 318 | |

TABLE 49-continued

| Compound No. | Structural formula |
|---|---|
| 319 | |
| 320 | |
| 321 | |
| 322 | |
| 323 | |
| 324 | |

TABLE 50
| Compound No. | Structural formula |
|---|---|
| 325 | 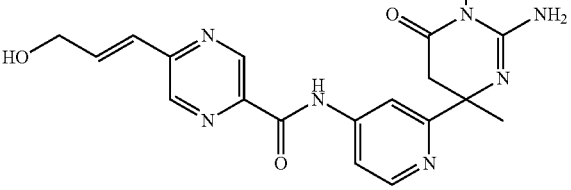 |
| 326 | 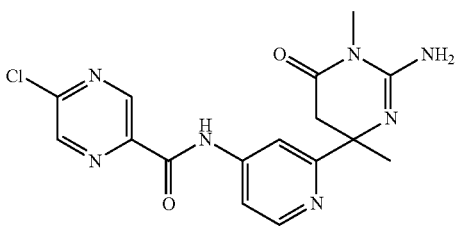 [SMILES: CN1C(=O)CC(C)(c2cc(NC(=O)c3cnc(Cl)cn3)ccn2)N=C1N] |
| 327 | 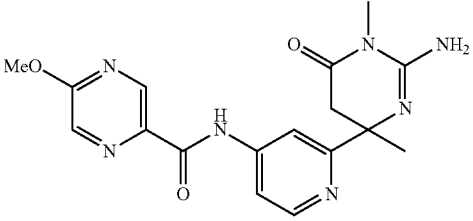 [SMILES: COc1cnc(C(=O)Nc2ccnc(C3(C)CC(=O)N(C)C(N)=N3)c2)cn1] |
| 328 | 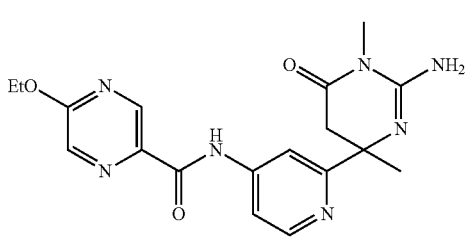 [SMILES: CCOc1cnc(C(=O)Nc2ccnc(C3(C)CC(=O)N(C)C(N)=N3)c2)cn1] |
| 329 | 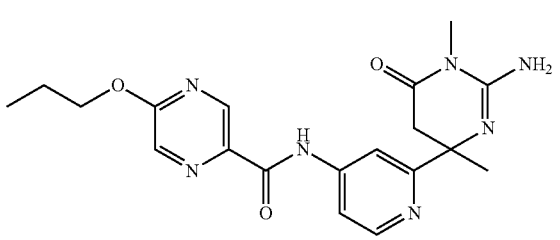 [SMILES: CCCOc1cnc(C(=O)Nc2ccnc(C3(C)CC(=O)N(C)C(N)=N3)c2)cn1] |
| 330 | 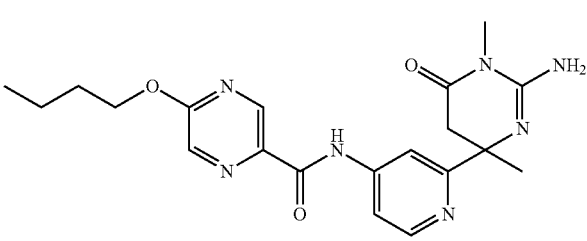 [SMILES: CCCCOc1cnc(C(=O)Nc2ccnc(C3(C)CC(=O)N(C)C(N)=N3)c2)cn1] |

141
TABLE 50-continued
| Compound No. | Structural formula |
|---|---|
| 331 | 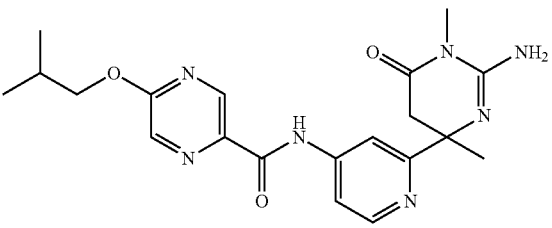 [SMILES: CC(C)COc1cnc(C(=O)Nc2ccnc(C3(C)CC(=O)N(C)C(N)=N3)c2)cn1] |
| 332 | 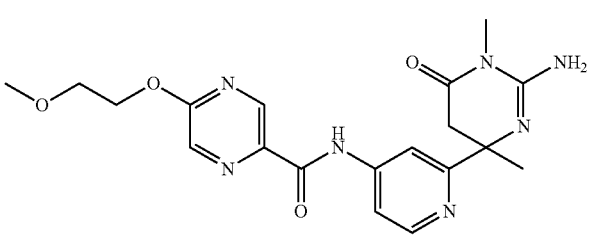 [SMILES: COCCOc1cnc(C(=O)Nc2ccnc(C3(C)CC(=O)N(C)C(N)=N3)c2)cn1] |
TABLE 51
| Compound No. | Structural formula |
|---|---|
| 333 | 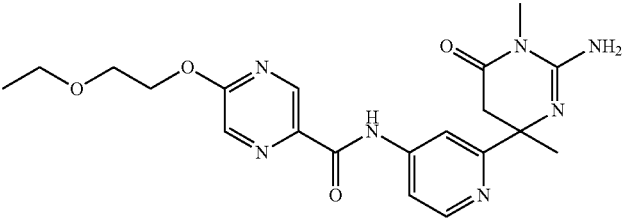 [SMILES: CCOCCOc1cnc(C(=O)Nc2ccnc(C3(C)CC(=O)N(C)C(N)=N3)c2)cn1] |
| 334 | 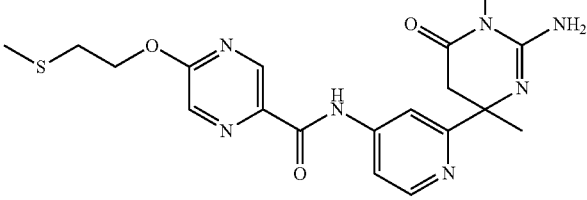 |
| 335 | 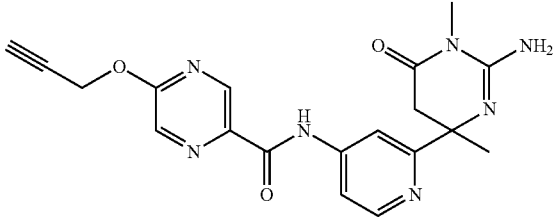 [SMILES: C#CCOc1cnc(C(=O)Nc2ccnc(C3(C)CC(=O)N(C)C(N)=N3)c2)cn1] |
| 336 | 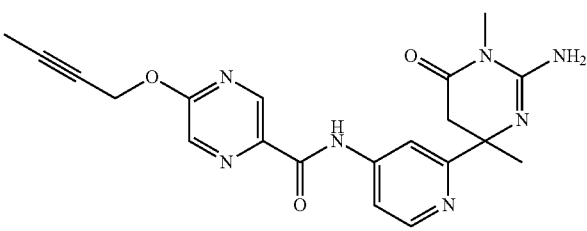 [SMILES: CC#CCOc1cnc(C(=O)Nc2ccnc(C3(C)CC(=O)N(C)C(N)=N3)c2)cn1] |

TABLE 51-continued

| Compound No. | Structural formula |
|---|---|
| 337 | |
| 338 | |
| 339 | |
| 340 | |

TABLE 52

| Compound No. | Structural formula |
|---|---|
| 341 | |
| 342 | |

TABLE 52-continued

| Compound No. | Structural formula |
|---|---|
| 343 | |
| 344 | |
| 345 | |
| 346 | |
| 347 | |
| 348 | |

TABLE 53
| Compound No. | Structural formula |
|---|---|
| 349 | 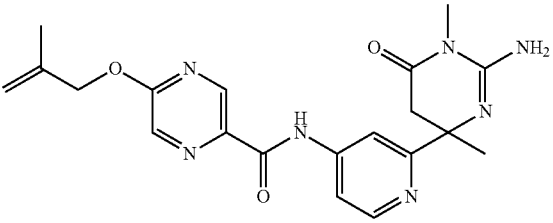 [SMILES: C=C(C)COc1cnc(C(=O)Nc2ccnc(C3(C)CC(=O)N(C)C(N)=N3)c2)cn1] |
| 350 | 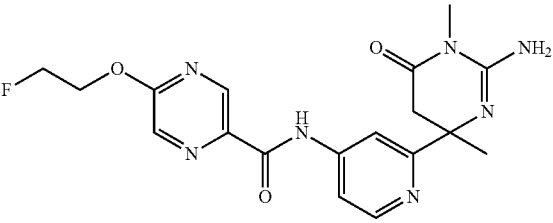 [SMILES: CN1C(=O)CC(C)(c2cc(NC(=O)c3cnc(OCCF)cn3)ccn2)N=C1N] |
| 351 | 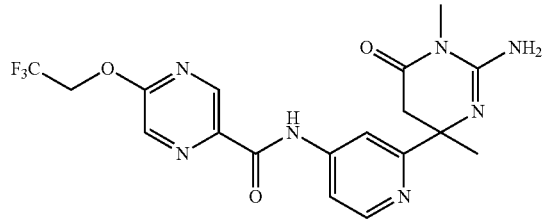 [SMILES: CN1C(=O)CC(C)(c2cc(NC(=O)c3cnc(OCC(F)(F)F)cn3)ccn2)N=C1N] |
| 352 | 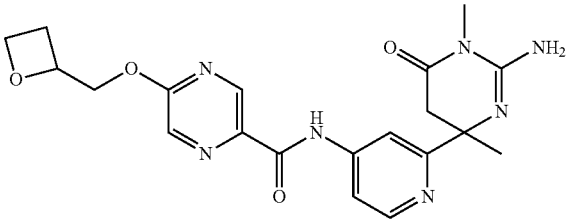 [SMILES: CN1C(=O)CC(C)(c2cc(NC(=O)c3cnc(OCC4CCO4)cn3)ccn2)N=C1N] |
| 353 | 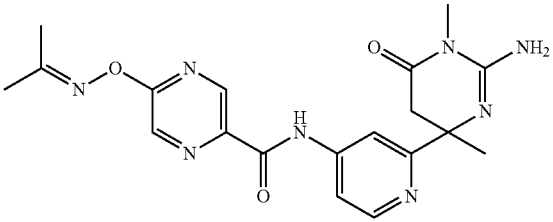 [SMILES: CC(C)=NOc1cnc(C(=O)Nc2ccnc(C3(C)CC(=O)N(C)C(N)=N3)c2)cn1] |
| 354 | 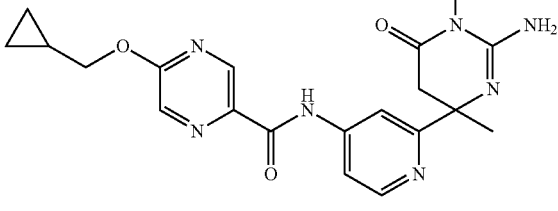 |

TABLE 53-continued

| Compound No. | Structural formula |
| --- | --- |
| 355 | |
| 356 | |

TABLE 54

| Compound No. | Structural formula |
| --- | --- |
| 357 | |
| 358 | |
| 359 | |
| 360 | |

TABLE 54-continued

| Compound No. | Structural formula |
|---|---|
| 361 | |
| 362 | |
| 363 | |
| 364 | |

TABLE 55

| Compound No. | Structural formula |
|---|---|
| 365 | |
| 366 | |
| 367 | |
| 368 | |

TABLE 55-continued
| Compound No. | Structural formula |
|---|---|
| 369 | 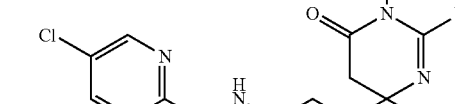 |
| 370 | |
| 371 | |
| 372 | |
TABLE 56
| Compound No. | Structural formula |
|---|---|
| 373 | 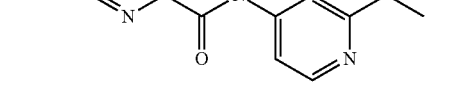 |
| 374 | |
| 375 | |
| 376 | |
| 377 | |
| 378 | |
| 379 | |
| 380 | |

TABLE 57

| Compound No. | Structural formula |
|---|---|
| 381 | 4-methoxybenzamide derivative |
| 382 | 1,5-dimethylpyrazole-carboxamide derivative |
| 383 | 3-cyano-1-methylpyrazole-carboxamide derivative |
| 384 | 1-tert-butyl-5-methylpyrazole-carboxamide derivative |
| 385 | 5-chloro-1-methylpyrazole-carboxamide derivative |
| 386 | 1,5-dimethylpyrazole-3-carboxamide derivative |

TABLE 57-continued

| Compound No. | Structural formula |
|---|---|
| 387 | 5-cyano-1-methylpyrazole-carboxamide derivative |
| 388 | 1-methylimidazole-2-carboxamide derivative |

TABLE 58

| Compound No. | Structural formula |
|---|---|
| 389 | oxazole-4-carboxamide derivative |
| 390 | 2-methyloxazole-4-carboxamide derivative |
| 391 | 5-trifluoromethyloxazole-4-carboxamide derivative |
| 392 | 2-chlorooxazole-4-carboxamide derivative |

TABLE 58-continued
| Compound No. | Structural formula |
|---|---|
| 393 | 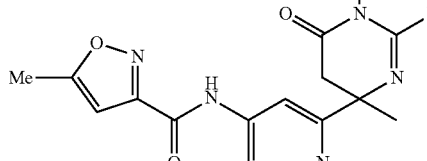 |
| 394 | |
| 395 | |
| 396 | |
TABLE 59
| Compound No. | Structural formula |
|---|---|
| 397 | |
| 398 | |
| 399 | 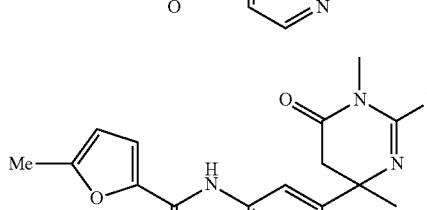 |
| 400 | |
| 401 | |
| 402 | |
| 403 | |
| 404 | |

TABLE 60

| Compound No. | Structural formula |
|---|---|
| 405 | |
| 406 | |
| 407 | |
| 408 | |
| 409 | |
| 410 | |
| 411 | |

TABLE 60-continued

| Compound No. | Structural formula |
|---|---|
| 412 | |

TABLE 61

| Compound No. | Structural formula |
|---|---|
| 413 | |
| 414 | |
| 415 | |
| 416 | |
| 417 | |

TABLE 61-continued
| Compound No. | Structural formula |
|---|---|
| 418 |  |
| 419 | |
| 420 | |
TABLE 62
| Compound No. | Structural formula |
|---|---|
| 421 | |
| 422 | |
| 423 | |
TABLE 62-continued
| Compound No. | Structural formula |
|---|---|
| 424 | 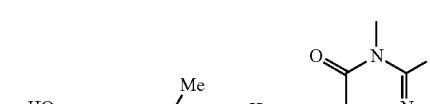 |
| 425 | |
| 426 | |
| 427 | |
| 428 | |
TABLE 63
| Compound No. | Structural formula |
|---|---|
| 429 | 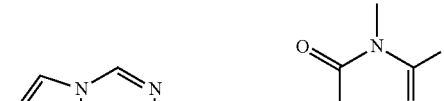 |

TABLE 63-continued

| Compound No. | Structural formula |
|---|---|
| 430 | |
| 431 | |
| 432 | |
| 433 | |
| 434 | |
| 435 | |

TABLE 63-continued

| Compound No. | Structural formula |
|---|---|
| 436 | |

TABLE 64

| Compound No. | Structural formula |
|---|---|
| 437 | |
| 438 | |

4) A compound of formula (I'):

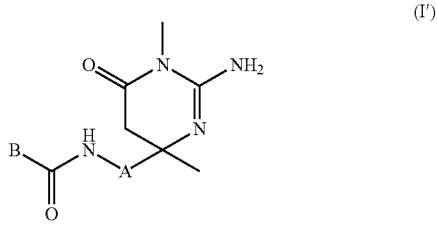

(I')

wherein A is optionally substituted benzenediyl (the substituent is one or more groups selected from lower alkyl, lower alkenyl and the substituent group α), and B is optionally substituted pyrazinediyl (the substituent is one or more groups selected from lower alkyl, lower alkenyl, lower alkynyl, lower alkenyloxy, lower alkynyloxy and the substituent group α).

Preferable among the above compounds is a compound in which A is optionally substituted benzenediyl (the substituent is one or more groups selected from halogen, lower alkyl, lower alkoxy, lower alkylthio, amino and lower alkylamino) and B is optionally substituted pyrazinediyl (the substituent is one or more groups selected from halogen, lower alkyl, lower alkenyl, lower alkoxy, lower alkoxy lower alkoxy and lower alkynyloxy).

More preferable among the above compounds is a compound in which A is unsubstituted benzenediyl and B is optionally substituted pyrazinediyl (the substituent is one or more groups selected from halogen, lower alkyl, lower alkenyl, lower alkoxy, lower alkoxy lower alkoxy and lower alkynyloxy).

Further, the compound of the present invention is preferably as follows.

5) A compound of formula (II'):

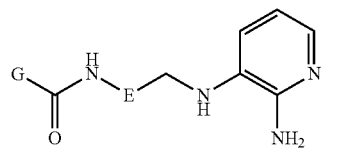
(II')

wherein

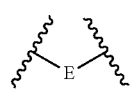

is any one of the following.

TABLE 65

| | |
|---|---|
| | 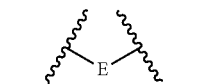 |
| E1 | 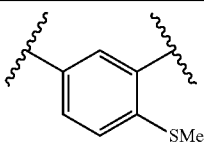 |
| E2 | |
| E3 | |
| E4 | |
| E5 | |

TABLE 65-continued

| | |
|---|---|
| | 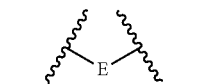 |
| E6 | 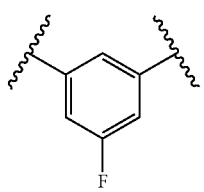 [SMILES: *c1cc(*)cc(F)c1] |
| E7 | 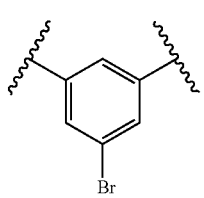 [SMILES: *c1cc(*)cc(Br)c1] |
| E8 | |
| E9 | 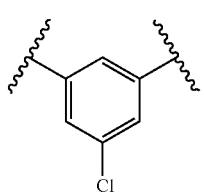 [SMILES: *c1cc(*)cc(Cl)c1] |
| E10 | 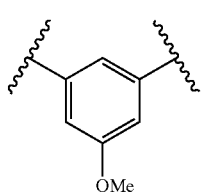 [SMILES: *c1cc(*)cc(OC)c1] |
| E11 | 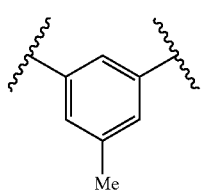 [SMILES: *c1cc(*)cc(C)c1] |
| E12 | 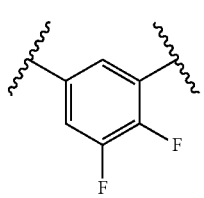 [SMILES: *c1cc(*)c(F)c(F)c1] |
| E13 | 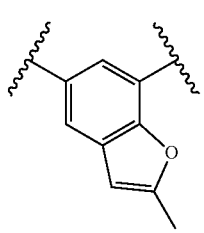 [SMILES: *c1cc(*)c2oc(C)cc2c1] |

TABLE 65-continued

| | |
|---|---|
| E14 | pyridine-2,6-diyl |
| E15 | pyridine-3,5-diyl |
| E16 | pyridine-2,4-diyl |
| E17 | 2-chloropyridine-3,5-diyl |
| E18 | pyrazine-2,6-diyl |
| E19 | benzene-1,3-diyl |
| E20 | 4-fluorobenzene-1,3-diyl |
| E21 | pyridine-2,4-diyl |

6) A compound of formula (II'):

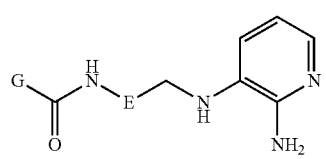

wherein

is any one of the following.

TABLE 66

| | G |
|---|---|
| G1 | 5-chloropyridin-2-yl |
| G2 | 5-bromopyridin-2-yl |
| G3 | 5-fluoropyridin-2-yl |
| G4 | 3,5-dichloropyridin-2-yl |
| G5 | 3-fluoropyridin-2-yl |
| G6 | 3,5-difluoropyridin-2-yl |
| G7 | 3-amino-5-chloropyridin-2-yl |
| G8 | 5-methylpyridin-2-yl |

TABLE 66-continued
| | G⌇ |
|---|---|
| G9 |  |
| G10 | 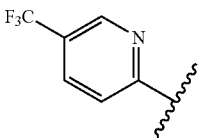 [SMILES: *c1ccc(C(F)(F)F)cn1] |
| G11 | 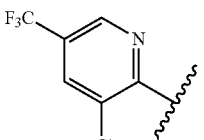 |
| G12 | 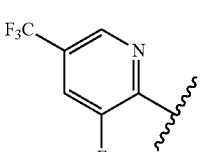 |
| G13 | 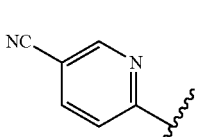 |
| G14 | 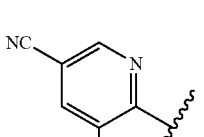 |
| G15 | 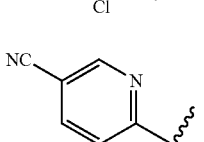 |
| G16 | 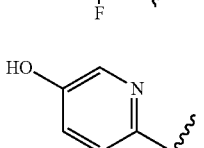 |
| G17 | 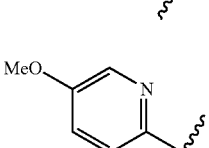 |
TABLE 66-continued
| | G⌇ |
|---|---|
| G18 |  |
| G19 | 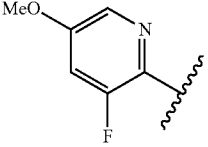 |
| G20 | 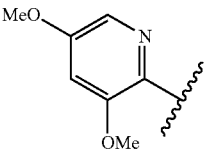 |
| G21 | 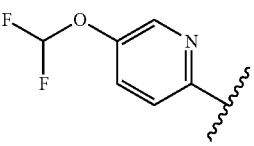 [SMILES: *c1ccc(OC(F)F)cn1] |
| G22 | 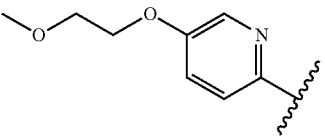 [SMILES: *c1ccc(OCCOC)cn1] |
| G23 | 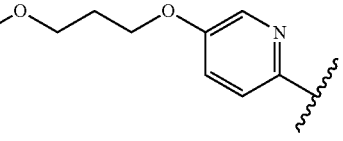 |
| G24 | 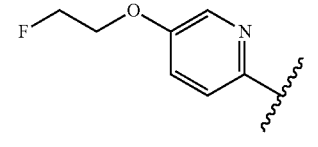 [SMILES: *c1ccc(OCCF)cn1] |
| G25 | 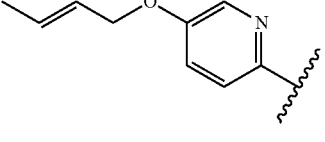 |
| G26 | 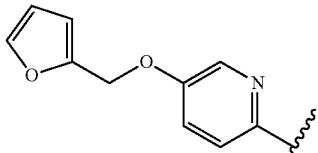 |

TABLE 67
| | G group | | G group |
|---|---|---|---|
| G27 | 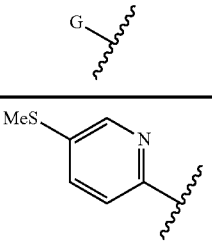 | G37 | 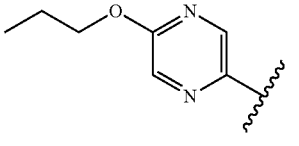 |
| G28 | 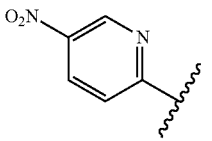 [SMILES: *c1ccc([N+](=O)[O-])cn1] | G38 | 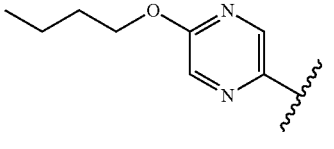 |
| G29 | 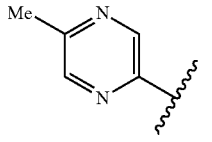 [SMILES: *c1cnc(C)cn1] | G39 | 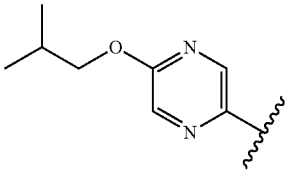 |
| G30 | 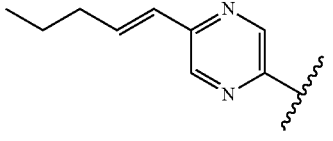 [SMILES: *c1cnc(/C=C/CCC)cn1] | G40 | 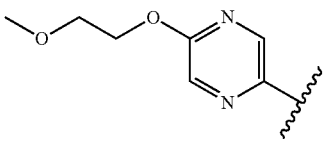 |
| G31 | 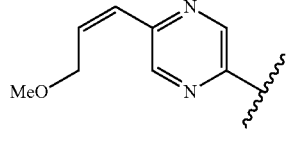 [SMILES: *c1cnc(/C=C\COC)cn1] | G41 | 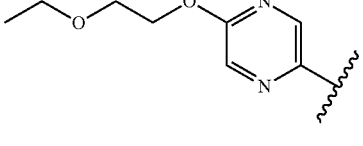 |
| G32 | 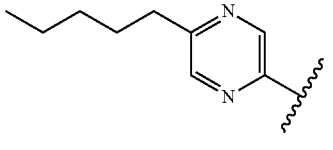 [SMILES: *c1cnc(CCCCC)cn1] | G42 | 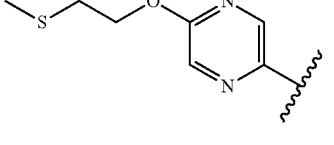 |
| G33 | 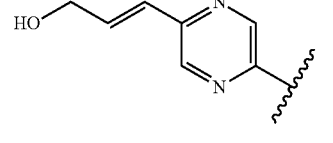 | G43 | 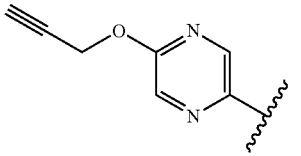 |
| G34 | 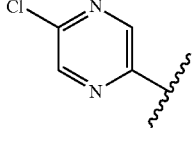 [SMILES: *c1cnc(Cl)cn1] | G44 | 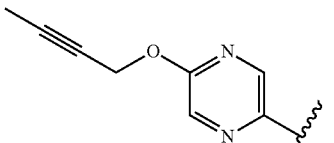 |
| G35 | 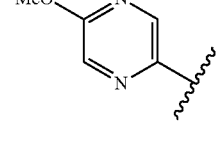 | G45 | 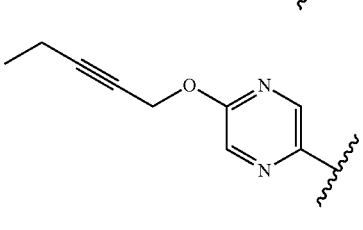 |
| G36 | 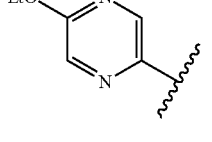 | | |

TABLE 67-continued
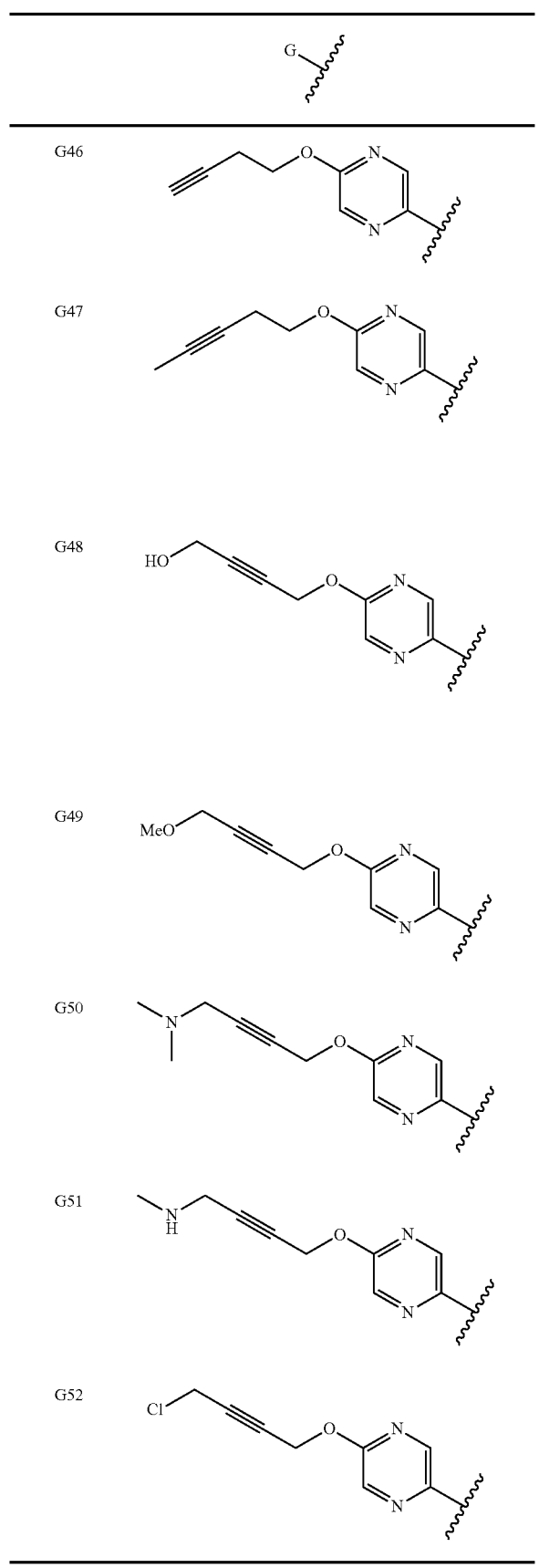
TABLE 68
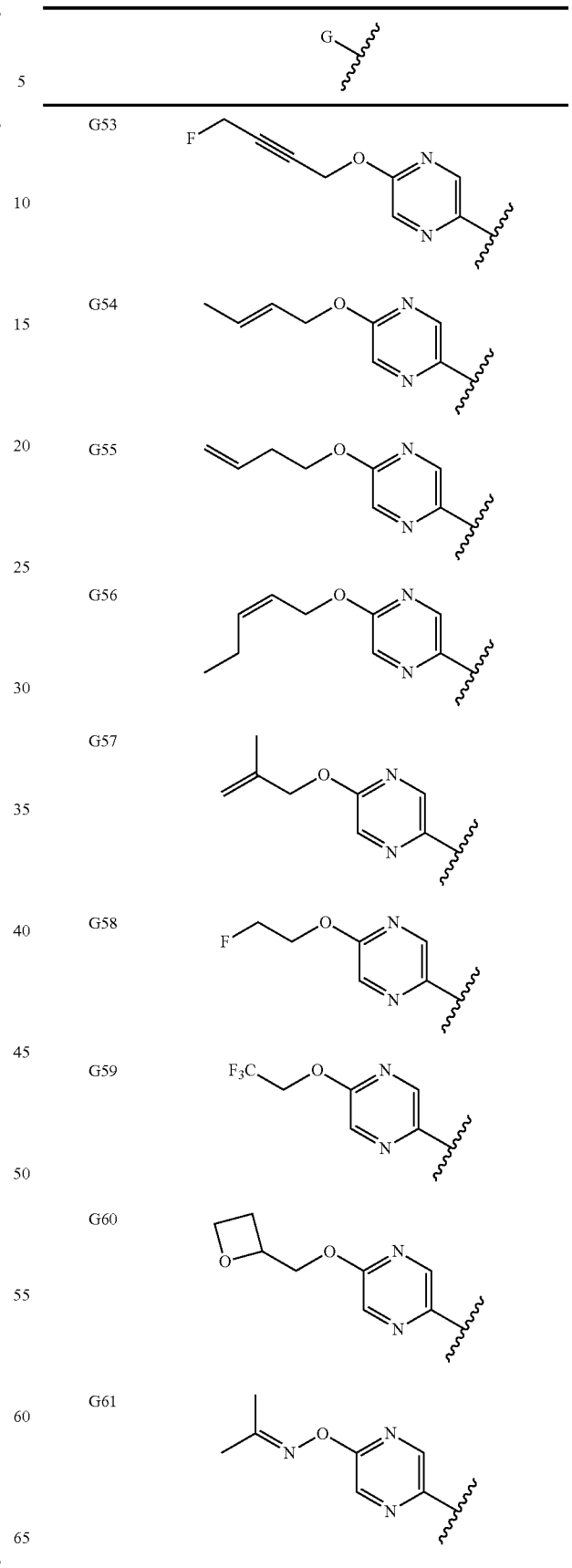

TABLE 68-continued

| | G↝ |
|---|---|
| G62 | cyclopropylmethoxy-pyrazinyl |
| G63 | 3-amino-6-methoxypyrazinyl |
| G64 | 3-amino-6-(2,2,2-trifluoroethoxy)pyrazinyl |
| G65 | 3-amino-6-(2-methoxyethoxy)pyrazinyl |
| G66 | 5-azidopyrazinyl |
| G67 | 5-(but-2-yn-1-ylamino)pyrazinyl |
| G68 | 5-(methylthio)pyrazinyl |
| G69 | 5-(ethylthio)pyrazinyl |
| G70 | 5-(2H-1,2,3-triazol-2-yl)pyrazinyl |
| G71 | 5-(1H-1,2,3-triazol-1-yl)pyrazinyl |
| G72 | 5-(1H-1,2,4-triazol-1-yl)pyrazinyl |
| G73 | 5-(1H-pyrazol-1-yl)pyrazinyl |
| G74 | 5-(1H-pyrrol-2-yl)pyrazinyl |
| G75 | 5-(oxazol-2-yl)pyrazinyl |
| G76 | 5-(thiazol-2-yl)pyrazinyl |
| G77 | 5-(thiophen-3-yl)pyrazinyl |

TABLE 68-continued
| | G |
|---|---|
| G78 | 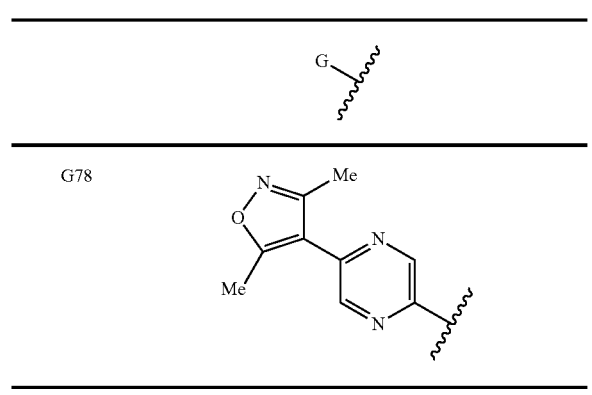 |
TABLE 69
| | G |
|---|---|
| G79 | |
| G80 | |
| G81 | |
| G82 | |
| G83 | |
| G84 | |
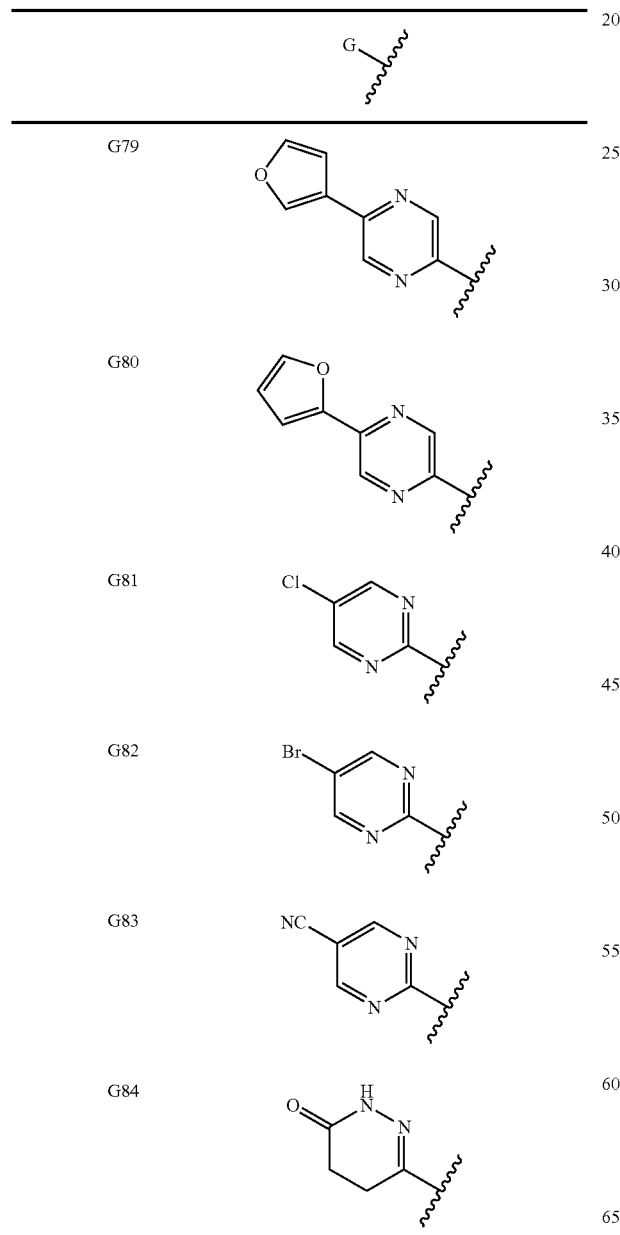
TABLE 69-continued
| | G |
|---|---|
| G85 | |
| G86 | |
| G87 | |
| G88 | |
| G89 | |
| G90 | |
| G91 | |
| G92 | |
| G93 | |
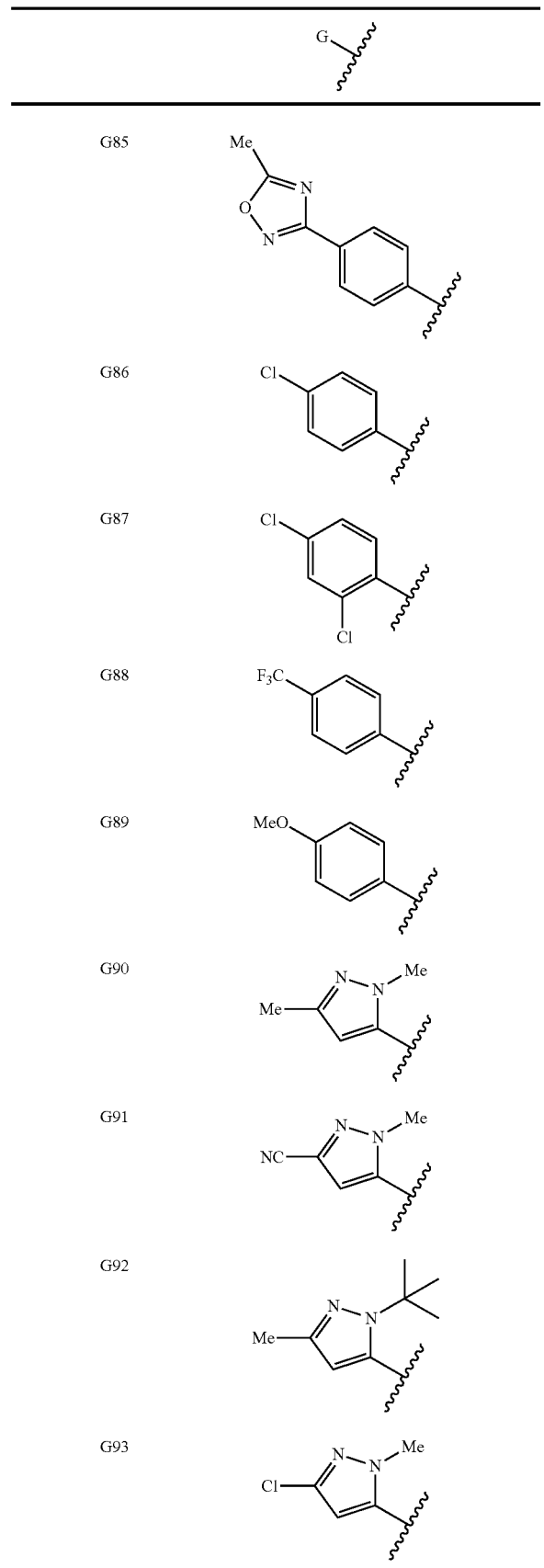

TABLE 69-continued
| | |
|---|---|
| G94 | 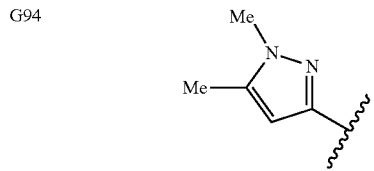 |
| G95 | 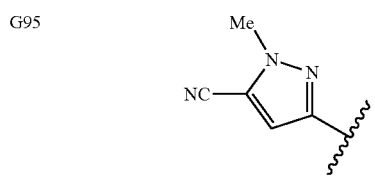 |
| G96 | 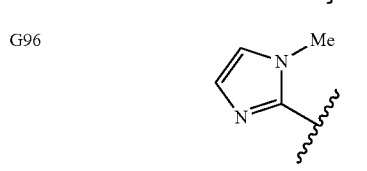 |
| G97 | 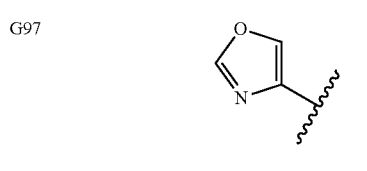 |
| G98 | 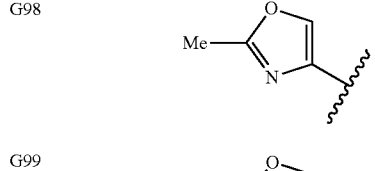 |
| G99 | 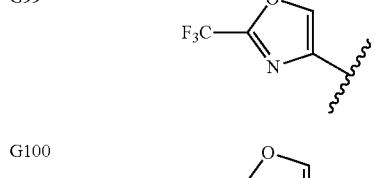 |
| G100 | 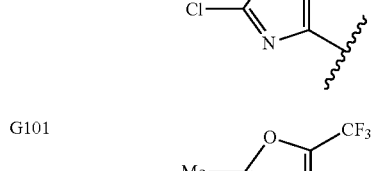 |
| G101 | 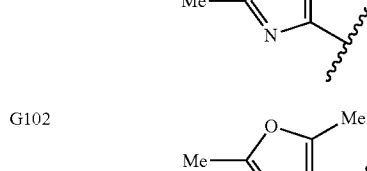 |
| G102 | 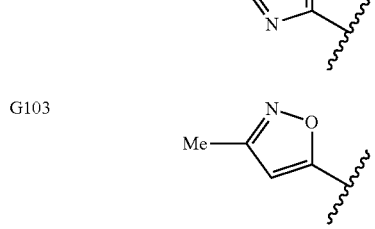 |
| G103 |  |
TABLE 69-continued
| | |
|---|---|
| G104 | 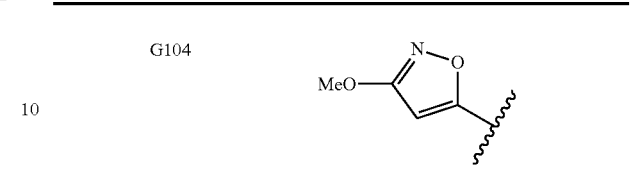 |
TABLE 70
| | |
|---|---|
| G105 | 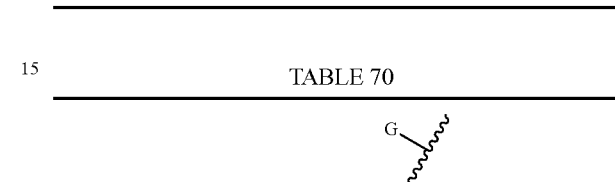 |
| G106 | 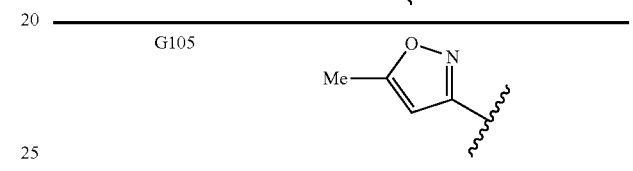 |
| G107 | 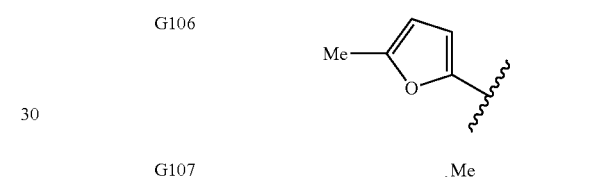 |
| G108 | 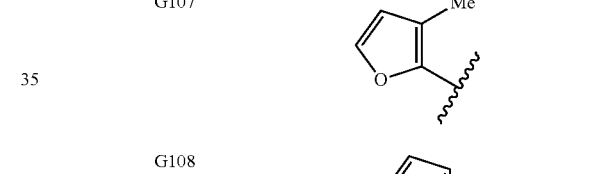 |
| G109 | 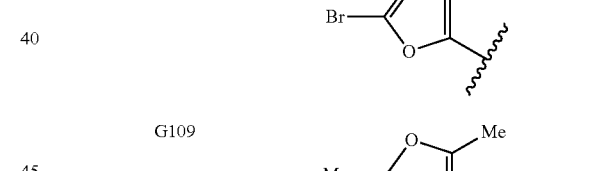 |
| G110 | 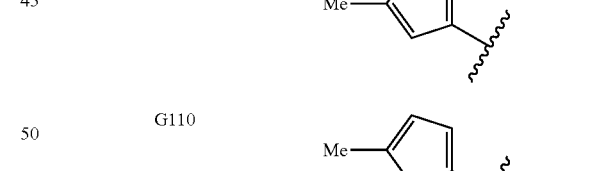 |
| G111 | 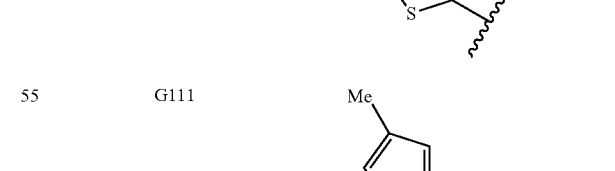 |
| G112 | |

TABLE 70-continued
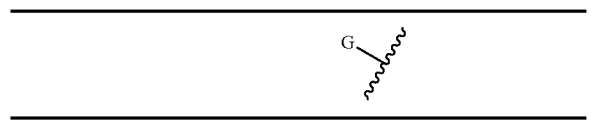
| | |
|---|---|
| G113 | 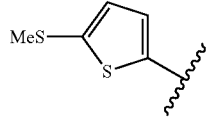 [SMILES: *c1ccc(SC)s1] |
| G114 | 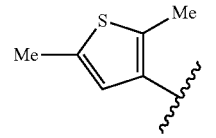 [SMILES: *c1cc(C)sc1C] |
| G115 | 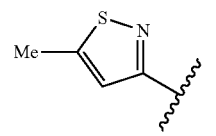 |
| G116 | 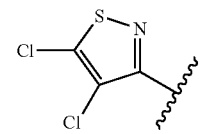 [SMILES: *c1nsc(Cl)c1Cl] |
| G117 | 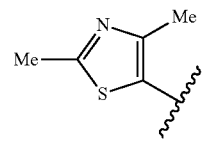 [SMILES: *c1sc(C)nc1C] |
| G118 | 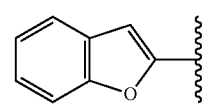 [SMILES: *c1cc2ccccc2o1] |
| G119 | 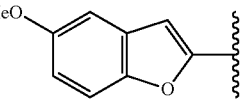 |
| G120 | 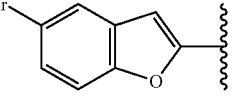 |
| G121 | 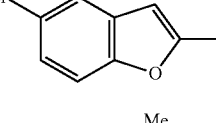 |
| G122 | 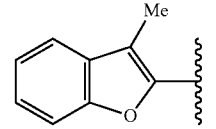 [SMILES: *c1oc2ccccc2c1C] |
| G123 | 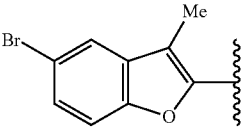 [SMILES: *c1oc2ccc(Cl)cc2c1C] |
TABLE 70-continued
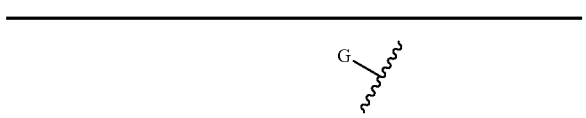
| | |
|---|---|
| G124 | 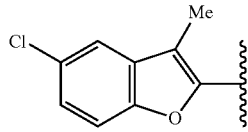 |
| G125 | 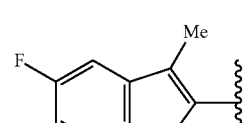 |
| G126 | 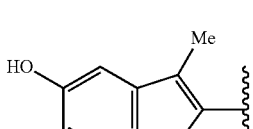 |
| G127 | 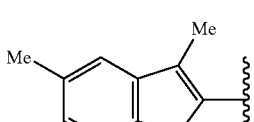 |
| G128 | 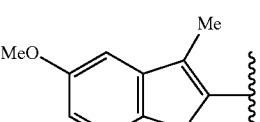 |
| G129 | 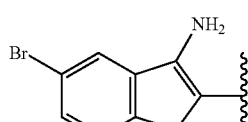 |
| G130 | 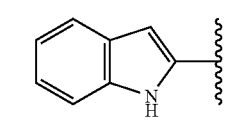 [SMILES: *c1cc2ccccc2[nH]1] |
TABLE 71
| | |
|---|---|
| G131 | 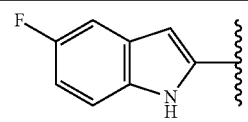 |
| G132 | 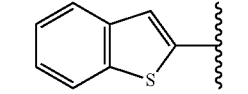 |

TABLE 71-continued

| | G⌇ | | | G⌇ |
|---|---|---|---|---|
| G133 | 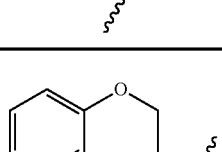 | | G143 | 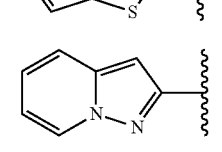 |
| G134 | | | G144 | |
| G135 | | | G145 | |
| G136 | | | G146 | |
| G137 | | | | |
| G138 | | | | |
| G139 | 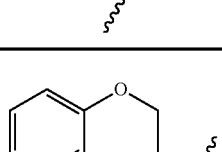 | | | |
| G140 | | | | |
| G141 | | | | |
| G142 | 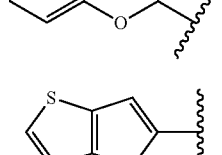 | | | |

7) A compound of formula (II'):

(II')

wherein the combination of

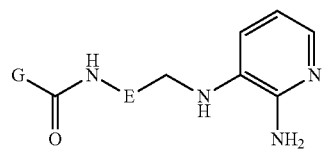 and 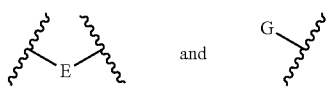

is any one of the following:
(E1, G1), (E1, G2), (E1, G3), (E1, G4), (E1, G5), (E1, G6), (E1, G7), (E1, G8), (E1, G9), (E1, G10), (E1, G11), (E1, G12), (E1, G13), (E1, G14), (E1, G15), (E1, G16), (E1, G17), (E1, G18), (E1, G19), (E1, G20), (E1, G21), (E1, G22), (E1, G23), (E1, G24), (E1, G25), (E1, G26), (E1, G27), (E1, G28), (E1, G29), (E1, G30), (E1, G31), (E1, G32), (E1, G33), (E1, G34), (E1, G35), (E1, G36), (E1, G37), (E1, G38), (E1, G39), (E1, G40), (E1, G41), (E1, G42), (E1, G43), (E1, G44), (E1, G45), (E1, G46), (E1, G47), (E1, G48), (E1, G49), (E1, G50), (E1, G51), (E1, G52), (E1, G53), (E1, G54), (E1, G55), (E1, G56), (E1, G57), (E1, G58), (E1, G59), (E1, G60), (E1, G61), (E1, G62), (E1, G63), (E1, G64), (E1, G65), (E1, G66), (E1, G67), (E1, G68), (E1, G69), (E1, G70), (E1, G71), (E1, G72), (E1, G73), (E1, G74), (E1, G75), (E1, G76), (E1, G77), (E1, G78), (E1, G79), (E1, G80), (E1, G81), (E1, G82), (E1, G83), (E1, G84), (E1, G85), (E1, G86), (E1, G87), (E1, G88), (E1, G89), (E1, G90), (E1, G91), (E1, G92), (E1, G93), (E1, G94), (E1, G95), (E1, G96), (E1, G97), (E1, G98), (E1, G99), (E1, G100), (E1, G101), (E1, G102), (E1, G103), (E1, G104), (E1, G105), (E1, G106), (E1, G107), (E1, G108), (E1, G109), (E1, G110), (E1, G111), (E1, G112), (E1, G113), (E1, G114), (E1, G115), (E1, G116), (E1, G117), (E1, G118), (E1, G119), (E1, G120), (E1, G121), (E1, G122), (E1, G123), (E1, G124), (E1, G125), (E1, G126), (E1, G127), (E1, G128), (E1, G129), (E1, G130), (E1, G131), (E1, G132), (E1, G133), (E1, G134), (E1, G135), (E1, G136), (E1, G137), (E1, G138), (E1, G139), (E1, G140), (E1, G141), (E1, G142), (E1, G143), (E1, G144), (E1, G145), (E1, G146), (E2, G1) (E2, G2), (E2, G3), (E2, G4), (E2, G5), (E2, G6), (E2, G7), (E2, G8), (E2, G9), (E2, G10) (E2, G11) (E2, G12), (E2, G13), (E2, G14), (E2, G15) (E2, G16), (E2, G17), (E2, G18), (E2, G19) (E2, G20), (E2, G21), (E2, G22), (E2, G23), (E2, G24), (E2, G25), (E2, G26), (E2, G27), (E2, G28), (E2, G29), (E2, G30), (E2, G31), (E2, G32), (E2, G33), (E2, G34), (E2, G35), (E2, G36), (E2, G37), (E2, G38), (E2, G39), (E2, G40), (E2, G41), (E2, G42), (E2, G43), (E2, G44), (E2, G45), (E2, G46), (E2, G47), (E2, G48), (E2, G49), (E2, G50), (E2, G51), (E2, G52), (E2, G53), (E2, G54), (E2, G55), (E2, G56), (E2, G57), (E2, G58), (E2, G59), (E2, G60), (E2, G61), (E2, G62), (E2, G63), (E2, G64), (E2, G65), (E2, G66), (E2, G67), (E2, G68), (E2, G69), (E2, G70), (E2, G71) (E2, G72), (E2, G73), (E2, G74), (E2, G75), (E2, G76), (E2, G77), (E2, G78), (E2, G79), (E2, G80), (E2, G81), (E2, G82), (E2, G83), (E2, G84), (E2, G85), (E2, G86), (E2, G87), (E2, G88), (E2, G89), (E2, G90), (E2, G91) (E2, G92), (E2, G93), (E2, G94), (E2, G95), (E2, G96), (E2, G97), (E2, G98), (E2, G99), (E2, G100) (E2, G101) (E2, G102), (E2, G103), (E2, G104) (E2, G105), (E2, G106), (E2, G107), (E2, G108) (E2, G109), (E2, G110), (E2, G111) (E2, G112) (E2, G113), (E2, G114), (E2, G115), (E2, G116), (E2, G117) (E2, G118) (E2, G119), (E2, G120), (E2, G121), (E2, G122), (E2, G123), (E2, G124), (E2, G125), (E2, G126), (E2, G127), (E2, G128), (E2, G129) (E2, G130), (E2, G131), (E2, G132), (E2, G133), (E2, G134), (E2, G135), (E2, G136), (E2, G137), (E2, G138) (E2, G139), (E2, G140), (E2, G141) (E2, G142), (E2, G143), (E2, G144), (E2, G145), (E2, G146), (E3, G1) (E3, G2), (E3, G3), (E3, G4), (E3, G5), (E3, G6), (E3, G7), (E3, G8), (E3, G9), (E3, G10) (E3, G11), (E3, G12), (E3, G13) (E3, G14), (E3, G15), (E3, G16), (E3, G17), (E3, G18), (E3, G19), (E3, G20), (E3, G21), (E3, G22), (E3, G23), (E3, G24), (E3, G25), (E3, G26), (E3, G27), (E3, G28), (E3, G29), (E3, G30), (E3, G31), (E3, G32), (E3, G33), (E3, G34), (E3, G35), (E3, G36), (E3, G37), (E3, G38), (E3, G39), (E3, G40), (E3, G41), (E3, G42), (E3, G43), (E3, G44), (E3, G45), (E3, G46), (E3, G47), (E3, G48), (E3, G49), (E3, G50), (E3, G51), (E3, G52), (E3, G53), (E3, G54), (E3, G55), (E3, G56), (E3, G57), (E3, G58), (E3, G59), (E3, G60), (E3, G61), (E3, G62), (E3, G63), (E3, G64), (E3, G65), (E3, G66), (E3, G67), (E3, G68), (E3, G69), (E3, G70), (E3, G71), (E3, G72), (E3, G73), (E3, G74), (E3, G75), (E3, G76), (E3, G77), (E3, G78), (E3, G79), (E3, G80), (E3, G81), (E3, G82), (E3, G83), (E3, G84), (E3, G85), (E3, G86), (E3, G87), (E3, G88), (E3, G89), (E3, G90), (E3, G91), (E3, G92), (E3, G93), (E3, G94), (E3, G95), (E3, G96), (E3, G97), (E3, G98), (E3, G99), (E3, G100), (E3, G101), (E3, G102), (E3, G103), (E3, G104), (E3, G105), (E3, G106), (E3, G107), (E3, G108), (E3, G109), (E3, G110), (E3, G111), (E3, G112), (E3, G113), (E3, G114), (E3, G115), (E3, G116), (E3, G117), (E3, G118), (E3, G119), (E3, G120), (E3, G121), (E3, G122), (E3, G123), (E3, G124), (E3, G125), (E3, G126), (E3, G127), (E3, G128), (E3, G129), (E3, G130), (E3, G131), (E3, G132), (E3, G133), (E3, G134), (E3, G135), (E3, G136), (E3, G137), (E3, G138), (E3, G139), (E3, G140), (E3, G141), (E3, G142), (E3, G143), (E3, G144), (E3, G145), (E3, G146), (E4, G1), (E4, G2), (E4, G3), (E4, G4), (E4, G5), (E4, G6), (E4, G7), (E4, G8), (E4, G9), (E4, G10), (E4, G11), (E4, G12), (E4, G13), (E4, G14), (E4, G15), (E4, G16), (E4, G17), (E4, G18), (E4, G19), (E4, G20), (E4, G21), (E4, G22), (E4, G23), (E4, G24), (E4, G25), (E4, G26), (E4, G27), (E4, G28), (E4, G29), (E4, G30), (E4, G31), (E4, G32), (E4, G33), (E4, G34), (E4, G35), (E4, G36), (E4, G37), (E4, G38), (E4, G39), (E4, G40), (E4, G41), (E4, G42), (E4, G43), (E4, G44), (E4, G45), (E4, G46), (E4, G47), (E4, G48), (E4, G49), (E4, G50), (E4, G51), (E4, G52), (E4, G53), (E4, G54), (E4, G55), (E4, G56), (E4, G57), (E4, G58), (E4, G59), (E4, G60), (E4, G61), (E4, G62), (E4, G63), (E4, G64), (E4, G65), (E4, G66), (E4, G67), (E4, G68), (E4, G69), (E4, G70), (E4, G71), (E4, G72), (E4, G73), (E4, G74), (E4, G75), (E4, G76), (E4, G77), (E4, G78), (E4, G79), (E4, G80), (E4, G81), (E4, G82), (E4, G83), (E4, G84), (E4, G85), (E4, G86), (E4, G87), (E4, G88), (E4, G89), (E4, G90), (E4, G91), (E4, G92), (E4, G93), (E4, G94), (E4, G95), (E4, G96), (E4, G97), (E4, G98), (E4, G99), (E4, G100), (E4, G101), (E4, G102), (E4, G103), (E4, G104), (E4, G105), (E4, G106), (E4, G107), (E4, G108), (E4, G109), (E4, G110), (E4, G111), (E4, G112), (E4, G113), (E4, G114), (E4, G115), (E4, G116), (E4, G117), (E4, G118), (E4, G119), (E4, G120), (E4, G121), (E4, G122), (E4, G123), (E4, G124), (E4, G125) (E4, G126), (E4, G127) (E4, G128) (E4, G129), (E4, G130), (E4, G131), (E4, G132), (E4, G133), (E4, G134), (E4, G135), (E4, G136), (E4, G137), (E4, G138), (E4, G139), (E4, G140), (E4, G141), (E4, G142), (E4, G143), (E4, G144), (E4, G145), (E4, G146), (E5, G1), (E5, G2), (E5, G3), (E5, G4), (E5, G5), (E5, G6), (E5, G7), (E5, G8), (E5, G9), (E5, G10), (E5, G11), (E5, G12), (E5, G13) (E5, G14), (E5, G15), (E5, G16), (E5, G17) (E5, G18), (E5, G19), (E5, G20), (E5, G21), (E5, G22), (E5, G23), (E5, G24), (E5, G25), (E5, G26), (E5, G27), (E5, G28), (E5, G29), (E5, G30), (E5, G31), (E5, G32), (E5, G33), (E5, G34), (E5, G35), (E5, G36), (E5, G37), (E5, G38), (E5, G39), (E5, G40), (E5, G41), (E5, G42), (E5, G43), (E5, G44), (E5, G45), (E5, G46), (E5, G47), (E5, G48), (E5, G49), (E5, G50), (E5, G51), (E5, G52), (E5, G53), (E5, G54), (E5, G55), (E5, G56), (E5, G57), (E5, G58), (E5, G59), (E5, G60), (E5, G61), (E5, G62), (E5, G63), (E5, G64), (E5, G65), (E5, G66), (E5, G67) (E5, G68), (E5, G69), (E5, G70), (E5, G71), (E5, G72), (E5, G73), (E5, G74), (E5, G75) (E5, G76), (E5, G77), (E5, G78), (E5, G79), (E5, G80), (E5, G81), (E5, G82), (E5, G83), (E5, G84), (E5, G85), (E5, G86), (E5, G87), (E5, G88), (E5, G89), (E5, G90), (E5, G91), (E5, G92), (E5, G93), (E5, G94), (E5, G95), (E5, G96), (E5, G97), (E5, G98), (E5, G99), (E5, G100) (E5, G101), (E5, G102), (E5, G103), (E5, G104), (E5, G105), (E5, G106), (E5, G107), (E5, G108), (E5, G109), (E5, G110) (E5, G111) (E5, G112), (E5, G113), (E5, G114), (E5, G115), (E5, G116), (E5, G117), (E5, G118), (E5, G119), (E5, G120), (E5, G121), (E5, G122), (E5, G123), (E5, G124), (E5, G125), (E5, G126), (E5, G127) (E5, G128), (E5, G129), (E5, G130), (E5, G131) (E5, G132), (E5, G133), (E5, G134) (E5, G135) (E5, G136), (E5, G137), (E5, G138), (E5, G139) (E5, G140) (E5, G141), (E5, G142) (E5, G143), (E5, G144), (E5, G145), (E5, G146), (E6, G1), (E6, G2), (E6, G3), (E6, G4) (E6, G5), (E6, G6) (E6, G7), (E6, G8) (E6, G9), (E6, G10), (E6, G11), (E6, G12), (E6, G13), (E6, G14), (E6, G15), (E6, G16), (E6, G17) (E6, G18), (E6, G19), (E6, G20) (E6, G21) (E6, G22), (E6, G23), (E6, G24) (E6, G25) (E6, G26), (E6, G27) (E6, G28) (E6, G29), (E6, G30), (E6, G31) (E6, G32), (E6, G33), (E6, G34) (E6, G35), (E6, G36), (E6, G37), (E6, G38), (E6, G39), (E6, G40) (E6, G41), (E6, G42), (E6, G43), (E6, G44), (E6, G45), (E6, G46) (E6, G47) (E6, G48), (E6, G49) (E6, G50), (E6, G51), (E6, G52) (E6, G53), (E6, G54) (E6, G55), (E6, G56) (E6, G57), (E6, G58) (E6, G59), (E6, G60), (E6, G61), (E6, G62) (E6, G63), (E6, G64), (E6, G65), (E6, G66) (E6, G67), (E6, G68) (E6, G69) (E6, G70), (E6, G71) (E6, G72) (E6, G73), (E6, G74) (E6, G75), (E6, G76), (E6, G77), (E6, G78) (E6, G79), (E6, G80) (E6, G81) (E6, G82), (E6, G83), (E6, G84), (E6, G85), (E6, G86), (E6, G87), (E6, G88) (E6, G89), (E6, G90) (E6, G91), (E6, G92), (E6, G93) (E6, G94) (E6, G95) (E6, G96) (E6, G97), (E6, G98), (E6, G99), (E6, G100), (E6, G101) (E6, G102) (E6, G103), (E6, G104) (E6, G105) (E6, G106) (E6, G107), (E6, G108), (E6, G109), (E6, G110) (E6, G111), (E6, G112) (E6, G113), (E6, G114), (E6, G115) (E6, G116), (E6, G117), (E6, G118), (E6, G119), (E6, G120) (E6, G121), (E6, G122) (E6, G123), (E6, G124), (E6, G125) (E6, G126), (E6, G127) (E6, G128) (E6, G129) (E6, G130), (E6, G131), (E6, G132), (E6, G133), (E6, G134), (E6, G135), (E6, G136), (E6, G137), (E6, G138), (E6, G139), (E6, G140), (E6, G141), (E6, G142), (E6, G143), (E6, G144), (E6, G145), (E6, G146)
(E7, G1) (E7, G2), (E7, G3), (E7, G4), (E7, G5), (E7, G6), (E7, G7), (E7, G8) (E7, G9), (E7, G10), (E7, G11) (E7, G12), (E7, G13), (E7, G14), (E7, G15), (E7, G16), (E7, G17), (E7, G18), (E7, G19), (E7, G20), (E7, G21), (E7, G22), (E7, G23), (E7, G24), (E7, G25), (E7, G26), (E7, G27), (E7, G28), (E7, G29), (E7, G30), (E7, G31), (E7, G32), (E7, G33), (E7, G34), (E7, G35) (E7, G36) (E7, G37), (E7, G38), (E7, G39), (E7, G40), (E7, G41) (E7, G42), (E7, G43), (E7, G44), (E7, G45), (E7, G46), (E7, G47), (E7, G48), (E7, G49), (E7, G50), (E7, G51), (E7, G52), (E7, G53), (E7, G54), (E7, G55), (E7, G56), (E7, G57), (E7, G58), (E7, G59), (E7, G60), (E7, G61), (E7, G62), (E7, G63), (E7, G64), (E7, G65), (E7, G66), (E7, G67), (E7, G68), (E7, G69), (E7, G70), (E7, G71), (E7, G72), (E7, G73), (E7, G74), (E7, G75), (E7, G76), (E7, G77), (E7, G78), (E7, G79), (E7, G80), (E7, G81), (E7, G82), (E7, G83), (E7, G84), (E7, G85), (E7, G86), (E7, G87), (E7, G88), (E7, G89), (E7, G90), (E7, G91), (E7, G92), (E7, G93), (E7, G94), (E7, G95), (E7, G96), (E7, G97), (E7, G98), (E7, G99), (E7, G100) (E7, G101) (E7, G102), (E7, G103), (E7, G104), (E7, G105), (E7, G106), (E7, G107), (E7, G108), (E7, G109), (E7, G110) (E7, G111), (E7, G112), (E7, G113), (E7, G114), (E7, G115) (E7, G116), (E7, G117), (E7, G118), (E7, G119), (E7, G120), (E7, G121), (E7, G122), (E7, G123), (E7, G124), (E7, G125), (E7, G126), (E7, G127), (E7, G128), (E7, G129), (E7, G130), (E7, G131) (E7, G132), (E7, G133), (E7, G134), (E7, G135), (E7, G136), (E7, G137), (E7, G138), (E7, G139), (E7, G140), (E7, G141) (E7, G142), (E7, G143), (E7, G144), (E7, G145), (E7, G146),
(E8, G1) (E8, G2), (E8, G3), (E8, G4), (E8, G5), (E8, G6), (E8, G7), (E8, G8), (E8, G9), (E8, G10) (E8, G11), (E8, G12), (E8, G13) (E8, G14), (E8, G15), (E8, G16), (E8, G17), (E8, G18), (E8, G19), (E8, G20), (E8, G21), (E8, G22), (E8, G23), (E8, G24), (E8, G25), (E8, G26), (E8, G27), (E8, G28), (E8, G29), (E8, G30), (E8, G31), (E8, G32), (E8, G33), (E8, G34), (E8, G35), (E8, G36), (E8, G37), (E8, G38), (E8, G39), (E8, G40), (E8, G41), (E8, G42), (E8, G43), (E8, G44), (E8, G45), (E8, G46), (E8, G47), (E8, G48), (E8, G49), (58, G50), (E8, G51), (E8, G52), (E8, G53), (E8, G54), (E8, G55), (E8, G56), (E8, G57), (E8, G58), (E8, G59), (E8, G60), (E8, G61), (E8, G62), (E8, G63), (E8, G64), (E8, G65), (E8, G66), (58, G67), (E8, G68), (E8, G69), (E8, G70), (E8, G71), (E8, G72), (E8, G73), (E8, G74), (E8, G75), (E8, G76), (E8, G77), (E8, G78), (E8, G79), (E8, G80), (E8, G81), (E8, G82), (E8, G83), (E8, G84), (E8, G85), (E8, G86), (E8, G87), (E8, G88), (E8, G89), (E8, G90), (E8, G91), (E8, G92), (E8, G93), (E8, G94), (E8, G95), (E8, G96), (E8, G97), (E8, G98), (E8, G99), (E8, G100), (E8, G101), (E8, G102), (E8, G103), (E8, G104), (E8, G105), (E8, G106), (E8, G107), (E8, G108), (E8, G109), (E8, G110), (E8, G111), (E8, G112), (E8, G113), (E8, G114), (E8, G115), (E8, G116), (E8, G117), (E8, G118), (E8, G119), (E8, G120), (E8, G121), (E8, G122), (E8, G123), (E8, G124), (E8, G125), (E8, G126), (E8, G127), (E8, G128), (E8, G129), (E8, G130), (E8, G131), (E8, G132), (E8, G133), (E8, G134), (E8, G135), (E8, G136), (E8, G137), (E8, G138), (E8, G139), (E8, G140), (E8, G141), (E8, G142), (E8, G143), (E8, G144), (E8, G145), (E8, G146),
(E9, G1), (E9, G2), (E9, G3), (E9, G4), (E9, G5), (E9, G6), (E9, G7), (E9, G8), (E9, G9), (E9, G10), (E9, G11), (E9, G12), (E9, G13), (E9, G14), (E9, G15), (E9, G16), (E9, G17), (E9, G18), (E9, G19), (E9, G20), (E9, G21), (E9, G22), (E9, G23), (E9, G24), (E9, G25), (E9, G26), (E9, G27), (E9, G28), (E9, G29), (E9, G30), (E9, G31), (E9, G32), (E9, G33), (E9, G34), (E9, G35), (E9, G36), (E9, G37), (E9, G38), (E9, G39), (E9, G40), (E9, G41), (E9, G42), (E9, G43), (E9, G44), (E9, G45), (E9, G46), (E9, G47), (E9, G48), (E9, G49), (E9, G50), (E9, G51), (E9, G52), (E9, G53), (E9, G54), (E9, G55), (E9, G56), (E9, G57), (E9, G58), (E9, G59), (E9, G60), (E9, G61), (E9, G62), (E9, G63), (E9, G64), (E9, G65), (E9, G66), (E9, G67), (E9, G68), (E9, G69), (E9, G70), (E9, G71), (E9, G72), (E9, G73), (E9, G74), (E9, G75), (E9, G76), (E9, G77), (E9, G78), (E9, G79), (E9, G80), (E9, G81), (E9, G82), (E9, G83), (E9, G84), (E9, G85), (E9, G86), (E9, G87), (E9, G88), (E9, G89), (E9, G90), (E9, G91), (E9, G92), (E9, G93), (E9, G94), (E9, G95), (E9, G96), (E9, G97), (E9, G98), (E9, G99), (E9, G100), (E9, G101), (E9, G102), (E9, G103), (E9, G104), (E9, G105), (E9, G106), (E9, G107), (E9, G108), (E9, G109), (E9, G110), (E9, G111), (E9, G112), (E9, G113), (E9, G114), (E9, G115), (E9, G116), (E9, G117), (E9, G118), (E9, G119), (E9, G120), (E9, G121), (E9, G122), (E9, G123), (E9, G124), (E9, G125), (E9, G126), (E9, G127), (E9, G128), (E9, G129), (E9, G130), (E9, G131), (E9, G132), (E9, G133), (E9, G134), (E9, G135), (E9, G136), (E9, G137), (E9, G138), (E9, G139), (E9, G140), (E9, G141), (E9, G142), (E9, G143), (E9, G144), (E9, G145), (E9, G146),
(E10, G1), (E10, G2), (E10, G3), (E10, G4), (E10, G5), (E10, G6), (E10, G7), (E10, G8), (E10, G9), (E10, G10), (E10, G11), (E10, G12), (E10, G13), (E10, G14), (E10, G15), (E10, G16), (E10, G17), (E10, G18), (E10, G19), (E10, G20), (E10, G21), (E10, G22), (E10, G23), (E10, G24), (E10, G25), (E10, G26), (E10, G27), (E10, G28), (E10, G29), (E10, G30), (E10, G31), (E10, G32), (E10, G33), (E10, G34), (E10, G35), (E10, G36), (E10, G37), (E10, G38), (E10, G39), (E10, G40), (E10, G41), (E10, G42), (E10, G43), (E10, G44), (E10, G45), (E10, G46), (E10, G47), (E10, G48), (E10, G49), (E10, G50), (E10, G51), (E10, G52), (E10, G53), (E10, G54), (E10, G55), (E10, G56), (E10, G57), (E10, G58), (E10, G59), (E10, G60), (E10, G61), (E10, G62), (E10, G63), (E10, G64), (E10, G65), (E10, G66), (E10, G67), (E10, G68), (E10, G69), (E10, G70), (E10, G71), (E10, G72), (E10, G73), (E10, G74), (E10, G75), (E10, G76), (E10, G77), (E10, G78), (E10, G79), (E10, G80), (E10, G81), (E10, G82), (E10, G83), (E10, G84), (E10, G85), (E10, G86), (E10, G87), (E10, G88), (E10, G89), (E10, G90), (E10, G91), (E10, G92), (E10, G93), (E10, G94), (E10, G95), (E10, G96), (E10, G97), (E10, G98), (E10, G99), (E10, G100), (E10, G101), (E10, G102), (E10, G103), (E10, G104), (E10, G105), (E10, G106), (E10, G107), (E10, G108), (E10, G109), (E10, G110), (E10, G111), (E10, G112), (E10, G113), (E10, G114), (E10, G115), (E10, G116), (E10, G117), (E10, G118), (E10, G119), (E10, G120), (E10, G121), (E10, G122), (E10, G123), (E10, G124), (E10, G125), (E10, G126), (E10, G127), (E10, G128), (E10, G129), (E10, G130), (E10, G131), (E10, G132), (E10, G133), (E10, G134), (E10, G135), (E10, G136), (E10, G137), (E10, G138), (E10, G139), (E10, G140), (E10, G141), (E10, G142), (E10, G143), (E10, G144), (E10, G145), (E10, G146),
(E11, G1), (E11, G2), (E11, G3), (E11, G4), (E11, G5), (E11, G6), (E11, G7), (E11, G8), (E11, G9), (E11, G10), (E11, G11), (E11, G12), (E11, G13), (E11, G14), (E11, G15), (E11, G16), (E11, G17), (E11, G18), (E11, G19), (E11, G20), (E11, G21), (E11, G22), (E11, G23), (E11, G24), (E11, G25), (E11, G26), (E11, G27), (E11, G28), (E11, G29), (E11, G30), (E11, G31), (E11, G32), (E11, G33), (E11, G34), (E11, G35), (E11, G36), (E11, G37), (E11, G38), (E11, G39), (E11, G40), (E11, G41), (E11, G42), (E11, G43), (E11, G44), (E11, G45), (E11, G46), (E11, G47), (E11, G48), (E11, G49), (E11, G50), (E11, G51), (E11, G52), (E11, G53), (E11, G54), (E11, G55), (E11, G56), (E11, G57), (E11, G58), (E11, G59), (E11, G60), (E11, G61), (E11, G62), (E11, G63), (E11, G64), (E11, G65), (E11, G66), (E11, G67), (E11, G68), (E11, G69), (E11, G70), (E11, G71), (E11, G72), (E11, G73), (E11, G74), (E11, G75), (E11, G76), (E11, G77), (E11, G78), (E11, G79), (E11, G80), (E11, G81), (E11, G82), (E11, G83), (E11, G84), (E11, G85), (E11, G86), (E11, G87), (E11, G88), (E11, G89), (E11, G90), (E11, G91), (E11, G92), (E11, G93), (E11, G94), (E11, G95), (E11, G96), (E11, G97), (E11, G98), (E11, G99), (E11, G100), (E11, G101), (E11, G102), (E11, G103), (E11, G104), (E11, G105), (E11, G106), (E11, G107), (E11, G108), (E11, G109), (E11, G110), (E11, G111), (E11, G112), (E11, G113), (E11, G114), (E11, G115), (E11, G116), (E11, G117), (E11, G118), (E11, G119), (E11, G120), (E11, G121), (E11, G122), (E11, G123), (E11, G124), (E11, G125), (E11, G126), (E11, G127), (E11, G128), (E11, G129), (E11, G130), (E11, G131), (E11, G132), (E11, G133), (E11, G134), (E11, G135), (E11, G136), (E11, G137), (E11, G138), (E11, G139), (E11, G140), (E11, G141), (E11, G142), (E11, G143), (E11, G144), (E11, G145), (E11, G146),
(E12, G1), (E12, G2), (E12, G3), (E12, G4), (E12, G5), (E12, G6), (E12, G7), (E12, G8), (E12, G9), (E12, G10), (E12, G11), (E12, G12), (E12, G13), (E12, G14), (E12, G15), (E12, G16), (E12, G17), (E12, G18), (E12, G19), (E12, G20), (E12, G21), (E12, G22), (E12, G23), (E12, G24), (E12, G25), (E12, G26), (E12, G27), (E12, G28), (E12, G29), (E12, G30), (E12, G31), (E12, G32), (E12, G33), (E12, G34), (E12, G35), (E12, G36), (E12, G37), (E12, G38), (E12, G39), (E12, G40), (E12, G41), (E12, G42), (E12, G43), (E12, G44), (E12, G45), (E12, G46), (E12, G47), (E12, G48), (E12, G49), (E12, G50), (E12, G51), (E12, G52), (E12, G53), (E12, G54), (E12, G55), (E12, G56), (E12, G57), (E12, G58), (E12, G59), (E12, G60), (E12, G61), (E12, G62), (E12, G63), (E12, G64), (E12, G65), (E12, G66), (E12, G67), (E12, G68), (E12, G69), (E12, G70), (E12, G71), (E12, G72), (E12, G73), (E12, G74), (E12, G75), (E12, G76), (E12, G77), (E12, G78), (E12, G79), (E12, G80), (E12, G81), (E12, G82), (E12, G83), (E12, G84), (E12, G85), (E12, G86), (E12, G87), (E12, G88), (E12, G89), (E12, G90), (E12, G91), (E12, G92), (E12, G93), (E12, G94), (E12, G95), (E12, G96), (E12, G97), (E12, G98), (E12, G99), (E12, G100), (E12, G101), (E12, G102), (E12, G103), (E12, G104), (E12, G105), (E12, G106), (E12, G107), (E12, G108), (E12, G109), (E12, G110), (E12, G111), (E12, G112), (E12, G113), (E12, G114), (E12, G115), (E12, G116), (E12, G117), (E12, G118), (E12, G119), (E12, G120), (E12, G121), (E12, G122), (E12, G123), (E12, G124), (E12, G125), (E12, G126), (E12, G127), (E12, G128), (512, G129), (E12, G130), (E12, G131), (E12, G132), (E12, G133), (E12, G134), (E12, G135), (E12, G136), (E12, G137), (E12, G138), (E12, G139), (E12, G140), (E12, G141), (E12, G142), (E12, G143), (E12, G144), (E12, G145), (E12, G146),
(E13, G1), (E13, G2), (E13, G3), (E13, G4), (E13, G5), (E13, G6), (E13, G7), (E13, G8), (E13, G9), (E13, G10), (E13, G11), (E13, G12), (E13, G13), (E13, G14), (E13, G15), (E13, G16), (E13, G17), (E13, G18), (E13, G19), (E13, G20), (E13, G21), (E13, G22), (E13, G23), (E13, G24), (E13, G25), (E13, G26), (E13, G27), (E13, G28), (E13, G29), (E13, G30), (E13, G31), (E13, G32), (E13, G33), (E13, G34), (E13, G35), (E13, G36), (E13, G37), (E13, G38), (E13, G39), (E13, G40), (E13, G41), (E13, G42), (E13, G43), (E13, G44), (E13, G45), (E13, G46), (E13, G47), (E13, G48), (E13, G49), (E13, G50), (E13, G51), (E13, G52), (E13, G53), (E13, G54), (E13, G55), (E13, G56), (E13, G57), (E13, G58), (E13, G59), (E13, G60), (E13, G61), (E13, G62), (E13, G63), (E13, G64), (E13, G65), (E13, G66), (E13, G67), (E13, G68), (E13, G69), (E13, G70), (E13, G71), (E13, G72), (E13, G73), (E13, G74), (E13, G75), (E13, G76), (E13, G77), (E13, G78), (E13, G79), (E13, G80), (E13, G81), (E13, G82), (E13, G83), (E13, G84), (E13, G85), (E13, G86), (E13, G87), (E13, G88), (E13, G89), (E13, G90), (E13, G91), (E13, G92), (E13, G93), (E13, G94), (E13, G95), (E13, G96), (E13, G97), (E13, G98), (E13, G99), (E13, G100), (E13, G101), (E13, G102), (E13, G103), (E13, G104), (E13, G105), (E13, G106), (E13, G107), (E13, G108), (E13, G109), (E13, G110), (E13, G111), (E13, G112), (E13, G113), (E13, G114), (E13, G115), (E13, G116), (E13, G117), (E13, G118), (E13, G119), (E13, G120), (E13, G121), (E13, G122), (E13, G123), (E13, G124), (E13, G125), (E13, G126), (E13, G127), (E13, G128), (E13, G129), (E13, G130), (E13, G131), (E13, G132), (E13, G133), (E13, G134), (E13, G135), (E13, G136), (E13, G137), (E13, G138), (E13, G139), (E13, G140), (E13, G141), (E13, G142), (E13, G143), (E13, G144), (E13, G145), (E13, G146),
(E14, G1), (E14, G2), (E14, G3), (E14, G4), (E14, G5), (E14, G6), (E14, G7), (E14, G8), (E14, G9), (E14, G10), (E14, G11), (E14, G12), (E14, G13), (E14, G14), (E14, G15), (E14, G16), (E14, G17), (E14, G18), (E14, G19), (E14, G20), (E14, G21), (E14, G22), (E14, G23), (E14, G24), (E14, G25), (E14, G26), (E14, G27), (E14, G28), (E14, G29), (E14, G30), (E14, G31), (E14, G32), (E14, G33), (E14, G34), (E14, G35), (E14, G36), (E14, G37), (E14, G38), (E14, G39), (E14, G40), (E14, G41), (E14, G42), (E14, G43), (E14, G44), (E14, G45), (E14, G46), (E14, G47), (E14, G48), (E14, G49), (E14, G50), (E14, G51), (E14, G52), (E14, G53), (E14, G54), (E14, G55), (E14, G56), (E14, G57), (E14, G58), (E14, G59), (E14, G60), (E14, G61), (E14, G62), (E14, G63), (E14, G64), (E14, G65), (E14, G66), (E14, G67), (E14, G68), (E14, G69), (E14, G70), (E14, G71), (E14, G72), (E14, G73), (E14, G74), (E14, G75), (E14, G76), (E14, G77), (E14, G78), (E14, G79), (E14, G80), (E14, G81), (E14, G82), (E14, G83), (E14, G84), (E14, G85), (E14, G86), (E14, G87), (E14, G88), (E14, G89), (E14, G90), (E14, G91), (E14, G92), (E14, G93), (E14, G94), (E14, G95), (E14, G96), (E14, G97), (E14, G98), (E14, G99), (E14, G100), (E14, G101), (E14, G102), (E14, G103), (E14, G104), (E14, G105), (E14, G106), (E14, G107), (E14, G108), (E14, G109), (E14, G110), (E14, G111), (E14, G112), (E14, G113), (E14, G114), (E14, G115), (E14, G116), (E14, G117), (E14, G118), (E14, G119), (E14, G120), (E14, G121), (E14, G122), (E14, G123), (E14, G124), (E14, G125), (E14, G126), (E14, G127), (E14, G128), (E14, G129), (E14, G130), (E14, G131), (E14, G132), (E14, G133), (E14, G134), (E14, G135), (E14, G136), (E14, G137), (E14, G138), (E14, G139), (E14, G140), (E14, G141), (E14, G142), (E14, G143), (E14, G144), (E14, G145), (E14, G146), (E15, G1), (E15, G2), (E15, G3), (E15, G4), (E15, G5), (E15, G6), (E15, G7), (E15, G8), (E15, G9), (E15, G10), (E15, G11), (E15, G12), (E15, G13), (E15, G14), (E15, G15), (E15, G16), (E15, G17), (E15, G18), (E15, G19), (E15, G20), (E15, G21), (E15, G22), (E15, G23), (E15, G24), (E15, G25), (E15, G26), (E15, G27), (E15, G28), (E15, G29), (E15, G30), (E15, G31), (E15, G32), (E15, G33), (E15, G34), (E15, G35), (E15, G36), (E15, G37), (E15, G38), (E15, G39), (E15, G40), (E15, G41), (E15, G42), (E15, G43), (E15, G44), (E15, G45), (E15, G46), (E15, G47), (E15, G48), (E15, G49), (E15, G50), (E15, G51), (E15, G52), (E15, G53), (E15, G54), (E15, G55), (E15, G56), (E15, G57), (E15, G58), (E15, G59), (E15, G60), (E15, G61), (E15, G62), (E15, G63), (E15, G64), (E15, G65), (E15, G66), (E15, G67), (E15, G68), (E15, G69), (E15, G70), (E15, G71), (E15, G72), (E15, G73), (E15, G74), (E15, G75), (E15, G76), (E15, G77), (E15, G78), (E15, G79), (E15, G80), (E15, G81), (E15, G82), (E15, G83), (E15, G84), (E15, G85), (E15, G86), (E15, G87), (E15, G88), (E15, G89), (E15, G90), (E15, G91), (E15, G92), (E15, G93), (E15, G94), (E15, G95), (E15, G96), (E15, G97), (E15, G98), (E15, G99), (E15, G100), (E15, G101), (E15, G102), (E15, G103), (E15, G104), (E15, G105), (E15, G106), (E15, G107), (E15, G108), (E15, G109), (E15, G110), (E15, G111), (E15, G112), (E15, G113), (E15, G114), (E15, G115), (E15, G116), (E15, G117), (E15, G118), (E15, G119), (E15, G120), (E15, G121), (E15, G122), (E15, G123), (E15, G124), (E15, G125), (E15, G126), (E15, G127), (E15, G128), (E15, G129), (E15, G130), (E15, G131), (E15, G132), (E15, G133), (E15, G134), (E15, G135), (E15, G136), (E15, G137), (E15, G138), (E15, G139), (E15, G140), (E15, G141), (E15, G142), (E15, G143), (E15, G144), (E15, G145), (E15, G146), (E16, G1), (E16, G2), (E16, G3), (E16, G4), (E16, G5), (E16, G6), (E16, G7), (E16, G8), (E16, G9), (E16, G10), (E16, G11), (E16, G12), (E16, G13), (E16, G14), (E16, G15), (E16, G16), (E16, G17), (E16, G18), (E16, G19), (E16, G20), (E16, G21), (E16, G22), (E16, G23), (E16, G24), (E16, G25), (E16, G26), (E16, G27), (E16, G28), (E16, G29), (E16, G30), (E16, G31), (E16, G32), (E16, G33), (E16, G34), (E16, G35), (E16, G36), (E16, G37), (E16, G38), (E16, G39), (E16, G40), (E16, G41), (E16, G42), (E16, G43), (E16, G44), (E16, G45), (E16, G46), (E16, G47), (E16, G48), (E16, G49), (E16, G50), (E16, G51), (E16, G52), (E16, G53), (E16, G54), (E16, G55), (E16, G56), (E16, G57), (E16, G58), (E16, G59), (E16, G60), (E16, G61), (E16, G62), (E16, G63), (E16, G64), (E16, G65), (E16, G66), (E16, G67), (E16, G68), (E16, G69), (E16, G70), (E16, G71), (E16, G72), (E16, G73), (E16, G74), (E16, G75), (E16, G76), (E16, G77), (E16, G78), (E16, G79), (E16, G80), (E16, G81), (E16, G82), (E16, G83), (E16, G84), (E16, G85), (E16, G86), (E16, G87), (E16, G88), (E16, G89), (E16, G90), (E16, G91), (E16, G92), (E16, G93), (E16, G94), (E16, G95), (E16, G96), (E16, G97), (E16, G98), (E16, G99), (E16, G100), (E16, G101), (E16, G102), (E16, G103), (E16, G104), (E16, G105), (E16, G106), (E16, G107), (E16, G108), (E16, G109), (E16, G110), (E16, G111), (E16, G112), (E16, G113), (E16, G114), (E16, G115), (E16, G116), (E16, G117), (E16, G118), (E16, G119), (E16, G120), (E16, G121), (E16, G122), (E16, G123), (E16, G124), (E16, G125), (E16, G126), (E16, G127), (E16, G128), (E16, G129), (E16, G130), (E16, G131), (E16, G132), (E16, G133), (E16, G134), (E16, G135), (E16, G136), (E16, G137), (E16, G138), (E16, G139), (E16, G140), (E16, G141), (E16, G142), (E16, G143), (E16, G144), (E16, G145), (E16, G146), (E17, G1), (E17, G2), (E17, G3), (E17, G4), (E17, G5), (E17, G6), (E17, G7), (E17, G8), (E17, G9), (E17, G10), (E17, G11), (E17, G12), (E17, G13), (E17, G14), (E17, G15), (E17, G16), (E17, G17), (E17, G18), (E17, G19), (E17, G20), (E17, G21), (E17, G22), (E17, G23), (E17, G24), (E17, G25), (E17, G26), (E17, G27), (E17, G28), (E17, G29), (E17, G30), (E17, G31), (E17, G32), (E17, G33), (E17, G34), (E17, G35), (E17, G36), (E17, G37), (E17, G38), (E17, G39), (E17, G40), (E17, G41), (E17, G42), (E17, G43), (E17, G44), (E17, G45), (E17, G46), (E17, G47), (E17, G48), (E17, G49), (E17, G50), (E17, G51), (E17, G52), (E17, G53), (E17, G54), (E17, G55), (E17, G56), (E17, G57), (E17, G58), (E17, G59), (E17, G60), (E17, G61), (E17, G62), (E17, G63), (E17, G64), (E17, G65), (E17, G66), (E17, G67), (E17, G68), (E17, G69), (E17, G70), (E17, G71), (E17, G72), (E17, G73), (E17, G74), (E17, G75), (E17, G76), (E17, G77), (E17, G78), (E17, G79), (E17, G80), (E17, G81), (E17, G82), (E17, G83), (E17, G84), (E17, G85), (E17, G86), (E17, G87), (E17, G88), (E17, G89), (E17, G90), (E17, G91), (E17, G92), (E17, G93), (E17, G94), (E17, G95), (E17, G96), (E17, G97), (E17, G98), (E17, G99), (E17, G100), (E17, G101), (E17, G102), (E17, G103), (E17, G104), (E17, G105), (E17, G106), (E17, G107), (E17, G108), (E17, G109), (E17, G110), (E17, G111), (E17, G112), (E17, G113), (E17, G114), (E17, G115), (E17, G116), (E17, G117), (E17, G118), (E17, G119), (E17, G120), (E17, G121), (E17, G122), (E17, G123), (E17, G124), (E17, G125), (E17, G126), (E17, G127), (E17, G128), (E17, G129), (E17, G130), (E17, G131), (E17, G132), (E17, G133), (E17, G134), (E17, G135), (E17, G136), (E17, G137), (E17, G138), (E17, G139), (E17, G140), (E17, G141), (E17, G142), (E17, G143), (E17, G144), (E17, G145), (E17, G146), (E18, G1), (E18, G2), (E18, G3), (E18, G4), (E18, G5), (E18, G6), (E18, G7), (E18, G8), (E18, G9), (E18, G10), (E18, G11), (E18, G12), (E18, G13), (E18, G14), (E18, G15), (E18, G16), (E18, G17), (E18, G18), (E18, G19), (E18, G20), (E18, G21), (E18, G22), (E18, G23), (E18, G24), (E18, G25), (E18, G26), (E18, G27), (E18, G28), (E18, G29), (E18, G30), (E18, G31), (E18, G32), (E18, G33), (E18, G34), (E18, G35), (E18, G36), (E18, G37), (E18, G38), (E18, G39), (E18, G40), (E18, G41), (E18, G42), (E18, G43), (E18, G44), (E18, G45), (E18, G46), (E18, G47), (E18, G48), (E18, G49), (E18, G50), (E18, G51), (E18, G52), (E18, G53), (E18, G54), (E18, G55), (E18, G56), (E18, G57), (E18, G58), (E18, G59), (E18, G60), (E18, G61), (E18, G62), (E18, G63), (E18, G64), (E18, G65), (E18, G66), (E18, G67), (E18, G68), (E18, G69), (E18, G70), (E18, G71), (E18, G72), (E18, G73), (E18, G74), (E18, G75), (E18, G76), (E18, G77), (E18, G78), (E18, G79), (E18, G80), (E18, G81), (E18, G82), (E18, G83), (E18, G84), (E18, G85), (E18, G86), (E18, G87), (E18, G88), (E18, G89), (E18, G90), (E18, G91), (E18, G92), (E18, G93), (E18, G94), (E18, G95), (E18, G96), (E18, G97), (E18, G98), (E18, G99), (E18, G100), (E18, G101), (E18, G102), (E18, G103), (E18, G104), (E18, G105), (E18, G106), (E18, G107), (E18, G108), (E18, G109), (E18, G110), (E18, G111), (E18, G112), (E18, G113), (E18, G114), (E18, G115), (E18, G116), (E18, G117), (E18, G118), (E18, G119), (E18, G120), (E18, G121), (E18, G122), (E18, G123), (E18, G124), (E18, G125), (E18, G126), (E18, G127), (E18, G128), (E18, G129), (E18, G130), (E18, G131), (E18, G132), (E18, G133), (E18, G134), (E18, G135), (E18, G136), (E18, G137), (E18, G138), (E18, G139), (E18, G140), (E18, G141), (E18, G142), (E18, G143), (E18, G144), (E18, G145), (E18, G146), (E19, G1), (E19, G2), (E19, G3), (E19, G4), (E19, G5), (E19, G6), (E19, G7), (E19, G8), (E19, G9), (E19, G10), (E19, G11), (E19, G12), (E19, G13), (E19, G14), (E19, G15), (E19, G16), (E19, G17), (E19, G18), (E19, G19), (E19, G20), (E19, G21), (E19, G22), (E19, G23), (E19, G24), (E19, G25), (E19, G26), (E19, G27), (E19, G28), (E19, G29), (E19, G30), (E19, G31), (E19, G32), (E19, G33), (E19, G34), (E19, G35), (E19, G36), (E19, G37), (E19, G38), (E19, G39), (E19, G40), (E19, G41), (E19, G42), (E19, G43), (E19, G44), (E19, G45), (E19, G46), (E19, G47), (E19, G48), (E19, G49), (E19, G50), (E19, G51), (E19, G52), (E19, G53), (E19, G54), (E19, G55), (E19, G56), (E19, G57), (E19, G58), (E19, G59), (E19, G60), (E19, G61), (E19, G62), (E19, G63), (E19, G64), (E19, G65), (E19, G66), (E19, G67), (E19, G68), (E19, G69), (E19, G70), (E19, G71), (E19, G72), (E19, G73), (E19, G74), (E19, G75), (E19, G76), (E19, G77), (E19, G78), (E19, G79), (E19, G80), (E19, G81), (E19, G82), (E19, G83), (E19, G84), (E19, G85), (E19, G86), (E19, G87), (E19, G88), (E19, G89), (E19, G90), (E19, G91), (E19, G92), (E19, G93), (E19, G94), (E19, G95), (E19, G96), (E19, G97), (E19, G98), (E19, G99), (E19, G100), (E19, G101), (E19, G102), (E19, G103), (E19, G104), (E19, G105), (E19, G106), (E19, G107), (E19, G108), (E19, G109), (E19, G110), (E19, G111), (E19, G112), (E19, G113), (E19, G114), (E19, G115), (E19, G116), (E19, G117), (E19, G118), (E19, G119), (E19, G120), (E19, G121), (E19, G122), (E19, G123), (E19, G124), (E19, G125), (E19, G126), (E19, G127), (E19, G128), (E19, G129), (E19, G130), (E19, G131), (E19, G132), (E19, G133), (E19, G134), (E19, G135), (E19, G136), (E19, G137), (E19, G138), (E19, G139), (E19, G140), (E19, G141), (E19, G142), (E19, G143), (E19, G144), (E19, G145), (E19, G146), (E20, G1), (E20, G2), (E20, G3), (E20, G4), (E20, G5), (E20, G6), (E20, G7), (E20, G8), (E20, G9), (E20, G10), (E20, G11), (E20, G12), (E20, G13), (E20, G14), (E20, G15), (E20, G16), (E20, G17), (E20, G18), (E20, G19), (E20, G20), (E20, G21), (E20, G22), (E20, G23), (E20, G24), (E20, G25), (E20, G26), (E20, G27), (E20, G28), (E20, G29), (E20, G30), (E20, G31), (E20, G32), (E20, G33), (E20, G34), (E20, G35), (E20, G36), (E20, G37), (E20, G38), (E20, G39), (E20, G40), (E20, G41), (E20, G42), (E20, G43), (E20, G44), (E20, G45), (E20, G46), (E20, G47), (E20, G48), (E20, G49), (E20, G50), (E20, G51), (E20, G52), (E20, G53), (E20, G54), (E20, G55), (E20, G56), (E20, G57), (E20, G58), (E20, G59), (E20, G60), (E20, G61), (E20, G62), (E20, G63), (E20, G64), (E20, G65), (E20, G66), (E20, G67), (E20, G68), (E20, G69), (E20, G70), (E20, G71), (E20, G72), (E20, G73), (E20, G74), (E20, G75), (E20, G76), (E20, G77), (E20, G78), (E20, G79), (E20, G80), (E20, G81), (E20, G82), (E20, G83), (E20, G84), (E20, G85), (E20, G86), (E20, G87), (E20, G88), (E20, G89), (E20, G90), (E20, G91), (E20, G92), (E20, G93), (E20, G94), (E20, G95), (E20, G96), (E20, G97), (E20, G98), (E20, G99), (E20, G100), (E20, G101), (E20, G102), (E20, G103), (E20, G104), (E20, G105), (E20, G106), (E20, G107), (E20, G108), (E20, G109), (E20, G110), (E20, G111), (E20, G112), (E20, G113), (E20, G114), (E20, G115), (E20, G116), (E20, G117), (E20, G118), (E20, G119), (E20, G120), (E20, G121), (E20, G122), (E20, G123), (E20, G124), (E20, G125), (E20, G126), (E20, G127), (E20, G128), (E20, G129), (E20, G130), (E20, G131), (E20, G132), (E20, G133), (E20, G134), (E20, G135), (E20, G136), (E20, G137), (E20, G138), (E20, G139), (E20, G140), (E20, G141), (E20, G142), (E20, G143), (E20, G144), (E20, G145), (E20, G146), (E21, G1), (E21, G2), (E21, G3), (E21, G4), (E21, G5), (E21, G6), (E21, G7), (E21, G8), (E21, G9), (E21, G10), (E21, G11), (E21, G12), (E21, G13), (E21, G14), (E21, G15), (E21, G16), (E21, G17), (E21, G18), (E21, G19), (E21, G20), (E21, G21), (E21, G22), (E21, G23), (E21, G24), (E21, G25), (E21, G26), (E21, G27), (E21, G28), (E21, G29), (E21, G30), (E21, G31), (E21, G32), (E21, G33), (E21, G34), (E21, G35), (E21, G36), (E21, G37), (E21, G38), (E21, G39), (E21, G40), (E21, G41), (E21, G42), (E21, G43), (E21, G44), (E21, G45), (E21, G46), (E21, G47), (E21, G48), (E21, G49), (E21, G50), (E21, G51), (E21, G52), (E21, G53), (E21, G54), (E21, G55), (E21, G56), (E21, G57), (E21, G58), (E21, G59), (E21, G60), (E21, G61), (E21, G62), (E21, G63), (E21, G64), (E21, G65), (E21, G66), (E21, G67), (E21, G68), (E21, G69), (E21, G70), (E21, G71), (E21, G72), (E21, G73), (E21, G74), (E21, G75), (E21, G76), (E21, G77), (E21, G78), (E21, G79), (E21, G80), (E21, G81), (E21, G82), (E21, G83), (E21, G84), (E21, G85), (E21, G86), (E21, G87), (E21, G88), (E21, G89), (E21, G90), (E21, G91), (E21, G92), (E21, G93), (E21, G94), (E21, G95), (E21, G96), (E21, G97), (E21, G98), (E21, G99), (E21, G100), (E21, G101), (E21, G102), (E21, G103), (E21, G104), (E21, G105), (E21, G106), (E21, G107), (E21, G108), (E21, G109), (E21, G110), (E21, G111), (E21, G112), (E21, G113), (E21, G114), (E21, G115), (E21, G116), (E21, G117), (E21, G118), (E21, G119), (E21, G120), (E21, G121), (E21, G122), (E21, G123), (E21, G124), (E21, G125), (E21, G126), (E21, G127), (E21, G128), (E21, G129), (E21, G130), (E21, G131), (E21, G132), (E21, G133), (E21, G134), (E21, G135), (E21, G136), (E21, G137), (E21, G138), (E21, G139), (E21, G140), (E21, G141), (E21, G142), (E21, G143), (E21, G144), (E21, G145), (E21, G146).

In particular, the following compounds are preferable.

TABLE 72

| Compound No. | Structural formula |
|---|---|
| 439 | 5-Cl pyridine-2-carboxamide-N-(3-((2-aminopyridin-3-yl)aminomethyl)phenyl) |
| 440 | 5-Br pyridine-2-carboxamide-N-(3-((2-aminopyridin-3-yl)aminomethyl)phenyl) |
| 441 | 5-F pyridine-2-carboxamide-N-(3-((2-aminopyridin-3-yl)aminomethyl)phenyl) |
| 442 | 3,5-diCl pyridine-2-carboxamide-N-(3-((2-aminopyridin-3-yl)aminomethyl)phenyl) |
| 443 | 3-F pyridine-2-carboxamide-N-(3-((2-aminopyridin-3-yl)aminomethyl)phenyl) |
| 444 | 3,5-diF pyridine-2-carboxamide-N-(3-((2-aminopyridin-3-yl)aminomethyl)phenyl) |
| 445 | 5-Cl-3-NH$_2$ pyridine-2-carboxamide-N-(3-((2-aminopyridin-3-yl)aminomethyl)phenyl) |
| 446 | 5-Me pyridine-2-carboxamide-N-(3-((2-aminopyridin-3-yl)aminomethyl)phenyl) |

TABLE 73

| Compound No. | Structural formula |
|---|---|
| 447 | 5-CF$_3$ pyridine-2-carboxamide-N-(3-((2-aminopyridin-3-yl)aminomethyl)phenyl) |
| 448 | 5-CF$_3$-3-Cl pyridine-2-carboxamide-N-(3-((2-aminopyridin-3-yl)aminomethyl)phenyl) |
| 449 | 5-CF$_3$-3-F pyridine-2-carboxamide-N-(3-((2-aminopyridin-3-yl)aminomethyl)phenyl) |
| 450 | 5-CN pyridine-2-carboxamide-N-(3-((2-aminopyridin-3-yl)aminomethyl)phenyl) |
| 451 | 5-CN-3-Cl pyridine-2-carboxamide-N-(3-((2-aminopyridin-3-yl)aminomethyl)phenyl) |
| 452 | 5-CN-3-F pyridine-2-carboxamide-N-(3-((2-aminopyridin-3-yl)aminomethyl)phenyl) |
| 453 | 5-OH pyridine-2-carboxamide-N-(3-((2-aminopyridin-3-yl)aminomethyl)phenyl) |
| 454 | 5-OMe pyridine-2-carboxamide-N-(3-((2-aminopyridin-3-yl)aminomethyl)phenyl) |

TABLE 74
| Compound No. | Structural formula |
|---|---|
| 455 | 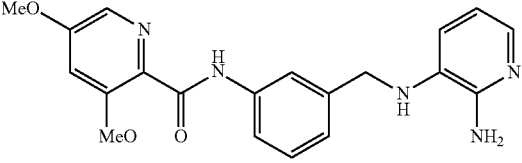 [SMILES: COc1cnc(C(=O)Nc2cccc(CNc3cccnc3N)c2)c(OC)c1] |
| 456 | 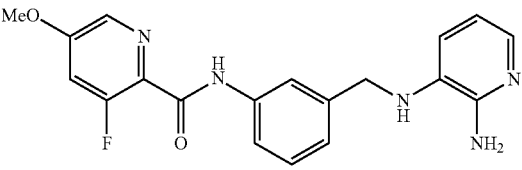 |
| 457 | 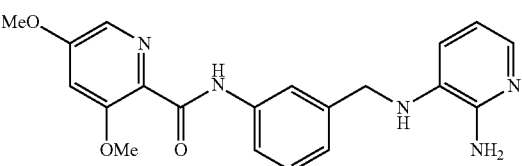 |
| 458 | 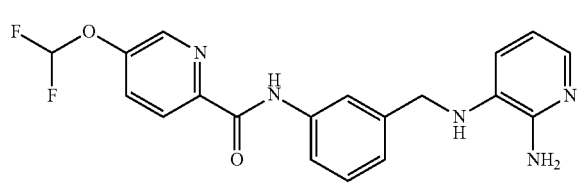 |
| 459 | 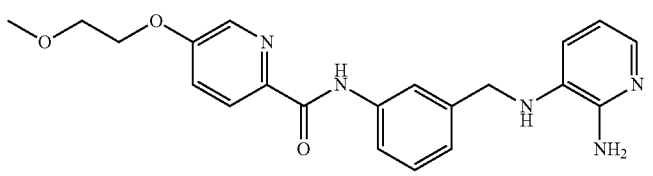 [SMILES: COCCOc1ccc(C(=O)Nc2cccc(CNc3cccnc3N)c2)nc1] |
| 460 | 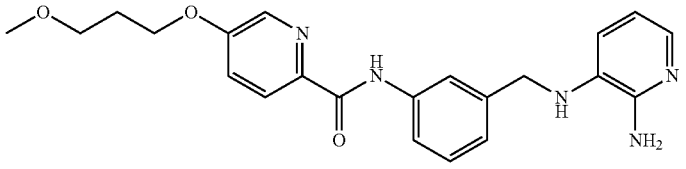 |
| 461 | 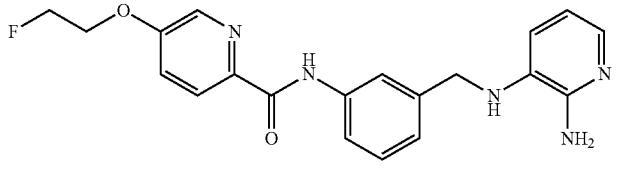 [SMILES: Nc1ncccc1NCc1cccc(NC(=O)c2ccc(OCCF)cn2)c1] |
| 462 | 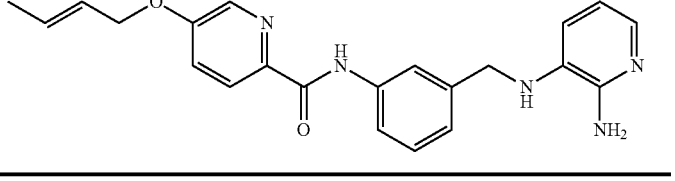 |

TABLE 75

| Compound No. | Structural formula |
|---|---|
| 463 | furan-CH2-O-(pyridine)-C(=O)NH-(phenyl)-CH2-NH-(pyridine-NH2) |
| 464 | CH3-C≡C-CH2-O-(pyridine)-C(=O)NH-(phenyl)-CH2-NH-(pyridine-NH2) |
| 465 | MeS-(pyridine)-C(=O)NH-(phenyl)-CH2-NH-(pyridine-NH2) |
| 466 | O2N-(pyridine)-C(=O)NH-(phenyl)-CH2-NH-(pyridine-NH2) |
| 467 | Me-(pyrazine)-C(=O)NH-(phenyl)-CH2-NH-(pyridine-NH2) |
| 468 | CH3CH2CH2-CH=CH-(pyrazine)-C(=O)NH-(phenyl)-CH2-NH-(pyridine-NH2) |
| 469 | MeO-CH2CH2-CH=CH-(pyrazine)-C(=O)NH-(phenyl)-CH2-NH-(pyridine-NH2) |
| 470 | CH3(CH2)4-(pyrazine)-C(=O)NH-(phenyl)-CH2-NH-(pyridine-NH2) |

TABLE 76

| Compound No. | Structural formula |
|---|---|
| 471 | (5-((E)-3-hydroxyprop-1-en-1-yl)pyrazine-2-carboxamide linked to N-(3-((2-aminopyridin-3-yl)amino)methyl)phenyl) |
| 472 | 5-chloropyrazine-2-carboxamide analog |
| 473 | 5-methoxypyrazine-2-carboxamide analog |
| 474 | 5-ethoxypyrazine-2-carboxamide analog |
| 475 | 5-propoxypyrazine-2-carboxamide analog |
| 476 | 5-butoxypyrazine-2-carboxamide analog |
| 477 | 5-isobutoxypyrazine-2-carboxamide analog |
| 478 | 5-(2-methoxyethoxy)pyrazine-2-carboxamide analog |

TABLE 77
| Compound No. | Structural formula |
|---|---|
| 479 | 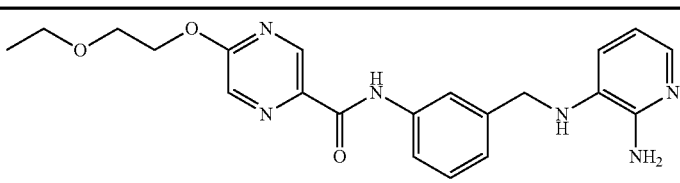 |
| 480 | 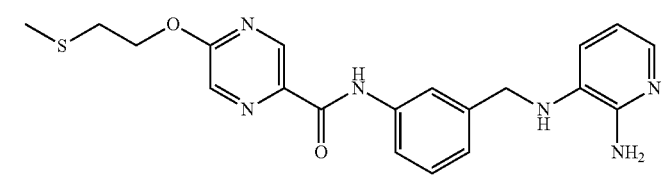 [SMILES: CSCCOc1cnc(C(=O)Nc2cccc(CNc3cccnc3N)c2)cn1] |
| 481 | 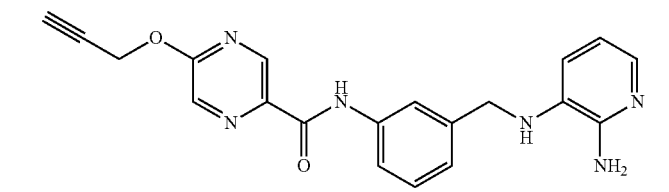 [SMILES: C#CCOc1cnc(C(=O)Nc2cccc(CNc3cccnc3N)c2)cn1] |
| 482 | 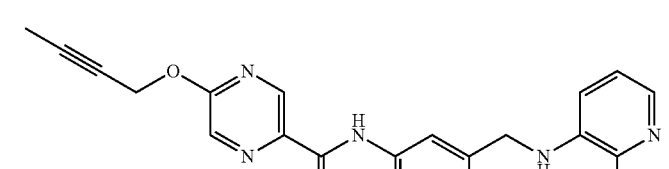 |
| 483 | 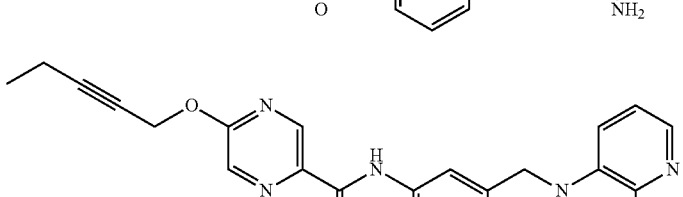 |
| 484 | 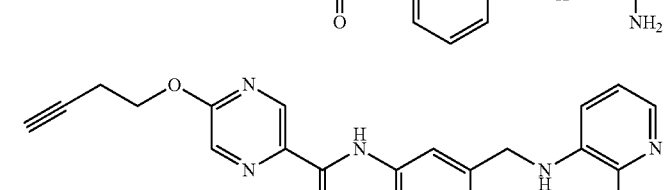 |
| 485 | 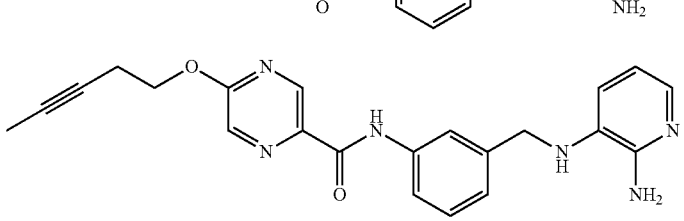 |
| 486 | 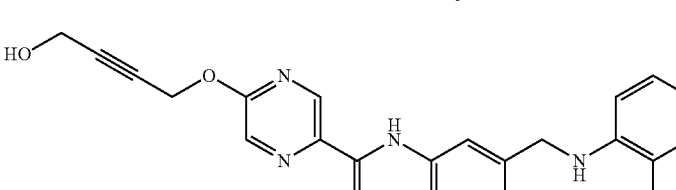 |

TABLE 78

| Compound No. | Structural formula |
|---|---|
| 487 | |
| 488 | |
| 489 | |
| 490 | |
| 491 | |
| 492 | |
| 493 | |

TABLE 78-continued

| Compound No. | Structural formula |
|---|---|
| 494 | |

TABLE 79

| Compound No. | Structural formula |
|---|---|
| 495 | |
| 496 | |
| 497 | |
| 498 | |

TABLE 79-continued

| Compound No. | Structural formula |
|---|---|
| 499 | |
| 500 | |
| 501 | |
| 502 | |

TABLE 80

| Compound No. | Structural formula |
|---|---|
| 503 | |
| 504 | |

TABLE 80-continued
| Compound No. | Structural formula |
|---|---|
| 505 | 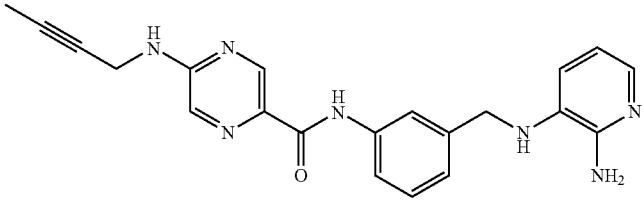 [SMILES: CC#CCNc1cnc(C(=O)Nc2cccc(CNc3cccnc3N)c2)cn1] |
| 506 | 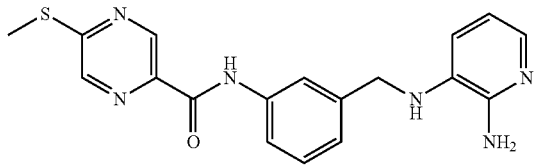 [SMILES: CSc1cnc(C(=O)Nc2cccc(CNc3cccnc3N)c2)cn1] |
| 507 | 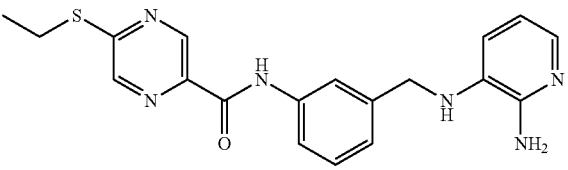 [SMILES: CCSc1cnc(C(=O)Nc2cccc(CNc3cccnc3N)c2)cn1] |
| 508 | 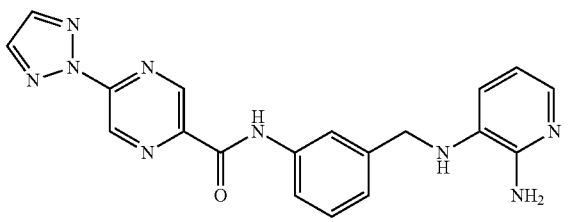 [SMILES: Nc1ncccc1NCc1cccc(NC(=O)c2cnc(-n3nccn3)cn2)c1] |
| 509 | 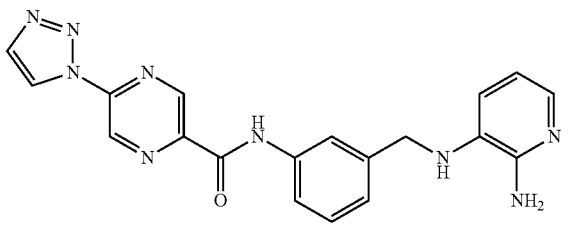 [SMILES: Nc1ncccc1NCc1cccc(NC(=O)c2cnc(-n3ccnn3)cn2)c1] |
| 510 | 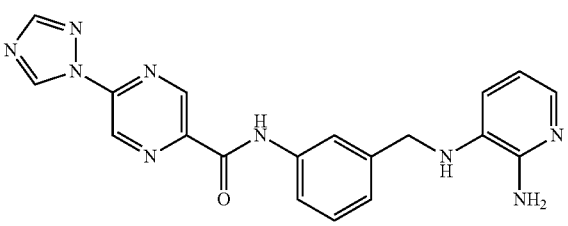 |

TABLE 81
| Compound No. | Structural formula |
|---|---|
| 511 | 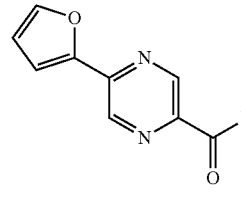 |
| 512 | |
| 513 | |
| 514 | |
| 515 | |
| 516 | |
| 517 | |
TABLE 81-continued
| Compound No. | Structural formula |
|---|---|
| 518 | 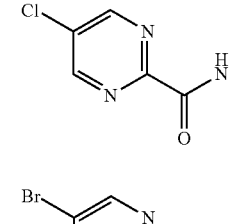 |
TABLE 82
| Compound No. | Structural formula |
|---|---|
| 519 | 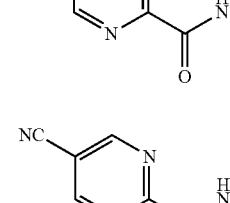 |
| 520 | 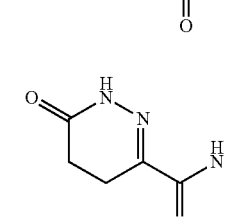 |
| 521 | 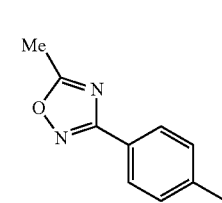 |
| 522 | |
| 523 | 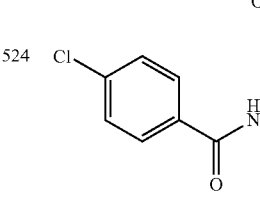 |
| 524 |  |

TABLE 82-continued
| Compound No. | Structural formula |
|---|---|
| 525 | 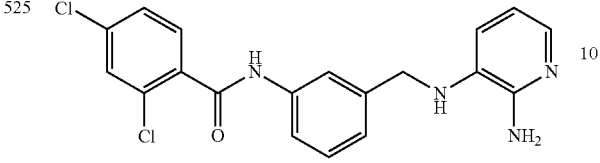 |
| 526 | 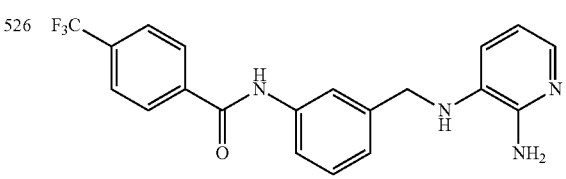 |
TABLE 83
| Compound No. | Structural formula |
|---|---|
| 527 | 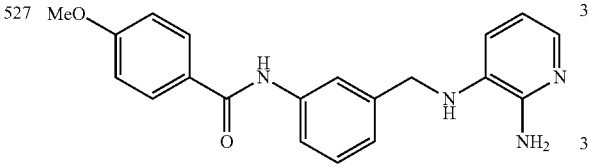 |
| 528 | 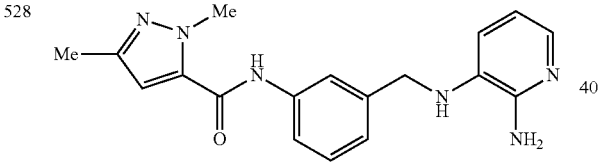 |
| 529 | 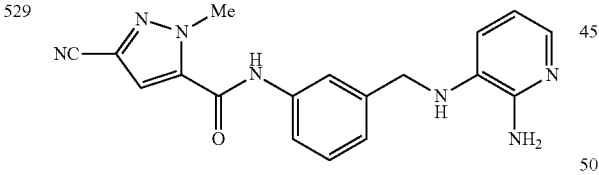 |
| 530 | 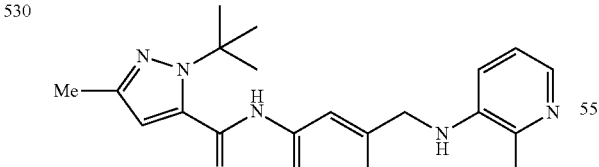 |
| 531 | 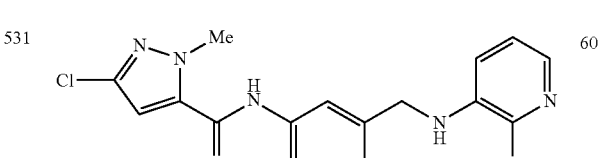 |
TABLE 83-continued
| Compound No. | Structural formula |
|---|---|
| 532 | 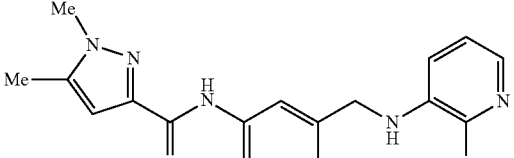 |
| 533 | 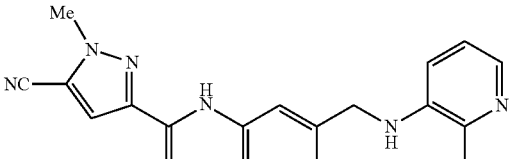 |
| 534 | 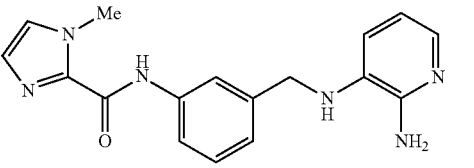 [SMILES: Cn1ccnc1C(=O)Nc1cccc(CNc2cccnc2N)c1] |
TABLE 84
| Compound No. | Structural formula |
|---|---|
| 535 | 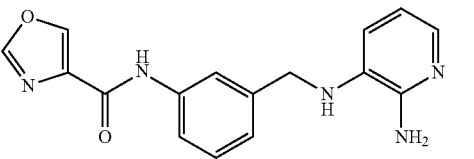 [SMILES: Nc1ncccc1NCc1cccc(NC(=O)c2cocn2)c1] |
| 536 | 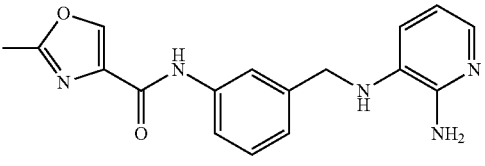 |
| 537 | 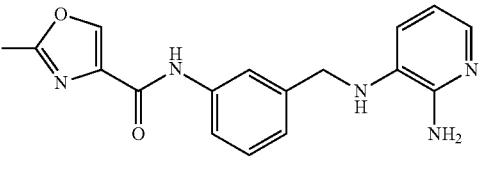 |
| 538 | 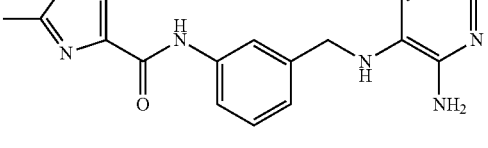 |

TABLE 84-continued
| Compound No. | Structural formula |
|---|---|
| 539 | 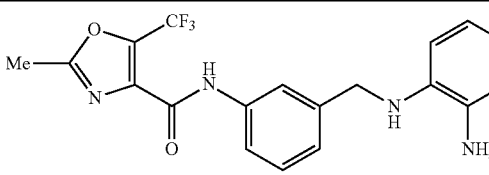 |
| 540 | |
| 541 | |
| 542 | |
TABLE 85
| Compound No. | Structural formula |
|---|---|
| 543 | 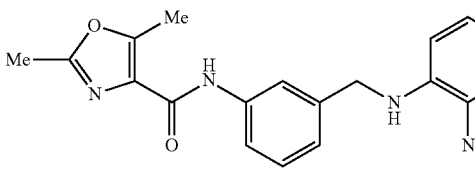 |
| 544 | |
| 545 | |
| 546 | |
TABLE 85-continued
| Compound No. | Structural formula |
|---|---|
| 547 | 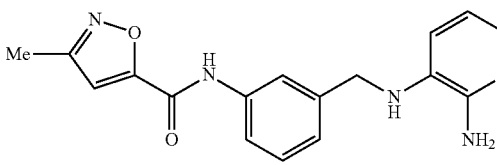 |
| 548 | |
| 549 | |
| 550 | |
TABLE 86
| Compound No. | Structural formula |
|---|---|
| 551 | 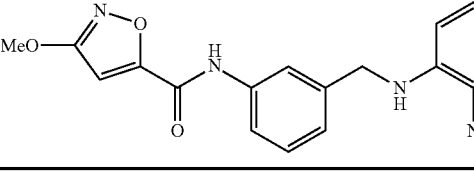 |
| 552 | |
| 553 | |

TABLE 86-continued
| Compound No. | Structural formula |
|---|---|
| 554 | 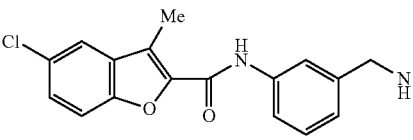 |
| 555 | 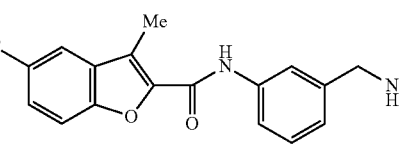 |
| 556 | 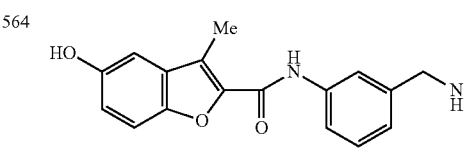 |
| 557 | 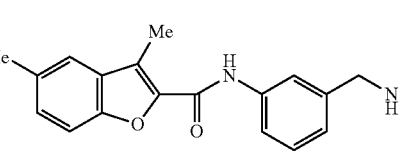 |
| 558 | 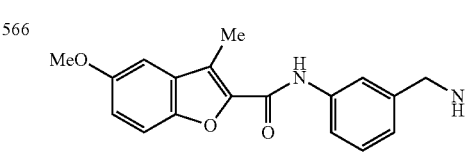 |
TABLE 87
| Compound No. | Structural formula |
|---|---|
| 559 | 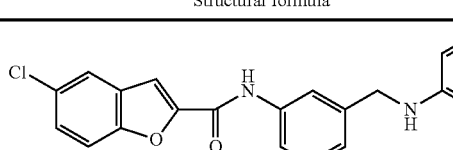 |
| 560 | 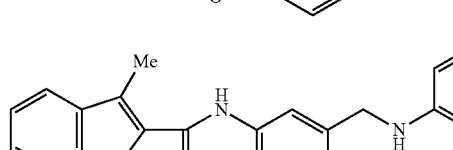 |
| 561 | 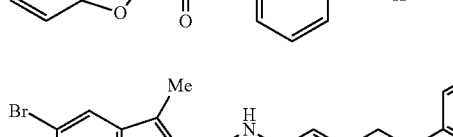 |
TABLE 87-continued
| Compound No. | Structural formula |
|---|---|
| 562 | 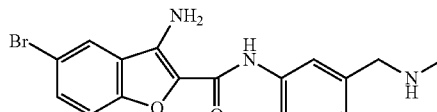 |
| 563 | |
| 564 | |
| 565 | |
| 566 | |
TABLE 88
| Compound No. | Structural formula |
|---|---|
| 567 | 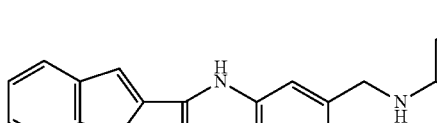 |
| 568 | |
| 569 | 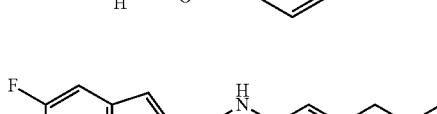 |

TABLE 88-continued
| Compound No. | Structural formula |
|---|---|
| 570 | 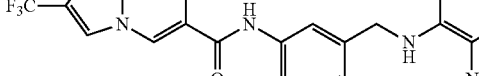 |
| 571 | |
| 572 | |
| 573 | |
| 574 | |
TABLE 89
| Compound No. | Structural formula |
|---|---|
| 575 | |
| 576 | |
| 577 | |
TABLE 89-continued
| Compound No. | Structural formula |
|---|---|
| 578 | 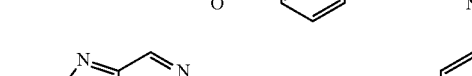 |
| 579 | |
| 580 | |
| 581 | |
| 582 | |
TABLE 90
| Compound No. | Structural formula |
|---|---|
| 583 | |
| 584 | |

TABLE 91
| Compound No. | Structural formula |
|---|---|
| 585 |  |
| 586 | |
| 587 | |
| 588 | |
| 589 | |
| 590 | |
| 591 | |
| 592 | |
TABLE 92
| Compound No. | Structural formula |
|---|---|
| 593 |  |
| 594 | |
| 595 | |
| 596 | |
| 597 | |
| 598 | |
| 599 | |
| 600 | |

TABLE 93

| Compound No. | Structural formula |
|---|---|
| 601 | (structure) |
| 602 | (structure) |
| 603 | (structure) |
| 604 | (structure) |
| 605 | (structure) |
| 606 | (structure) |
| 607 | (structure) |
| 608 | (structure) |

TABLE 94

| Compound No. | Structural formula |
|---|---|
| 609 | (structure) |
| 610 | (structure) |
| 611 | (structure) |
| 612 | (structure) |
| 613 | (structure) |
| 614 | (structure) |
| 615 | (structure) |
| 616 | (structure) |

TABLE 95

| Compound No. | Structural formula |
|---|---|
| 617 | (5-((E)-3-hydroxyprop-1-en-1-yl)pyrazine-2-carboxylic acid [3-[(2-amino-pyridin-3-ylamino)methyl]-4-fluorophenyl]amide) |
| 618 | 5-chloro-pyrazine-2-carboxylic acid [3-[(2-amino-pyridin-3-ylamino)methyl]-4-fluorophenyl]amide |
| 619 | 5-methoxy-pyrazine-2-carboxylic acid [3-[(2-amino-pyridin-3-ylamino)methyl]-4-fluorophenyl]amide |
| 620 | 5-ethoxy-pyrazine-2-carboxylic acid [3-[(2-amino-pyridin-3-ylamino)methyl]-4-fluorophenyl]amide |
| 621 | 5-propoxy-pyrazine-2-carboxylic acid [3-[(2-amino-pyridin-3-ylamino)methyl]-4-fluorophenyl]amide |
| 622 | 5-butoxy-pyrazine-2-carboxylic acid [3-[(2-amino-pyridin-3-ylamino)methyl]-4-fluorophenyl]amide |
| 623 | 5-isobutoxy-pyrazine-2-carboxylic acid [3-[(2-amino-pyridin-3-ylamino)methyl]-4-fluorophenyl]amide |
| 624 | 5-(2-methoxyethoxy)-pyrazine-2-carboxylic acid [3-[(2-amino-pyridin-3-ylamino)methyl]-4-fluorophenyl]amide |

TABLE 96

| Compound No. | Structural formula |
|---|---|
| 625 | (structure) |
| 626 | (structure) |
| 627 | (structure) |
| 628 | (structure) |
| 629 | (structure) |
| 630 | (structure) |
| 631 | (structure) |

TABLE 96-continued

| Compound No. | Structural formula |
|---|---|
| 632 | (HO-CH2-C≡C-CH2-O-pyrazine-C(=O)-NH-(3-position of 4-fluorophenyl)-CH2-NH-(3-position of 2-aminopyridine)) |

TABLE 97

| Compound No. | Structural formula |
|---|---|
| 633 | (MeO-CH2-C≡C-CH2-O-pyrazine-C(=O)-NH-(3-position of 4-fluorophenyl)-CH2-NH-(3-position of 2-aminopyridine)) |
| 634 | ((CH3)2N-CH2-C≡C-CH2-O-pyrazine-C(=O)-NH-(3-position of 4-fluorophenyl)-CH2-NH-(3-position of 2-aminopyridine)) |
| 635 | (CH3-NH-CH2-C≡C-CH2-O-pyrazine-C(=O)-NH-(3-position of 4-fluorophenyl)-CH2-NH-(3-position of 2-aminopyridine)) |
| 636 | (Cl-CH2-C≡C-CH2-O-pyrazine-C(=O)-NH-(3-position of 4-fluorophenyl)-CH2-NH-(3-position of 2-aminopyridine)) |
| 637 | (F-CH2-C≡C-CH2-O-pyrazine-C(=O)-NH-(3-position of 4-fluorophenyl)-CH2-NH-(3-position of 2-aminopyridine)) |

TABLE 97-continued

| Compound No. | Structural formula |
|---|---|
| 638 | (2-butenyl)oxy-pyrazine-carboxamide-N-(4-fluoro-3-{[(2-aminopyridin-3-yl)amino]methyl}phenyl) |
| 639 | (3-butenyl)oxy-pyrazine-carboxamide-N-(4-fluoro-3-{[(2-aminopyridin-3-yl)amino]methyl}phenyl) |
| 640 | (cis-2-pentenyl)oxy-pyrazine-carboxamide-N-(4-fluoro-3-{[(2-aminopyridin-3-yl)amino]methyl}phenyl) |

TABLE 98

| Compound No. | Structural formula |
|---|---|
| 641 | (2-methylallyl)oxy-pyrazine-carboxamide-N-(4-fluoro-3-{[(2-aminopyridin-3-yl)amino]methyl}phenyl) |
| 642 | (2-fluoroethyl)oxy-pyrazine-carboxamide-N-(4-fluoro-3-{[(2-aminopyridin-3-yl)amino]methyl}phenyl) |
| 643 | (2,2,2-trifluoroethyl)oxy-pyrazine-carboxamide-N-(4-fluoro-3-{[(2-aminopyridin-3-yl)amino]methyl}phenyl) |
| 644 | (oxetan-2-ylmethyl)oxy-pyrazine-carboxamide-N-(4-fluoro-3-{[(2-aminopyridin-3-yl)amino]methyl}phenyl) |

TABLE 98-continued
| Compound No. | Structural formula |
|---|---|
| 645 | 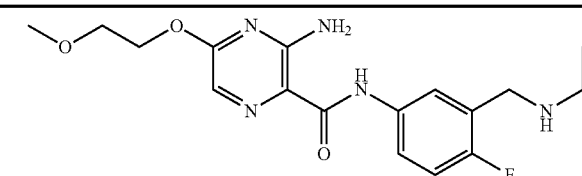 |
| 646 | |
| 647 | |
| 648 | |
TABLE 99
| Compound No. | Structural formula |
|---|---|
| 649 | 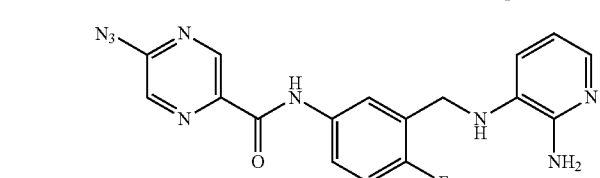 |
| 650 | |
| 651 | |

TABLE 99-continued
| Compound No. | Structural formula |
|---|---|
| 652 | 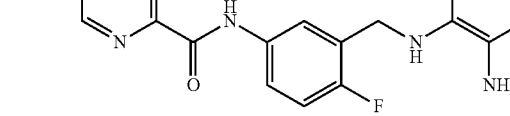 |
| 653 | 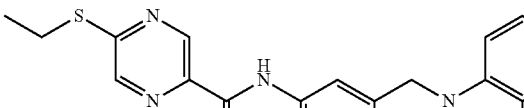 |
| 654 | 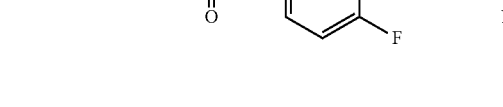 |
| 655 |  |
| 656 | 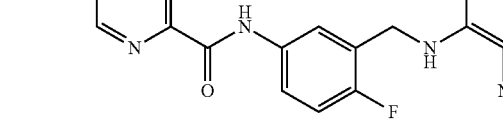 |
TABLE 100
| Compound No. | Structural formula |
|---|---|
| 657 | |
| 658 | |

TABLE 100-continued

| Compound No. | Structural formula |
|---|---|
| 659 | (oxazol-2-yl)-pyrazine-carboxamide derivative |
| 660 | (thiazol-2-yl)-pyrazine-carboxamide derivative |
| 661 | (thiophen-3-yl)-pyrazine-carboxamide derivative |
| 662 | (3,5-dimethylisoxazol-4-yl)-pyrazine-carboxamide derivative |
| 663 | (furan-3-yl)-pyrazine-carboxamide derivative |
| 664 | (furan-2-yl)-pyrazine-carboxamide derivative |

TABLE 101

| Compound No. | Structural formula |
|---|---|
| 665 | 5-chloro-pyrimidine-2-carboxamide derivative |
| 666 | 5-bromo-pyrimidine-2-carboxamide derivative |
| 667 | 5-cyano-pyrimidine-2-carboxamide derivative |
| 668 | 6-oxo-1,4,5,6-tetrahydropyridazine-3-carboxamide derivative |
| 669 | 4-(5-methyl-1,2,4-oxadiazol-3-yl)benzamide derivative |
| 670 | 4-chlorobenzamide derivative |
| 671 | 2,4-dichlorobenzamide derivative |
| 672 | 4-(trifluoromethyl)benzamide derivative |

US 8,703,785 B2
TABLE 102
| Compound No. | Structural formula |
|---|---|
| 673 | 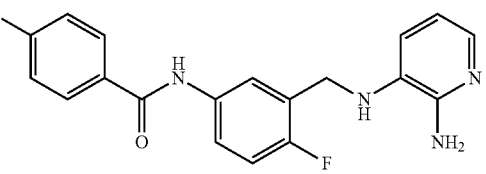 |
| 674 | 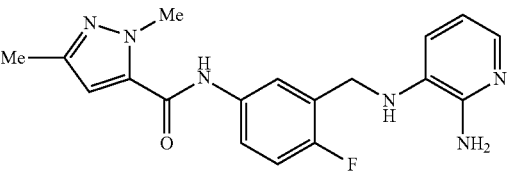 [SMILES: Cc1cc(C(=O)Nc2ccc(F)c(CNc3cccnc3N)c2)n(C)n1] |
| 675 | 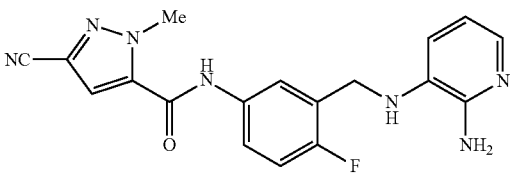 [SMILES: Cn1nc(C#N)cc1C(=O)Nc1ccc(F)c(CNc2cccnc2N)c1] |
| 676 | 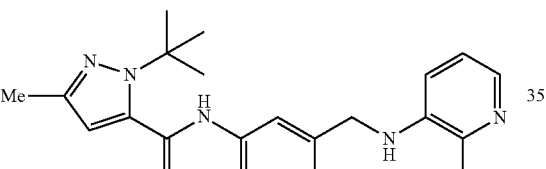 |
| 677 | 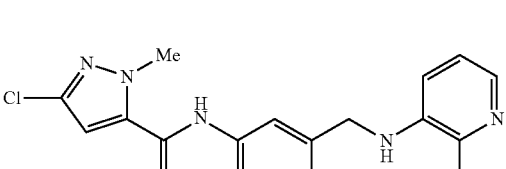 |
| 678 | 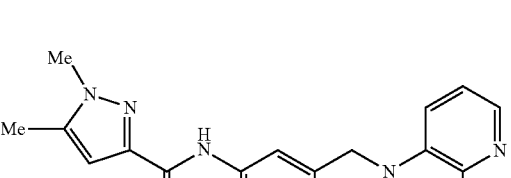 |
| 679 | 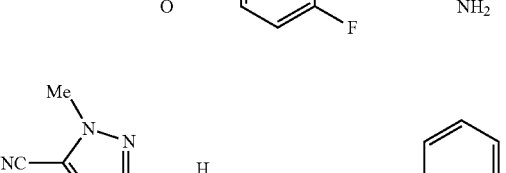 |
TABLE 102-continued
| Compound No. | Structural formula |
|---|---|
| 680 | 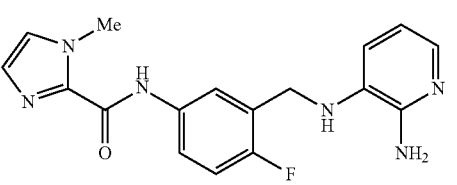 [SMILES: Cn1ccnc1C(=O)Nc1ccc(F)c(CNc2cccnc2N)c1] |
TABLE 103
| Compound No. | Structural formula |
|---|---|
| 681 | 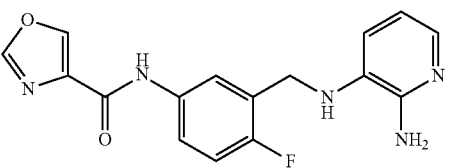 [SMILES: Nc1ncccc1NCc1cc(NC(=O)c2cocn2)ccc1F] |
| 682 | 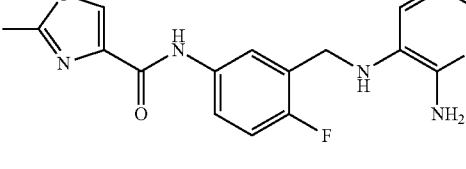 |
| 683 | 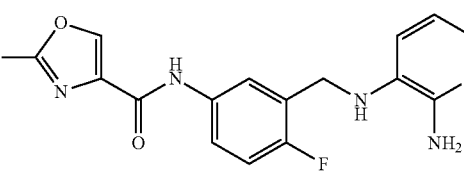 |
| 684 | 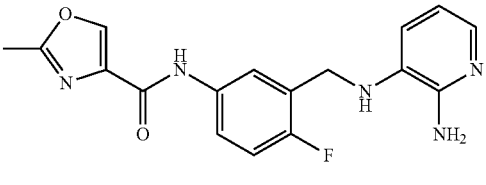 |
| 685 | 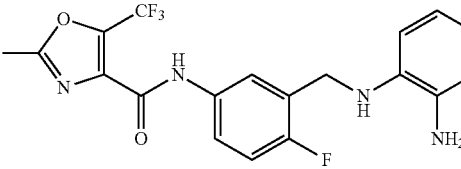 |
| 686 | 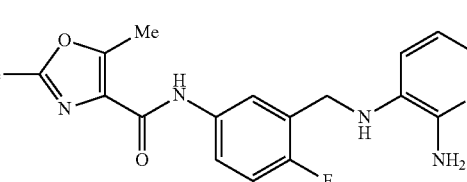 |

TABLE 103-continued
| Compound No. | Structural formula |
|---|---|
| 687 | 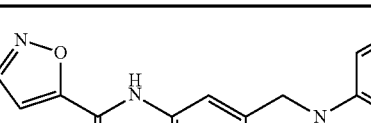 |
| 688 | |
TABLE 104
| Compound No. | Structural formula |
|---|---|
| 689 | 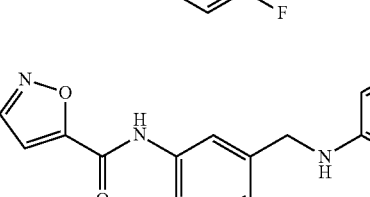 |
| 690 | |
| 691 | |
| 692 | 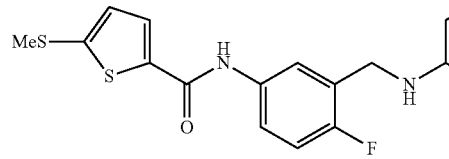 |
| 693 | |
TABLE 104-continued
| Compound No. | Structural formula |
|---|---|
| 694 | 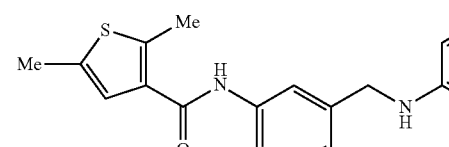 |
| 695 | |
| 696 | |
TABLE 105
| Compound No. | Structural formula |
|---|---|
| 697 | 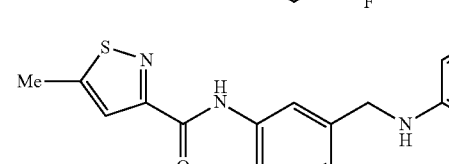 |
| 698 | |
| 699 | |
| 700 | 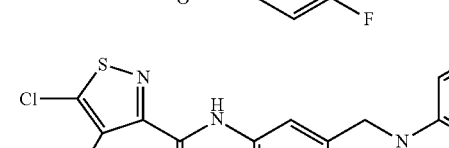 |

TABLE 105-continued
| Compound No. | Structural formula |
|---|---|
| 701 | 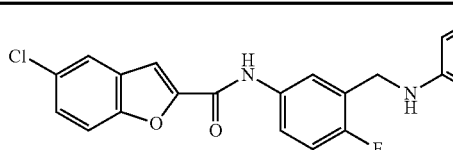 |
| 702 | |
| 703 | |
| 704 | |
TABLE 106
| Compound No. | Structural formula |
|---|---|
| 705 | 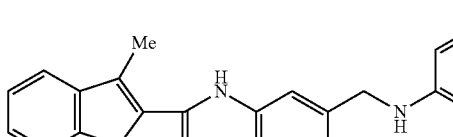 |
| 706 | |
| 707 | |
| 708 | |
TABLE 106-continued
| Compound No. | Structural formula |
|---|---|
| 709 | 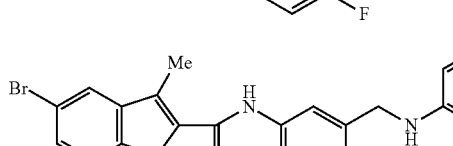 |
| 710 | |
| 711 | |
| 712 | |
TABLE 107
| Compound No. | Structural formula |
|---|---|
| 713 | 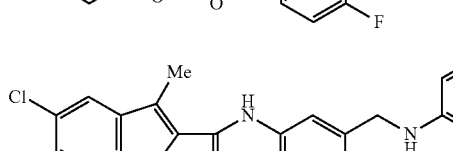 |
| 714 | |
| 715 | |
| 716 | |

TABLE 107-continued

| Compound No. | Structural formula |
|---|---|
| 717 | 3-methyl-6-hydroxy-benzothiophene-2-carboxamide linked to N-(4-fluoro-3-((2-aminopyridin-3-ylamino)methyl)phenyl) |
| 718 | pyrrolo[1,2-c]pyrimidine-3-carboxamide linked to N-(4-fluoro-3-((2-aminopyridin-3-ylamino)methyl)phenyl) |
| 719 | 6-chloro-pyrrolo[1,2-c]pyrimidine-3-carboxamide linked to N-(4-fluoro-3-((2-aminopyridin-3-ylamino)methyl)phenyl) |
| 720 | 2-methyl-imidazo[1,2-a]pyrazine-6-carboxamide linked to N-(4-fluoro-3-((2-aminopyridin-3-ylamino)methyl)phenyl) |

TABLE 108

| Compound No. | Structural formula |
|---|---|
| 721 | 2-trifluoromethyl-imidazo[1,2-a]pyrazine-6-carboxamide linked to N-(4-fluoro-3-((2-aminopyridin-3-ylamino)methyl)phenyl) |
| 722 | 2-cyano-imidazo[1,2-a]pyrazine-6-carboxamide linked to N-(4-fluoro-3-((2-aminopyridin-3-ylamino)methyl)phenyl) |
| 723 | quinoxaline-2-carboxamide linked to N-(4-fluoro-3-((2-aminopyridin-3-ylamino)methyl)phenyl) |
| 724 | quinoline-2-carboxamide linked to N-(4-fluoro-3-((2-aminopyridin-3-ylamino)methyl)phenyl) |

TABLE 108-continued

| Compound No. | Structural formula |
|---|---|
| 725 | isoquinoline-3-carboxamide linked to N-(4-fluoro-3-((2-aminopyridin-3-ylamino)methyl)phenyl) |
| 726 | 3,4-dihydro-2H-benzo[b][1,4]oxazine-2-carboxamide linked to N-(4-fluoro-3-((2-aminopyridin-3-ylamino)methyl)phenyl) |
| 727 | 2,3-dihydrobenzo[b][1,4]dioxine-2-carboxamide linked to N-(4-fluoro-3-((2-aminopyridin-3-ylamino)methyl)phenyl) |
| 728 | thieno[3,2-b]thiophene-2-carboxamide linked to N-(4-fluoro-3-((2-aminopyridin-3-ylamino)methyl)phenyl) |

TABLE 109

| Compound No. | Structural formula |
|---|---|
| 729 | pyrazolo[1,5-a]pyridine-2-carboxamide linked to N-(4-fluoro-3-((2-aminopyridin-3-ylamino)methyl)phenyl) |
| 730 | imidazo[2,1-b]thiazole-6-carboxamide linked to N-(4-fluoro-3-((2-aminopyridin-3-ylamino)methyl)phenyl) |

TABLE 110

| Compound No. | Structural formula |
|---|---|
| 731 | 5-chloro-pyridine-2-carboxamide linked to N-(2-((2-aminopyridin-3-ylamino)methyl)pyridin-4-yl) |

TABLE 110-continued

| Compound No. | Structural formula |
|---|---|
| 732 | 5-Br-pyridine-2-carboxamide-N-(2-((2-aminopyridin-3-ylamino)methyl)pyridin-4-yl) |
| 733 | 5-F-pyridine-2-carboxamide-N-(2-((2-aminopyridin-3-ylamino)methyl)pyridin-4-yl) |
| 734 | 3,5-diCl-pyridine-2-carboxamide-N-(2-((2-aminopyridin-3-ylamino)methyl)pyridin-4-yl) |
| 735 | 3-F-pyridine-2-carboxamide-N-(2-((2-aminopyridin-3-ylamino)methyl)pyridin-4-yl) |
| 736 | 3,5-diF-pyridine-2-carboxamide-N-(2-((2-aminopyridin-3-ylamino)methyl)pyridin-4-yl) |
| 737 | 3-NH$_2$-5-Cl-pyridine-2-carboxamide-N-(2-((2-aminopyridin-3-ylamino)methyl)pyridin-4-yl) |
| 738 | 5-Me-pyridine-2-carboxamide-N-(2-((2-aminopyridin-3-ylamino)methyl)pyridin-4-yl) |

TABLE 111

| Compound No. | Structural formula |
|---|---|
| 739 | 5-CF$_3$-pyridine-2-carboxamide-N-(2-((2-aminopyridin-3-ylamino)methyl)pyridin-4-yl) |
| 740 | 3-Cl-5-CF$_3$-pyridine-2-carboxamide-N-(2-((2-aminopyridin-3-ylamino)methyl)pyridin-4-yl) |
| 741 | 3-F-5-CF$_3$-pyridine-2-carboxamide-N-(2-((2-aminopyridin-3-ylamino)methyl)pyridin-4-yl) |
| 742 | 5-CN-pyridine-2-carboxamide-N-(2-((2-aminopyridin-3-ylamino)methyl)pyridin-4-yl) |
| 743 | 3-Cl-5-CN-pyridine-2-carboxamide-N-(2-((2-aminopyridin-3-ylamino)methyl)pyridin-4-yl) |
| 744 | 3-F-5-CN-pyridine-2-carboxamide-N-(2-((2-aminopyridin-3-ylamino)methyl)pyridin-4-yl) |
| 745 | 5-OH-pyridine-2-carboxamide-N-(2-((2-aminopyridin-3-ylamino)methyl)pyridin-4-yl) |
| 746 | 5-OMe-pyridine-2-carboxamide-N-(2-((2-aminopyridin-3-ylamino)methyl)pyridin-4-yl) |

TABLE 112
| Compound No. | Structural formula |
|---|---|
| 747 | 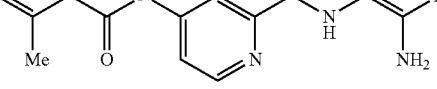 |
| 748 | 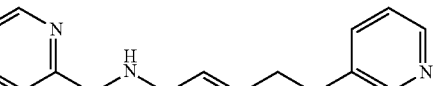 |
| 749 | 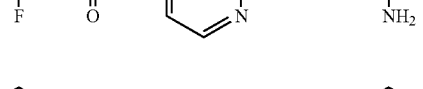 |
| 750 | 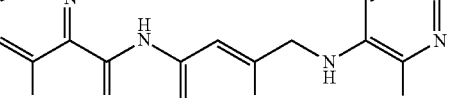 |
| 751 |  |
| 752 | 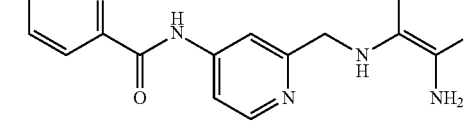 |
| 753 |  |
| 754 | 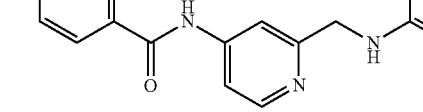 |

TABLE 113

| Compound No. | Structural formula |
|---|---|
| 755 | (furan-2-ylmethoxy)pyridine-carboxamide linked to pyridine-CH$_2$-NH-(2-aminopyridin-3-yl) |
| 756 | (but-2-yn-1-yloxy)pyridine-carboxamide linked to pyridine-CH$_2$-NH-(2-aminopyridin-3-yl) |
| 757 | 5-(MeS)pyridine-2-carboxamide linked to pyridine-CH$_2$-NH-(2-aminopyridin-3-yl) |
| 758 | 5-(O$_2$N)pyridine-2-carboxamide linked to pyridine-CH$_2$-NH-(2-aminopyridin-3-yl) |
| 759 | 5-Me-pyrazine-2-carboxamide linked to pyridine-CH$_2$-NH-(2-aminopyridin-3-yl) |
| 760 | 5-(pent-1-en-1-yl)pyrazine-2-carboxamide linked to pyridine-CH$_2$-NH-(2-aminopyridin-3-yl) |
| 761 | 5-(3-methoxyprop-1-en-1-yl)pyrazine-2-carboxamide linked to pyridine-CH$_2$-NH-(2-aminopyridin-3-yl) |
| 762 | 5-pentylpyrazine-2-carboxamide linked to pyridine-CH$_2$-NH-(2-aminopyridin-3-yl) |

TABLE 114

| Compound No. | Structural formula |
|---|---|
| 763 | (E)-5-(3-hydroxyprop-1-en-1-yl)-N-(2-(((2-aminopyridin-3-yl)amino)methyl)pyridin-4-yl)pyrazine-2-carboxamide |
| 764 | 5-chloro-N-(2-(((2-aminopyridin-3-yl)amino)methyl)pyridin-4-yl)pyrazine-2-carboxamide |
| 765 | 5-methoxy-N-(2-(((2-aminopyridin-3-yl)amino)methyl)pyridin-4-yl)pyrazine-2-carboxamide |
| 766 | 5-ethoxy-N-(2-(((2-aminopyridin-3-yl)amino)methyl)pyridin-4-yl)pyrazine-2-carboxamide |
| 767 | 5-propoxy-N-(2-(((2-aminopyridin-3-yl)amino)methyl)pyridin-4-yl)pyrazine-2-carboxamide |
| 768 | 5-butoxy-N-(2-(((2-aminopyridin-3-yl)amino)methyl)pyridin-4-yl)pyrazine-2-carboxamide |
| 769 | 5-isobutoxy-N-(2-(((2-aminopyridin-3-yl)amino)methyl)pyridin-4-yl)pyrazine-2-carboxamide |
| 770 | 5-(2-methoxyethoxy)-N-(2-(((2-aminopyridin-3-yl)amino)methyl)pyridin-4-yl)pyrazine-2-carboxamide |

TABLE 115
| Compound No. | Structural formula |
|---|---|
| 771 | |
| 772 | |
| 773 | |
| 774 | |
| 775 | |
| 776 | |
| 777 | |
| 778 | |
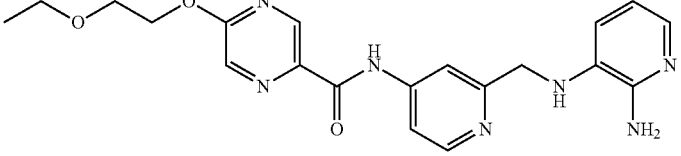

TABLE 116

| Compound No. | Structural formula |
|---|---|
| 779 | (structure) |
| 780 | (structure) |
| 781 | (structure) |
| 782 | (structure) |
| 783 | (structure) |
| 784 | (structure) |
| 785 | (structure) |
| 786 | (structure) |

TABLE 117

| Compound No. | Structural formula |
|---|---|
| 787 | |
| 788 | |
| 789 | |
| 790 | |
| 791 | |
| 792 | |
| 793 | |
| 794 | |

TABLE 118

| Compound No. | Structural formula |
| --- | --- |
| 795 | (structure) |
| 796 | (structure) |
| 797 | (structure) |
| 798 | (structure) |
| 799 | (structure) |
| 800 | (structure) |
| 801 | (structure) |

TABLE 118-continued

| Compound No. | Structural formula |
| --- | --- |
| 802 | (1,2,4-triazol-1-yl)-pyrazine-carboxamide-N-(pyridin-4-yl)methyl-NH-(2-aminopyridin-3-yl) |

TABLE 119

| Compound No. | Structural formula |
| --- | --- |
| 803 | (pyrazol-1-yl)-pyrazine-carboxamide-N-(pyridin-4-yl)methyl-NH-(2-aminopyridin-3-yl) |
| 804 | (1H-pyrrol-2-yl)-pyrazine-carboxamide-N-(pyridin-4-yl)methyl-NH-(2-aminopyridin-3-yl) |
| 805 | (oxazol-2-yl)-pyrazine-carboxamide-N-(pyridin-4-yl)methyl-NH-(2-aminopyridin-3-yl) |
| 806 | (thiazol-2-yl)-pyrazine-carboxamide-N-(pyridin-4-yl)methyl-NH-(2-aminopyridin-3-yl) |
| 807 | (thiophen-3-yl)-pyrazine-carboxamide-N-(pyridin-4-yl)methyl-NH-(2-aminopyridin-3-yl) |

TABLE 119-continued
| Compound No. | Structural formula |
|---|---|
| 808 | 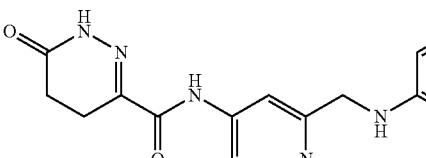 |
| 809 | |
| 810 | |
TABLE 120
| Compound No. | Structural formula |
|---|---|
| 811 | 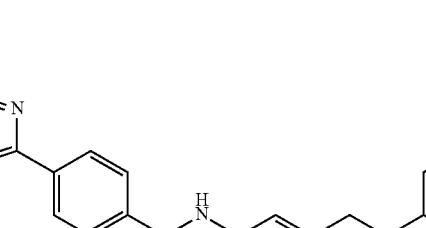 |
| 812 | |
| 813 | |
| 814 | |
| 815 | |
| 816 | |

TABLE 120-continued
| Compound No. | Structural formula |
|---|---|
| 817 | 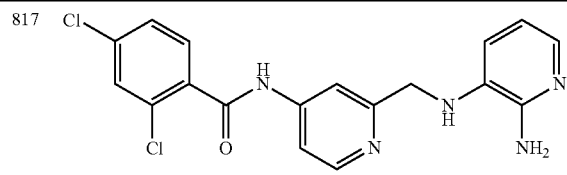 |
| 818 | 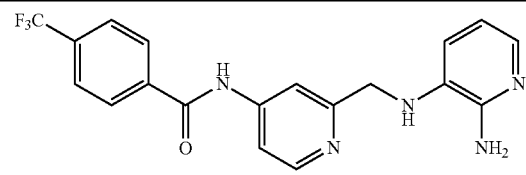 |
TABLE 121
| Compound No. | Structural formula |
|---|---|
| 819 | 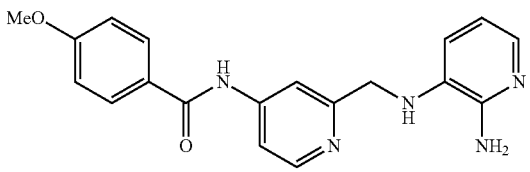 [SMILES: COc1ccc(C(=O)Nc2ccnc(CNc3cccnc3N)c2)cc1] |
| 820 | 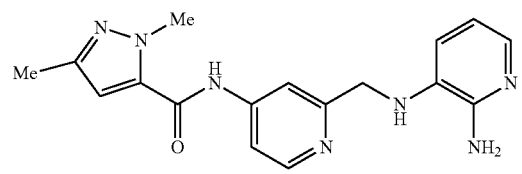 [SMILES: Cc1cc(C(=O)Nc2ccnc(CNc3cccnc3N)c2)n(C)n1] |
| 821 | 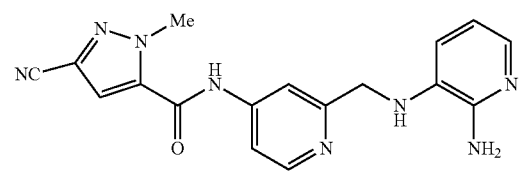 [SMILES: Cn1nc(C#N)cc1C(=O)Nc1ccnc(CNc2cccnc2N)c1] |
| 822 | 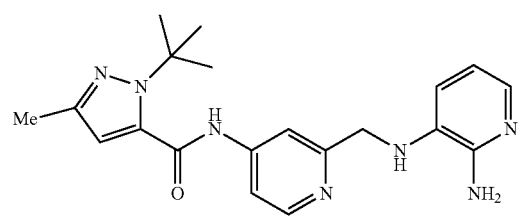 [SMILES: Cc1cc(C(=O)Nc2ccnc(CNc3cccnc3N)c2)n(C(C)(C)C)n1] |
| 823 | 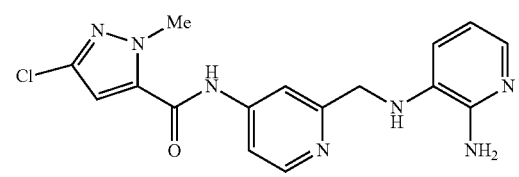 [SMILES: Cn1nc(Cl)cc1C(=O)Nc1ccnc(CNc2cccnc2N)c1] |
| 824 | 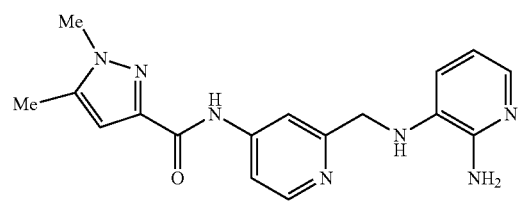 [SMILES: Cc1cc(C(=O)Nc2ccnc(CNc3cccnc3N)c2)nn1C] |

TABLE 121-continued

| Compound No. | Structural formula |
|---|---|
| 825 | (structure) |
| 826 | (structure) |

TABLE 122

| Compound No. | Structural formula |
|---|---|
| 827 | (structure) |
| 828 | (structure) |
| 829 | (structure) |
| 830 | (structure) |
| 831 | (structure) |
| 832 | (structure) |
| 833 | (structure) |
| 834 | (structure) |

TABLE 123

| Compound No. | Structural formula |
|---|---|
| 835 | (structure) |
| 836 | (structure) |
| 837 | (structure) |

TABLE 123-continued

| Compound No. | Structural formula |
| --- | --- |
| 838 | 5-bromo-furan-2-carboxamide linked to N-(2-((2-aminopyridin-3-ylamino)methyl)pyridin-4-yl) |
| 839 | 2,5-dimethyl-furan-3-carboxamide linked to N-(2-((2-aminopyridin-3-ylamino)methyl)pyridin-4-yl) |
| 840 | 5-methyl-thiophene-2-carboxamide linked to N-(2-((2-aminopyridin-3-ylamino)methyl)pyridin-4-yl) |
| 841 | 4-methyl-thiophene-2-carboxamide linked to N-(2-((2-aminopyridin-3-ylamino)methyl)pyridin-4-yl) |
| 842 | 5-bromo-thiophene-2-carboxamide linked to N-(2-((2-aminopyridin-3-ylamino)methyl)pyridin-4-yl) |

TABLE 124

| Compound No. | Structural formula |
| --- | --- |
| 843 | 5-methoxy-thiophene-2-carboxamide linked to N-(2-((2-aminopyridin-3-ylamino)methyl)pyridin-4-yl) |
| 844 | 2,5-dimethyl-thiophene-3-carboxamide linked to N-(2-((2-aminopyridin-3-ylamino)methyl)pyridin-4-yl) |
| 845 | 5-methyl-isothiazole-3-carboxamide linked to N-(2-((2-aminopyridin-3-ylamino)methyl)pyridin-4-yl) |
| 846 | 4,5-dichloro-isothiazole-3-carboxamide linked to N-(2-((2-aminopyridin-3-ylamino)methyl)pyridin-4-yl) |
| 847 | 2,4-dimethyl-thiazole-5-carboxamide linked to N-(2-((2-aminopyridin-3-ylamino)methyl)pyridin-4-yl) |

TABLE 124-continued

| Compound No. | Structural formula |
|---|---|
| 848 | (benzofuran-2-carboxamide linked to N-(pyridin-4-yl), with CH2-NH-(2-aminopyridin-3-yl)) |
| 849 | 5-MeO-benzofuran-2-carboxamide linked analogously |
| 850 | 5-Br-benzofuran-2-carboxamide linked analogously |

TABLE 125

| Compound No. | Structural formula |
|---|---|
| 851 | 5-Cl-benzofuran-2-carboxamide linked analogously |
| 852 | 3-Me-benzofuran-2-carboxamide linked analogously |
| 853 | 5-Br-3-Me-benzofuran-2-carboxamide linked analogously |
| 854 | 5-Cl-3-Me-benzofuran-2-carboxamide linked analogously |
| 855 | 5-F-3-Me-benzofuran-2-carboxamide linked analogously |

TABLE 125-continued

| Compound No. | Structural formula |
|---|---|
| 856 | 5-hydroxy-3-methyl-benzofuran-2-carboxylic acid [2-[(2-amino-pyridin-3-ylamino)-methyl]-pyridin-4-yl]-amide |
| 857 | 3,5-dimethyl-benzofuran-2-carboxylic acid [2-[(2-amino-pyridin-3-ylamino)-methyl]-pyridin-4-yl]-amide |
| 858 | 5-methoxy-3-methyl-benzofuran-2-carboxylic acid [2-[(2-amino-pyridin-3-ylamino)-methyl]-pyridin-4-yl]-amide |

TABLE 126

| Compound No. | Structural formula |
|---|---|
| 859 | 3-amino-5-bromo-benzofuran-2-carboxylic acid [2-[(2-amino-pyridin-3-ylamino)-methyl]-pyridin-4-yl]-amide |
| 860 | 1H-indole-2-carboxylic acid [2-[(2-amino-pyridin-3-ylamino)-methyl]-pyridin-4-yl]-amide |
| 861 | 5-fluoro-1H-indole-2-carboxylic acid [2-[(2-amino-pyridin-3-ylamino)-methyl]-pyridin-4-yl]-amide |
| 862 | benzo[b]thiophene-2-carboxylic acid [2-[(2-amino-pyridin-3-ylamino)-methyl]-pyridin-4-yl]-amide |
| 863 | 5-hydroxy-3-methyl-benzo[b]thiophene-2-carboxylic acid [2-[(2-amino-pyridin-3-ylamino)-methyl]-pyridin-4-yl]-amide |

TABLE 126-continued

| Compound No. | Structural formula |
| --- | --- |
| 864 | (pyrrolo[1,2-c]pyrimidine-3-carboxamide linked to N-[2-[[(2-aminopyridin-3-yl)amino]methyl]pyridin-4-yl]) |
| 865 | 7-chloro analog of 864 |
| 866 | 7-methyl-imidazo[1,2-a]pyrazine-3-carboxamide linked to N-[2-[[(2-aminopyridin-3-yl)amino]methyl]pyridin-4-yl] |

TABLE 127

| Compound No. | Structural formula |
| --- | --- |
| 867 | 7-trifluoromethyl-imidazo[1,2-a]pyrazine-3-carboxamide linked to N-[2-[[(2-aminopyridin-3-yl)amino]methyl]pyridin-4-yl] |
| 868 | 7-cyano-imidazo[1,2-a]pyrazine-3-carboxamide linked to N-[2-[[(2-aminopyridin-3-yl)amino]methyl]pyridin-4-yl] |
| 869 | quinoxaline-2-carboxamide linked to N-[2-[[(2-aminopyridin-3-yl)amino]methyl]pyridin-4-yl] |
| 870 | quinoline-2-carboxamide linked to N-[2-[[(2-aminopyridin-3-yl)amino]methyl]pyridin-4-yl] |
| 871 | isoquinoline-3-carboxamide linked to N-[2-[[(2-aminopyridin-3-yl)amino]methyl]pyridin-4-yl] |

TABLE 127-continued

| Compound No. | Structural formula |
|---|---|
| 872 | |
| 873 | |
| 874 | |

TABLE 128

| Compound No. | Structural formula |
|---|---|
| 875 | |
| 876 | |

8) A compound of formula (II'):

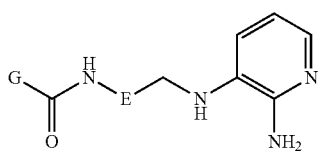

(II')

wherein E is optionally substituted benzenediyl (the substituent is one or more groups selected from lower alkyl, lower alkenyl and the substituent group α) and G is optionally substituted pyrazinediyl (the substituent is one or more groups selected from lower alkyl, lower alkenyl, lower alkynyl, lower alkenyloxy, lower alkynyloxy and the substituent group α).

Preferable among the above compounds is a compound in which E is optionally substituted benzenediyl (the substituent is one or more groups selected from halogen, lower alkyl, lower alkoxy, lower alkylthio, amino and lower alkylamino) and G is optionally substituted pyrazinediyl (the substituent is one or more groups selected from halogen, lower alkyl, lower alkenyl, lower alkoxy, lower alkoxy lower alkoxy and lower alkynyloxy).

Further, preferable among the above compounds is a compound in which E is unsubstituted benzenediyl and G is optionally substituted pyrazinediyl (the substituent is one or more groups selected from halogen, lower alkyl, lower alkenyl, lower alkoxy, lower alkoxy lower alkoxy and lower alkynyloxy).

The compound according to the present invention is useful against diseases induced by production, secretion or deposition of amyloid-β proteins. For example, the compound is effective for treating and/or preventing, and ameliorating symptoms of diseases such as dementia of the Alzheimer's type (e.g. Alzheimer's disease and senile dementia of the Alzheimer's type), Down syndrome, memory disorder, prion diseases (e.g. Creutzfeldt-Jakob disease), mild cognitive impairment (MCI), hereditary cerebral hemorrhage with amyloidosis-Dutch type, cerebral amyloid angiopathy, other degenerative dementia, vascular and degenerative mixed dementia, dementia associated with Parkinson's disease, dementia associated with progressive supranuclear palsy, dementia associated with corticobasal degeneration, Alzheimer's disease with diffuse Lewy bodies, age-related macular degeneration, Parkinson's disease and amyloid angiopathy.

The compound according to the present invention has effects such as a high inhibitory activity on BACE1, in particular, an inhibitory activity on production of amyloid-β in cell lines and high selectivity against other enzymes. Thus, the compound can be used as pharmaceuticals with reduced side effects. Further, the compound of the present invention can be pharmaceuticals which achieves a wider safety margin for side effects by preparing the compound as an optically active substance with an appropriate stereochemical structure. In addition, the compound according to the present invention has various advantages such as high metabolic stability, high solubility, a long half life, low hERG channel inhibition and low CYP inhibition. Thus, the compound can be excellent pharmaceuticals.

When the compound according to the present invention is administered, other medicaments (e.g. other therapeutic agents for Alzheimer's disease such as acetylcholine esterase) may be used in combination. For example, anti-dementia drugs such as donepezil hydrochloride, tacrine, galantamine, rivastigmine, zanapezil, memantine and vinpocetine may be used in combination.

When the compound according to the present invention is administered to humans, it may be orally administered as powders, granules, tablets, capsules, pills, liquids and the like, or may be parenterally administered as injections, suppositories, transdermal systems, inhalant and the like. In addition, if needed, an effective amount of the present compound may be mixed with pharmaceutical additives such as diluents, binders, humectants, disintegrants and lubricants suitable for its dosage form, and thereby the compound may be formed into a pharmaceutical preparation.

The dosage depends on disease conditions, the route of administration, the age or the weight of a patient. In the case of oral administration to adults, the dosage is generally 0.1 μg to 1 g/day, and preferably 0.01 to 200 mg/day. In the case of parenteral administration, the dosage is generally 1 μg to 10 g/day, and preferably 0.1 to 2 g/day.

EXAMPLES

The present invention will be described in more detail with reference to, but not limited to, the following examples and test examples.

In the examples, meaning of each abbreviation is as follows.
Et: ethyl
Me: methyl
Boc: t-butoxycarbonyl
HATU: O-(7-azabenzotriazol-1-yl)-N,N,N',N'-tetramethyluronium hexafluorophosphate
Ac: acetyl
TFA: trifluoroacetic acid Reference Example 1

Synthesis of Fused Cyclic Compound (6)

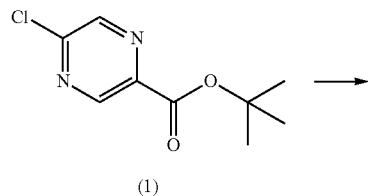

(1)

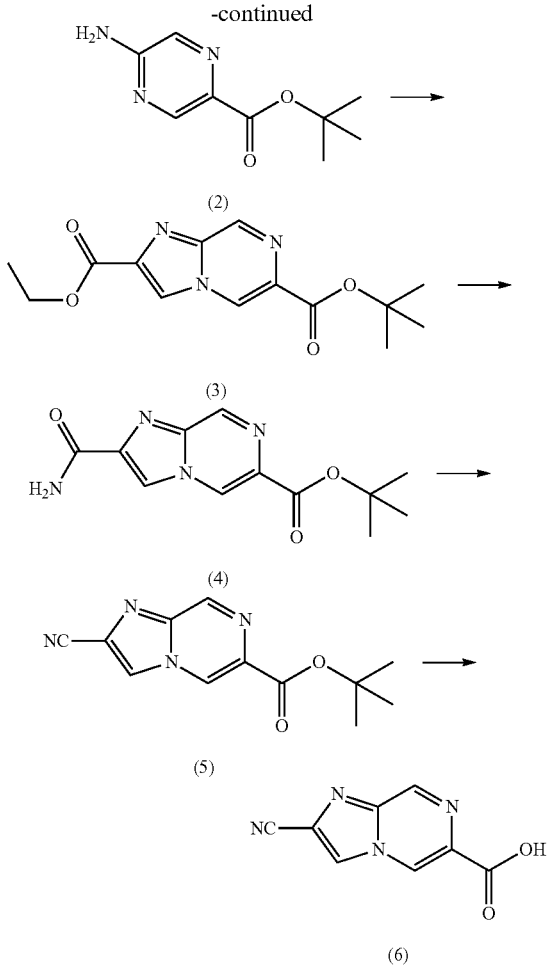

Compound (1) (1000 mg), dioxane (2 ml), and 28% aqueous ammonia solution (2 ml) were mixed with each other, and the mixture was stirred for 19 hours at 50° C. The reaction solution was concentrated under reduced pressure. Water was added to the residue, and the residue was extracted with ethyl acetate. The extract was dried with anhydrous magnesium sulfate, and the solvent was distilled away under reduced pressure. The residue was subjected to silica gel column chromatography. Compound (2) (476 mg) was thereby obtained.

$^1$H-NMR (CDCl$_3$) δ: 1.63 (9H, s), 5.04 (2H, br s), 8.03 (1H, s), 8.69 (1H, s).

Compound (2) (475 mg) was mixed with 3-bromo-2-oxopropanoic acid ethyl ester (1582 mg) in dimethoxyethane (4 ml), and the mixture was stirred for 2.5 hours at 75° C. The reaction solution was diluted with diisopropyl ether. Insoluble matter was collected by filtration, rinsed with diisopropyl ether and hexane, and dried under reduced pressure. The residue was stirred for 2 hours at 95° C. in t-butyl alcohol (7.5 ml). The solvent was distilled away under reduced pressure, and the residue was subjected to silica gel column chromatography. Compound (3) (709 mg) was thereby obtained.

$^1$H-NMR (CDCl$_3$) δ: 1.46 (3H, t, J=7.1 Hz), 1.66 (9H, s), 4.50 (2H, q, J=7.1 Hz), 8.35 (1H, s), 8.89 (1H, s), 9.24 (1H, s).

Compound (3) (270 mg), dioxane (3 ml), and 28% aqueous ammonia solution (2.5 ml) were mixed with each other. The mixture was stirred for 6 hours at 50° C. in a pressure bottle, and the reaction solution was concentrated under reduced pressure. A crude product of Compound (4) (249 mg) was thereby obtained.

$^1$H-NMR of crude product (CDCl$_3$) δ: 1.67 (9H, s), 5.79 (1H, br s), 8.35 (1H, s), 8.90 (1H, s), 9.15 (1H, s).

Compound (4) (146 mg), triethylamine (282 mg), and dimethylaminopyridine (6.8 mg) were mixed with each other in tetrahydrofuran (9 ml), and 2,2,2-trichloroacetyl chloride (253 mg) was added to the mixture at 0° C. They were then stirred for 2 hours at room temperature. The reaction solution was diluted with ethyl acetate, and a saturated aqueous solution of sodium hydrogen carbonate was added thereto to terminate the reaction. The reaction product was extracted with ethyl acetate. The extract was dried with anhydrous magnesium sulfate, and the solvent was distilled away under reduced pressure. A crude product of Compound (5) (99 mg) was thereby obtained.

Compound (5) (95 mg) was dissolved in chloroform (3 ml). Trifluoroacetic acid (1330 mg) was added thereto, and the mixture was stirred for 4 hours at room temperature. The reaction solution was concentrated under reduced pressure, and thereby a crude product was obtained. The residue was suspended with ethyl acetate and diisopropyl ether. Insoluble matter was collected by filtration and rinsed with diisopropyl ether. The residue was dried under reduced pressure. A composition of Compound (6) was thereby obtained.

A compound which forms a side chain such as the above-listed B136 may be prepared in the same manner as mentioned above.

Example 1

Synthesis of Compound 35

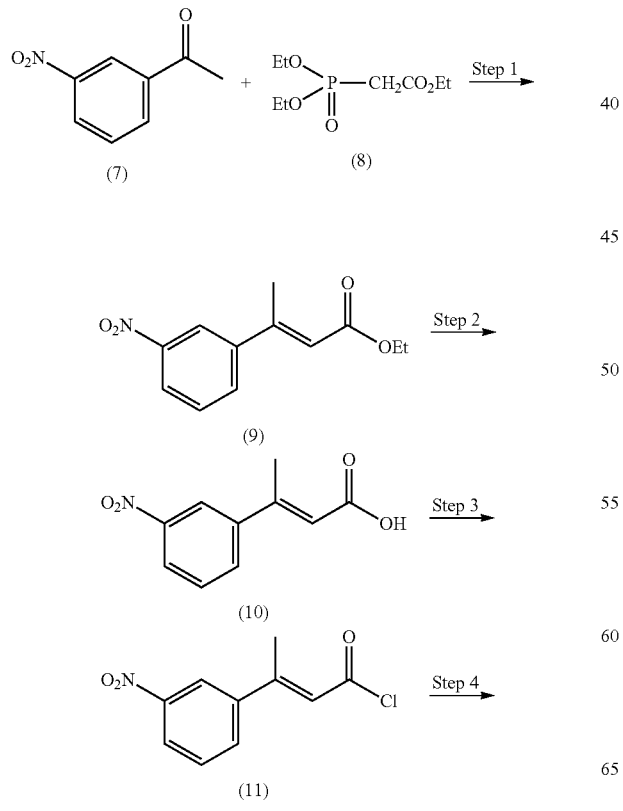
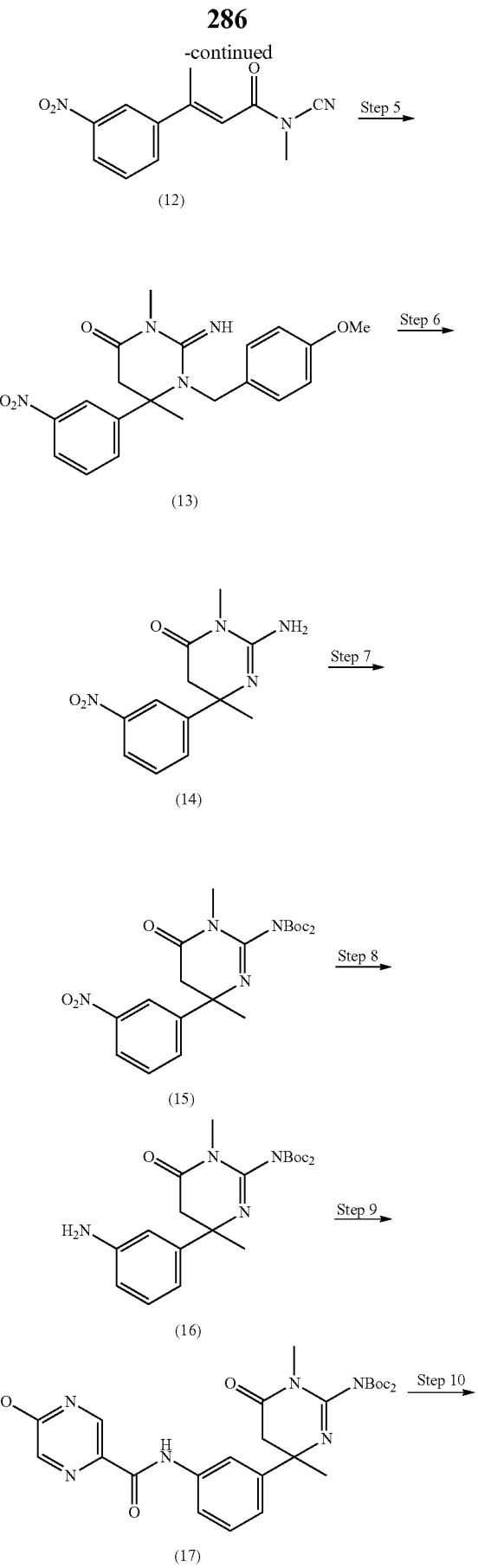

-continued

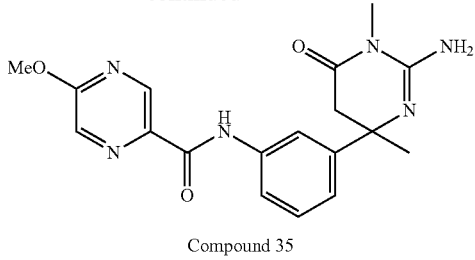

Compound 35

Step 1

Compound (8) (14.93 g) was dissolved in tetrahydrofuran (100 ml). A 1.6 M solution of n-butyl lithium in hexane (4.4 g) was dropwise added thereto at −78° C., and the mixture was stirred for 30 minutes. Compound (7) (10 g) was added thereto over 30 minutes, and the mixture was further stirred for 30 minutes. The mixture was warmed up to room temperature, and further stirred for 18 hours. The solvent was concentrated under reduced pressure, and the residue was purified by chromatography. Compound (9) (7.5 g) was thereby obtained.

$^1$H-NMR (CDCl$_3$) δ: 1.3 (3H, t), 2.6 (3H, s), 4.2-4.3 (2H, q), 6.2 (1H, s), 7.5 (1H, t), 7.8 (1H, d), 8.2 (1H, d), 8.3 (1H, s).

Step 2

Compound (9) (20.0 g) was dissolved in methanol (200 ml) and water (70 ml). Sodium hydroxide (10.2 g) was added thereto, and they were stirred overnight at room temperature. Methanol was removed under reduced pressure, and 1 M hydrochloric acid was added to the product so as to control the pH to 7. Then, the reaction product was extracted with ethyl acetate. The organic phase was rinsed with water and saturated aqueous NaCl solution, and dried with anhydrous sodium sulfate. The solvent was then distilled away under reduced pressure. Petroleum ether was added to the residue, and the precipitated solid was collected by filtration. Compound (10) (15 g) was thereby obtained.

$^1$H-NMR (DMSO-d$_6$) δ: 2.6 (3H, s), 6.3 (1H, s), 8.3-7.9 (4H, m), 12.4 (1H, s).

Step 3

Compound (10) (0.7 g) was suspended in dichloromethane (5 ml). Oxalyl chloride (0.4 ml), and then a small amount of dimethylformamide were added thereto at room temperature, and the mixture was stirred for 2 hours at room temperature. Trifluoroacetic anhydride (13.6 ml) and pyridine (7.8 ml) were added thereto, and they were stirred for 30 minutes. The solvent was then distilled away under reduced pressure. The residue of Compound (11) (0.7 g) was thereby obtained, and it was used in the following step without purification.

Step 4

Cyanogen bromide (1.17 g) was dissolved in tetrahydrofuran (10 ml). Potassium carbonate (2.17 g), and then a 1 M solution of methylamine in tetrahydrofuran (11 ml) were added thereto at −68° C., and the mixture was stirred for 2 hours at −65° C. The reaction solution was filtered through Celite under nitrogen stream. A solution of Compound (11) (1.0 g) in tetrahydrofuran (2 ml) and diisopropylethylamine (1.15 ml) were added to the filtrate at −65° C., and the mixture was stirred for 4 hours at the same temperature. The solvent was distilled away under reduced pressure, and the residue was purified by chromatography. Compound (12) (550 mg) was thereby obtained.

$^1$H-NMR (CDCl$_3$) δ: 2.6 (3H, s), 3.3 (3H, s), 6.8 (1H, s), 7.6 (1H, t), 7.8 (1H, d), 8.3 (2H, s).

Step 5

Compound (12) (1.7 g) was dissolved in dimethylformamide (4 ml). 4-Methoxybenzylamine (2.37 g) was added thereto at room temperature, and the mixture was stirred overnight. Cold water was added thereto, and the mixture was extracted with ethyl acetate. The organic phase was rinsed with water and saturated aqueous NaCl solution, and was dried with anhydrous sodium sulfate. Then, the solvent was distilled away under reduced pressure, and the residue was purified by chromatography. Compound (13) (1.32 g) was thereby obtained.

$^1$H-NMR (CDCl$_3$) δ: 1.7 (3H, s), 3.0 (1H, s), 3.1 (1H, s), 3.2 (3H, s), 3.8 (3H, s), 4.4-4.3 (1H, d), 4.8 (1H, d), 6.9 (2H, d), 7.1 (2H, d), 7.4-7.5 (2H, m), 8.1-8.2 (2H, m).

Step 6

Compound (13) (2.5 g) was suspended in acetonitrile (50 ml) and water (12.5 ml). Diammonium cerium nitrate (10.75 g) was added thereto at room temperature, and the mixture was stirred for 4 hours at 85° C. The reaction solution was added to ethyl acetate (200 ml) and a 2 M aqueous sodium hydroxide solution (50 ml). Insoluble matter was filtered out through Celite, and the filtrate was extracted with ethyl acetate. The organic phase was rinsed with water and saturated aqueous NaCl solution, and dried with anhydrous sodium sulfate. Then, the solvent was distilled away under reduced pressure, and the residue was purified by chromatography. Compound (14) (967 mg) was thereby obtained.

$^1$H-NMR (CDCl$_3$) δ: 1.52 (3H, s), 2.81, 2.89 (2H, ABq, J=16.1 Hz), 3.20 (3H, s), 4.5 (2H, brs), 7.51 (1H, t, J=8.0 Hz), 7.72-7.80 (2H, m), 8.11 (1H, ddd, J=8.0, 2.1, 1.2 Hz), 8.39 (1H, t, J=2.1 Hz).

Step 7

Compound (14) (500 mg) was dissolved in dichloromethane (5 ml) and tetrahydrofuran (5 ml). Di-t-butyl dicarbonate (1.11 ml) and 4-dimethylaminopyridine (47 mg) were added thereto, and the mixture was stirred for 45 minutes at room temperature. The solvent was distilled away under reduced pressure, and the residue was purified by chromatography. Compound (15) (683 mg) was thereby obtained.

$^1$H-NMR (CDCl$_3$) δ: 1.49 (9H, s), 1.53 (9H, s), 1.58 (3H, s), 2.70, 2.87 (2H, ABq, J=16.2 Hz), 3.14 (3H, s), 7.55 (1H, t, J=8.1 Hz), 7.84 (1H, ddd, J=8.1, 2.1, 1.2 Hz), 8.15 (1H, ddd, J=8.0, 2.1, 1.2 Hz), 8.41 (1H, t, J=2.1 Hz).

Step 8

Compound (15) (553 mg) was dissolved in methanol (5.5 ml). 10% Palladium-carbon (111 mg) was added thereto, and the mixture was stirred for 4 hours at room temperature under hydrogen atmosphere. Palladium-carbon was filtered out through Celite, and the filtrate was distilled away under reduced pressure. The residue of Compound (16) (345 mg) was thereby obtained.

$^1$H-NMR (CDCl$_3$) δ: 1.44 (9H, s), 1.50 (3H, s), 1.51 (9H, s), 2.75 (2H, s), 3.11 (3H, s), 3.69 (2H, s), 6.58 (1H, ddd, J=7.8, 2.1, 1.2 Hz), 6.81 (1H, ddd, J=7.8, 2.1, 1.2 Hz), 6.87 (1H, t, J=2.1 Hz), 7.13 (1H, t, J=7.8 Hz).

Step 9

5-Methoxypyrazine-2-carboxylic acid (37 mg) was dissolved in dimethylformamide (0.8 ml). HATU (91 mg), triethylamine (0.038 ml), and then a solution of Compound (16) (88 mg) in dimethylformamide (0.7 ml) were added thereto, and the mixture was stirred for 3 hours at room temperature. Ethyl acetate and water were added thereto, and the mixture was extracted with ethyl acetate. The organic phase was rinsed with water and saturated aqueous NaCl solution, and then dried with anhydrous sodium sulfate. The solvent was then distilled away under reduced pressure. The residue of Compound (17) (143 mg) was thereby obtained, and was used in the following step without purification.

Step 10

The residue of Compound (17) (143 mg) was dissolved in dichloromethane (1.4 ml), and TFA (0.7 ml) was added thereto in ice-cold conditions. The mixture was stirred for 1 hour and 15 minutes at room temperature, and then the solvent was distilled away under reduced pressure. Ethyl acetate and a 5% solution of potassium carbonate were added thereto, and the mixture was extracted with ethyl acetate. The organic phase was rinsed with water and saturated aqueous NaCl solution, and dried with anhydrous sodium sulfate. The solvent was then distilled away under reduced pressure, and the residue was purified by chromatography. Compound 35 (25 mg) was thereby obtained.

$^1$H-NMR (DMSO-$d_6$) δ: 1.38 (3H, s), 2.65-2.95 (2H, m), 2.99 (3H, s), 4.03 (3H, s), 5.94 (2H, brs), 7.18 (1H, d, J=8.1 Hz), 7.29 (1H, t, J=8.1 Hz), 7.74 (1H, t, J=8.1 Hz), 7.89 (1H, s), 8.42 (1H, d, J=1.1 Hz), 8.90 (1H, d, J=1.1 Hz), 10.38 (1H, s).

Example 2

Synthesis of Compound 482

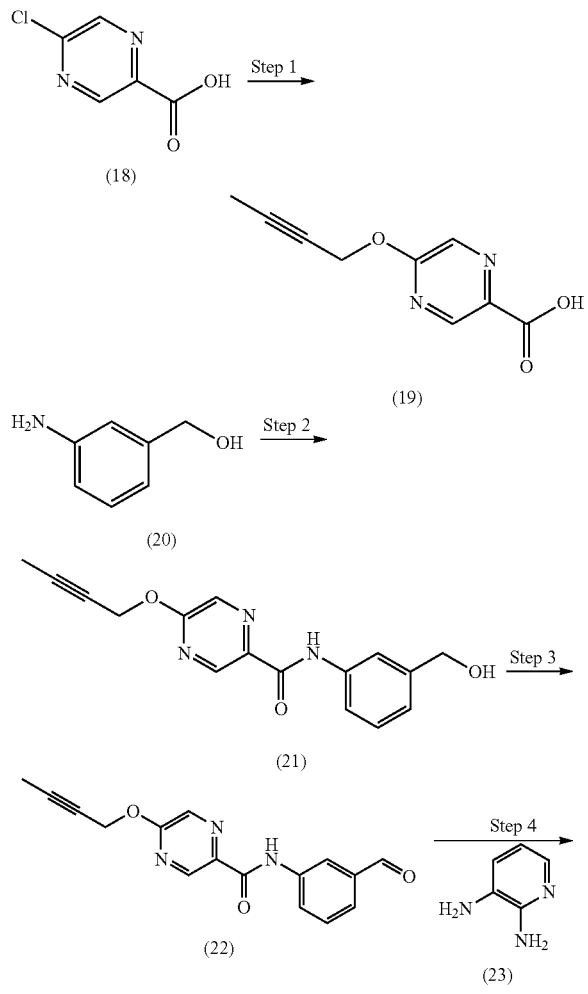

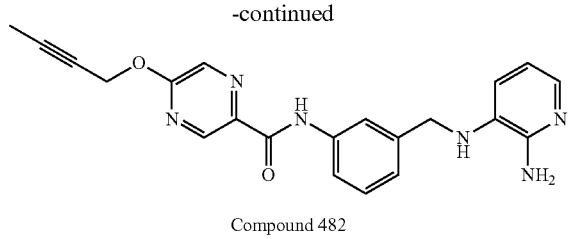

Compound 482

Step 1

Potassium t-butoxide (4.25 g) and 2-butyn-1-ol (10 ml) were added to ice-cold dimethylformamide (10 ml) under nitrogen stream. Compound (18) (1.5 g) was further added thereto. The temperature of the mixture was raised to room temperature, and the mixture was heated and stirred for 8 hours at 65° C. The temperature of the mixture was lowered to room temperature, and 2 M aqueous hydrochloric acid was added thereto. The solvent was then distilled away under reduced pressure. Thereafter, water was added and ultrasound treatment was performed. Compound (19) (1.37 g) was thereby obtained as solid matter.

$^1$H-NMR (DMSO-$d_6$) δ: 1.84 (3H, s), 5.04 (2H, s), 8.39 (1H, s), 8.79 (1H, s)

Step 2

Dimethylformamide (2 ml) was added to Compound (19) (104 mg) and HATU (205 mg), and then Compound (20) (73 mg) and triethylamine (92 µl) were added thereto. The mixture was stirred for 1 hour at room temperature, and the reaction solution was concentrated under reduced pressure. Thereafter, methanol was added and ultrasound treatment was performed. Compound (21) (112 mg) was thereby obtained as solid matter.

$^1$H-NMR (DMSO-$d_6$) δ: 1.85 (3H, s), 4.50 (2H, d, J=5.56 Hz), 5.09 (2H, d, J=2.27 Hz), 5.22 (1H, t, J=5.68 Hz), 7.08 (1H, d, J=7.33 Hz), 7.30 (1H, t, J=7.83 Hz), 7.70 (1H, d, J=8.59 Hz), 7.87 (1H, s), 8.44 (1H, s), 8.89 (1H, s), 10.42 (1H, s).

Step 3

A 0.3 M solution of Dess-Martin reagent in dichloromethane (2.24 ml) was added to Compound (21) (100 mg) under nitrogen stream, and the mixture was stirred for 2 hours at room temperature. The reaction solution was concentrated under reduced pressure. Thereafter, methanol was added and ultrasound treatment was performed. Compound (22) (68 mg) was thereby obtained as solid matter.

$^1$H-NMR (DMSO-$d_6$) δ: 1.86 (3H, s), 5.09 (2H, d, J=2.27 Hz), 7.60 (1H, t, J=7.71 Hz), 7.68 (1H, d, J=7.58 Hz), 8.13 (1H, d, J=8.34 Hz), 8.46 (1H, s), 8.52 (1H, s), 8.91 (1H, s), 10.01 (1H, s), 10.81 (1H, s).

Step 4

Dichloromethane (1 ml) and a catalytic amount of acetic acid were added to Compound (22) (50 mg) and Compound (23) (18 mg), and the mixture was stirred for 20 minutes at room temperature. NaBH(OAc)$_3$ (113 mg) was further added thereto, and the mixture was stirred for 7 hours at room temperature. The reaction solution was treated with a 2 M aqueous sodium hydroxide solution, and then extracted with ethyl acetate. The organic phase was rinsed with aqueous NaCl solution, and dried with magnesium sulfate. The solvent was then distilled away under reduced pressure, and the residue was purified by thin layer chromatography. Compound 482 (22 mg) was thereby obtained.

$^1$H-NMR (DMSO-$d_6$) δ: 1.85 (3H, s), 4.29 (2H, d, J=5.05 Hz), 5.09 (2H, d, J=2.27 Hz), 5.46-5.49 (1H, m), 5.53 (2H, s), 6.35-6.39 (1H, m), 6.46-6.48 (1H, m), 7.11-7.13 (1H, m), 7.25-7.26 (1H, m), 7.31 (1H, t, J=7.96 Hz), 7.72-7.74 (1H, m), 7.91 (1H, s), 8.43 (1H, s), 8.89 (1H, s), 10.45 (1H, s).

The other compounds were synthesized in the same manner as mentioned above. The structures and the physical constants thereof are listed below. With respect to LC-MS, the unit of retention time in the table is "minute", and the measurement conditions were as follows.

Method A

Column: Luna C18 (2) (5 μm, i.d. 4.6×50 mm) (Phenomenex)

Flow rate: 3 mL/min.

UV detection wavelength: 254 nm

Mobile phase: [A] 0.1% formic acid-containing aqueous solution; [B] 0.1% formic acid-containing acetonitrile solution Gradient: performing linear gradient of 10% to 100% solvent [B] for 3 minutes, and keeping 100% solvent [B] for 1 minute Method B Column: Shim-pack XR-ODS (2.2 μm, i.d. 50×3.0 mm) (Shimadzu)

Flow rate: 1.6 mL/min.

UV detection wavelength: 254 nm

Mobile phase: [A] 0.1% formic acid-containing aqueous solution; [B] 0.1% formic acid-containing acetonitrile solution Gradient: performing linear gradient of 10% to 100% solvent [B] for 3 minutes, and keeping 100% solvent [B] for 1 minute Test Example 1

Measurement of BACE1 Inhibitory Activity

First, 48.5 μl portions of a solution of substrate peptide (Biotin-XSEVNLDAEFRHDSGC-Eu: X=ε-amino-n-capronic acid, Eu=Europium cryptate) were put into respective wells of a 96-well half area microplate (black microplate, Costar). Then, 0.5 μl of a test compound (DMSO (dimethyl sulfoxide) solution) and 1 μl of Recombinant human BACE-1 (R&D systems) were added to each of the wells, and they were reacted for 3 hours at 30° C. The substrate peptide was synthesized by reacting Biotin-XSEVNLDAEFRHDSGC (PEPTIDE INSTITUTE, INC.) with Cryptate TBPCOOH mono SMP (CIS bio international). The final concentration of the substrate peptide was set to 18 nM, and the final concentration of Recombinant human BACE-1 was set to 7.4 nM. The reaction buffer used was a sodium acetate buffer (50 mM sodium acetate, pH 5.0, 0.008% Triton X-100). After the reaction finished, 50 μl portions of a 8.0 μg/ml solution of Streptavidin-XL665 (CIS bio international) in a phosphate buffer (150 mM $K_2HPO_4$—$KH_2PO_4$, pH 7.0, 0.008% Triton X-100, 0.8 M KF) were added to the respective wells, and the plate was left standing for 1 hour at 30° C. Thereafter, the fluorescence intensity (excitation wavelength: 320 nm, measurement wavelength: 620 nm and 665 nm) was measured with a Wallac 1420 multilabel counter (Perkin Elmer life sciences). The enzyme activity was determined from the count rate at each measurement wavelength (10000× Count

TABLE 129

| Compound No. | MS (M + H)+ | Retention time (min.) | Measurement method | NMR |
|---|---|---|---|---|
| 34 | 372.9 | 0.89 | Method A | |
| 35 | 368.9 | 0.89 | Method A | $^1$H-NMR (DMSO-$d_6$) δ: 1.38 (3H, s), 2.65-2.95 (2H, m), 2.99 (3H, s), 4.03 (3H, s), 5.94 (2H, brs), 7.18 (1H, d, J = 8.1 Hz), 7.29 (1H, t, J = 8.1 Hz), 7.74 (1H, t, J = 8.1 Hz), 7.89 (1H, s), 8.42 (1H, d, J = 1.1 Hz), 8.90 (1H, d, J = 1.1 Hz), 10.38 (1H, s). |
| 40 | 413.6 | 1.04 | Method B | |
| 43 | 393.1 | 1.12 | Method B | |
| 44 | 407 | 1.13 | Method A | |
| 473 | 351.1 | 1.16 | Method B | |
| 478 | 395.35 | 1.19 | Method B | |
| 481 | 375.1 | 1.26 | Method B | |
| 482 | 389.4 | 1.46 | Method B | $^1$H-NMR (DMSO-$d_6$) δ: 1.85 (3H, s), 4.29 (2H, d, J = 5.05 Hz), 5.09 (2H, d, J = 2.27 Hz), 5.46-5.49 (1H, m), 5.53 (2H, s), 6.35-6.39 (1H, m), 6.46-6.48 (1H, m), 7.11-7.13 (1H, m), 7.25-7.26 (1H, m), 7.31 (1H, t, J = 7.96 Hz), 7.72-7.74 (1H, m), 7.91 (1H, s), 8.43 (1H, s), 8.89 (1H, s), 10.45 (1H, s). |

665/Count 620), and the amount needed to inhibit the enzyme activity by 50% (IC$_{50}$) was calculated. Table 130 shows IC$_{50}$ value of each test compound. Here, a BACE1 inhibitor having the following structure, disclosed in the document (J. Med. Chem., 2004, 47, 6447), was used as a reference compound.

TABLE 130

| Compound No. | IC$_{50}$ (μM) |
| --- | --- |
| 34 | 0.037 |
| 35 | 0.042 |
| 40 | 0.014 |
| 43 | 0.056 |
| 44 | 0.012 |
| 473 | 1.985 |
| 478 | 3.176 |
| 481 | 0.180 |
| 482 | 0.073 |
| Reference Compound | 0.019 |

The above results show that the compound of the present invention greatly inhibits BACE1 enzyme activity.

Test Example 2

Measurement of β-amyloid (Aβ) Production Inhibitory Effect in Cell

Neuroblastoma SH-SY5Y cells (SH/APPwt) with human wild-type β-APP excessively expressed therein were prepared at 8×10$^5$ cells/mL, and 150 μl portions thereof were inoculated into respective wells of a 96-well culture plate (Falcon). The cells were cultured for 2 hours at 37° C. in a 5% gaseous carbon dioxide incubator. Then, a solution which had been preliminarily prepared by adding and suspending the test compound (DMSO (dimethyl sulfoxide) solution) so as to be 2 μl/50 μl medium was added to the cell sap. Namely, the final DMSO concentration was 1%, and the amount of the cell culture was 200 μl. After the incubation was performed for 24 hours from the addition of the test compound, 100 μl of the culture supernatant was collected from each fraction. The amount of the Aβ in each fraction was measured.

The Aβ amount was measured as follows. 10 μl of a homogeneous time resolved fluorescence (HTRF) measurement reagent (Amyloid-β 1-40 peptide; IBA Molecular Holding, S.A.) and 10 μl of the culture supernatant were put into a 384-well half area microplate (black microplate, Costar) and mixed with each other, and then left standing overnight at 4° C. while the light was shielded. Then, the fluorescence intensity (excitation wavelength: 337 nm, measurement wavelength: 620 nm and 665 nm) was measured with a Wallac 1420 multilabel counter (Perkin Elmer life sciences). The Aβ amount was determined from the count rate at each measurement wavelength (10000×Count 665/Count 620), and the amount needed to inhibit Aβ production by 50% (IC$_{50}$) was calculated from at least six different dosages. Table 131 shows the IC$_{50}$ value of each test compound.

TABLE 131

| Compound No. | IC$_{50}$ (μM) |
| --- | --- |
| 34 | 0.0762 |
| 35 | 0.0066 |
| 40 | 0.0009 |
| 43 | 0.0286 |
| 44 | 0.0007 |
| 473 | 0.4787 |
| 478 | 0.8114 |
| 481 | 0.0768 |
| 482 | 0.0438 |
| Reference Compound | 0.0368 |

The above results show that the compounds of the present invention greatly inhibit Aβ production.

Test Example 3

CYP3A4 Fluorescent MBI Test

The CYP3A4 fluorescent MBI test is a test to examine enhancement of CYP3A4 inhibition by metabolic reaction of the compound. Here, E. coli-expressing CYP3A4 was used as an enzyme, and a reaction wherein 7-benzyloxy trifluoromethylcumarin (7-BFC) was debenzylated by the CYP3A4 enzyme into a fluorescent metabolite 7-hydroxytrifluoromethylcumarin (HFC) was employed as an indicator reaction. The reaction conditions were as follows.
Substrate: 5.6 μmol/L 7-BFC
Pre-reaction time: 0 or 30 minutes
Reaction time: 15 minutes
Reaction temperature: 25° C. (room temperature)
CYP3A4 content (E. coli-expressing enzyme): 62.5 pmol/mL at pre-reaction, 6.25 μmol/mL at reaction (10-fold diluted)
Test compound concentration: 0.625, 1.25, 2.5, 5, 10, and 20 μmol/L (six different concentrations).

The enzyme and a test compound solution were added to a K-Pi buffer (pH 7.4) in the aforementioned amounts for the pre-reaction so that a pre-reaction solution was prepared, and this solution was put into a 96-well microplate. Part of this solution was transferred to another 96-well microplate such that it was diluted with the substrate and the K-Pi buffer to get a 10-fold diluted solution. NADPH, which is a coenzyme, was added so as to trigger the indicator reaction (without pre-reaction). As the reaction proceeded for a predetermined time period, acetonitrile/0.5 mol/L Tris (tris hydroxyaminomethane)=4/1 was added to terminate the reaction. NADPH was also added to the residual pre-reaction solution so as to trigger the pre-reaction (with pre-reaction). As the pre-reaction proceeded for a predetermined time period, part of the solution was transferred to another microplate so that the solution was diluted with the substrate and the K-Pi buffer to get a 10-fold diluted solution, and then the indicator reaction was triggered. As the reaction proceeded for a predetermined time period, acetonitrile/0.5 mol/L Tris (tris hydroxyaminomethane)=4/1 was added so as to terminate the reaction. With respect to each of the microplates on which the indicator reaction was performed, the fluorescence value of the metabolite 7-HFC was measured with a fluorescence plate reader (Ex=420 nm, Em=535 nm). Control (100%) was prepared by adding only DMSO, which was used as a solvent to dissolve the drug, to the reaction system. The remaining activity (%) at each concentration after adding the test compound solution was calculated, and the $IC_{50}$ value was calculated from the concentration and inhibition percentage by inverse estimation with the logistic model. When the difference of the $IC_{50}$ values was 5 µM or higher, it was regarded as (+), and when the difference was 3 µM or lower, it was regarded as (−).
(Results)
Compound No. 40: (−)
Compound No. 43: (−)

Test Example 4

CYP Inhibition Test

Using commercially available pooled human liver microsomes and employing typical substrate metabolic reactions of 5 major species of human CYP enzymes (CYP1A2, 2C9, 2C19, 2D6, 3A4), namely, O-deethylation of 7-ethoxyresorufin (CYP1A2), methyl-hydroxylation of tolbutamide (CYP2C9), 4'-hydroxylation of mephenyloin (CYP2C19), O-demethylation of dextromethorphan (CYP2D6), and hydroxylation of terfenadine (CYP3A4), as indicator reactions, the degree of inhibition of each metabolite production by each test compound was evaluated.

The reaction conditions were as follows:
Substrate: 0.5 µmol/L of ethoxyresorufin (CYP1A2), 100 µmol/L of tolbutamide (CYP2C9), 50 µmol/L of S-mephenyloin (CYP2C19), 5 µmol/L of dextromethorphan (CYP2D6), 1 µmol/L of terfenadine (CYP3A4);
Reaction time period: 15 minutes;
Reaction temperature: 37° C.;
Enzyme: pooled human liver microsomes 0.2 mg protein/mL;
Test compound concentration: 1, 5, 10 and 20 µmol/L (four different concentrations).

As a reaction solution, the respective five substrates, human liver microsomes, and test compound in the aforementioned amounts were added to a 50 mM Hepes buffer in a 96-well microplate. NADPH, which is a coenzyme, was added thereto to start the indicator metabolic reaction. The reaction proceeded for 15 minutes at 37° C., and the solution of methanol/acetonitrile=1/1 (v/v) was added so as to terminate the reaction. Centrifugation was performed for 15 minutes at 3000 rpm, and each metabolite in the centrifuged supernatant was quantified. Namely, resorufin (CYP1A2 metabolite) was quantified with a fluorescence multilabel counter, and hydroxylated tolbutamide (CYP2C9 metabolite), 4'-hydroxylated mephenyloin (CYP2C19 metabolite), dextrorphan (CYP2D6 metabolite) and alcoholized terfenadine (CYP3A4 metabolite) were quantified with LC/MS/MS.

Control (100%) was prepared by adding only DMSO, which was used as a solvent to dissolve the drug, to the reaction system. The remaining activity (%) at each concentration after adding the test compound solution was calculated, and the $IC_{50}$ value was calculated from the concentration and inhibition percentage by inverse estimation with the logistic model.
(Results)
Compound No. 44: five species >20 µM
Compound No. 473: five species >20 µM Test Example 5

FAT Test

20 µL of each strain of cryopreserved *Salmonella typhimurium* (TA98, TA100) is inoculated to 10 mL of a nutrient broth (2.5% Oxoid nutrient broth No. 2), and cultured for 10 hours at 37° C. before shaking. With respect to TA98, 9 mL of the bacterial culture is centrifuged (2000×g, 10 minutes) so that the culture medium is removed. The bacteria are suspended in 9 mL of a Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4.7H_2O$: 0.1 g/L), and added to 110 mL of an Exposure medium (Micro F buffer containing: biotin (8 µg/mL), histidine (0.2 µg/mL), and glucose (8 mg/mL)) to prepare a test bacterial culture. With respect to TA100, 3.16 mL of the bacterial culture is added to 120 mL of an Exposure medium to prepare a test bacterial culture. 588 µL of each test bacterial culture (mixed solution of 498 µL of the test bacterial culture and 90 µL of S9 mix for a metabolic activation condition) is mixed with 12 µL each of a solution of the test compound in DMSO (8-step 2-fold serial dilution from the maximum dosage of 50 mg/mL), DMSO as negative control, and positive controls (non-metabolic activation condition: a 50 µg/mL solution of 4-nitroquinoline-1-oxide in DMSO for TA98, a 0.25 µg/mL solution of 2-(2-furyl)-3-(5-nitro-2-furyl)acrylamide in DMSO for TA100; metabolic activation condition: a 40 µg/mL solution of 2-aminoanthracene in DMSO for TA98, a 20 µg/mL solution of 2-aminoanthracene in DMSO for TA100). The mixture is shake-cultured for 90 minutes at 37° C. 460 µL of the bacterial culture exposed to the test compound is added to 2300 µL of an Indicator medium (Micro F buffer containing biotin (8 µg/mL), histidine (0.2 µg/mL), glucose (8 mg/mL), and bromocresol purple (37.5 µg/mL)), and 50 µL portions of the mixture are dispensed in a microplate 48 wells/dosage. The mixture is stationarily cultured for 3 days at 37° C. In the wells containing bacteria which acquired proliferation potency due to mutation of the amino acid (histidine) synthase gene, the color of the mixture changes from purple to yellow due to pH change. Thus, the number of bacterial proliferation wells in which the color of the mixture has turned into yellow is counted among the 48 wells for each dosage, and evaluation is performed in comparison with the negative control group. Negative mutagenicity is evaluated as (−), while positive mutagenicity as (+).

Test Example 6

Solubility Test

The solubility of each compound was determined under 1% DMSO addition conditions. A 10 mM solution of the compound was prepared with DMSO, and 6 µL of the compound solution was added to 594 µL of an artificial intestinal juice (water and 118 mL of 0.2 mol/L NaOH reagent were added to 250 mL of 0.2 mol/L potassium dihydrogen phosphate reagent to reach 1000 mL) with a pH of 6.8. The mixture was left standing for 16 hours at 25° C., and the mixture was vacuum-filtered. The filtrate was two-fold diluted with methanol/water=1/1, and the compound concentration in the filtrate was measured with HPLC or LC/MS/MS by the absolute calibration method.
(Results)
Compound No. 473: >50 µM
Compound No. 478: >50 µM Test Example 7

Metabolic Stability Test

The target compound was reacted with commercially available pooled human liver microsomes for a predetermined time period. The residual rate was calculated by comparing the reacted sample and unreacted sample, and thus the degree of metabolism in liver was evaluated.

In 0.2 mL of a buffer (50 mmol/L tris-HCl pH 7.4, 150 mmol/L potassium chloride, 10 mmol/L magnesium chloride) containing human liver microsomes 0.5 mg protein/mL, reaction was carried out in the presence of 1 mmol/L NADPH for 0 minute or 30 minutes at 37° C. (oxidative reaction). After the reaction, 50 μL of the reaction solution was added to and mixed with 100 μL of a solution of methanol/acetonitrile=1/1 (v/v), and the mixture was centrifuged for 15 minutes at 3000 rpm. The test compound in the centrifuged supernatant was quantified by LC/MS/MS, and the residual amount of the test compound after the reaction was calculated based on the compound amount at 0-minute reaction set as 100%.

(Results) The residual rate at a compound concentration of 2 μM is shown below.

Compound No. 35: 99.5%

Test Example 8 hERG Test

For the purpose of risk assessment for QT prolongation on an electrocardiogram, the action on delayed rectifier K+ current ($I_{Kr}$) which plays an important role on a process of ventricular repolarization was studied using a HEK293 cell with a human ether-a-go-go related gene (hERG) channel expressed therein.

A cell was maintained at a membrane potential of −80 mV, and then +40 mV of a depolarizing stimulus was applied to the cell for 2 seconds and further −50 mV of a repolarizing stimulus was applied thereto for 2 seconds by a whole-cell patch clamp technique with a fully-automatic patch clamp system (PatchXpress 7000A, Axon Instruments Inc.), and the induced $I_{Kr}$ was recorded. As the current generated was stabilized, an extracellular fluid with the test compound dissolved therein at a target concentration (NaCl: 135 mmol/L, KCl: 5.4 mmol/L, $NaH_2PO_4$: 0.3 mmol/L, $CaCl_2.2H_2O$: 1.8 mmol/L, $MgCl_2\text{-}6H_2O$: 1 mmol/L, glucose: 10 mmol/L, HEPES (4-(2-hydroxyethyl)-1-piperazineethanesulfonic acid): 10 mmol/L, pH=7.4) was applied to the cell for 10 minutes under room temperature conditions. The absolute value of the maximum tail current was determined from the obtained $I_{Kr}$ with an analysis software (DataXpress ver. 1, Molecular Devices Corporation) based on a current value at a maintained membrane potential. Further, an inhibitory percentage relative to the maximum tail current before application of the test compound was calculated, and influence of the test compound on $I_{Kr}$ was evaluated in comparison with the medium application group (0.1% dimethyl sulfoxide solution).

(Results) The inhibitory percentage at a compound concentration of 5 μM is shown below.

Compound No. 40: 4.1%

Test Example 9

Powder Solubility Test

Appropriate amounts of the test substances are put into appropriate containers. To the respective containers are added 200 μL of JP-1 fluid (sodium chloride 2.0 g, hydrochloric acid 7.0 mL and water to reach 1000 mL), 200 μL of JP-2 fluid (phosphate buffer (pH 6.8) 500 mL and water 500 mL), and 200 μL of 20 mmol/L TCA (sodium taurocholate)/JP-2 fluid (TCA 1.08 g and water to reach 100 mL). In the case that the test compound is dissolved after the addition of the test fluid, the bulk powder is added as appropriate. The containers are sealed, and shaken for 1 hour at 37° C. The mixtures are filtered, and 100 μL of methanol is added to each of the filtrate (100 μL) so that the filtrates are two-fold diluted. The dilution ratio may be changed if necessary. The dilutions are observed for bubbles and precipitates, and then the containers are sealed and shaken. Quantification is performed by HPLC with an absolute calibration method.

Test Example 10

BA Test

Materials and Methods for Studies on Oral Absorption (1) Animal: SD rats (2) Breeding conditions: rats are allowed to freely take solid feed and sterilized tap water (3) Dose and grouping: orally or intravenously administered at a predetermined dose; grouping is as follows (Dose depends on the compound)

Oral administration: 1 to 30 mg/kg (n=2 to 3)

Intravenous administration: 0.5 to 10 mg/kg (n=2 to 3)

(4) Preparation of dosing solution: for oral administration, in a solution or a suspension state; for intravenous administration, in a solubilized state (5) Administration method: in oral administration, forcedly administer into ventriculus with oral probe; in intravenous administration, administer from caudal vein with a needle-equipped syringe (6) Evaluation items: blood is collected over time, and the plasma concentration of drug is measured by LC/MS/MS (7) Statistical analysis: regarding the transition of the plasma concentration, the area under the plasma concentration-time curve (AUC) is calculated by non-linear least squares program WinNonlin (Registered trademark), and the bioavailability (BA) is calculated from the AUCs of the oral administration group and intravenous administration group Formulation Example 1

Granules containing the following ingredients are prepared.

| Ingredients | Compound of formula (I) | 10 mg |
|---|---|---|
| | Lactose | 700 mg |
| | Corn starch | 274 mg |
| | HPC-L | 16 mg |
| | | 1000 mg |

Compound of formula (I) and lactose are screened through a 60-mesh sieve. Corn starch is screened through a 120-mesh sieve. These ingredients are mixed by a V-shaped mixer. An aqueous solution of HPC-L (low-viscosity hydroxypropyl cellulose) is added to the mixed powders, and the mixture is kneaded, granulated (extrusion-granulation, pore-size: 0.5 to 1 mm), and dried. The dried granules obtained are screened through a vibrating sieve (12/60 meshes), and thereby granules are obtained.

Formulation Example 2

Granules to be capsulated containing the following ingredients are prepared.

| Ingredients | Compound of formula (I) | 15 mg |
|---|---|---|
| | Lactose | 90 mg |
| | Corn starch | 42 mg |
| | HPC-L | 3 mg |
| | | 150 mg |

Compound of formula (I) and lactose are screened through a 60-mesh sieve. Corn starch is screened through a 120-mesh sieve. Then, these ingredients are mixed with each other. An HPC-L solution is added to the mixed powders, and the mixture is kneaded, granulated, and dried. The dried granules obtained are subjected to sizing, and 150 mg of the sized granules are capsulated into a size #4 hard gelatin capsule.

Formulation Example 3

A tablet containing the following ingredients is prepared.

| Ingredients | Compound of formula (I) | 10 mg |
|---|---|---|
| | Lactose | 90 mg |
| | Fine crystal cellulose | 30 mg |
| | CMC-Na | 15 mg |
| | Magnesium stearate | 5 mg |
| | | 150 mg |

Compound of formula (I), lactose, fine crystal cellulose, and CMC-Na (carboxymethyl cellulose sodium salt) are screened through a 60-mesh sieve, and they are mixed with each other. Magnesium stearate is added to the mixed powders, and thereby mixed powders for tablet are obtained. The mixed powders are directly compressed, so that a 150-mg tablet is obtained.

Formulation Example 4

The following ingredients are mixed under heating, and then sterilized to be an injection.

| Ingredients | Compound of formula (I) | 3 mg |
|---|---|---|
| | Nonionic surfactant | 15 mg |
| | Purified water for injection | 1 ml |

Formulation Example 5

Granules containing the following ingredients are produced.

| Ingredients | Compound of formula (II) | 10 mg |
|---|---|---|
| | Lactose | 700 mg |
| | Corn starch | 274 mg |
| | HPC-L | 16 mg |
| | | 1000 mg |

Compound of formula (II) and lactose are screened through a 60-mesh sieve. Corn starch is screened through a 120-mesh sieve. They are mixed by a V-shaped mixer. An aqueous solution of HPC-L (low-viscosity hydroxypropyl cellulose) is added to the mixed powders, and the mixture is kneaded, granulated (extrusion-granulation, pore-size: 0.5 to 1 mm), and dried. The dried granules obtained are screened through a vibrating sieve (12/60 meshes), and thereby granules are obtained.

Formulation Example 6

Granules to be capsulated containing the following ingredients are prepared.

| Ingredients | Compound of formula (II) | 15 mg |
|---|---|---|
| | Lactose | 90 mg |
| | Corn starch | 42 mg |
| | HPC-L | 3 mg |
| | | 150 mg |

Compound of formula (II) and lactose are screened through a 60-mesh sieve. Corn starch is screened through a 120-mesh sieve. Then, these ingredients are mixed with each other. An HPC-L solution is added to the mixed powders, and the mixture is kneaded, granulated, and dried. The dried granules obtained are subjected to sizing, and 150 mg of the sized granules are capsulated into a size #4 hard gelatin capsule.

Formulation Example 7

A tablet containing the following ingredients is prepared.

| Ingredients | Compound of formula (II) | 10 mg |
|---|---|---|
| | Lactose | 90 mg |
| | Fine crystal cellulose | 30 mg |
| | CMC-Na | 15 mg |
| | Magnesium stearate | 5 mg |
| | | 150 mg |

Compound of formula (II), lactose, fine crystal cellulose, and CMC-Na (carboxymethyl cellulose sodium salt) are screened through a 60-mesh sieve, and they are mixed with each other. Magnesium stearate is added to the mixed powder, and thereby mixed powders for tablet are obtained. The mixed powders are directly compressed, so that a 150-mg tablet is obtained.

Formulation Example 8

The following ingredients are mixed under heating, and then sterilized to be an injection.

| Ingredients | Compound of formula (II) | 3 mg |
|---|---|---|
| | Nonionic surfactant | 15 mg |
| | Purified water for injection | 1 ml |

Industrial Applicability

The compound of the present invention may be a medicament useful as a therapeutic agent for diseases induced by production, secretion and/or deposition of amyloid-β proteins.

The invention claimed is:

1. A compound represented by formula (I) or a pharmaceutically acceptable salt or solvate thereof,

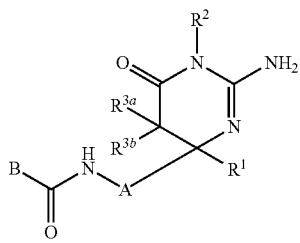

wherein A is an optionally substituted carbocyclic diyl or an optionally substituted heterocyclic diyl;
wherein a heterocyclic portion of the heterocyclic diyl is selected from the group consisting of pyrrolyl, imidazolyl, pyrazolyl, pyridyl, pyridazinyl, pyrimidinyl, pyrazinyl, triazolyl, triazinyl, tetrazolyl, furyl, isoxazolyl, oxazolyl, oxadiazolyl, isothiazolyl, thiazolyl, thiadiazolyl, dioxanyl, thiiranyl, oxiranyl, oxetanyl, oxathioranyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl, tetrahydropyridazinyl, indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzotriazolyl, benzisoxazolyl, benzoxazolyl, benzoxadiazolyl, benzoisothiazolyl, benzothiazolyl, benzothiadiazolyl, benzofuryl, isobenzofuryl, benzothienyl, benzotriazolyl, thienopyridyl, thienopyrrolyl, thienopyrazolyl, thienopyrazinyl, furopyrrolyl, thienothienyl, imidazopyrazyl, imidazopyridyl, pyrazolopyridyl, thiazolopyridyl, pyrazolopyrimidinyl, pyrrolopyrimidinyl, pyrazolotriazinyl, pyridazolopyridyl, triazolopyridyl, imidazothiazolyl, pirazinopyridazinyl, quinazolinyl, quinolyl, isoquinolyl, naphthyridinyl, dihydrothiazolopyrimidinyl, tetrahydroquinolyl, tetrahydroisoquinolyl, dihydrobenzofuryl, dihydrobenzoxazinyl, dihydrobenzimidazolyl, tetrahydrobenzothienyl, tetrahydrobenzofuryl, benzodioxolyl, benzodioxonyl, chromanyl, chromenyl, octahydrochromenyl, dihydrobenzodioxinyl, dihydrobenzooxedinyl, dihydrobenzodioxepinyl, dihydrothienodioxinyl, carbazolyl, acridinyl, xanthenyl, phenothiazinyl, phenoxathiinyl, phenoxazinyl, dibenzofuryl, imidazoquinolyl and tetrahydrocarbazolyl;
B is an optionally substituted heterocyclic group;
$R^1$ is an optionally substituted lower alkyl, an optionally substituted lower alkenyl, or an optionally substituted lower alkynyl, or $R^1$ forms a bond together with $R^{3a}$ or $R^{3b}$;
$R^2$ is hydrogen, an optionally substituted lower alkyl, an optionally substituted lower alkenyl, an optionally substituted lower alkynyl, an optionally substituted acyl or an optionally substituted lower alkoxycarbonyl; and
$R^{3a}$ and $R^{3b}$ are each independently hydrogen, halogen, hydroxy, an optionally substituted lower alkyl, an optionally substituted lower alkenyl, an optionally substituted acyl, an optionally substituted lower alkoxy, an optionally substituted aralkyl, an optionally substituted heteroarylalkyl, an optionally substituted aralkyloxy, an optionally substituted heteroarylalkyloxy, an optionally substituted lower alkylthio, carboxy, an optionally substituted lower alkoxycarbonyl, an optionally substituted amino, an optionally substituted carbamoyl, an optionally substituted carbocyclic group or an optionally substituted heterocyclic group, or $R^{3a}$ or $R^{3b}$ forms a bond together with $R^1$,
provided that the following compound is excluded

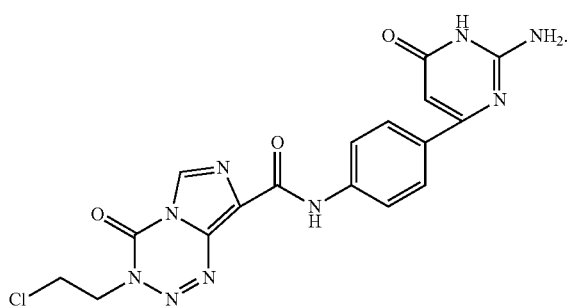 [SMILES: Nc1nc(-c2ccc(NC(=O)c3ncn4c(=O)n(CCCl)nnc34)cc2)cc(=O)[nH]1]

2. The compound or a pharmaceutically acceptable salt or solvate thereof according to claim 1,
wherein A is an optionally substituted benzenediyl, an optionally substituted pyridinediyl, an optionally substituted pyrazinediyl or an optionally substituted benzofurandiyl.

3. The compound or a pharmaceutically acceptable salt or solvate thereof according to claim 1,
wherein the substituent of the heterocyclic group for B is an optionally substituted lower alkoxy, an optionally substituted lower alkenyloxy or an optionally substituted lower alkynyloxy.

4. The compound or a pharmaceutically acceptable salt or solvate thereof according to claim 1,
wherein $R^{3a}$ and $R^{3b}$ are both hydrogen.

5. The compound or a pharmaceutically acceptable salt or solvate thereof according to claim 1,
wherein $R^1$ and $R^{3a}$ together form a bond, and $R^{3b}$ is hydrogen.

6. The compound or a pharmaceutically acceptable salt or solvate thereof according to claim 1,
wherein $R^1$ is C1-C3 alkyl.

7. The compound or a pharmaceutically acceptable salt or solvate thereof according to claim 1,
wherein $R^2$ is an optionally substituted lower alkyl.

8. A pharmaceutical composition, comprising
the compound or a pharmaceutically acceptable salt or solvate thereof according to claim 1 as an active ingredient.

9. The pharmaceutical composition according to claim 8, which has a BACE1 inhibitory activity.

* * * * *